US011608499B2

(12) United States Patent
Neuteboom et al.

(10) Patent No.: US 11,608,499 B2

(45) Date of Patent: Mar. 21, 2023

(54) METHODS FOR MODIFICATION OF TARGET NUCLEIC ACIDS

(71) Applicant: BASF PLANT SCIENCE COMPANY GMBH, Ludwigshafen am Rhein (DE)

(72) Inventors: Leendert W. Neuteboom, Research Triangle Park, NC (US); John A. McElver, Research Triangle Park, NC (US); Rosa De Pinho Barroco, Ghent (BE); Chris De Wilde, Ghent (BE); Max Fabian Felle, Ludwigshafen (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 914 days.

(21) Appl. No.: 16/097,300

(22) PCT Filed: Apr. 20, 2017

(86) PCT No.: PCT/EP2017/059331

§ 371 (c)(1),
(2) Date: Oct. 29, 2018

(87) PCT Pub. No.: WO2017/186550

PCT Pub. Date: Nov. 2, 2017

(65) Prior Publication Data

US 2019/0309290 A1 Oct. 10, 2019

(30) Foreign Application Priority Data

Apr. 29, 2016 (EP) .................................... 16167773
Apr. 29, 2016 (EP) .................................... 16167774
Feb. 14, 2017 (EP) .................................... 17156018

(51) Int. Cl.

| | |
|---|---|
| ***C12N 15/11*** | (2006.01) |
| ***C12N 15/10*** | (2006.01) |
| ***C12N 15/70*** | (2006.01) |
| ***C12N 15/75*** | (2006.01) |
| ***C12N 15/82*** | (2006.01) |
| ***C12N 15/85*** | (2006.01) |
| ***C12N 15/90*** | (2006.01) |
| ***C12N 15/81*** | (2006.01) |

(52) U.S. Cl.

CPC ............ *C12N 15/11* (2013.01); *C12N 15/102* (2013.01); *C12N 15/111* (2013.01); *C12N 15/70* (2013.01); *C12N 15/75* (2013.01); *C12N 15/81* (2013.01); *C12N 15/8274* (2013.01); *C12N 15/8509* (2013.01); *C12N 15/902* (2013.01); *C12N 15/905* (2013.01); *C12N 15/907* (2013.01); *C12N 2310/20* (2017.05)

(58) Field of Classification Search

CPC C12N 15/09; C12N 15/907; C12N 2310/111; C12N 2310/3519

See application file for complete search history.

(56) References Cited

U.S. PATENT DOCUMENTS

| | | | | |
|---|---|---|---|---|
| 2014/0315985 | A1 | 10/2014 | May et al. | |
| 2018/0223313 | A1* | 8/2018 | Uchida ................ | C07K 14/155 |

FOREIGN PATENT DOCUMENTS

| | | | |
|---|---|---|---|
| EP | 1152058 | A1 | 11/2001 |
| WO | WO-2007/025097 | A2 | 3/2007 |
| WO | WO-2014/150624 | A1 | 9/2014 |
| WO | WO-2014/204728 | | 12/2014 |
| WO | WO-2015/013583 | A2 | 1/2015 |
| WO | 2015191693 | A2 | 12/2015 |
| WO | WO-2016/065364 | A1 | 4/2016 |
| WO | WO-2016/183448 | A1 | 11/2016 |
| WO | WO-2017/024047 | A1 | 2/2017 |
| WO | 2017059241 | A1 | 4/2017 |
| WO | 2017064546 | A1 | 4/2017 |
| WO | WO-2017/092201 | A1 | 6/2017 |
| WO | 2017180711 | A1 | 10/2017 |
| WO | 2018094356 | A2 | 5/2018 |

OTHER PUBLICATIONS

Cong et al., Multiplex Genome Engineering Using CRISPR/Cas Systems, Science, vol. 339, Issue 6121, 2013, pp. 819-823.

Doudna et al., The new frontier of genome engineering with CRISPR-Cas9, Science, vol. 346, Issue 6213, Nov. 28, 2014, pp. 1258096-1-1258096-09.

European Search Report for EP Patent Application No. 16167774.5, dated Oct. 24, 2016, 3 pages.

Guilinger et al., Fusion of catalytically inactive Cas9 to FokI nuclease improves the specificity of genome modification, Nature Biotechnology, vol. 32, Issue 6, 2014, pp. 577-582.

International Search Report for PCT Application No. PCT/EP2017/059331, dated Jul. 17, 2017, 06 pages.

Li et al., Novel HDAd/EBV Reprogramming Vector and Highly Efficient Ad/CRISPR-Cas Sickle Cell Disease Gene Correction, Scientific Reports, vol. 6, 2016, 10 pages.

(Continued)

*Primary Examiner* — Karen Cochrane Carlson

(74) *Attorney, Agent, or Firm* — ArentFox Schiff LLP

(57) ABSTRACT

Methods for modification of target nucleic acids. The method involves a construct in which guide RNA is covalently linked to donor RNA (fusion NA) to be introduced into the target nucleic acid by homologous recombination and is based on the introduction of a nuclease, e.g. CRISPR or TALEN, into the cell containing the target nucleic acid. The fusion NA may be introduced as a DNA vector.

20 Claims, 26 Drawing Sheets

Figure 1:
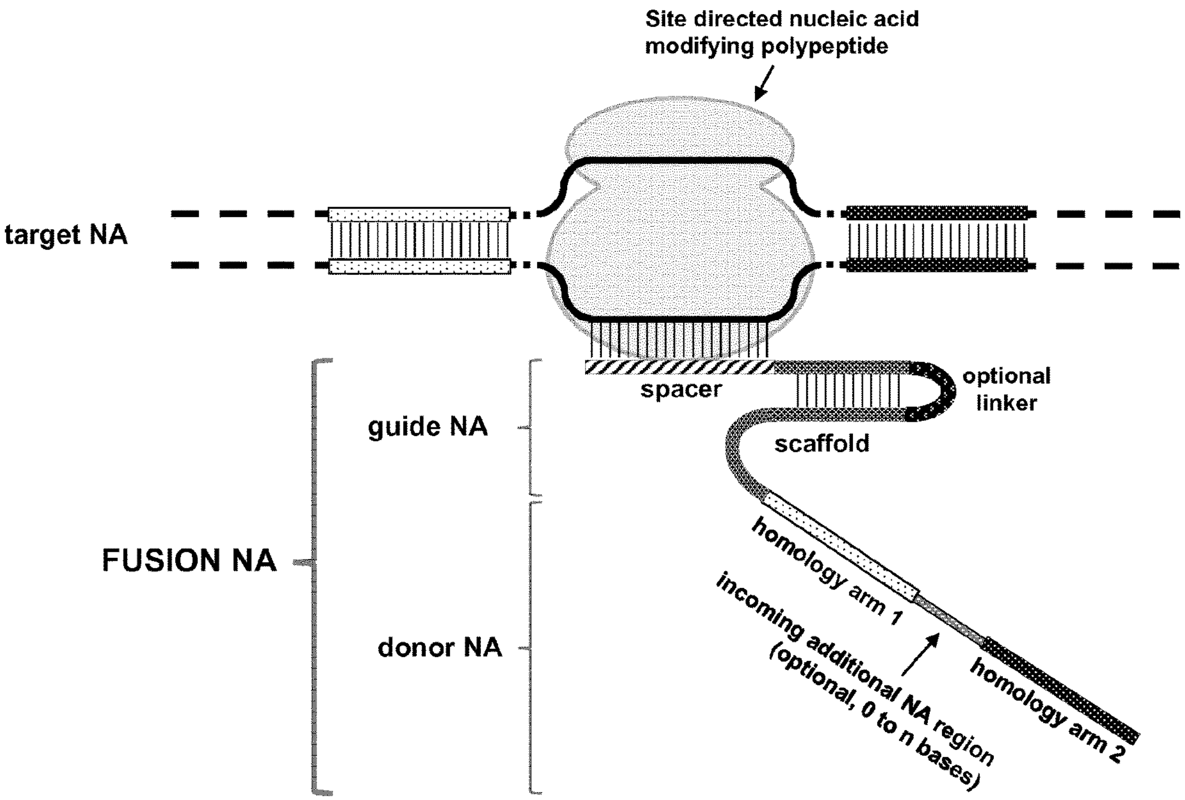

Specification includes a Sequence Listing.

(56) References Cited

OTHER PUBLICATIONS

Maeder et al., Genome-editing Technologies for Gene and Cell Therapy, Molecular Therapy, vol. 24, Issue 3, Mar. 2016, pp. 430-446.
Mali et al., RNA-Guided Human Genome Engineering via Cas9, Science, vol. 339, Issue 6121, Feb. 15, 2013, pp. 823-826.
Maurisse et al., A New Method (Gorec) for Directed Mutagenesis and Gene Repair by Homologous Recombination, Gene Therapy, Nature Publishing Group, vol. 9, Issue 11, 2002, pp. 703-707.
Salmon et al., A conserved amino acid residue critical for product and substrate specificity in plant triterpene synthases, Proceedings of the National Academy of Sciences of the United States of America, vol. 113, Issue 30, pp. E4407-E4414.
Shalem et al., Genome-scale CRISPR-Cas9 knockout screening in human cells, Science, vol. 343, Issue 6166, 2014, pp. 84-87.
Standage-Beier et al., Targeted Large-Scale Deletion of Bacterial Genomes Using CRISPR-Nickases, ACS Synthetic Biology, vol. 4, Issue 11, 2015, pp. 1217-1225.
Tsai et al., Dimeric CRISPR RNA-guided Fokl nucleases for highly specific genome editing, Nature Biotechnology, vol. 32, Issue 6, 2014, pp. 569-576.
Wade, High-Throughput Silencing Using the CRISPR-Cas9 System: A Review of the Benefits and Challenges, Journal of Biomolecular Screening, vol. 20, Issue 8, 2015, pp. 1027-1039.
Xu et al., Efficient Genome Editing in Clostridium cellulolyticum via CRISPR-Cas9 Nickase, Applied and Environmental Microbiology, vol. 81, Issue 13, 2015, pp. 4423-4431.
Hsu, et al., "Development and Applications of CRISPR-Cas9 for Genome Engineering", Cell, vol. 157, Issue 6, Jun. 5, 2014, pp. 1262-1278.
European Search Report for EP Patent Application No. 21162462.2, dated Jul. 28, 2021, 4 pages.
Jeffrey M. Bono et al., "Connecting genotypes, phenotypes and fitness: harnessing the power of CRISPR/Cas9 genome editing," Molecular Ecology (2015), 24, pp. 3810-3822.
F Ann Ran et al., "Genome engineering using the CRISPR-Cas9 system," Nature Protocols, 2013, vol. 8, No. 11, pp. 2281-2308.
Alexandre Paix et al., "Scalable and Versatile Genome Editing Using Linear DNAs with Microhomology to Cas9 Sites in Caenorhabditis elegans," Genetics, Dec. 2014, vol. 198, pp. 1347-1356.
Alexandro E. Trevino et al., "Genome Editing Using Cas9 Nickases," Methods in Enzymology, 2014, vol. 546, Chapter 8, pp. 161-174.
Zengrong Zhu et al., "The iCRISPR Platform for Rapid Genome Editing in Human Pluripotent Stem Cells," Methods in Enzymology, 2014, vol. 546, Chapter 11, pp. 215-250.
Supratim Choudhuri, "Bioinformatics for Beginners: Genes, Genomes, Molecular Evolution, Databases and Analytical Tools," 2014, Elsevier Inc., pp. 64.
Martin Jinek et al., "A Programmable Dual-RNA-Guided DNA Endonuclease in Adaptive Bacterial Immunity," Science, Aug. 17, 2012, vol. 337.
"ProQuest™ Two-Hybrid System: A sensitive method for detecting protein-protein interactions," invitrogen, Oct. 24, 2005, pp. i-160.
Josef Altenbuchner, "Editing of the Bacillus subtilis Genome by the CRISPR-Cas9 System," Applied and Environmental Microiology, Sep. 2016, vol. 82, No. 17, pp. 5421-5427.
U.S. Appl. No. 62/322,099, filed Apr. 13, 2016.
U.S. Appl. No. 62/236,223, filed Oct. 2, 2015.
EPO Communication dated Aug. 4, 2022 in European Patent Application No. 17720040.9 (EP Patent No. EP3448990), 78 pages.
Makarova et al., An updated evolutionary classification of CRISPR—Cas systems, Nature Reviews Microbiology 13, 722-736, doi:10.1038/nrmicro3569, published Sep. 28, 2015.
Zetsche et al., Cpf1 Is a Single RNA-Guided Endonuclease of a Class 2 CRISPR—Cas System, Cell vol. 163(3), Oct. 22, 2015, published Sep. 25, 2015.
Doerr, Cas9 and the importance of asymmetry, Nature Methods, pp. 286-287, vol. 13, No. 4, published online Mar. 30, 2016 (Apr. 2016 print edition).
Richardson et al., Enhancing homology-directed genome editing by catalytically active and inactive CRISPR-Cas9 using asymmetric donor DNA, Nature Biotechnology, vol. 34(3), Mar. 2016, published online Jan. 20, 2016.
Lehrbuch der Molekularen Zellbiologie; Alberts, Johnson, Lewis, Raff, Roberts, Walter (authors); Wiley-VCH Verlag GmbH, printed 1999.
Alberts et al. (editors): Essential Cell Biology (third edition), Garland Science, p. 47 (2010).
Shen et al., Mutation Research/Fundamental and Molecular Mechanisms of Mutagenesis; Mutation Research 717 (2011) 91-98.
Hisano et al., Precise in-frame integration of exogenous DNA mediated by CRISPR/Cas9 system in zebrafish, Scientific Reports, 5:8841; DOI:10.1038/srep08841; published Mar. 5, 2015.
Simone et al., Chimeric RNA: DNA TracrRNA Improves Homology-Directed Repair In Vitro and In Vivo, The CRISPR Journal vol. 5, No. 1, 2022, Mary Ann Liebert, Inc., DOI: 10.1089/crispr.2021.0087.
Komor et al., Programmable editing of a target base in genomic DNA without double-stranded DNA cleavage, Nature. ;533(7603): 420-424. doi: 10.1038/naturel7946, published Apr. 20, 2016.
Kiani et al., Cas9gRNA engineering for genome editing, activation and repression; Nat Methods.; 12(11):1051-1054; doi:10.1038/nmeth.3580; published Nov. 2015.
Konermann et al., Genome-scale transcriptional activation by an engineered CRISPR-Cas9 complex; Nature vol. 517; doi:10.1038/nature14136; Jan. 29, 2015.
Dahlman et al., Orthogonal gene knockout and activation with a catalytically active Cas9 nuclease; Nature Biotechnology; 33(11); published online Oct. 5, 2015; doi :10.1038/nbt.3390.
Giifliths: Modem Genetic Analysis; 2nd Edition 1999, pp. 4 and 5, printed 2002, Freeman and Company.
Girffiths: Modern Genetic Analysis; 2nd Edition 1999, p. 217, printed 2002, Freeman and Company.
Tycko et al., Methods for Optimizing CRISPR-Cas9 Genome Editing Specificity; Molecular Cell 63, Aug. 4, 2016; pp. 355-370; http://dx.doi.org/10.1016/j.molcel.2016.07.004.
Yin et al., Therapeutic genome editing by combined viral and non-viral delivery of CRISPR system components in vivo; Nature Biotechnology; Advance online publication; published online Feb. 1, 2016; doi:10.1038/nbt.3471.
Anderson et al., Systematic analysis of CRISPR—Cas9 mismatch tolerance reveals low levels of off-target activity; Journal of Biotechnology 211 (2015) 56-65, available online Jul. 17, 2015.
GE Healthcare; 2015, Brochure: DharmaconTM Edit-RTM CRISPR-Cas9 Genome Editing Products.
GE Healthcare; 2015, Brochure: A CRISPR-Cas9 gene engineering workflow: generating functional knockouts using Edit-RTM Cas9 and synthetic crRNA and tracrRNA.
Liang et al., Rapid and highly efficient mammalian cell engineering via Cas9 protein transfection; Journal of Biotechnology 208 (2015) 44-53; available online May 21, 2015.
Park et al., Extension of the crRNA enhances Cpf1 gene editing in vitro and in vivo; Nature Communications; (2018) 9:3313; DOI:10.1038/s41467-018-05641-3.
EPO Communication dated Dec. 20, 2022 in European Patent Application No. 17720040.9 (European Patent No. EP3448990B1) including Experimental Report (document D37), 83 pages.
Reply of Patent Proprietor dated Jan. 25, 2023 in European Patent Application No. 17720040.9 (European Patent No. EP3448990B1) including Declaration of Dr. Maarten H. Stuiver (document D38); and documents D39 and D40, 47 pages.

* cited by examiner

SEQUENCE LISTING

<160> NUMBER OF SEQ ID NOS: 75

<210> SEQ ID NO 1
<211> LENGTH: 4140
<212> TYPE: DNA
<213> ORGANISM: Artificial Sequence
<220> FEATURE:
<223> OTHER INFORMATION: Cas9 yeast

<400> SEQUENCE: 1
atggataaaa aatattctat tggtttggat attggtacta attctgttgg ttgggctgtt 60
attactgatg aatataaagt tccatctaaa aaatttaaag ttttgggtaa tactgataga 120
cattctatta aaaaaaattt gattggtgct ttgttgtttg attctggtga aactgctgaa 180
gctactagat tgaaaagaac tgctagaaga agatatacta gaagaaaaaa tagaatttgt 240
tatttgcaag aaatttttc taatgaaatg gctaaagttg atgattcttt ttttcataga 300
ttggaagaat cttttttggt tgaagaagat aaaaaacatg aaagacatcc aatttttggt 360
aatattgttg atgaagttgc ttatcatgaa aaatatccaa ctatttatca tttgagaaaa 420
aaattggttg attctactga taaagctgat ttgagattga tttatttggc tttggctcat 480
atgattaaat ttagaggtca ttttttgatt gaaggtgatt tgaatccaga taattctgat 540
gttgataaat tgtttattca attggttcaa acttataatc aattgtttga agaaaatcca 600
attaatgctt ctggtgttga tgctaaagct attttgtctg ctagattgtc taaatctaga 660
agattggaaa atttgattgc tcaattgcca ggtgaaaaaa aaaatggttt gtttggtaat 720
ttgattgctt tgtctttggg tttgactcca aattttaaat ctaattttga tttggctgaa 780
gatgctaaat tgcaattgtc taaagatact tatgatgatg atttggataa tttgttggct 840
caaattggtg atcaatatgc tgatttgttt ttggctgcta aaaatttgtc tgatgctatt 900
ttgttgtctg atattttgag agttaatact gaaattacta aagctccatt gtctgcttct 960
atgattaaaa gatatgatga acatcatcaa gatttgactt tgttgaaagc tttggttaga 1020
caacaattgc cagaaaaata taaagaaatt ttttttgatc aatctaaaaa tggttatgct 1080
ggttatattg atggtggtgc ttctcaagaa gaattttata aatttattaa accaattttg 1140
gaaaaaatgg atggtactga agaattgttg gttaaattga atagagaaga tttgttgaga 1200
aaacaaagaa cttttgataa tggttctatt ccacatcaaa ttcatttggg tgaattgcat 1260
gctattttga gaagacaaga agatttttat ccatttttga aagataatag agaaaaaatt 1320
gaaaaaattt tgacttttag aattccatat tatgttggtc cattggctag aggtaattct 1380
agatttgctt ggatgactag aaaatctgaa gaaactatta ctccatggaa ttttgaagaa 1440
gttgttgata aaggtgcttc tgctcaatct tttattgaaa gaatgactaa ttttgataaa 1500
aatttgccaa atgaaaaagt tttgccaaaa cattctttgt tgtatgaata ttttactgtt 1560
tataatgaat tgactaaagt taaatatgtt actgaaggta tgagaaaacc agctttttttg 1620 tctggtgaac aaaaaaaagc tattgttgat ttgttgttta aaactaatag aaaagttact 1680
gttaaacaat tgaaagaaga ttattttaaa aaaattgaat gttttgattc tgttgaaatt 1740
tctggtgttg aagatagatt taatgcttct ttgggtactt atcatgattt gttgaaaatt 1800
attaaagata aagatttttt ggataatgaa gaaaatgaag atattttgga agatattgtt 1860
ttgactttga ctttgtttga agatagagaa atgattgaag aaagattgaa aacttatgct 1920
catttgtttg atgataaagt tatgaaacaa ttgaaaagaa gaagatatac tggttggggt 1980
agattgtcta gaaaattgat taatggtatt agagataaac aatctggtaa aactattttg 2040 gatttttga aatctgatgg ttttgctaat agaaatttta tgcaattgat tcatgatgat 2100
tctttgactt ttaaagaaga tattcaaaaa gctcaagttt ctggtcaagg tgattctttg 2160
catgaacata ttgctaattt ggctggttct ccagctatta aaaaaggtat tttgcaaact 2220
gttaaagttg ttgatgaatt ggttaaagtt atgggtagac ataaaccaga aaatattgtt 2280
attgaaatgg ctagagaaaa tcaaactact caaaaaggtc aaaaaaattc tagagaaaga 2340
atgaaaagaa ttgaagaagg tattaaagaa ttgggttctc aaattttgaa agaacatcca 2400
gttgaaaata ctcaattgca aaatgaaaaa ttgtatttgt attatttgca aaatggtaga 2460
gatatgtatg ttgatcaaga attggatatt aatagattgt ctgattatga tgttgatcat 2520
attgttccac aatctttttt gaaagatgat tctattgata ataaagtttt gactagatct 2580
gataaaaata gaggtaaatc tgataatgtt ccatctgaag aagttgttaa aaaaatgaaa 2640
aattattgga gacaattgtt gaatgctaaa ttgattactc aaagaaaatt tgataatttg 2700
actaaagctg aaagaggtgg tttgtctgaa ttggataaag ctggttttat taaaagacaa 2760
ttggttgaaa ctagacaaat tactaaacat gttgctcaaa ttttggattc tagaatgaat 2820
actaaatatg atgaaaatga taaattgatt agagaagtta aagttattac tttgaaatct 2880
aaattggttt ctgattttag aaaagatttt caattttata aagttagaga aattaataat 2940
tatcatcatg ctcatgatgc ttatttgaat gctgttgttg gtactgcttt gattaaaaaa 3000
tatccaaaat tggaatctga atttgtttat ggtgattata aagtttatga tgttagaaaa 3060
atgattgcta aatctgaaca agaaattggt aaagctactg ctaaatattt tttttattct 3120
aatattatga attttttttaa aactgaaatt actttggcta atggtgaaat tagaaaaaga 3180
ccattgattg aaactaatgg tgaaactggt gaaattgttt gggataaagg tagagatttt 3240
gctactgtta gaaaagtttt gtctatgcca caagttaata ttgttaaaaa aactgaagtt 3300
caaactggtg gtttttctaa agaatctatt ttgccaaaaa gaaattctga taaattgatt 3360
gctagaaaaa aagattggga tccaaaaaaa tatggtggtt ttgattctcc aactgttgct 3420
tattctgttt tggttgttgc taaagttgaa aaaggtaaat ctaaaaaatt gaaatctgtt 3480

-continued

```
aaagaattgt tgggtattac tattatggaa agatcttctt ttgaaaaaaa tccaattgat   3540

tttttggaag ctaaaggtta taaagaagtt aaaaaagatt tgattattaa attgccaaaa   3600

tattctttgt ttgaattgga aaatggtaga aaaagaatgt tggcttctgc tggtgaattg   3660

caaaaaggta atgaattggc tttgccatct aaatatgtta attttttgta tttggcttct   3720

cattatgaaa aattgaaagg ttctccagaa gataatgaac aaaaacaatt gtttgttgaa   3780

caacataaac attatttgga tgaaattatt gaacaaattt ctgaattttc taaaagagtt   3840

attttggctg atgctaattt ggataaagtt ttgtctgctt ataataaaca tagagataaa   3900

ccaattagag aacaagctga aaatattatt catttgttta ctttgactaa tttgggtgct   3960

ccagctgctt ttaaatattt tgatactact attgatagaa aaagatatac ttctactaaa   4020

gaagttttgg atgctacttt gattcatcaa tctattactg gtttgtatga aactagaatt   4080

gatttgtctc aattgggtgg tgattctaga gctgatccaa aaaaaaaaag aaaagtttaa   4140
```

<210> SEQ ID NO 2
<211> LENGTH: 1379
<212> TYPE: PRT
<213> ORGANISM: Artificial Sequence
<220> FEATURE:
<223> OTHER INFORMATION: Cas9 yeast protein

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255
```

-continued

```
Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

-continued

```
Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
```

```
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

Ser Arg  Ala Asp Pro Lys Lys  Lys Arg Lys Val
    1370                1375
```

<210> SEQ ID NO 3
<211> LENGTH: 4140
<212> TYPE: DNA
<213> ORGANISM: Artificial Sequence
<220> FEATURE:
<223> OTHER INFORMATION: Cas9 D10A H840A inactive

<400> SEQUENCE: 3

```
atggataaaa aatattctat tggtttggct attggtacta attctgttgg ttgggctgtt     60

attactgatg aatataaagt tccatctaaa aaatttaaag ttttgggtaa tactgataga    120

cattctatta aaaaaaattt gattggtgct ttgttgtttg attctggtga aactgctgaa    180

gctactagat tgaaaagaac tgctagaaga agatatacta gaagaaaaaa tagaatttgt    240

tatttgcaag aaattttttc taatgaaatg gctaaagttg atgattcttt ttttcataga    300
```

-continued

```
ttggaagaat ctttttttggt tgaagaagat aaaaaacatg aaagacatcc aatttttggt    360
aatattgttg atgaagttgc ttatcatgaa aaatatccaa ctatttatca tttgagaaaa    420
aaattggttg attctactga taaagctgat ttgagattga tttatttggc tttggctcat    480
atgattaaat ttagaggtca ttttttgatt gaaggtgatt tgaatccaga taattctgat    540
gttgataaat tgtttattca attggttcaa acttataatc aattgtttga agaaaatcca    600
attaatgctt ctggtgttga tgctaaagct attttgtctg ctagattgtc taaatctaga    660
agattggaaa atttgattgc tcaattgcca ggtgaaaaaa aaaatggttt gtttggtaat    720
ttgattgctt tgtctttggg tttgactcca aattttaaat ctaattttga tttggctgaa    780
gatgctaaat tgcaattgtc taaagatact tatgatgatg atttggataa tttgttggct    840
caaattggtg atcaatatgc tgatttgttt ttggctgcta aaaatttgtc tgatgctatt    900
ttgttgtctg atattttgag agttaatact gaaattacta aagctccatt gtctgcttct    960
atgattaaaa gatatgatga acatcatcaa gatttgactt tgttgaaagc tttggttaga   1020
caacaattgc cagaaaaata taaagaaatt ttttttgatc aatctaaaaa tggttatgct   1080
ggttatattg atggtggtgc ttctcaagaa gaattttata aatttattaa accaattttg   1140
gaaaaaatgg atggtactga agaattgttg gttaaattga atagagaaga tttgttgaga   1200
aaacaaagaa cttttgataa tggttctatt ccacatcaaa ttcatttggg tgaattgcat   1260
gctattttga gaagacaaga agatttttat ccattttttga aagataatag agaaaaaatt   1320
gaaaaaattt tgacttttag aattccatat tatgttggtc cattggctag aggtaattct   1380
agatttgctt ggatgactag aaaatctgaa gaaactatta ctccatggaa ttttgaagaa   1440
gttgttgata aaggtgcttc tgctcaatct tttattgaaa gaatgactaa ttttgataaa   1500
aatttgccaa atgaaaaagt tttgccaaaa cattctttgt tgtatgaata ttttactgtt   1560
tataatgaat tgactaaagt taaatatgtt actgaaggta tgagaaaacc agctttttttg   1620
tctggtgaac aaaaaaaagc tattgttgat ttgttgttta aaactaatag aaaagttact   1680
gttaaacaat tgaaagaaga ttattttaaa aaaattgaat gttttgattc tgttgaaatt   1740
tctggtgttg aagatagatt taatgcttct ttgggtactt atcatgattt gttgaaaatt   1800
attaaagata aagatttttt ggataatgaa gaaaatgaag atattttgga agatattgtt   1860
ttgactttga ctttgtttga agatagagaa atgattgaag aaagattgaa aacttatgct   1920
catttgtttg atgataaagt tatgaaacaa ttgaaaagaa gaagatatac tggttggggt   1980
agattgtcta gaaaattgat taatggtatt agagataaac aatctggtaa aactattttg   2040
gatttttttga aatctgatgg ttttgctaat agaaatttta tgcaattgat tcatgatgat   2100
tctttgactt ttaaagaaga tattcaaaaa gctcaagttt ctggtcaagg tgattctttg   2160
catgaacata ttgctaattt ggctggttct ccagctatta aaaaaggtat tttgcaaact   2220
gttaaagttg ttgatgaatt ggttaaagtt atgggtagac ataaaccaga aaatattgtt   2280
attgaaatgg ctagagaaaa tcaaactact caaaaaggtc aaaaaaaattc tagagaaaga   2340
atgaaaagaa ttgaagaagg tattaaagaa ttgggttctc aaattttgaa agaacatcca   2400
gttgaaaata ctcaattgca aaatgaaaaa ttgtatttgt attatttgca aaatggtaga   2460
gatatgtatg ttgatcaaga attggatatt aatagattgt ctgattatga tgttgatgct   2520
attgttccac aatctttttt gaaagatgat tctattgata ataaagtttt gactagatct   2580
gataaaaata gaggtaaatc tgataatgtt ccatctgaag aagttgttaa aaaaatgaaa   2640
aattattgga gacaattgtt gaatgctaaa ttgattactc aaagaaaatt tgataatttg   2700
```

```
actaaagctg aaagaggtgg tttgtctgaa ttggataaag ctggttttat taaaagacaa   2760

ttggttgaaa ctagacaaat tactaaacat gttgctcaaa ttttggattc tagaatgaat   2820

actaaatatg atgaaaatga taaattgatt agagaagtta aagttattac tttgaaatct   2880

aaattggttt ctgattttag aaaagatttt caattttata aagttagaga aattaataat   2940

tatcatcatg ctcatgatgc ttatttgaat gctgttgttg gtactgcttt gattaaaaaa   3000

tatccaaaat tggaatctga atttgtttat ggtgattata aagtttatga tgttagaaaa   3060

atgattgcta aatctgaaca agaaattggt aaagctactg ctaaatattt tttttattct   3120

aatattatga attttttaa aactgaaatt actttggcta atggtgaaat tagaaaaaga   3180

ccattgattg aaactaatgg tgaaactggt gaaattgttt gggataaagg tagagatttt   3240

gctactgtta gaaaagtttt gtctatgcca caagttaata ttgttaaaaa aactgaagtt   3300

caaactggtg gtttttctaa agaatctatt ttgccaaaaa gaaattctga taaattgatt   3360

gctagaaaaa aagattggga tccaaaaaaa tatggtggtt ttgattctcc aactgttgct   3420

tattctgttt tggttgttgc taaagttgaa aaaggtaaat ctaaaaaatt gaaatctgtt   3480

aaagaattgt tgggtattac tattatggaa agatcttctt ttgaaaaaaa tccaattgat   3540

tttttggaag ctaaaggtta taaagaagtt aaaaaagatt tgattattaa attgccaaaa   3600

tattctttgt ttgaattgga aaatggtaga aaaagaatgt tggcttctgc tggtgaattg   3660

caaaaaggta atgaattggc tttgccatct aaatatgtta attttttgta tttggcttct   3720

cattatgaaa aattgaaagg ttctccagaa gataatgaac aaaaacaatt gtttgttgaa   3780

caacataaac attatttgga tgaaattatt gaacaaattt ctgaattttc taaaagagtt   3840

attttggctg atgctaattt ggataaagtt ttgtctgctt ataataaaca tagagataaa   3900

ccaattagag aacaagctga aaatattatt catttgttta ctttgactaa tttgggtgct   3960

ccagctgctt ttaaatattt tgatactact attgatagaa aaagatatac ttctactaaa   4020

gaagttttgg atgctacttt gattcatcaa tctattactg gtttgtatga aactagaatt   4080

gatttgtctc aattgggtgg tgattctaga gctgatccaa aaaaaaaaag aaaagtttaa   4140
```

<210> SEQ ID NO 4
<211> LENGTH: 1379
<212> TYPE: PRT
<213> ORGANISM: Artificial Sequence
<220> FEATURE:
<223> OTHER INFORMATION: Cas9 D10A H840A inactive protein

<400> SEQUENCE: 4

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110
```

-continued

```
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525
```

-continued

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
```

-continued

```
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350
```

```
Gly Leu  Tyr Glu Thr Arg Ile  Asp Leu Ser Gln Leu  Gly Gly Asp
    1355                 1360                 1365

Ser Arg  Ala Asp Pro Lys Lys  Lys Arg Lys Val
    1370                 1375


<210> SEQ ID NO 5
<211> LENGTH: 4155
<212> TYPE: DNA
<213> ORGANISM: Artificial Sequence
<220> FEATURE:
<223> OTHER INFORMATION: Cas9 rice

<400> SEQUENCE: 5

atggacaaga agtatagtat tggtctggac attgggacga attccgttgg ctgggccgtg     60

atcaccgatg agtacaaggt cccttccaag aagtttaagg ttctggggaa caccgatcgg    120

cacagcatca agaagaatct cattggagcc ctcctgttcg actcaggcga gaccgccgaa    180

gcaacaaggc tcaagagaac cgcaaggaga cggtatacaa gaaggaagaa taggatctgc    240

tacctgcagg agattttcag caacgaaatg gcgaaggtgg acgattcgtt ctttcataga    300

ttggaggaga gtttcctcgt cgaggaagat aagaagcacg agaggcatcc tatctttggc    360

aacattgtcg acgaggttgc ctatcacgaa aagtacccca caatctatca tctgcggaag    420

aagcttgtgg actcgactga taaggcggac cttagattga tctacctcgc tctggcacac    480

atgattaagt tcaggggcca ttttctgatc gagggggatc ttaacccgga caatagcgat    540

gtggacaagt tgttcatcca gctcgtccaa acctacaatc agctctttga ggaaaaccca    600

attaatgctt caggcgtcga cgccaaggcg atcctgtctg cacgcctttc aaagtctcgc    660

cggcttgaga acttgatcgc tcaactcccg ggcgaaaaga agaacggctt gttcgggaat    720

ctcattgcac tttcgttggg gctcacacca aacttcaaga gtaattttga tctcgctgag    780

gacgcaaagc tgcagctttc caaggacact tatgacgatg acctggataa cctttttggcc    840

caaatcggcg atcagtacgc ggacttgttc ctcgccgcga agaatttgtc ggacgcgatc    900

ctcctgagtg atattctccg cgtgaacacc gagattacaa aggccccgct ctcggcgagt    960

atgatcaagc gctatgacga gcaccatcag gatctgaccc ttttgaaggc tttggtccgg   1020

cagcaactcc cagagaagta caaggaaatc ttctttgatc aatccaagaa cggctacgct   1080

ggttatattg acggcggggc atcgcaggag gaattctaca agtttatcaa gccaattctg   1140

gagaagatgg atggcacaga ggaactcctg gtgaagctca atagggagga cctttttgcgg   1200

aagcaaagaa ctttcgataa cggcagcatc cctcaccaga ttcatctcgg ggagctgcac   1260

gccatcctga gaaggcagga agacttctac ccctttctta aggataaccg ggagaagatc   1320

gaaaagattc tgacgttcag aattccgtac tatgtcggac cactcgcccg gggtaattcc   1380

agatttgcgt ggatgaccag aaagagcgag gaaaccatca caccttggaa cttcgaggaa   1440

gtggtcgata agggcgcttc cgcacagagc ttcattgagc gcatgacaaa ttttgacaag   1500

aacctgccta atgagaaggt ccttcccaag cattccctcc tgtacgagta tttcactgtt   1560

tataacgaac tcacgaaggt gaagtatgtg accgagggaa tgcgcaagcc cgccttcctg   1620

agcggcgagc aaaagaaggc gatcgtggac cttttgttta agaccaatcg gaaggtcaca   1680

gttaagcagc tcaaggagga ctacttcaag aagattgaat gcttcgattc cgttgagatc   1740

agcggcgtgg aagacaggtt taacgcgtca ctggggactt accacgatct cctgaagatc   1800

attaaggata aggacttctt ggacaacgag gaaaatgagg atatcctcga agacattgtc   1860
```

-continued

```
ctgactctta cgttgtttga ggatagggaa atgatcgagg aacgcttgaa gacgtatgcc   1920
catctcttcg atgacaaggt tatgaagcag ctcaagagaa gaagatacac cggatgggga   1980
aggctgtccc gcaagcttat caatggcatt agagacaagc aatcagggaa gacaatcctt   2040
gactttttga agtctgatgg cttcgcgaac aggaatttta tgcagctgat tcacgatgac   2100
tcacttactt tcaaggagga tatccagaag gctcaagtgt cgggacaagg tgacagtctg   2160
cacgagcata tcgccaacct tgcgggatct cctgcaatca agaagggtat tctgcagaca   2220
gtcaaggttg tggatgagct tgtgaaggtc atgggacggc ataagcccga gaacatcgtt   2280
attgagatgg ccagagaaaa tcagaccaca caaaagggtc agaagaactc gagggagcgc   2340
atgaagcgca tcgaggaagg cattaaggag ctggggagtc agatccttaa ggagcacccg   2400
gtggaaaaca cgcagttgca aaatgagaag ctctatctgt actatctgca aaatggcagg   2460
gatatgtatg tggaccagga gttggatatt aaccgcctct cggattacga cgtcgatcat   2520
atcgttcctc agtccttcct taaggatgac agcattgaca ataaggttct caccaggtcc   2580
gacaagaacc gcgggaagtc cgataatgtg cccagcgagg aagtcgttaa gaagatgaag   2640
aactactgga ggcaactttt gaatgccaag ttgatcacac agaggaagtt tgataacctc   2700
actaaggccg agcgcggagg tctcagcgaa ctggacaagg cgggcttcat taagcggcaa   2760
ctggttgaga ctagacagat cacgaagcac gtggcgcaga ttctcgattc acgcatgaac   2820
acgaagtacg atgagaatga caagctgatc cgggaagtga aggtcatcac cttgaagtca   2880
aagctcgttt ctgacttcag gaaggatttc caattttata aggtgcgcga gatcaacaat   2940
tatcaccatg ctcatgacgc atacctcaac gctgtggtcg gaacagcatt gattaagaag   3000
tacccgaagc tcgagtccga attcgtgtac ggtgactata aggtttacga tgtgcgcaag   3060
atgatcgcca agtcagagca ggaaattggc aaggccactg cgaagtattt cttttactct   3120
aacattatga atttctttaa gactgagatc acgctggcta atggcgaaat ccggaagaga   3180
ccacttattg agaccaacgg cgagacaggg gaaatcgtgt gggacaaggg gagggatttc   3240
gccacagtcc gcaaggttct ctctatgcct caagtgaata ttgtcaagaa gactgaagtc   3300
cagacgggcg ggttctcaaa ggaatctatt ctgcccaagc ggaactcgga taagcttatc   3360
gccagaaaga aggactggga cccgaagaag tatggaggtt tcgactcacc aacggtggct   3420
tactctgtcc tggttgtggc aaaggtggag aagggaaagt caaagaagct caagtctgtc   3480
aaggagctcc tgggtatcac cattatggag aggtccagct tcgaaaagaa tccgatcgat   3540
tttctcgagg cgaagggata taaggaagtg aagaaggacc tgatcattaa gcttccaaag   3600
tacagtcttt tcgagttgga aaacggcagg aagcgcatgt tggcttccgc aggagagctc   3660
cagaagggta acgagcttgc tttgccgtcc aagtatgtga acttcctcta tctggcatcc   3720
cactacgaga agctcaaggg cagcccagag gataacgaac agaagcaact gtttgtggag   3780
caacacaagc attatcttga cgagatcatt gaacagattt cggagttcag taagcgcgtc   3840
atcctcgccg acgcgaattt ggataaggtt ctctcagcct acaacaagca ccgggacaag   3900
cctatcagag agcaggcgga aaatatcatt catctcttca ccctgacaaa ccttggggct   3960
cccgctgcat tcaagtattt tgacactacg attgatcgga agagatacac ttctacgaag   4020
gaggtgctgg atgcaaccct tatccaccaa tcgattactg gcctctacga gacgcggatc   4080
gacttgagtc agctcggggg ggataagaga ccagcggcaa ccaagaaggc aggacaagcg   4140
aagaagaaga agtag                                                    4155
```

-continued

<210> SEQ ID NO 6
<211> LENGTH: 24
<212> TYPE: DNA
<213> ORGANISM: Artificial Sequence
<220> FEATURE:
<223> OTHER INFORMATION: SV40 Nuclear Localizaion Signal

<400> SEQUENCE: 6
cccaagaaga agcggaaggt ctcg 24

<210> SEQ ID NO 7
<211> LENGTH: 957
<212> TYPE: DNA
<213> ORGANISM: Artificial Sequence
<220> FEATURE:
<223> OTHER INFORMATION: GAL4

<400> SEQUENCE: 7
atgaagctac tgtcttctat cgaacaagca tgcgatattt gccgacttaa aaagctcaag 60
tgctccaaag aaaaaccgaa gtgcgccaag tgtctgaaga acaactggga gtgtcgctac 120
tctcccaaaa ccaaaaggtc tccgctgact agggcacatc tgacagaagt ggaatcaagg 180
ctagaaagac tggaacagct atttctactg atttttcctc gagaagacct tgacatgatt 240
ttgaaaatgg attctttaca ggatataaaa gcattgttaa caggattatt tgtacaagat 300
aatgtgaata aagatgccgt cacagataga ttggcttcag tggagactga tatgcctcta 360
acattgagac agcatagaat aagtgcgaca tcatcatcgg aagagagtag taacaaaggt 420
caaagacagt tgactgtatc gccggaattt gtaatacgac tcactatagg gcgagccgcc 480
atcatggagg agcagaagct gatctcagag gaggacctgc atatggccat ggaggccgaa 540
ttcatggata aagcggaatt aattcccgag cctccaaaaa agaagagaaa ggtcgaattg 600
ggtaccgccg ccaattttaa tcaaagtggg aatattgctg atagctcatt gtccttcact 660
ttcactaaca gtagcaacgg tccgaacctc ataacaactc aaacaaattc tcaagcgctt 720
tcacaaccaa ttgcctcctc taacgttcat gataacttca tgaataatga aatcacggct 780
agtaaaattg atgatggtaa taattcaaaa ccactgtcac ctggttggac ggaccaaact 840
gcgtataacg cgtttggaat cactacaggg atgtttaata ccactacaat ggatgatgta 900
tataactatc tattcgatga tgaagatacc ccaccaaacc caaaaaaaga gatttaa 957

<210> SEQ ID NO 8
<211> LENGTH: 318
<212> TYPE: PRT
<213> ORGANISM: Artificial Sequence
<220> FEATURE:
<223> OTHER INFORMATION: GAL4 protein

<400> SEQUENCE: 8

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu

-continued

```
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Val Ile Arg Leu Thr Ile Gly Arg Ala Ala
145                 150                 155                 160

Ile Met Glu Glu Gln Lys Leu Ile Ser Glu Glu Asp Leu His Met Ala
                165                 170                 175

Met Glu Ala Glu Phe Met Asp Lys Ala Glu Leu Ile Pro Glu Pro Pro
            180                 185                 190

Lys Lys Lys Arg Lys Val Glu Leu Gly Thr Ala Ala Asn Phe Asn Gln
        195                 200                 205

Ser Gly Asn Ile Ala Asp Ser Ser Leu Ser Phe Thr Phe Thr Asn Ser
    210                 215                 220

Ser Asn Gly Pro Asn Leu Ile Thr Thr Gln Thr Asn Ser Gln Ala Leu
225                 230                 235                 240

Ser Gln Pro Ile Ala Ser Ser Asn Val His Asp Asn Phe Met Asn Asn
                245                 250                 255

Glu Ile Thr Ala Ser Lys Ile Asp Asp Gly Asn Asn Ser Lys Pro Leu
            260                 265                 270

Ser Pro Gly Trp Thr Asp Gln Thr Ala Tyr Asn Ala Phe Gly Ile Thr
        275                 280                 285

Thr Gly Met Phe Asn Thr Thr Thr Met Asp Asp Val Tyr Asn Tyr Leu
    290                 295                 300

Phe Asp Asp Glu Asp Thr Pro Pro Asn Pro Lys Lys Glu Ile
305                 310                 315
```

<210> SEQ ID NO 9
<211> LENGTH: 958
<212> TYPE: DNA
<213> ORGANISM: Artificial Sequence
<220> FEATURE:
<223> OTHER INFORMATION: GAL4 target 1

<400> SEQUENCE: 9

```
atgaagctac tgtcttctat cgaacaagca tgcgatattt gccgacttaa aaagctcaag      60

tgctccaaag aaaaaccgaa gtgcgccaag tgtctgaaga actaactggg agtgtcgcta     120

ctctcccaaa accaaaaggt ctccgctgac tagggcacat ctgacagaag tggaatcaag     180

gctagaaaga ctggaacagc tatttctact gatttttcct cgagaagacc ttgacatgat     240

tttgaaaatg gattctttac aggatataaa agcattgtta acaggattat ttgtacaaga     300

taatgtgaat aaagatgccg tcacagatag attggcttca gtggagactg atatgcctct     360

aacattgaga cagcatagaa taagtgcgac atcatcatcg gaagagagta gtaacaaagg     420

tcaaagacag ttgactgtat cgccggaatt tgtaatacga ctcactatag ggcgagccgc     480

catcatggag gagcagaagc tgatctcaga ggaggacctg catatggcca tggaggccga     540

attcatggat aaagcggaat taattcccga gcctccaaaa aagaagagaa aggtcgaatt     600

gggtaccgcc gccaatttta atcaaagtgg gaatattgct gatagctcat tgtccttcac     660

tttcactaac agtagcaacg gtccgaacct cataacaact caaacaaatt ctcaagcgct     720

ttcacaacca attgcctcct ctaacgttca tgataacttc atgaataatg aaatcacggc     780
```

tagtaaaatt gatgatggta ataattcaaa accactgtca cctggttgga cggaccaaac 840
tgcgtataac gcgtttggaa tcactacagg gatgtttaat accactacaa tggatgatgt 900
atataactat ctattcgatg atgaagatac cccaccaaac ccaaaaaaag agatttaa 958

<210> SEQ ID NO 10
<211> LENGTH: 938
<212> TYPE: DNA
<213> ORGANISM: Artificial Sequence
<220> FEATURE:
<223> OTHER INFORMATION: GAL4 target 2

<400> SEQUENCE: 10
atgaagctac tgtcttctat cgaacaagca tgcgatattt gccgacttaa aaagctcaag 60
tgctccaaag aaaaaccgaa gtgcgccaag tgtctgaaga actaactgga accaaaaggt 120
ctccgctgac tagggcacat ctgacagaag tggaatcaag gctagaaaga ctggaacagc 180
tatttctact gatttttcct cgagaagacc ttgacatgat tttgaaaatg gattctttac 240
aggatataaa agcattgtta acaggattat ttgtacaaga taatgtgaat aaagatgccg 300
tcacagatag attggcttca gtggagactg atatgcctct aacattgaga cagcatagaa 360
taagtgcgac atcatcatcg gaagagagta gtaacaaagg tcaaagacag ttgactgtat 420
cgccggaatt tgtaatacga ctcactatag ggcgagccgc catcatggag gagcagaagc 480
tgatctcaga ggaggacctg catatggcca tggaggccga attcatggat aaagcggaat 540
taattcccga gcctccaaaa aagaagagaa aggtcgaatt gggtaccgcc gccaatttta 600
atcaaagtgg gaatattgct gatagctcat tgtccttcac tttcactaac agtagcaacg 660
gtccgaacct cataacaact caaacaaatt ctcaagcgct ttcacaacca attgcctcct 720
ctaacgttca tgataacttc atgaataatg aaatcacggc tagtaaaatt gatgatggta 780
ataattcaaa accactgtca cctggttgga cggaccaaac tgcgtataac gcgtttggaa 840
tcactacagg gatgtttaat accactacaa tggatgatgt atataactat ctattcgatg 900
atgaagatac cccaccaaac ccaaaaaaag agatttaa 938

<210> SEQ ID NO 11
<211> LENGTH: 920
<212> TYPE: DNA
<213> ORGANISM: Artificial Sequence
<220> FEATURE:
<223> OTHER INFORMATION: GAL4 target 3

<400> SEQUENCE: 11
atgaagctac tgtcttctat cgaacaagca tgcgatattt gccgacttaa aaagctcaag 60
tgctccaaag aaaacaagtg tctgaagaac taactggaag gtctccgctg actagggcac 120
atctgacaga agtggaatca aggctagaaa gactggaaca gctatttcta ctgatttttc 180
ctcgagaaga ccttgacatg attttgaaaa tggattcttt acaggatata aaagcattgt 240
taacaggatt atttgtacaa gataatgtga ataaagatgc cgtcacagat agattggctt 300
cagtggagac tgatatgcct ctaacattga gacagcatag aataagtgcg acatcatcat 360
cggaagagag tagtaacaaa ggtcaaagac agttgactgt atcgccggaa tttgtaatac 420
gactcactat agggcgagcc gccatcatgg aggagcagaa gctgatctca gaggaggacc 480
tgcatatggc catggaggcc gaattcatgg ataaagcgga attaattccc gagcctccaa 540
aaaagaagag aaaggtcgaa ttgggtaccg ccgccaattt taatcaaagt gggaatattg 600

-continued ctgatagctc attgtccttc actttcacta acagtagcaa cggtccgaac ctcataacaa 660
ctcaaacaaa ttctcaagcg ctttcacaac caattgcctc ctctaacgtt catgataact 720
tcatgaataa tgaaatcacg gctagtaaaa ttgatgatgg taataattca aaaccactgt 780
cacctggttg gacggaccaa actgcgtata acgcgtttgg aatcactaca gggatgttta 840
ataccactac aatggatgat gtatataact atctattcga tgatgaagat accccaccaa 900
acccaaaaaa agagatttaa 920

<210> SEQ ID NO 12
<211> LENGTH: 560
<212> TYPE: DNA
<213> ORGANISM: Artificial Sequence
<220> FEATURE:
<223> OTHER INFORMATION: GAL4 target 4

<400> SEQUENCE: 12
atgaagctac tgtcttctat cgaacaagca tgcgatattt gccgacttaa aaagctcaag 60
tgctccaaag aaaaaccgaa gtgcgccaag tgtctgaaga acaactggga gtgtcgctac 120
tctcccaaaa ccaaaaggtc tccgctgact agggcacatc tgacagaagt ggaatcaagg 180
ctagaaagac tggaacagct atttctactg atttttcctc gagaagacct tgacatgatt 240
ttgaaaatgg attctttaca ggatataaaa gcattgttaa caggattatt tgtacaagat 300
aatgtgaata aagatgccgt cacagataga ttggcttcag tggagactga tatgcctcta 360
acattgagac agcatagaat aagtgcgaca tcatcatcgg aagagagtag taacaaaggt 420
caaagacagt tgactgtata acgccggaac gcgtttggaa tcacttaaca gggatgttta 480
ataccactac aatggatgat gtatataact atctattcga tgatgaagat accccaccaa 540
acccaaaaaa agagatttaa 560

<210> SEQ ID NO 13
<211> LENGTH: 708
<212> TYPE: DNA
<213> ORGANISM: Artificial Sequence
<220> FEATURE:
<223> OTHER INFORMATION: GAL4 target 5

<400> SEQUENCE: 13
atgaagctac tgtcttctat cgaacaagca tgcgatattt gccgacttaa aaagctcaag 60
tgctccaaag aaaaaccgaa gtgcgccaag tgtctgaaga acaactggga gtgtcgctac 120
tctcccaaaa ccaaaaggtc tccgctgact agggcacatc tgacagaagt ggaatcaagg 180
ctagaaagac tggaacagct atttctactg atttttcctc gagaagacct tgacatgatt 240
ttgaaaatgg attctttaca ggatataaaa gcattgttaa caggattatt tgtacaagat 300
aatgtgaata aagatgccgt cacagataga ttggcttcag tggagactga tatgcctcta 360
acattgagac agcatagaat aagtgcgaca tcatcatcgg aagagagtag taacaaaggt 420
caaagacagt tgactgtatc gccggaattt gtaatacgac tcactatagg gcgagccgcc 480
atcatggagg agcagaagct gatctcagag gaggacctgc atatggccat ggaggccgaa 540
ttcatgtgat aaagcggaat taattcccca cctggttgga cggaccaaac tgcgtataac 600
gcgtttggaa tcactacagg gatgtttaat accactacaa tggatgatgt atataactat 660
ctattcgatg atgaagatac cccaccaaac ccaaaaaaag agatttaa 708

<210> SEQ ID NO 14
<211> LENGTH: 240

<212> TYPE: DNA
<213> ORGANISM: Artificial Sequence
<220> FEATURE:
<223> OTHER INFORMATION: GAL4 target 6

<400> SEQUENCE: 14
atgaagctac tgtcttctat cgaacaagca tgcgatattt gccgacttaa aaagctcaag 60
tgctccaaag aaaaaccgaa gtgcgccaag tgtctgaaga actaactgga ctgcgtccaa 120
actgcgtata acgcgtttgg aatcactaca gggatgttta ataccactac aatggatgat 180
gtatataact atctattcga tgatgaagat accccaccaa acccaaaaaa agagatttaa 240

<210> SEQ ID NO 15
<211> LENGTH: 356
<212> TYPE: DNA
<213> ORGANISM: Artificial Sequence
<220> FEATURE:
<223> OTHER INFORMATION: GAL4 target 7

<400> SEQUENCE: 15
atgaagctac tgtcttctat cgaacaagca tgcgatattt gccgacttaa aaagctcaag 60
tgctccaaag aaaaaccgaa gtgcgccaag tgtctgaaga acaactggga gtgtcgctac 120
tctcccaaaa ccaaaaggtc tccgctgact agggcacatc tgacagaagt ggaatcaagg 180
ctagaaagac tggaacagct atttctactg atttttcctc gagaagacct tgactgattt 240
tgtataacgc gtttggaatc actacaggga tgtttaatac cactacaatg gatgatgtat 300
ataactatct attcgatgat gaagataccc caccaaaccc aaaaaaagag atttaa 356

<210> SEQ ID NO 16
<211> LENGTH: 268
<212> TYPE: DNA
<213> ORGANISM: Saccharomyces cerevisiae
<220> FEATURE:
<221> NAME/KEY: misc_feature
<223> OTHER INFORMATION: SNR52 promoter

<400> SEQUENCE: 16
ctttgaaaag ataatgtatg attatgcttt cactcatatt tatacagaaa cttgatgttt 60
tctttcgagt atatacaagg tgattacatg tacgtttgaa gtacaactct agattttgta 120
gtgccctctt gggctagcgg taaaggtgcg catttttca caccctacaa tgttctgttc 180
aaaagatttt ggtcaaacgc tgtagaagtg aaagttggtg cgcatgtttc ggcgttcgaa 240
acttctccgc agtgaaagat aaatgatc 268

<210> SEQ ID NO 17
<211> LENGTH: 20
<212> TYPE: DNA
<213> ORGANISM: Saccharomyces cerevisiae
<220> FEATURE:
<221> NAME/KEY: misc_feature
<223> OTHER INFORMATION: SUP4 terminator

<400> SEQUENCE: 17
tttttttgtt ttttatgtct 20

<210> SEQ ID NO 18
<211> LENGTH: 75
<212> TYPE: DNA
<213> ORGANISM: Artificial Sequence
<220> FEATURE:
<223> OTHER INFORMATION: scaffold guide RNA Cas9

-continued

<400> SEQUENCE: 18
ttttagagct agaaatagca agttaaaata aggctagtcc gttatcaact tgaaaaagtg 60
gcaccgagtc ggtgc 75

<210> SEQ ID NO 19
<211> LENGTH: 20
<212> TYPE: DNA
<213> ORGANISM: Artificial Sequence
<220> FEATURE:
<223> OTHER INFORMATION: spacer 1

<400> SEQUENCE: 19
caagtgtctg aagaactaac 20

<210> SEQ ID NO 20
<211> LENGTH: 20
<212> TYPE: DNA
<213> ORGANISM: Artificial Sequence
<220> FEATURE:
<223> OTHER INFORMATION: spacer 2

<400> SEQUENCE: 20
gacagttgac tgtataacgc 20

<210> SEQ ID NO 21
<211> LENGTH: 20
<212> TYPE: DNA
<213> ORGANISM: Artificial Sequence
<220> FEATURE:
<223> OTHER INFORMATION: spacer 3

<400> SEQUENCE: 21
gcgtttggaa tcacttaaca 20

<210> SEQ ID NO 22
<211> LENGTH: 20
<212> TYPE: DNA
<213> ORGANISM: Artificial Sequence
<220> FEATURE:
<223> OTHER INFORMATION: spacer 4

<400> SEQUENCE: 22
gcatatggcc atggaggccg 20

<210> SEQ ID NO 23
<211> LENGTH: 20
<212> TYPE: DNA
<213> ORGANISM: Artificial Sequence
<220> FEATURE:
<223> OTHER INFORMATION: spacer 5

<400> SEQUENCE: 23
acgcgtttgg aatcactaca 20

<210> SEQ ID NO 24
<211> LENGTH: 20
<212> TYPE: DNA
<213> ORGANISM: Artificial Sequence
<220> FEATURE:
<223> OTHER INFORMATION: spacer 6

<400> SEQUENCE: 24
atggtctcaa aacccttggt 20

-continued

<210> SEQ ID NO 25
<211> LENGTH: 20
<212> TYPE: DNA
<213> ORGANISM: Artificial Sequence
<220> FEATURE:
<223> OTHER INFORMATION: spacer 7

<400> SEQUENCE: 25
acacgcttac tgcctgacta 20

<210> SEQ ID NO 26
<211> LENGTH: 44
<212> TYPE: DNA
<213> ORGANISM: Artificial Sequence
<220> FEATURE:
<223> OTHER INFORMATION: donor 1

<400> SEQUENCE: 26
cctcgagaag accttgacat gattttgaaa atggattctt taca 44

<210> SEQ ID NO 27
<211> LENGTH: 108
<212> TYPE: DNA
<213> ORGANISM: Artificial Sequence
<220> FEATURE:
<223> OTHER INFORMATION: donor 2

<400> SEQUENCE: 27
aaagactgga acagctattt ctactgattt ttcctcgaga agaccttgac atgattttga 60
aaatggattc tttacaggat ataaaagcat tgttaacagg attatttg 108

<210> SEQ ID NO 28
<211> LENGTH: 520
<212> TYPE: DNA
<213> ORGANISM: Artificial Sequence
<220> FEATURE:
<223> OTHER INFORMATION: donor 3

<400> SEQUENCE: 28
tcatcatcgg aagagagtag taacaaaggt caaagacagt tgactgtatc gccggaattt 60
gtaatacgac tcactatagg gcgagccgcc atcatggagg agcagaagct gatctcagag 120
gaggacctgc atatggccat ggaggccgaa ttcatggata aagcggaatt aattcccgag 180
cctccaaaaa agaagagaaa ggtcgaattg ggtaccgccg ccaattttaa tcaaagtggg 240
aatattgctg atagctcatt gtccttcact ttcactaaca gtagcaacgg tccgaacctc 300
ataacaactc aaacaaattc tcaagcgctt tcacaaccaa ttgcctcctc taacgttcat 360
gataacttca tgaataatga aatcacggct agtaaaattg atgatggtaa taattcaaaa 420
ccactgtcac ctggttggac ggaccaaact gcgtataacg cgtttggaat cactacaggg 480
atgtttaata ccactacaat ggatgatgta tataactatc 520

<210> SEQ ID NO 29
<211> LENGTH: 635
<212> TYPE: DNA
<213> ORGANISM: Artificial Sequence
<220> FEATURE:
<223> OTHER INFORMATION: donor 4

<400> SEQUENCE: 29
cagatagatt ggcttcagtg gagactgata tgcctctaac attgagacag catagaataa 60
gtgcgacatc atcatcggaa gagagtagta acaaaggtca aagacagttg actgtatcgc 120

-continued

```
cggaatttgt aatacgactc actatagggc gagccgccat catggaggag cagaagctga    180

tctcagagga ggacctgcat atggccatgg aggccgaatt catggataaa gcggaattaa    240

ttcccgagcc tccaaaaaag aagagaaagg tcgaattggg taccgccgcc aattttaatc    300

aaagtgggaa tattgctgat agctcattgt ccttcacttt cactaacagt agcaacggtc    360

cgaacctcat aacaactcaa acaaattctc aagcgctttc acaaccaatt gcctcctcta    420

acgttcatga taacttcatg aataatgaaa tcacggctag taaaattgat gatggtaata    480

attcaaaacc actgtcacct ggttggacgg accaaactgc gtataacgcg tttggaatca    540

ctacagggat gtttaatacc actacaatgg atgatgtata taactatcta ttcgatgatg    600

aagataccc accaaaccca aaaaaagaga tttaa                                635
```

<210> SEQ ID NO 30
<211> LENGTH: 957
<212> TYPE: DNA
<213> ORGANISM: Artificial Sequence
<220> FEATURE:
<223> OTHER INFORMATION: donor 5

<400> SEQUENCE: 30

```
atgaagctac tgtcttctat cgaacaagca tgcgatattt gccgacttaa aaagctcaag     60

tgctccaaag aaaaaccgaa gtgcgccaag tgtctgaaga acaactggga gtgtcgctac    120

tctcccaaaa ccaaaaggtc tccgctgact agggcacatc tgacagaagt ggaatcaagg    180

ctagaaagac tggaacagct atttctactg atttttcctc gagaagacct tgacatgatt    240

ttgaaaatgg attctttaca ggatataaaa gcattgttaa caggattatt tgtacaagat    300

aatgtgaata aagatgccgt cacagataga ttggcttcag tggagactga tatgcctcta    360

acattgagac agcatagaat aagtgcgaca tcatcatcgg aagagagtag taacaaaggt    420

caaagacagt tgactgtatc gccggaattt gtaatacgac tcactatagg gcgagccgcc    480

atcatggagg agcagaagct gatctcagag gaggacctgc atatggccat ggaggccgaa    540

ttcatggata aagcggaatt aattcccgag cctccaaaaa agaagagaaa ggtcgaattg    600

ggtaccgccg ccaattttaa tcaaagtggg aatattgctg atagctcatt gtccttcact    660

ttcactaaca gtagcaacgg tccgaacctc ataacaactc aaacaaattc tcaagcgctt    720

tcacaaccaa ttgcctcctc taacgttcat gataacttca tgaataatga aatcacggct    780

agtaaaattg atgatggtaa taattcaaaa ccactgtcac ctggttggac ggaccaaact    840

gcgtataacg cgtttggaat cactacaggg atgtttaata ccactacaat ggatgatgta    900

tataactatc tattcgatga tgaagatacc ccaccaaacc caaaaaaaga gatttaa       957
```

<210> SEQ ID NO 31
<211> LENGTH: 4155
<212> TYPE: DNA
<213> ORGANISM: Artificial Sequence
<220> FEATURE:
<223> OTHER INFORMATION: Cas9 rice codon-optimized

<400> SEQUENCE: 31

```
atggacaaga agtatagtat tggtctggac attgggacga attccgttgg ctgggccgtg     60

atcaccgatg agtacaaggt cccttccaag aagtttaagg ttctggggaa caccgatcgg    120

cacagcatca agaagaatct cattggagcc ctcctgttcg actcaggcga gaccgccgaa    180

gcaacaaggc tcaagagaac cgcaaggaga cggtatacaa gaaggaagaa taggatctgc    240

tacctgcagg agattttcag caacgaaatg gcgaaggtgg acgattcgtt ctttcataga    300
```

-continued

```
ttggaggaga gtttcctcgt cgaggaagat aagaagcacg agaggcatcc tatctttggc    360
aacattgtcg acgaggttgc ctatcacgaa aagtacccca caatctatca tctgcggaag    420
aagcttgtgg actcgactga taaggcggac cttagattga tctacctcgc tctggcacac    480
atgattaagt tcaggggcca ttttctgatc gagggggatc ttaacccgga caatagcgat    540
gtggacaagt tgttcatcca gctcgtccaa acctacaatc agctctttga ggaaaaccca    600
attaatgctt caggcgtcga cgccaaggcg atcctgtctg cacgcctttc aaagtctcgc    660
cggcttgaga acttgatcgc tcaactcccg ggcgaaaaga agaacggctt gttcgggaat    720
ctcattgcac tttcgttggg gctcacacca aacttcaaga gtaattttga tctcgctgag    780
gacgcaaagc tgcagctttc caaggacact tatgacgatg acctggataa ccttttggcc    840
caaatcggcg atcagtacgc ggacttgttc ctcgccgcga agaatttgtc ggacgcgatc    900
ctcctgagtg atattctccg cgtgaacacc gagattacaa aggccccgct ctcggcgagt    960
atgatcaagc gctatgacga gcaccatcag gatctgaccc ttttgaaggc tttggtccgg   1020
cagcaactcc cagagaagta caaggaaatc ttctttgatc aatccaagaa cggctacgct   1080
ggttatattg acggcggggc atcgcaggag gaattctaca agtttatcaa gccaattctg   1140
gagaagatgg atggcacaga ggaactcctg gtgaagctca atagggagga ccttttgcgg   1200
aagcaaagaa ctttcgataa cggcagcatc cctcaccaga ttcatctcgg ggagctgcac   1260
gccatcctga gaaggcagga agacttctac ccctttctta aggataaccg ggagaagatc   1320
gaaaagattc tgacgttcag aattccgtac tatgtcggac cactcgcccg gggtaattcc   1380
agatttgcgt ggatgaccag aaagagcgag gaaaccatca caccttggaa cttcgaggaa   1440
gtggtcgata agggcgcttc cgcacagagc ttcattgagc gcatgacaaa ttttgacaag   1500
aacctgccta atgagaaggt ccttcccaag cattccctcc tgtacgagta tttcactgtt   1560
tataacgaac tcacgaaggt gaagtatgtg accgagggaa tgcgcaagcc cgccttcctg   1620
agcggcgagc aaaagaaggc gatcgtggac cttttgttta agaccaatcg gaaggtcaca   1680
gttaagcagc tcaaggagga ctacttcaag aagattgaat gcttcgattc cgttgagatc   1740
agcggcgtgg aagacaggtt taacgcgtca ctggggactt accacgatct cctgaagatc   1800
attaaggata aggacttctt ggacaacgag gaaaatgagg atatcctcga agacattgtc   1860
ctgactctta cgttgtttga ggatagggaa atgatcgagg aacgcttgaa gacgtatgcc   1920
catctcttcg atgacaaggt tatgaagcag ctcaagagaa gaagatacac cggatgggga   1980
aggctgtccc gcaagcttat caatggcatt agagacaagc aatcagggaa gacaatcctt   2040
gactttttga agtctgatgg cttcgcgaac aggaatttta tgcagctgat tcacgatgac   2100
tcacttactt tcaaggagga tatccagaag gctcaagtgt cgggacaagg tgacagtctg   2160
cacgagcata tcgccaacct tgcgggatct cctgcaatca agaagggtat tctgcagaca   2220
gtcaaggttg tggatgagct tgtgaaggtc atgggacggc ataagcccga gaacatcgtt   2280
attgagatgg ccagagaaaa tcagaccaca caaaagggtc agaagaactc gagggagcgc   2340
atgaagcgca tcgaggaagg cattaaggag ctggggagtc agatccttaa ggagcacccg   2400
gtggaaaaca cgcagttgca aaatgagaag ctctatctgt actatctgca aaatggcagg   2460
gatatgtatg tggaccagga gttggatatt aaccgcctct cggattacga cgtcgatcat   2520
atcgttcctc agtccttcct taaggatgac agcattgaca ataaggttct caccaggtcc   2580
gacaagaacc gcgggaagtc cgataatgtg cccagcgagg aagtcgttaa gaagatgaag   2640
```

-continued aactactgga ggcaactttt gaatgccaag ttgatcacac agaggaagtt tgataacctc 2700
actaaggccg agcgcggagg tctcagcgaa ctggacaagg cgggcttcat taagcggcaa 2760
ctggttgaga ctagacagat cacgaagcac gtggcgcaga ttctcgattc acgcatgaac 2820
acgaagtacg atgagaatga caagctgatc cgggaagtga aggtcatcac cttgaagtca 2880
aagctcgttt ctgacttcag gaaggatttc caattttata aggtgcgcga gatcaacaat 2940
tatcaccatg ctcatgacgc atacctcaac gctgtggtcg gaacagcatt gattaagaag 3000
tacccgaagc tcgagtccga attcgtgtac ggtgactata aggtttacga tgtgcgcaag 3060
atgatcgcca agtcagagca ggaaattggc aaggccactg cgaagtattt cttttactct 3120
aacattatga atttctttaa gactgagatc acgctggcta atggcgaaat ccggaagaga 3180
ccacttattg agaccaacgg cgagacaggg gaaatcgtgt gggacaaggg gagggatttc 3240
gccacagtcc gcaaggttct ctctatgcct caagtgaata ttgtcaagaa gactgaagtc 3300
cagacgggcg ggttctcaaa ggaatctatt ctgcccaagc ggaactcgga taagcttatc 3360
gccagaaaga aggactggga cccgaagaag tatggaggtt tcgactcacc aacggtggct 3420
tactctgtcc tggttgtggc aaaggtggag aagggaaagt caaagaagct caagtctgtc 3480
aaggagctcc tgggtatcac cattatggag aggtccagct tcgaaaagaa tccgatcgat 3540
tttctcgagg cgaagggata taaggaagtg aagaaggacc tgatcattaa gcttccaaag 3600
tacagtcttt tcgagttgga aaacggcagg aagcgcatgt tggcttccgc aggagagctc 3660
cagaagggta acgagcttgc tttgccgtcc aagtatgtga acttcctcta tctggcatcc 3720
cactacgaga agctcaaggg cagcccagag gataacgaac agaagcaact gtttgtggag 3780
caacacaagc attatcttga cgagatcatt gaacagattt cggagttcag taagcgcgtc 3840
atcctcgccg acgcgaattt ggataaggtt ctctcagcct acaacaagca ccgggacaag 3900
cctatcagag agcaggcgga aaatatcatt catctcttca ccctgacaaa ccttggggct 3960
cccgctgcat tcaagtattt tgacactacg attgatcgga agagatacac ttctacgaag 4020
gaggtgctgg atgcaaccct tatccaccaa tcgattactg gcctctacga gacgcggatc 4080
gacttgagtc agctcggggg ggataagaga ccagcggcaa ccaagaaggc aggacaagcg 4140
aagaagaaga agtag 4155

<210> SEQ ID NO 32
<211> LENGTH: 1995
<212> TYPE: DNA
<213> ORGANISM: Zea mays
<220> FEATURE:
<221> NAME/KEY: misc_feature
<223> OTHER INFORMATION: maize Ubi promoter containing MubG1 intron

<400> SEQUENCE: 32
tgcagtgcag cgtgacccgg tcgtgcccct ctctagagat aatgagcatt gcatgtctaa 60
gttataaaaa attaccacat attttttttg tcacacttgt ttgaagtgca gtttatctat 120
ctttatacat atatttaaac tttactctac gaataatata atctatagta ctacaataat 180
atcagtgttt tagagaatca tataaatgaa cagttagaca tggtctaaag gacaattgag 240
tattttgaca acaggactct acagttttat ctttttagtg tgcatgtgtt ctcctttttt 300
tttgcaaata gcttcaccta tataatactt catccatttt attagtacat ccatttaggg 360
tttagggtta atggttttta tagactaatt tttttagtac atctatttta ttctatttta 420
gcctctaaat taagaaaact aaaactctat tttagttttt ttatttaata gtttagatat 480

```
aaaatagaat aaaataaagt gactaaaaat taaacaaata ccctttaaga aattaaaaaa    540

actaaggaaa catttttctt gtttcgagta gataatgcca gcctgttaaa cgccgtcgac    600

gagtctaacg gacaccaacc agcgaaccag cagcgtcgcg tcgggccaag cgaagcagac    660

ggcacggcat ctctgtcgct gcctctggac ccctctcgag agttccgctc caccgttgga    720

cttgctccgc tgtcggcatc cagaaattgc gtggcggagc ggcagacgtg agccggcacg    780

gcaggcggcc tcctcctcct ctcacggcac cggcagctac gggggattcc tttcccaccg    840

ctccttcgct ttcccttcct cgcccgccgt aataaataga cacccctcc acaccctctt    900

tccccaacct cgtgttgttc ggagcgcaca cacacacaac cagatctccc ccaaatccac    960

ccgtcggcac ctccgcttca aggtacgccg ctcgtcctcc cccccccccc cccctctcta   1020

ccttctctag atcggcgttc cggtccatgg ttagggcccg gtagttctac ttctgttcat   1080

gtttgtgtta gatccgtgtt tgtgttagat ccgtgctgct agcgttcgta cacggatgcg   1140

acctgtacgt cagacacgtt ctgattgcta acttgccagt gtttctcttt ggggaatcct   1200

gggatggctc tagccgttcc gcagacggga tcgatttcat gatttttttt gtttcgttgc   1260

atagggtttg gtttgccctt ttcctttatt tcaatatatg ccgtgcactt gtttgtcggg   1320

tcatcttttc atgctttttt ttgtcttggt tgtgatgatg tggtctggtt gggcggtcgt   1380

tctagatcgg agtagaattc tgtttcaaac tacctggtgg atttattaat tttggatctg   1440

tatgtgtgtg ccatacatat tcatagttac gaattgaaga tgatggatgg aaatatcgat   1500

ctaggatagg tatacatgtt gatgcgggtt ttactgatgc atatacagag atgctttttg   1560

ttcgcttggt tgtgatgatg tggtgtggtt gggcggtcgt tcattcgttc tagatcggag   1620

tagagtactg tttcaaacta cctggtgtat ttattaattt tggaactgta tgtgtgtgtc   1680

atacatcttc atagttacga gtttaagatg gatggaaata tcgatctagg ataggtatac   1740

atgttgatgt gggttttact gatgcatata catgatggca tatgcagcat ctattcatat   1800

gctctaacct tgagtaccta tctattataa taaacaagta tgttttataa ttatttcgat   1860

cttgatatac ttggatgatg gcatatgcag cagctatatg tggatttttt tagccctgcc   1920

ttcatacgct atttatttgc ttggtactgt ttcttttgtc gatgctcacc ctgttgtttg   1980

gtgttacttc tgcag                                                    1995
```

<210> SEQ ID NO 33
<211> LENGTH: 294
<212> TYPE: DNA
<213> ORGANISM: Agrobacterium tumefaciens
<220> FEATURE:
<221> NAME/KEY: misc_feature
<223> OTHER INFORMATION: nopaline synthase terminator (tnos)

<400> SEQUENCE: 33

```
agcggccgcc cggctgcaga tcgttcaaac atttggcaat aaagtttctt aagattgaat     60

cctgttgccg gtcttgcgat gattatcata taatttctgt tgaattacgt taagcatgta    120

ataattaaca tgtaatgcat gacgttattt atgagatggg tttttatgat tagagtcccg    180

caattataca tttaatacgc gatagaaaac aaaatatagc gcgcaaacta ggataaatta    240

tcgcgcgcgg tgtcatctat gttactagat ccgatgataa gctgtcaaac atga          294
```

<210> SEQ ID NO 34
<211> LENGTH: 377
<212> TYPE: DNA
<213> ORGANISM: Oryza sativa
<220> FEATURE:

<221> NAME/KEY: misc_feature
<223> OTHER INFORMATION: RNA pol III promoter promoter from the rice U3
small nucle ar RNA gene (OsU3)

<400> SEQUENCE: 34
aagggatctt taaacatacg aacagatcac ttaaagttct tctgaagcaa cttaaagtta 60
tcaggcatgc atggatcttg gaggaatcag atgtgcagtc agggaccata gcacaggaca 120
ggcgtcttct actggtgcta ccagcaaatg ctggaagccg ggaacactgg gtacgttgga 180
aaccacgtga tgtggagtaa gataaactgt aggagaaaag catttcgtag tgggccatga 240
agcctttcag gacatgtatt gcagtatggg ccggcccatt acgcaattgg acgacaacaa 300
agactagtat tagtaccacc tcggctatcc acatagatca aagctggttt aaaagagttg 360
tgcagatgat ccgtggc 377

<210> SEQ ID NO 35
<211> LENGTH: 7787
<212> TYPE: DNA
<213> ORGANISM: Oryza sativa
<220> FEATURE:
<221> NAME/KEY: misc_feature
<223> OTHER INFORMATION: rice Protoporphyrinogen Oxidase (PPO2)

<400> SEQUENCE: 35
atgctctctc ctgccaccac cttctcctcc tcctcctcct cctcgtcgcc gtcgcgcgcc 60
cacgctcgcg ctcccacccg cttcgcggtc gcagcatccg cgcgcgccgc acggttccgc 120
cccgcgcgcg ccatggccgc ctccgacgac ccccgcggcg ggaggtccgt cgccgtcgtc 180
ggcgccggcg tcaggtgggt ggggagccgc gcgcgctctc cgtgggttca gttctgccct 240
aggtttgggg tgccgtgtgc gtgtgagtgg ggaggttgtt ttttttgatg attgatgaaa 300
tggttgcctc tctgcagtgg gctcgcggcg gcgtacaggc tgaggaagcg cggcgtgcag 360
gtgacggtgt tcgaggcggc cgacagggcg ggtgggaaga tacggaccaa ctccgagggc 420
gggttcatct gggacgaagg ggccaacacc atggtgagcg cgctttggtg tgcctcgctg 480
cttctgtttg atcacaatct cgggctgtgt tggtctgcat tgctgcaaat gctgcttctg 540
tatgttttgg attgtggcgc actggcgctg ctgcggctat ttgagggctg gagcacacta 600
gcgagtagtg ctccttggtg cgcaggctga ggaaacttgt gtttgtgaac gaaatgcaag 660
ctgctcacta atgcagacag ttgttcctgc aaatggagaa gtgttttctt ctgcattcgt 720
atcccacaac agacgtgaac cctttctgct atgagcatca ttgaacaccg ttatgtaact 780
tatcatagcc tgattcgatt tcattcacca tgatctataa ctattatact taccatatta 840
gttactttgt actactctta gtaaaataaa taaattattt taatactcca ctgacaaaat 900
aggttaagat tgtttcattg cttgggcaca tgtgcaatac tagtcgcatt ttttttacct 960
gcgtgcaaat cttatcatgc ctgcttgatt caatttgccg ttctctctgt aatttaatta 1020
ttttgcctcc agacagagag tgaattggag gcaagcaggc ttattgacga tcttggccta 1080
caaggcaaac agcagtatgt atgtgctaat gttatctgtg atggttaact gctttgaatg 1140
tcttctgttt cataatttac actgatatgt ttaatatttc gatatccttt agcctaactc 1200
acaacacaag cgttacattg tcaaagatgg agcaccaaca ctggtaaata gacttttcat 1260
gatatgatgc attttgtttt gttcttccta tagtatgcct cacttttgaa tatatttttt 1320
tgtcacataa gattccctca gatcccattg cgctcatgaa aagcactgtt ctttctacaa 1380
aatcaaaggt atgtaagtta ttgagtgcta attgctacaa catatcatga cctcctgacc 1440

-continued

```
tatttgcaac aagttgcttg ttgtttccac ttgtcactga tggattaaaa ttcactagtg   1500
tagaaacaat catattaaac tgatcaccgt gacttgattt acttgttttc agttcactat   1560
tacaaatttg tacatttcct gatctttcgt gttcaagctg tgtgatcgac tgattgcaac   1620
cgtcatatta tattactgta ttgagtttag taaaacatgg tcttatcttt gcagctcaag   1680
ctatttctgg aaccatttct ctatgagaaa tctagcagaa ggacctcggg aaaagtgtct   1740
gatgaacatt taagtgagag gtgagccttc atactgatgt tattttgagt tgttgtaaac   1800
ttgaaccact gataatatag ttatatgttt ttttcctgtg ttcttccttc attctcatgc   1860
ccttgtgaaa tacaaatata tacttcatat cacacactcc ctttggtcat ttttcatgtc   1920
aaacttttaa aactttgtac ataaaatcag ttcaatattt agattgaacg catgagaaag   1980
tattttcata atattatgat tttaccattt ttttcatata cgttgcaaca gaatttagtg   2040
gtcaaagcta cactttgaag accttattga tgtcaaaaac agcatgtttt ctgaccagag   2100
agaatacatt tgcagtgtga tttttctgtg tatatgtaga gataatcagg tttctctttt   2160
gcagtgttgc aagtttcttt gaacgccact ttggaaaaga ggcaagttca tttttaatga   2220
agaaatttat ggattgttaa gtgaatacaa tcaacacttt gcaacttaca tgcccattat   2280
aatcagtaga gggtaagaat ttataacttt attacaggtt gttgattatc ttattgatcc   2340
atttgtggct ggaacaagcg gaggagatcc tgagtcatta tcagtaagtt attataacat   2400
gtctcactat ttgcattttc catatcagca cctttgcatt tctacagtaa attgtagtca   2460
taattatttt tatgtaaatt gtgcgtataa acaacatatg tgcttgactt tgtgatgtgt   2520
tcttggggat gataactgat acggctagaa cttttggggg ctaatctcct tgagccgtat   2580
cagtaagtca taacaattct cattcataat gatcaaaaca tatcaccttc ttgtgtagaa   2640
ctgttctggt tttgagtaat attttcttct gtgcagattc gtcatgcatt tccagcatta   2700
tggaatttgg agaataagta agtttgtagt agtttgtttg gagaataagt aagtttgtag   2760
tttgtgcatt gatgttcatt caagatttac cttatcaata attcacttgt ccacgtccat   2820
atgctcgtgc tatatcctgt ccattcaaat gtcaacaccg ccatgtgaat ttactgcata   2880
gtgcatttta atgatttcat ttatccttgt tgcttgcatc tctttttgg gctcctgctg   2940
ttagcttgtt tttggttcct gctgttacct atttcttttc tatcattttt tcattggaca   3000
gatggtgctc tcagtcctta ctgcttatta tttgttaacc tgatatgcac ctacttgaag   3060
ttaatgttat gatttttagt attttatagt catggtatca ttaatactta tttttggcaa   3120
tcgaaattaa aaaaacatga tgtcaaaata aaaaatcatg gcagttgaat gcagtgggta   3180
tatgtatcaa gaatttaaga tcttgaacat aagtccaatt gctatatgtt caattcgttg   3240
gagcataaca tgatctaatt tgtaagttaa atttatctga taaacgatgg aaggaaattc   3300
tggtaccact catgcaacta tacaagcttc aaaggcttct tacatgtgga ccattggacc   3360
tagaatagaa tctaaattta ttcataagta tataattttt tttccttcat gggccatgat   3420
agttaactat atgagcttgt agagtcaaaa taggcataat tgcttctttg ggtttccact   3480
taatttaccc tacaacactt ctattgcaat aaatatggtc aacaacattt ctttacggtc   3540
cgtttggttg gagggagttt ttaggaggga ttgggagttt agagggatgg agctattaac   3600
tgttttgttt ggttgggaga gatgggaatt ttggtgggat ggagatgggg aattgaggaa   3660
ggaactccct ccttttcaat acctgggtag ggggtggtaa ttgggaggga attcctcctt   3720
tactttgcct aaacaaatct cagccatccg ttttcattaa tgacctaatc tccaactaaa   3780
cttcctgtca atttccacca cctctgccaa acaagatatt gggattaaaa atcaaattcc   3840
```

-continued

```
catcttaatc tcaccatcaa ttccctcgtg taaactccca atccccttcc ctcaagttgc   3900
caaacaagcc attagtgccc agttatgttc tttggtcatc ttcttcataa tttgttgctc   3960
catgcacttt caatgctcac aggtatggct ctgtcattgc tggtgccatc ttgtccaaac   4020
tatccactaa gggtgattca gtgaagacag gaggtgcttc gccagggaaa ggaaggaata   4080
aacgtgtgtc attttcattt catggtggaa tgcaggtact ccacagatgt cctgtagttt   4140
cttttgtcag tgtcaaagat atcaaagaca gtgataaacc ctgaacttta gtttgagcaa   4200
ttctacatgc cactaaaaaa tgccgaattc atatgttgtg aattgaagac ctgttatttt   4260
cctgcaacta ggacatatgt ttagtcggtg aaacttcatt gctgctttaa gaagtcttac   4320
aggccagaga aaactgtctt gttttttttt tttttgattt gatgtcctgc tttatattta   4380
tgatccagcc aagcttatcc atccatctgc accctgatcc tgccataatc atttttttta   4440
tcagcctgac atgagcttat tatgttgcat aagttaggtt gaagctagat cgaacaaaaa   4500
actcaaagct actgataagt acaggatatg caacagaagt atcacacgag ccaaatctgc   4560
tataagaata aaacatacca agagccttag acaccactaa atagtgtgaa tggtagtgat   4620
agcgaataat ctcagaagat gacattttgg gaaatattat cgtgtagtat actttattaa   4680
ttgggagttg cgatacttgc cctgcacgct aaacatgctg aaaagtttca cagttatact   4740
acataacatc tgggtgtgta aaggttttat gttgttcatt gcttttcagt cactaataga   4800
tgcacttcac aatgaagttg gagatggtaa cgtgaagctt ggtacagaag tgttgtcatt   4860
ggcatgttgc tgtgatggag tctcttcttc tggtggttgg tcaatttctg ttgattcaaa   4920
agatgctaaa gggaaagatc tcagaaagaa ccaatctttc gatgctgtta taatgactgt   4980
aagaaaaaaa ttatctgtat tcatctcttt agaagcttga tcatttgaca gccacaaatt   5040
aaaatatttt accgtgtttt tctttttgcc cctttaggct ccattgtcta atgtccagag   5100
gatgaagttt acaaaaggtg gagttccctt tgtgctagac tttcttccta aggtcaggtt   5160
agaatcactc ttttagattt aacaaatgca gtgttgcact agcatgttct tgagaaattt   5220
gtgctggggg aaattcctct taatccttca aattgcattt aatttcatcc attaggtcga   5280
tggatccatg tcacagaaaa tattttgttt atcttctaga tttctattat atatgtaaga   5340
ctgtctctta gtttgtgaat ttacaggagt caatcatcac tcccttgaat ctgagcatat   5400
cagcagttca tcagcaatat ggtttatttg agaaggcaac ggaaactatt gtttccaaag   5460
gccacttgtt tgaaactttc accactgttt tgaacagtgt attaaagtaa cagtcatttg   5520
tatagcagca cctggtgatt tttaagtaaa ttttccattc ccaatcaaaa caagtaacat   5580
tatatgttga acatgtactg aattgaatat ggaactttat gctggagatg ccagacttta   5640
ttttactggc atgaatacac aattattgta acaatggtat tattgcttgg ttacttctcc   5700
gctgtgaaga catacctttc gtcacctttt cttgtttccc atattctgca ccttatggga   5760
ttgtcttcca catgttaaga tgccttgtag taccagttcc cctattattt gaatgtgttc   5820
ttccttagat atatgtgcat ttggaacgtg attggaaata caacagcaaa ctggtattgt   5880
tagctgcttg cctgccacag cctacatatg ctgccatatt acagaattat gagataggtg   5940
gactttgatt tctgtcataa tgattaacta acttgatata ctcaaactat gcagctccta   6000
gctggtatcc ttagaattta tcgagtatgc atagaagtct actcttaatc catatctatt   6060
tgatgtactc aaacttgaaa ctatgcagct cctagctggg ctccttagaa ttatcaagta   6120
tgcatagaaa tcttaatcca tatttattta ttatatgcag gtcgattatc taccactatc   6180
```

-continued

```
tctcatggta acagctttta agaaggaaga tgtcaaaaaa ccattggaag gatttggtgc   6240
cttgataccc tataaggaac agcaaaagca tggtctcaaa acccttggta ggttaattca   6300
gctttacact tatattttat ccagcttgta gctgcttata ttttgatttg cgaattaaaa   6360
attattaaaa cagccttgaa agaagaaacc atgttcgctg tggagactag aaattcccac   6420
attaattggg gaaagagaaa tatttacacc ctatgatttt ggcaagtgca agttttaatg   6480
gttgagattg atggattgaa tatatatcat atttggactc agtatgaaca aataccagat   6540
acataaatag atagtactaa ttcaacatgg atctgaactg ttgatcagac caattgagca   6600
cttggttgta attgctcgcg gactacacgc ttactgcctg actagggttc catgatgata   6660
aggttcgatt ttctaaaata ctattacaac aagatgacta tttaataaaa tttaaagaga   6720
ataacgtata taaaaattta gataaatttg gtgcaccgcg caattgcgca ggtcaccctg   6780
ctagctgtat tgaactcaat atacaaatca accttgctac attgctctac tttttctcag   6840
gtcttattta ctctgatttc tatttattct aatctataca tgtcgtcttg tacagggacc   6900
ctcttctcct cgatgatgtt tccagatcga gctcctaatg atcaatatct atatacatct   6960
ttcattgggg ggagccataa tagagacctc gctggggctc caacgtatac ttccatatta   7020
tgatcattta tgttttggtt gttttttctt ttcttgctag atttttctga tatatatact   7080
tatgtagggc tattctgaaa caacttgtga cctctgacct aagaaagctc ttgggtgttg   7140
agggacaacc tacttttgtg aagtaagtga taagaaacta ctgccatggt ttagagtatc   7200
tatatgtttt ctcttgttgt gcttgtgtta tggttttcca tcactatgga gttttgagga   7260
ttcattcagg tttttgcact accacttgcg aattcaatat gatgttcttt tacacaggca   7320
tgtacattgg agaaatgctt ttcctttata tggccagaat tatgatctgg tactggaagc   7380
tatagcaaaa atggagaaca atcttccagg gttcttttac gcaggcaagt caatgaaggc   7440
acccctattg tacaaaagaa atcttagata tttgaaacat attcctgttg attgagtacg   7500
tgaataattt gctgtttcta gtaagtcaat ttggtatttc tcatgcaact tatggggctc   7560
cttgatttgc tgagaatgat gagtttccta gagcaagcca ggaactgtaa tcccagcatg   7620
taatacttta ccttgaaatt aacttcaaaa aaataattga agctttttct gtatctgtag   7680
gaaataacaa ggatgggttg gctgttggaa atgttatagc ttcaggaagc aaggctgctg   7740
accttgtgat ctcttatctt gaatcttgca cagatcagga caattag                 7787
```

<210> SEQ ID NO 36
<211> LENGTH: 20
<212> TYPE: DNA
<213> ORGANISM: Artificial Sequence
<220> FEATURE:
<223> OTHER INFORMATION: spacer 8

<400> SEQUENCE: 36

```
atggtctcaa aacccttggt                                                 20
```

<210> SEQ ID NO 37
<211> LENGTH: 20
<212> TYPE: DNA
<213> ORGANISM: Artificial Sequence
<220> FEATURE:
<223> OTHER INFORMATION: spacer 9

<400> SEQUENCE: 37

```
acacgcttac tgcctgacta                                                 20
```

<210> SEQ ID NO 38
<211> LENGTH: 20
<212> TYPE: DNA
<213> ORGANISM: Artificial Sequence
<220> FEATURE:
<223> OTHER INFORMATION: spacer 10

<400> SEQUENCE: 38
tatatacatc tttcattggg 20

<210> SEQ ID NO 39
<211> LENGTH: 120
<212> TYPE: DNA
<213> ORGANISM: Artificial Sequence
<220> FEATURE:
<223> OTHER INFORMATION: donor 6

<400> SEQUENCE: 39
gaaggatttg gtgccttgat accctataag gaacagcaaa agcatggtct caaaaccttt 60
ggtagattaa ttcagcttta cacttatatt ttatccagct tgtagctgct tatattttga 120

<210> SEQ ID NO 40
<211> LENGTH: 794
<212> TYPE: DNA
<213> ORGANISM: Artificial Sequence
<220> FEATURE:
<223> OTHER INFORMATION: donor 7

<400> SEQUENCE: 40
gaaggatttg gtgccttgat accctataag gaacagcaaa agcatggtct caaaaccttt 60
ggtaggttaa ttcagcttta cacttatatt ttatccagct tgtagctgct tatattttga 120
tttgcgaatt aaaaattatt aaaacagcct tgaaagaaga aaccatgttc gctgtggaga 180
ctagaaattc ccacattaat tggggaaaga gaaatattta caccctatga ttttggcaag 240
tgcaagtttt aatggttgag attgatggat tgaatatata tcatatttgg actcagtatg 300
aacaaatacc agatacataa atagatagta ctaattcaac atggatctga actgttgatc 360
agaccaattg agcacttggt tgtaattgct cgcggactac acgcttactg cctgactagc 420
gttccatgat gataaggttc gattttctaa aatactatta caacaagatg actatttaat 480
aaaatttaaa gagaataacg tatataaaaa tttagataaa tttggtgcac cgcgcaattg 540
cgcaggtcac cctgctagct gtattgaact caatatacaa atcaaccttg ctacattgct 600
ctactttttc tcaggtctta tttactctga tttctattta ttctaatcta tacatgtcgt 660
cttgtacagg gaccctcttc tcctcgatga tgtttccaga tcgagctcct aatgatcaat 720
atctatatac atctgtaatt ggggggagcc ataatagaga cctcgctggg gctccaacgt 780
atacttccat atta 794

<210> SEQ ID NO 41
<211> LENGTH: 800
<212> TYPE: DNA
<213> ORGANISM: Artificial Sequence
<220> FEATURE:
<223> OTHER INFORMATION: donor 8

<400> SEQUENCE: 41
atggatctga actgttgatc agaccaattg agcacttggt tgtaattgct cgcggactac 60
acgcttactg cctgactagg gttccatgat gataaggttc gattttctaa aatactatta 120
caacaagatg actatttaat aaaatttaaa gagaataacg tatataaaaa tttagataaa 180

-continued

```
tttggtgcac cgcgcaattg cgcaggtcac cctgctagct gtattgaact caatatacaa    240

atcaaccttg ctacattgct ctactttttc tcaggtctta tttactctga tttctattta    300

ttctaatcta tacatgtcgt cttgtacagg gaccttcttc tcctcgatga tgtttccaga    360

tcgagctcct aatgatcaat atctatatac atctgtaatt ggcggcagcc ataatagaga    420

cctcgctggg gctccaacgt atacttccat attatgatca tttatgtttt ggttgttttt    480

tcttttcttg ctagattttt ctgatatata tacttatgta gggctattct gaaacaactt    540

gtgacctctg acctaagaaa gctcttgggt gttgagggac aacctacttt tgtgaagtaa    600

gtgataagaa actactgcca tggtttagag tatctatatg ttttctcttg ttgtgcttgt    660

gttatggttt tccatcacta tggagttttg aggattcatt caggtttttg cactaccact    720

tgcgaattca atatgatgtt cttttacaca ggcatgtaca ttggagaaat gcttttcctt    780

tatatggcca gaattatgat                                                800
```

```
<210> SEQ ID NO 42
<211> LENGTH: 138
<212> TYPE: DNA
<213> ORGANISM: Artificial Sequence
<220> FEATURE:
<223> OTHER INFORMATION: RecA FusionCRISPR

<400> SEQUENCE: 42

gatgtggaaa ccatctctac gttttagagc tagaaatagc aagttaaaat aaggctagtc     60

cgttatcaac ttgaaaaagt ggcaccgagt cggtgctttc catggatgtg gaaaccatcg    120

ctttcactgg atatcgcg                                                  138
```

```
<210> SEQ ID NO 43
<211> LENGTH: 1062
<212> TYPE: DNA
<213> ORGANISM: Escherichia coli
<220> FEATURE:
<221> NAME/KEY: misc_feature
<223> OTHER INFORMATION: RecA

<400> SEQUENCE: 43

atggctatcg acgaaaacaa acagaaagcg ttggcggcag cactgggcca gattgagaaa     60

caatttggta aaggctccat catgcgcctg ggtgaagacc gttccatgga tgtggaaacc    120

atctctaccg gttcgctttc actggatatc gcgcttgggg caggtggtct gccgatgggc    180

cgtatcgtcg aaatctacgg accggaatct tccggtaaaa ccacgctgac gctgcaggtg    240

atcgccgcag cgcagcgtga aggtaaaacc tgtgcgttta tcgatgctga acacgcgctg    300

gacccaatct acgcacgtaa actgggcgtc gatatcgaca acctgctgtg ctcccagccg    360

gacaccggcg agcaggcact ggaaatctgt gacgccctgg cgcgttctgg cgcagtagac    420

gttatcgtcg ttgactccgt ggcggcactg acgccgaaag cggaaatcga aggcgaaatc    480

ggcgactctc acatgggcct tgcggcacgt atgatgagcc aggcgatgcg taagctggcg    540

ggtaacctga agcagtccaa cacgctgctg atcttcatca accagatccg tatgaaaatt    600

ggtgtgatgt tcggtaaccc ggaaaccact accggtggta acgcgctgaa attctacgcc    660

tctgttcgtc tcgacatccg tcgtatcggc gcggtgaaag agggcgaaaa cgtggtgggt    720

agcgaaaccc gcgtgaaagt ggtgaagaac aaaatcgctg cgccgtttaa acaggctgaa    780

ttccagatcc tctacggcga aggtatcaac ttctacggcg aactggttga cctgggcgta    840

aaagagaagc tgatcgagaa agcaggcgcg tggtacagct acaaaggtga gaagatcggt    900
```

cagggtaaag cgaatgcgac tgcctggctg aaagataacc cggaaaccgc gaaagagatc 960
gagaagaaag tacgtgagtt gctgctgagc aacccgaact caacgccgga tttctctgta 1020
gatgatagcg aaggcgtagc agaaactaac gaagattttt aa 1062

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
atggctatcg acgaaaacaa a 21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
cgtcagcgtg gttttaccgg a 21

<210> SEQ ID NO 46
<211> LENGTH: 461
<212> TYPE: DNA
<213> ORGANISM: Artificial Sequence
<220> FEATURE:
<223> OTHER INFORMATION: Expression Cassette

<400> SEQUENCE: 46
tgtacaaaaa agcaggcttt aaaggaacca attcagtcga ctggatccgg taccaaggtc 60
gggcaggaag agggcctatt tcccatgatt ccttcatatt tgcatatacg atacaaggct 120
gttagagaga taattagaat taatttgact gtaaacacaa agatattagt acaaaatacg 180
tgacgtagaa agtaataatt tcttgggtag tttgcagttt taaaattatg ttttaaaatg 240
gactatcata tgcttaccgt aacttgaaag tatttcgatt tcttggcttt atatatcttg 300
tggaaaggac gaaacaccgg catccctcag gctgggctgt tttagagcta gaaatagcaa 360
gttaaaataa ggctagtccg ttatcaactt gaaaaagtgg caccgagtcg gtgctggcca 420
tcaggcatcc ctcagtatgg aatgaggcat ctgatttttt t 461

<210> SEQ ID NO 47
<211> LENGTH: 275
<212> TYPE: DNA
<213> ORGANISM: Homo sapiens
<220> FEATURE:
<221> NAME/KEY: misc_feature
<223> OTHER INFORMATION: PRDM9 exon ENSE00001804383

<400> SEQUENCE: 47
attgtgagat gtgtcagaac ttcttcattg acagctgtgc tgcccatggg ccccctacat 60
ttgtaaagga cagtgcagtg gacaaggggc accccaaccg ttcagccctc agtctgcccc 120
cagggctgag aattgggcca tcaggcatcc ctcaggctgg gcttggagta tggaatgagg 180
catctgatct gccgctgggt ctgcactttg gcccttatga gggccgaatt acagaagacg 240
aagaggcagc caacaatgga tactcctggc tgtgg 275

<210> SEQ ID NO 48

<211> LENGTH: 783
<212> TYPE: DNA
<213> ORGANISM: Artificial Sequence
<220> FEATURE:
<223> OTHER INFORMATION: Gene Fragment

<400> SEQUENCE: 48

```
cacctagggg ggaggtcgta gtaccccct atgttttctc ccctaaataa ccccaaaaat     60

ctaagaaaaa aagacctcaa aaaggtcttt aattaacatc tcaaatttcg catttattcc    120

aatttccttt ttgcgtgtga tgcgaattct tgaccgtgat tagagaattg agtaaaatgt    180

acctacgcga gacctcattc gccattcagg ctacgcaact gttgggaagg gcgatcggtg    240

cgggcctctt cgctattacg ccatgaggcg aaagggggat gtgctgcaag gcgattaagt    300

tgggtaacgc cagggttttc ccagtcacga cgttgtaaaa cgacggccag actattcgta    360

atcatggtca tagctgtttc ctgtgtgaaa ttgttatccg ctcacaattc cacacaacat    420

acgagccgga agcataaagt gtaaagcctg gggtgcctaa tgagtgagct aactcacatt    480

aattgcgttg cgctcactgc ccgctttcca gtcgggaaac ctgtcgtgcc agctcgatta    540

atgaatcggt ctcagtttta gagctagaaa tagcaagtta aaataaggct agtccgttat    600

caacttgaaa aagtggcacc gagtcggtgc tggccaacga ggcccgggcc aataaggcct    660

tttttactcc atctggattt gttcagaacg ctcggttgcc gccgggcgtt ttttatctaa    720

agcttaggcc cagtcgaaag actgggcctt tttaatacga ctcactatag ggtcgactct    780

aga                                                                  783
```

<210> SEQ ID NO 49
<211> LENGTH: 784
<212> TYPE: DNA
<213> ORGANISM: Artificial Sequence
<220> FEATURE:
<223> OTHER INFORMATION: Gene Fragment

<400> SEQUENCE: 49

```
cacctagggg ggaggtcgta gtaccccct atgttttctc ccctaaataa ccccaaaaat     60

ctaagaaaaa aagacctcaa aaaggtcttt aattaacatc tcaaatttcg catttattcc    120

aatttccttt ttgcgtgtga tgcgaattct tgaccgtgat tagagaattg agtaaaatgt    180

acctacggcc aacgaggccc gggccaataa ggcctacgcg agacctcatt cgccattcag    240

gctacgcaac tgttgggaag ggcgatcggt gcgggcctct tcgctattac gccatgaggc    300

gaaaggggga tgtgctgcaa ggcgattaag ttgggtaacg ccagggtttt cccagtcacg    360

acgttgtaaa acgacggcca gactattcgt aatcatggtc atagctgttt cctgtgtgaa    420

attgttatcc gctcacaatt ccacacaaca tacgagccgg aagcataaag tgtaaagcct    480

ggggtgccta atgagtgagc taactcacat taattgcgtt gcgctcactg cccgctttcc    540

agtcgggaaa cctgtcgtgc cagctcgatt aatgaatcgg tctcagtttt agagctagaa    600

atagcaagtt aaaataaggc tagtccgtta tcaacttgaa aaagtggcac cgagtcggtg    660

ctttttactc catctggatt tgttcagaac gctcggttgc cgccgggcgt tttttatcta    720

aagcttaggc ccagtcgaaa gactgggcct ttttaatacg actcactata gggtcgactc    780

taga                                                                 784
```

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide

<400> SEQUENCE: 50
tacgtgaaga tcaggctatc actg 24

<210> SEQ ID NO 51
<211> LENGTH: 24
<212> TYPE: DNA
<213> ORGANISM: Artificial Sequence
<220> FEATURE:
<223> OTHER INFORMATION: Oligonucleotide

<400> SEQUENCE: 51
aaaccagtga tagcctgatc ttca 24

<210> SEQ ID NO 52
<211> LENGTH: 52
<212> TYPE: DNA
<213> ORGANISM: Artificial Sequence
<220> FEATURE:
<223> OTHER INFORMATION: Oligonucleotide

<400> SEQUENCE: 52
gatcggccaa cgaggccgcg gcattatgtt tgaatttccg tttaaagaat gg 52

<210> SEQ ID NO 53
<211> LENGTH: 76
<212> TYPE: DNA
<213> ORGANISM: Artificial Sequence
<220> FEATURE:
<223> OTHER INFORMATION: Oligonucleotide

<400> SEQUENCE: 53
gatggtttct ttcggtaagt cccgtctagc cttgccctca tcttgacact ccttatttga 60
ttttttgaag acttac 76

<210> SEQ ID NO 54
<211> LENGTH: 40
<212> TYPE: DNA
<213> ORGANISM: Artificial Sequence
<220> FEATURE:
<223> OTHER INFORMATION: Oligonucleotide

<400> SEQUENCE: 54
tgagggcaag gctagacggg acttaccgaa agaaaccatc 40

<210> SEQ ID NO 55
<211> LENGTH: 56
<212> TYPE: DNA
<213> ORGANISM: Artificial Sequence
<220> FEATURE:
<223> OTHER INFORMATION: Oligonucleotide

<400> SEQUENCE: 55
gatcaggcct tattggcctt ggcaggccgc tgaatttcca tgttgcgtaa gtcagg 56

<210> SEQ ID NO 56
<211> LENGTH: 52
<212> TYPE: DNA
<213> ORGANISM: Artificial Sequence
<220> FEATURE:
<223> OTHER INFORMATION: Oligonucleotide

<400> SEQUENCE: 56
gatcggccaa cgaggccttg gcaggccgct gaatttccat gttgcgtaag tc 52

<210> SEQ ID NO 57
<211> LENGTH: 76
<212> TYPE: DNA
<213> ORGANISM: Artificial Sequence
<220> FEATURE:
<223> OTHER INFORMATION: Oligonucleotide

<400> SEQUENCE: 57
cgaagtaagt cttcaaaaaa tcaaataagg agtgtcaaga tgagggcaag gctagacggg 60
acttaccgaa agaaac 76

<210> SEQ ID NO 58
<211> LENGTH: 40
<212> TYPE: DNA
<213> ORGANISM: Artificial Sequence
<220> FEATURE:
<223> OTHER INFORMATION: Oligonucleotide

<400> SEQUENCE: 58
tcttgacact ccttatttga tttttgaag acttacttcg 40

<210> SEQ ID NO 59
<211> LENGTH: 57
<212> TYPE: DNA
<213> ORGANISM: Artificial Sequence
<220> FEATURE:
<223> OTHER INFORMATION: Oligonucleotide

<400> SEQUENCE: 59
gatcggcctt attggccgcg gcattatgtt tgaatttccg tttaaagaat ggtctgc 57

<210> SEQ ID NO 60
<211> LENGTH: 19
<212> TYPE: DNA
<213> ORGANISM: Artificial Sequence
<220> FEATURE:
<223> OTHER INFORMATION: Oligonucleotide

<400> SEQUENCE: 60
gactttcagg cgtgaatgg 19

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide

<400> SEQUENCE: 61
cgtgctctcc gataatatgc 20

<210> SEQ ID NO 62
<211> LENGTH: 6588
<212> TYPE: DNA
<213> ORGANISM: Artificial Sequence
<220> FEATURE:
<223> OTHER INFORMATION: Vector RLW121

<400> SEQUENCE: 62
ccgtttaaac ttagttacta atcagtgatc agattgtcgt ttcccgcctt cactttaaac 60
tatcagtgtt tgacaggata tattggcggg taaacctaag agaaaagagc gtttattaga 120
ataatcggat atttaaaagg gcgtgaaaag gtttatccgt tcgtccattt gtatgtcaat 180

-continued

```
attgggggg ggggaaagcc acgttgtgtc tcaaaatctc tgatgttaca ttgcacaaga    240
taaaaatata tcatcatgaa caataaaact gtctgcttac ataaacagta atacaagggg    300
tgttcgccac catgagccat atccagcgtg aaacctcgtg ctcccgcccg cgcctcaatt    360
ccaatatgga tgccgacctt tatggctaca agtgggcgcg cgacaacgtc ggccagtcgg    420
gcgcgaccat ttatcggctt tatggcaaac ccgatgcccc ggaactgttc ctgaagcacg    480
gcaaaggcag cgtcgcaaac gatgtcaccg atgagatggt ccgcctgaac tggcttaccg    540
agttcatgcc gctgccgacg attaagcatt tcatccgtac cccggacgat gcctggctct    600
tgaccacggc cattccgggc aaaacggcct ttcaggtcct tgaagagtac ccggactccg    660
gtgagaatat cgtggacgcc ctcgcggtct tcctccgccg tttgcatagc atccccgtgt    720
gcaactgccc cttcaactcg gaccgggttt tccgcctggc acaggcccag tcgcgcatga    780
ataacggcct cgttgacgcg agcgatttcg acgatgaacg gaatggctgg ccggtggaac    840
aggtttggaa ggaaatgcac aaactgcttc cgttctcgcc ggattcggtg gtcacgcatg    900
gtgatttttc cctggataat ctgatctttg acgagggcaa gctgatcggc tgcatcgacg    960
tgggtcgcgt cggtatcgcc gaccgctatc aggacctggc gatcttgtgg aattgcctcg   1020
gcgagttctc gccctcgctc cagaagcgcc tgttccagaa gtacggcatc gacaacccgg   1080
atatgaacaa gctccagttc cacctcatgc tggacgaatt tttttgaaca gaattggtta   1140
attggttgta acactggcag agcattacgc tgacttgacg ggacggcggc tttgttgaat   1200
aaatcgaact tttgctgagt tgaaggatcg atgagttgaa ggaccccgta gaaaagatca   1260
aaggatcttc ttgagatcct ttttttctgc gcgtaatctg ctgcttgcaa acaaaaaaac   1320
caccgctacc agcggtggtt tgtttgccgg atcaagagct accaactctt tttccgaagg   1380
taactggctt cagcagagcg cagataccaa atactgtcct tctagtgtag ccgtagttag   1440
gccaccactt caagaactct gtagcaccgc ctacatacct cgctctgcta atcctgttac   1500
cagtggctgc tgccagtggc gataagtcgt gtcttaccgg gttggactca agacgatagt   1560
taccggataa ggcgcagcgg tcgggctgaa cggggggttc gtgcacacag cccagcttgg   1620
agcgaacgac ctacaccgaa ctgagatacc tacagcgtga gctatgagaa agcgccacgc   1680
ttcccgaagg gagaaaggcg gacaggtatc cggtaagcgg cagggtcgga acaggagagc   1740
gcacgaggga gcttccaggg ggaaacgcct ggtatcttta tagtcctgtc gggtttcgcc   1800
acctctgact tgagcgtcga tttttgtgat gctcgtcagg ggggcggagc ctatggaaaa   1860
acgccagcaa cgcggccttt ttacggttcc tggccttttg ctggcctttt gctcacatgt   1920
tctttcctgc gttatcccct gattctgtgg ataaccgtat taccgccttt gagtgagctg   1980
ataccgctcg ccgcagccga acgaccgagc gcagcgagtc agtgagcgag gaagcggaag   2040
agcgcctgat gcggtatttt ctccttacgc atctgtgcgg tatttcacac cgcataggcc   2100
gcgataggcc gacgcgaagc ggcggggcgt agggagcgca gcgaccgaag ggtaggcgct   2160
ttttgcagct cttcggctgt gcgctggcca gacagttatg cacaggccag gcgggtttta   2220
agagttttaa taagttttaa agagttttag gcggaaaaat cgcctttttt ctcttttata   2280
tcagtcactt acatgtgtga ccggttccca atgtacggct ttgggttccc aatgtacggg   2340
ttccggttcc caatgtacgg ctttgggttc ccaatgtacg tgctatccac aggaaagaga   2400
ccttttcgac ctttttcccc tgctagggca atttgcccta gcatctgctc cgtacattag   2460
gaaccggcgg atgcttcgcc ctcgatcagg ttgcggtagc gcatgactag gatcgggcca   2520
```

-continued

```
gcctgccccg cctcctcctt caaatcgtac tccggcaggt catttgaccc gatcagcttg   2580
cgcacggtga aacagaactt cttgaactct ccggcgctgc cactgcgttc gtagatcgtc   2640
ttgaacaacc atctggcttc tgccttgcct gcggcgcggc gtgccaggcg gtagagaaaa   2700
cggccgatgc cggggtcgat caaaaagtaa tcggggtgaa ccgtcagcac gtccgggttc   2760
ttgccttctg tgatctcgcg gtacatccaa tcagcaagct cgatctcgat gtactccggc   2820
cgcccggttt cgctctttac gatcttgtag cggctaatca aggcttcacc ctcggatacc   2880
gtcaccaggc ggccgttctt ggccttcttg gtacgctgca tggcaacgtg cgtggtgttt   2940
aaccgaatgc aggtttctac caggtcgtct ttctgctttc cgccatcggc tcgccggcag   3000
aacttgagta cgtccgcaac gtgtggacgg aacacgcggc cgggcttgtc tcccttccct   3060
tcccggtatc ggttcatgga ttcggttaga tgggaaaccg ccatcagtac caggtcgtaa   3120
tcccacacac tggccatgcc ggcggggcct gcggaaacct ctacgtgccc gtctggaagc   3180
tcgtagcgga tcacctcgcc agctcgtcgg tcacgcttcg acagacggaa aacggccacg   3240
tccatgatgc tgcgactatc gcgggtgccc acgtcataga gcatcggaac gaaaaaatct   3300
ggttgctcgt cgcccttggg cggcttccta atcgacggcg caccggctgc cggcggttgc   3360
cgggattctt tgcggattcg atcagcggcc ccttgccacg attcaccggg gcgtgcttct   3420
gcctcgatgc gttgccgctg ggcggcctgc gcggccttca acttctccac caggtcatca   3480
cccagcgccg cgccgatttg taccgggccg gatggtttgc gaccgctcac gccgattcct   3540
cgggcttggg ggttccagtg ccattgcagg gccggcagac aacccagccg cttacgcctg   3600
gccaaccgcc cgttcctcca cacatggggc attccacggc gtcggtgcct ggttgttctt   3660
gattttccat gccgcctcct ttagccgcta aaattcatct actcatttat tcatttgctc   3720
atttactctg gtagctgcgc gatgtattca gatagcagct cggtaatggt cttgccttgg   3780
cgtaccgcgt acatcttcag cttggtgtga tcctccgccg gcaactgaaa gttgacccgc   3840
ttcatggctg gcgtgtctgc caggctggcc aacgttgcag ccttgctgct gcgtgcgctc   3900
ggacggccgg cacttagcgt gtttgtgctt ttgctcattt tctctttacc tcattaactc   3960
aaatgagttt tgatttaatt tcagcggcca gcgcctggac ctcgcgggca gcgtcgccct   4020
cgggttctga ttcaagaacg gttgtgccgg cggcggcagt gcctgggtag ctcacgcgct   4080
gcgtgatacg ggactcaaga atgggcagct cgtacccggc cagcgcctcg gcaacctcac   4140
cgccgatgcg cgtgcctttg atcgcccgcg acacgacaaa ggccgcttgt agccttccat   4200
ccgtgacctc aatgcgctgc ttaaccagct ccaccaggtc ggcggtggcc caaatgtcgt   4260
aagggcttgg ctgcaccgga atcagcacga agtcggctgc cttgatcgcg gacacagcca   4320
agtccgccgc ctggggcgct ccgtcgatca ctacgaagtc gcgccggccg atggccttca   4380
cgtcgcggtc aatcgtcggg cggtcgatgc cgacaacggt tagcggttga tcttcccgca   4440
cggccgccca atcgcgggca ctgccctggg gatcggaatc gactaacaga acatcggccc   4500
cggcgagttg cagggcgcgg gctagatggg ttgcgatggt cgtcttgcct gacccgcctt   4560
tctggttaag tacagcgata accttcatgc gttccccttg cgtatttgtt tatttactca   4620
tcgcatcata tacgcagcga ccgcatgacg caagctgttt tactcaaata cacatcacct   4680
ttttagatga tcagtgattt tgtgccgagc tgccggtcgg ggagctgttg gctggctggt   4740
ggcaggatat attgtggtgt aaacaaattg acgcttagac aacttaataa cacattgcgg   4800
acgtctttaa tgtactgaat ttagttactg atcactgatt aagtactgat aaatttaatt   4860
aacagatctc aactttgtat agaaaagttg aacgagaaac gtaaaatgat ataaatatca   4920
```

```
atatattaaa ttagattttg cataaaaaac agactacata atactgtaaa acacaacata   4980

tccagtcact atggtcgacc tgcagactgg ctgtgtataa gggagcctga catttatatt   5040

ccccagaaca tcaggttaat ggcgtttttg atgtcatttt cgcggtggct gagatcagcc   5100

acttcttccc cgataacgga gaccggcaca ctggccatat cggtggtcat catgcgccag   5160

ctttcatccc cgatatgcac caccgggtaa agttcacggg ggactttatc tgacagcaga   5220

cgtgcactgg ccagggggat caccatccgt cgcccgggcg tgtcaataat atcactctgt   5280

acatccacaa acagacgata acggctctct cttttatagg tgtaaacctt aaactgcatt   5340

tcaccagccc ctgttctcgt cggcaaaaga gccgttcatt tcaatgaacc gggcgacctc   5400

agccatccct tcctgatttt ccgctttcca gcgttcggca cgcagacgac gggcttcatt   5460

ctgcatggtt gtgcttaccg aaccggagat attgacatca tatatgcctt gagcaactga   5520

tagctgtcgc tgtcaactgt cactgtaata cgctgcttca tagcatacct ctttttgaca   5580

tacttcgggt atacatatca gtatatattc ttataccgca aaaatcagcg cgcaaatacg   5640

catactgtta tctggctttt agtaagccgg atcctctaga ttacgccccg cctgccactc   5700

atcgcagtac tgttgtaatt cattaagcat tctgccgaca tggaagccat cacaaacggc   5760

atgatgaacc tgaatcgcca gcggcatcag caccttgtcg ccttgcgtat aatatttgcc   5820

catggtgaaa acgggggcga agaagttgtc catattggcc acgtttaaat caaaactggt   5880

gaaactcacc cagggattgg ctgagacgaa aaacatattc tcaataaacc ctttagggaa   5940

ataggccagg ttttcaccgt aacacgccac atcttgcgaa tatatgtgta gaaactgccg   6000

gaaatcgtcg tggtattcac tccagagcga tgaaaacgtt tcagtttgct catggaaaac   6060

ggtgtaacaa gggtgaacac tatcccatat caccagctca ccgtctttca ttgccatacg   6120

gaattccgga tgagcattca tcaggcgggc aagaatgtga ataaaggccg gataaaactt   6180

gtgcttattt ttctttacgg tctttaaaaa ggccgtaata tccagctgaa cggtctggtt   6240

ataggtacat tgagcaactg actgaaatgc ctcaaaatgt tctttacgat gccattggga   6300

tatatcaacg gtggtatatc cagtgatttt tttctccatt ttagcttcct tagctcctga   6360

aaatctcgac ggatcctaac tcaaaatcca catattatac gagccggaag cataaagtgt   6420

aaagcctggg gtgcctaatg cggccgccat agtgactgga tatgttgtgt tttacagtat   6480

tatgtagtct gtttttttatg caaaatctaa tttaatatat tgatatttat atcattttac   6540

gtttctcgtt caactttatt atacatagtt gataattcac tgggccgg              6588
```

<210> SEQ ID NO 63
<211> LENGTH: 7443
<212> TYPE: DNA
<213> ORGANISM: Artificial Sequence
<220> FEATURE:
<223> OTHER INFORMATION: Vector CC003

<400> SEQUENCE: 63

```
ctaaattgta agcgttaata ttttgttaaa attcgcgtta aatttttgtt aaatcagctc     60

atttttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattggcgg aaggccgtca    360
```

-continued

```
aggccgcata aataatgatt ttattttgac tgatagtgac ctgttcgttg caacaaattg    420
ataagcaatg ctttttata atgccaactt tgtatagaaa agttgattta aatgaattca     480
agcttttaat taacttagcc actgcaacaa gttcttgaac cttagcacaa tcatattgtg    540
catgcacttg tttattgcaa agaatggtgc gtagggaaca cgcatgattt ttgaattgct    600
ggcacataat tttatcatta gaaactggaa tgcaacatgt accctttgtc atggtttctt    660
tccgagacat tgcactgttt tttttaatcc tatcattatc ataatgccaa gaactggtca    720
ccaaccagca ttttgcatca tggttagttg agctgtcccc atgtatcaat aggtgcattg    780
tattggtcca aaatataaat gcagtggatg caacctatct catggccgtc aacaaaagaa    840
atcaaaaggg aaatgcacca tcttatatct ccagtttata tgaacagatt ggataagatc    900
ataagatcaa gtggtttata ttattttgag gaatataaca tggattcatc ctaatcactc    960
gtctaggcag tatgtgtatt catgatggat atggtactat actacggagt tttttcttca   1020
caaaataacc tgttattttg acctccaacc aaacacgaat tataccaaaa attgggttat   1080
ttcatctata gtacaactct attataaaca tgcagtaaat tatcctacac atataccaaa   1140
attcaagtgt aataatccta atacacagac ttaaaaaaca aactatttcc tttttaagaa   1200
aaggaaaacc atttttttaa cggaaggaaa acaaattcgg gtcaaggcgg aagccagcgc   1260
gccaccccac gtcagcgaat acggaggcgc ggggttgacg gcgtcacccg gtcctaacgg   1320
cgaccaacaa accagccaga agaaattaca gtaaaaaaaa gtaaattgca ctttgatcca   1380
ccttttatta cccaagtttc aatttggacc acccttaaac ctatcttttc aaattgggcc   1440
gggttgtggt ttggactacc atgaacaact tttcgtcatg tctaacttcc ctttcggcaa   1500
acatatgaac catatataga ggagatcggc cgtatactag agctgatgtg tttaaggtcg   1560
ttgattgcac gagaaaaaaa aaatccaaat cgcaacaata gcaaatttat ctagttcaaa   1620
gtgaaaagat atgtttaaag gtagtccaaa gtaaaactta ggggctgttt ggttcccagc   1680
catactttac cattacttgc caacaaaagt tgccacacct tgtctaaggt gaggtgatca   1740
aattgttagc cacaacttac taagcctaag ggaatcttgc cacacttttt tgagccattg   1800
acacgtggga cttaatttgt tagagggaaa tcttgccaca actgtggcta caaccaaaca   1860
cctgtcaaat ttgcctaacc ttaggcgtgg caaactgtgg caaagtgtgg cttacaacca   1920
aacacaccct tagataataa aatgtggtcc aaagcgtaat tcactaaaaa aaaatcaacg   1980
agacgtgtac caaacggaga caaacggcat cttctcgaaa tttcccaacc gctcgctcgc   2040
ccgcctcgtc ttcccggaaa ccgcggtggt ttcagcgtgg cggattctcc aagcagacgg   2100
agacgtcacg gcacgggact cctcccacca cccaaccgcc ataaatacca gcccccctcat  2160
ctcctctcct cgcatcagct ccacccccga aaaatttctc cccaatctcg cgaggctctc   2220
gtcgtcgaat cgaatcctct cgcgtcctca agcttggcat ccaggtacgg atccgcgtcc   2280
catctccctc accccccgtg ttcttcgtgc ctgcttctgg gtcagatctg ggtggattcg   2340
cggttgttgg atgtgggggg ctgtgtttat ttgtcggtgg atctggttgt ctggatctgc   2400
gttttctctg tcgtagttag cggatctgat gaaatgttta gtgttcgtgt atactggtat   2460
ggtggatctg gtcctaggat gcgtggaatg gatatatgta ggcgaattgg aggatttatt   2520
ttgtgaattt tgctgaaatg atagttctaa acactggatc tgacctcggg atgctgttaa   2580
atgtggaaat catggtcgat gctgtcatga acatggtgtt cttatggtag atctgagcaa   2640
tgtatgtttc aaaattgttt gtcacatgga aatgctatgg ttctagatgc aatagaatga   2700
tacatgccga gatcccctct agttgatatg atagatcatg atgttttaca gctatgtcat   2760
```

-continued

```
atgaatatgt tcatttgtta ccgatgtatt tggatctact taacatttcc aaagcacgcc   2820
gcgttctaat tctagatctg gtagtcatgt ttgtacacgt cacccaccta atacaaatac   2880
atatgtctag tgtttggtga cactgcccgt cagatctgtt ttttccagat ctgtggaaca   2940
aatactccac gcatgtatgg tagttttgaa acgatcttgt atcttccatt gttgtagtaa   3000
caactaaata aagtacaatt gttcaattat tgggaatcgt attttctgta gtgccgatgt   3060
acagcatatt catagatgtc tatttaggaa ctcaaatttt aaattgagga ctagttattt   3120
attgtgggtc agtcttttga attgtgttat cttgctgtac tggcgcgcca ccatggccac   3180
cgccgccgcc gcgtctaccg cgctcactgg cgccactacc gctgcgccca aggcgaggcg   3240
ccgggcgcac ctcctggcca cccgccgcgc cctcgccgcg cccatcaggt gctcagcggc   3300
gtcacccgcc atgccgatgg ctcccccggc caccccgctc cggccgtggg gccccaccga   3360
tccccgcaag ggcgccgaca tcctcgtcga gtccctcgag cgctgcggcg tccgcgacgt   3420
cttcgcctac cccggcggca cgtccatgga gatccaccag gcactcaccc gctcccccgt   3480
catcgccaac cacctcttcc gccacgagca aggggaggcc tttgcggcct ccggctacgc   3540
gcgctcctcg ggccgcgtcg gcgtctgcat cgccacctcc ggccccggcg ccaccaacct   3600
tgtctccgcg ctcgccgacg cgctgctcga ttccgtcccc atggtcgcca tcacgggaca   3660
ggtgccgcga cgcatgattg gcaccgacgc cttccaggag acgcccatcg tcgaggtcac   3720
ccgctccatc accaagcaca actacctggt cctcgacgtc gacgacatcc cccgcgtcgt   3780
gcaggaggct ttcttcctcg cctcctctgg tcgaccgggg ccggtgcttg tcgacatccc   3840
caaggacatc cagcagcaga tggcggtgcc tgtctgggac aagcccatga gtctgcctgg   3900
gtacattgcg cgccttccca agccccctgc gactgagttg cttgagcagg tgctgcgtct   3960
tgttggtgaa tcccggcgcc ctgttcttta tgttggcggt ggctgcgcag catctggtga   4020
ggagttgcga cgctttgtgg agctgactgg aatcccggtc acaactactc ttatgggcct   4080
cggcaacttc cccagcgacg acccactgtc tctgcgcatg ctaggtatgc atggcacggt   4140
gtatgcaaat tatgcagtgg ataaggccga tctgttgctt gcacttggtg tgcggtttga   4200
tgatcgtgtg acagggaaga ttgaggcttt tgcaagcagg gctaagattg tgcacgttga   4260
tattgatccg gctgagattg gcaagaacaa gcagccacat gtgtccatct gtgcagatgt   4320
taagcttgct ttgcagggca tgaatgctct tcttgaagga agcacatcaa agaagagctt   4380
tgactttggc tcatggaacg atgagttgga tcagcagaag agggaattcc cccttgggta   4440
taaaacatct aatgaggaga tccagccaca atatgctatt caggttcttg atgagctgac   4500
gaaaggcgag gccatcatcg gcacaggtgt tgggcagcac cagatgtggg cggcacagta   4560
ctacacttac aagcggccaa ggcagtggtt gtcttcagct ggtcttgggg ctatgggatt   4620
tggtttgccg gctgctgctg gtgcttctgt ggccaaccca ggtgttactg ttgttgacat   4680
cgatggagat ggtagctttc tcatgaacgt tcaggagcta gctatgatcc gaattgagaa   4740
cctcccggtg aaggtctttg tgctaaacaa ccagcacctg ggatggtgg tgcagtggga   4800
ggacaggttc tataaggcca acagagcgca cacatacttg ggaaacccag agaatgaaag   4860
tgagatatat ccagatttcg tgacgatcgc caaagggttc aacattccag cggtccgtgt   4920
gacaaagaag aacgaagtcc gcgcagcgat aaagaagatg ctcgagactc cagggccgta   4980
cctcttggat ataatcgtcc cacaccagga gcatgtgttg cctatgatcc ctaatggtgg   5040
ggctttcaag gatatgatcc tggatggtga tggcaggact gtgtactagc ctgcaggcct   5100
```

-continued

```
aggatcgttc aaacatttgg caataaagtt tcttaagatt gaatcctgtt gccggtcttg   5160
cgatgattat catataattt ctgttgaatt acgttaagca tgtaataatt aacatgtaat   5220
gcatgacgtt atttatgaga tgggttttta tgattagagt cccgcaatta tacatttaat   5280
acgcgataga aaacaaaata tagcgcgcaa actaggataa attatcgcgc gcggtgtcat   5340
ctatgttact agatcggccg gccgtttaaa cagcctgctt ttttgtacaa agttggcatt   5400
ataaaaaagc attgctcatc aatttgttgc aacgaacagg tcactatcag tcaaaataaa   5460
atcattattt gctgggcctc atgggccttc cgctcactgc ccgctttcca gtcgggaaac   5520
ctgtcgtgcc agctgcatta acatggtcat agctgtttcc ttgcgtattg ggcgctctcc   5580
gcttcctcgc tcactgactc gctgcgctcg gtcgttcggg taaagcctgg ggtgcctaat   5640
gagcaaaagg ccagcaaaag gccaggaacc gtaaaaaggc cgcgttgctg gcgtttttcc   5700
ataggctccg cccccctgac gagcatcaca aaaatcgacg ctcaagtcag aggtggcgaa   5760
acccgacagg actataaaga taccaggcgt ttccccctgg aagctccctc gtgcgctctc   5820
ctgttccgac cctgccgctt accggatacc tgtccgcctt tctcccttcg ggaagcgtgg   5880
cgctttctca tagctcacgc tgtaggtatc tcagttcggt gtaggtcgtt cgctccaagc   5940
tgggctgtgt gcacgaaccc cccgttcagc ccgaccgctg cgccttatcc ggtaactatc   6000
gtcttgagtc caacccggta agacacgact tatcgccact ggcagcagcc actggtaaca   6060
ggattagcag agcgaggtat gtaggcggtg ctacagagtt cttgaagtgg tggcctaact   6120
acggctacac tagaagaaca gtatttggta tctgcgctct gctgaagcca gttaccttcg   6180
gaaaaagagt tggtagctct tgatccggca aacaaaccac cgctggtagc ggtggttttt   6240
ttgtttgcaa gcagcagatt acgcgcagaa aaaaaggatc tcaagaagat cctttgatct   6300
tttctacggg gtctgacgct cagtggaacg aaaactcacg ttaagggatt ttggtcatga   6360
gattatcaaa aaggatcttc acctagatcc ttttaaatta aaaatgaagt tttaaatcaa   6420
tctaaagtat atatgagtaa acttggtctg acagttacca atgcttaatc agtgaggcac   6480
ctatctcagc gatctgtcta tttcgttcat ccatagttgc ctgactcccc gtcgtgtaga   6540
taactacgat acgggagggc ttaccatctg gccccagtgc tgcaatgata ccgcgagaac   6600
cacgctcacc ggctccagat ttatcagcaa taaaccagcc agccggaagg gccgagcgca   6660
gaagtggtcc tgcaacttta tccgcctcca tccagtctat taattgttgc cgggaagcta   6720
gagtaagtag ttcgccagtt aatagtttgc gcaacgttgt tgccattgct acaggcatcg   6780
tggtgtcacg ctcgtcgttt ggtatggctt cattcagctc cggttcccaa cgatcaaggc   6840
gagttacatg atcccccatg ttgtgcaaaa aagcggttag ctccttcggt cctccgatcg   6900
ttgtcagaag taagttggcc gcagtgttat cactcatggt tatggcagca ctgcataatt   6960
ctcttactgt catgccatcc gtaagatgct tttctgtgac tggtgagtac tcaaccaagt   7020
cattctgaga atagtgtatg cggcgaccga gttgctcttg cccggcgtca atacgggata   7080
ataccgcgcc acatagcaga actttaaaag tgctcatcat tggaaaacgt tcttcggggc   7140
gaaaactctc aaggatctta ccgctgttga gatccagttc gatgtaaccc actcgtgcac   7200
ccaactgatc ttcagcatct tttactttca ccagcgtttc tgggtgagca aaaacaggaa   7260
ggcaaaatgc cgcaaaaaag ggaataaggg cgacacggaa atgttgaata ctcatactct   7320
tcctttttca atattattga agcatttatc agggttattg tctcatgagc ggatacatat   7380
ttgaatgtat ttagaaaaat aaacaaatag gggttccgcg cacatttccc cgaaaagtgc   7440
cac                                                                 7443
```

<210> SEQ ID NO 64
<211> LENGTH: 3734
<212> TYPE: DNA
<213> ORGANISM: Artificial Sequence
<220> FEATURE:
<223> OTHER INFORMATION: Vector CC018

<400> SEQUENCE: 64
cgcggatcat gaaccaacgg cctggctgta tttggtggtt gtgtagggag atggggagaa 60
gaaaagcccg attctcttcg ctgtgatggg ctggatgcat gcgggggagc gggaggccca 120
agtacgtgca cggtgagcgg cccacagggc gagtgtgagc gcgagaggcg ggaggaacag 180
tttagtacca cattgcccag ctaactcgaa cgcgaccaac ttataaaccc gcgcgctgtc 240
gcttgtgtgc attgagtgct atgctgaggt tttagagcta gaaatagcaa gttaaaataa 300
ggctagtccg ttatcaactt gaaaaagtgg caccgagtcg gtgctctgtt cctcgtgctg 360
gacaagtgtg gtttccagat tctgcaacca agactgcgca ggcattgctg gacttcaacc 420
gtgaaggatt acctctgttc atcctcgcta actggagagg cttctctggt ggacaaagag 480
atctctttga aggaattctt caggctggct cgactattgt tgagaacctt aggacataca 540
atcagcctgc ctttgtctac attcccatgg ctgcagagct acgaggaggg gcttgggttg 600
tggttgatag caagataaac ccagaccgca ttgagtgcta tgctgagaga actgcaaaat 660
ccaatgttct ggaaccgcaa gggttaattg agatcaagtt caggtcagag gaactccagg 720
attgcatgag tcggcttgac ccaacattaa ttgatctgaa agcaaaactc gaagtagcaa 780
ataaaaatgg aagtgctgac acaaaatcgc ttcaagaaaa tatagaagct cgaacaaaac 840
agttgatgcc tctatatact cagattgcga tacggtttgc tgaattgcat gatacatccc 900
tcagaatggc tgcgaaaggt gtgattaaga aagttgtgga ctgggaagaa tcacgatctt 960
tctttttttt gcggccgccc cggcctgca ggggatcccg atcgggccgg ccgtttaaac 1020
ccactttgta caagaaagtt gaacgagaaa cgtaaaatga tataaatatc aatatattaa 1080
attagatttt gcataaaaaa cagactacat aatactgtaa aacacaacat atgcagtcac 1140
tatgaaccaa ctacttagat ggtattagtg acctgtactg ggcctcatgg gccttccgct 1200
cactgcccgc tttccagtcg ggaaacctgt cgtgccagct gcattaacat ggtcatagct 1260
gtttccttgc gtattgggcg ctctccgctt cctcgctcac tgactcgctg cgctcggtcg 1320
ttcgggtaaa gcctggggtg cctaatgagc aaaaggccag caaaaggcca ggaaccgtaa 1380
aaaggccgcg ttgctggcgt ttttccatag gctccgcccc cctgacgagc atcacaaaaa 1440
tcgacgctca agtcagaggt ggcgaaaccc gacaggacta taaagatacc aggcgtttcc 1500
ccctggaagc tccctcgtgc gctctcctgt tccgaccctg ccgcttaccg gatacctgtc 1560
cgcctttctc ccttcgggaa gcgtggcgct ttctcatagc tcacgctgta ggtatctcag 1620
ttcggtgtag gtcgttcgct ccaagctggg ctgtgtgcac gaaccccccg ttcagcccga 1680
ccgctgcgcc ttatccggta actatcgtct tgagtccaac ccggtaagac acgacttatc 1740
gccactggca gcagccactg gtaacaggat tagcagagcg aggtatgtag gcggtgctac 1800
agagttcttg aagtggtggc ctaactacgg ctacactaga agaacagtat ttggtatctg 1860
cgctctgctg aagccagtta ccttcggaaa aagagttggt agctcttgat ccggcaaaca 1920
aaccaccgct ggtagcggtg gtttttttgt ttgcaagcag cagattacgc gcagaaaaaa 1980
aggatctcaa gaagatcctt tgatcttttc tacggggtct gacgctcagt ggaacgaaaa 2040

-continued

```
ctcacgttaa gggattttgg tcatgagatt atcaaaaagg atcttcacct agatcctttt   2100

aaattaaaaa tgaagtttta aatcaatcta aagtatatat gagtaaactt ggtctgacag   2160

ttaccaatgc ttaatcagtg aggcacctat ctcagcgatc tgtctatttc gttcatccat   2220

agttgcctga ctccccgtcg tgtagataac tacgatacgg gagggcttac catctggccc   2280

cagtgctgca atgataccgc gagaaccacg ctcaccggct ccagatttat cagcaataaa   2340

ccagccagcc ggaagggccg agcgcagaag tggtcctgca actttatccg cctccatcca   2400

gtctattaat tgttgccggg aagctagagt aagtagttcg ccagttaata gtttgcgcaa   2460

cgttgttgcc attgctacag gcatcgtggt gtcacgctcg tcgtttggta tggcttcatt   2520

cagctccggt tcccaacgat caaggcgagt tacatgatcc cccatgttgt gcaaaaaagc   2580

ggttagctcc ttcggtcctc cgatcgttgt cagaagtaag ttggccgcag tgttatcact   2640

catggttatg gcagcactgc ataattctct tactgtcatg ccatccgtaa gatgcttttc   2700

tgtgactggt gagtactcaa ccaagtcatt ctgagaatag tgtatgcggc gaccgagttg   2760

ctcttgcccg gcgtcaatac gggataatac cgcgccacat agcagaactt taaaagtgct   2820

catcattgga aaacgttctt cggggcgaaa actctcaagg atcttaccgc tgttgagatc   2880

cagttcgatg taacccactc gtgcacccaa ctgatcttca gcatctttta ctttcaccag   2940

cgtttctggg tgagcaaaaa caggaaggca aaatgccgca aaaaagggaa taagggcgac   3000

acggaaatgt tgaatactca tactcttcct ttttcaatat tattgaagca tttatcaggg   3060

ttattgtctc atgagcggat acatatttga atgtatttag aaaaataaac aaataggggt   3120

tccgcgcaca tttccccgaa aagtgccacc taaattgtaa gcgttaatat tttgttaaaa   3180

ttcgcgttaa atttttgtta aatcagctca ttttttaacc aataggccga aatcggcaaa   3240

atcccttata aatcaaaaga atagaccgag atagggttga gtggccgcta cagggcgctc   3300

ccattcgcca ttcaggctgc gcaactgttg ggaagggcgt ttcggtgcgg gcctcttcgc   3360

tattacgcca gctggcgaaa gggggatgtg ctgcaaggcg attaagttgg gtaacgccag   3420

ggttttccca gtcacgacgt tgtaaaacga cggccagtga gcgcgacgta atacgactca   3480

ctatagggcg aattggcgga aggccgtcaa ggccgcatta caggtcacta ataccatcta   3540

agtagttggt tcatagtgac tgcatatgtt gtgttttaca gtattatgta gtctgttttt   3600

tatgcaaaat ctaatttaat atattgatat ttatatcatt ttacgtttct cgttcaactt   3660

ttttgtacaa acttgattta aatgaattca agcttttaat taagcatgcg agctcggcgc   3720

gccggtaccg cgat                                                     3734
```

```
<210> SEQ ID NO 65
<211> LENGTH: 9506
<212> TYPE: DNA
<213> ORGANISM: Artificial Sequence
<220> FEATURE:
<223> OTHER INFORMATION: Vector CC006

<400> SEQUENCE: 65

ctaaattgta agcgttaata ttttgttaaa attcgcgtta aatttttgtt aaatcagctc     60

atttttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattggcgg aaggccgtca    360
```

```
aggccgcatc aaataatgat tttattttga ctgatagtga cctgttcgtt gcaacaaatt    420
gataagcaat gctttcttat aatgccaact ttgtacaaga aagctgggta tttaaatgaa    480
ttcaagcttt taattaatgc agtgcagcgt gacccggtcg tgcccctctc tagagataat    540
gagcattgca tgtctaagtt ataaaaaatt accacatatt ttttttgtca cacttgtttg    600
aagtgcagtt tatctatctt tatacatata tttaaacttt actctacgaa taatataatc    660
tatagtacta caataatatc agtgttttag agaatcatat aaatgaacag ttagacatgg    720
tctaaaggac aattgagtat tttgacaaca ggactctaca gttttatctt tttagtgtgc    780
atgtgttctc cttttttttt gcaaatagct tcacctatat aatacttcat ccattttatt    840
agtacatcca tttagggttt agggttaatg gtttttatag actaattttt ttagtacatc    900
tattttattc tattttagcc tctaaattaa gaaaactaaa actctatttt agttttttta    960
tttaatagtt tagatataaa atagaataaa ataaagtgac taaaaattaa acaaataccc   1020
tttaagaaat taaaaaaact aaggaaacat ttttcttgtt tcgagtagat aatgccagcc   1080
tgttaaacgc cgtcgacgag tctaacggac accaaccagc gaaccagcag cgtcgcgtcg   1140
ggccaagcga agcagacggc acggcatctc tgtcgctgcc tctggacccc tctcgagagt   1200
tccgctccac cgttggactt gctccgctgt cggcatccag aaattgcgtg gcggagcggc   1260
agacgtgagc cggcacggca ggcggcctcc tcctcctctc acggcaccgg cagctacggg   1320
ggattccttt cccaccgctc cttcgctttc ccttcctcgc ccgccgtaat aaatagacac   1380
cccctccaca ccctctttcc ccaacctcgt gttgttcgga gcgcacacac acacaaccag   1440
atctccccca aatccacccg tcggcacctc cgcttcaagg tacgccgctc gtcctccccc   1500
cccccccccc tctctacctt ctctagatcg gcgttccggt ccatggttag ggcccggtag   1560
ttctacttct gttcatgttt gtgttagatc cgtgtttgtg ttagatccgt gctgctagcg   1620
ttcgtacacg gatgcgacct gtacgtcaga cacgttctga ttgctaactt gccagtgttt   1680
ctctttgggg aatcctggga tggctctagc cgttccgcag acgggatcga tttcatgatt   1740
ttttttgttt cgttgcatag ggtttggttt gccctttttcc tttatttcaa tatatgccgt   1800
gcacttgttt gtcgggtcat cttttcatgc ttttttttgt cttggttgtg atgatgtggt   1860
ctggttgggc ggtcgttcta gatcggagta gaattctgtt tcaaactacc tggtggattt   1920
attaattttg gatctgtatg tgtgtgccat acatattcat agttacgaat tgaagatgat   1980
ggatggaaat atcgatctag gataggtata catgttgatg cgggttttac tgatgcatat   2040
acagagatgc tttttgttcg cttggttgtg atgatgtggt gtggttgggc ggtcgttcat   2100
tcgttctaga tcggagtaga atactgtttc aaactacctg gtgtatttat taattttgga   2160
actgtatgtg tgtgtcatac atcttcatag ttacgagttt aagatggatg gaaatatcga   2220
tctaggatag gtatacatgt tgatgtgggt tttactgatg catatacatg atggcatatg   2280
cagcatctat tcatatgctc taaccttgag tacctatcta ttataataaa caagtatgtt   2340
ttataattat ttcgatcttg atatacttgg atgatggcat atgcagcagc tatatgtgga   2400
tttttttagc cctgccttca tacgctattt atttgcttgg tactgtttct tttgtcgatg   2460
ctcaccctgt tgtttggtgt tacttctgca gggcgcgcca ccatggctcc taagaagaag   2520
cggaaggttg gtattcacgg ggtgcctgcg gctgacaaga agtactccat cggcctcgac   2580
atcggcacca acagcgtcgg ctgggcggtg atcaccgacg agtacaaggt cccgtccaag   2640
aagttcaagg tcctgggcaa caccgaccgc cactccatca agaagaacct catcggcgcc   2700
```

-continued

```
ctcctcttcg actccggcga gacggcggag gcgacccgcc tcaagcgcac cgcccgccgc   2760
cgctacaccc gccgcaagaa ccgcatctgc tacctccagg agatcttctc caacgagatg   2820
gcgaaggtcg acgactcctt cttccaccgc ctcgaggagt ccttcctcgt ggaggaggac   2880
aagaagcacg agcgccaccc catcttcggc aacatcgtcg acgaggtcgc ctaccacgag   2940
aagtacccca ctatctacca ccttcgtaag aagcttgttg actctactga taaggctgat   3000
cttcgtctca tctaccttgc tctcgctcac atgatcaagt tccgtggtca cttccttatc   3060
gagggtgacc ttaaccctga taactccgac gtggacaagc tcttcatcca gctcgtccag   3120
acctacaacc agctcttcga ggagaaccct atcaacgctt ccggtgtcga cgctaaggcg   3180
atcctttccg ctaggctctc caagtccagg cgtctcgaga acctcatcgc ccagctccct   3240
ggtgagaaga agaacggtct tttcggtaac ctcatcgctc tctccctcgg tctgacccct   3300
aacttcaagt ccaacttcga cctcgctgag gacgctaagc ttcagctctc caaggatacc   3360
tacgacgatg atctcgacaa cctcctcgct cagattggag atcagtacgc tgatctcttc   3420
cttgctgcta agaacctctc cgatgctatc ctcctttcgg atatccttag ggttaacact   3480
gagatcacta aggctcctct ttctgcttcc atgatcaagc gctacgacga gcaccaccag   3540
gacctcaccc tcctcaaggc tcttgttcgt cagcagctcc ccgagaagta caaggagatc   3600
ttcttcgacc agtccaagaa cggctacgcc ggttacattg acggtggagc tagccaggag   3660
gagttctaca agttcatcaa gccaatcctt gagaagatgg atggtactga ggagcttctc   3720
gttaagctta accgtgagga cctccttagg aagcagagga ctttcgataa cggctctatc   3780
cctcaccaga tccaccttgg tgagcttcac gccatccttc gtaggcagga ggacttctac   3840
cctttcctca aggacaaccg tgagaagatc gagaagatcc ttactttccg tattccttac   3900
tacgttggtc ctcttgctcg tggtaactcc cgtttcgctt ggatgactag gaagtccgag   3960
gagactatca ccccttggaa cttcgaggag gttgttgaca agggtgcttc cgcccagtcc   4020
ttcatcgagc gcatgaccaa cttcgacaag aacctcccca acgagaaggt cctccccaag   4080
cactccctcc tctacgagta cttcacggtc tacaacgagc tcaccaaggt caagtacgtc   4140
accgagggta tgcgcaagcc tgccttcctc tccggcgagc agaagaaggc tatcgttgac   4200
ctcctcttca agaccaaccg caaggtcacc gtcaagcagc tcaaggagga ctacttcaag   4260
aagatcgagt gcttcgactc cgtcgagatc agcggcgttg aggaccgttt caacgcttct   4320
ctcggcacct accacgatct cctcaagatc atcaaggaca aggacttcct cgacaacgag   4380
gagaacgagg acatcctcga ggacatcgtc ctcactctta ctctcttcga ggatagggag   4440
atgatcgagg agaggctcaa gacttacgct catctcttcg atgacaaggt tatgaagcag   4500
ctcaagcgtc gccgttacac cggttggggt aggctctccc gcaagctcat caacggtatc   4560
agggataagc agagcggcaa gactatcctc gacttcctca agtctgatgg tttcgctaac   4620
aggaacttca tgcagctcat ccacgatgac tctcttacct tcaaggagga tattcagaag   4680
gctcaggtgt ccggtcaggg cgactctctc cacgagcaca ttgctaacct tgctggttcc   4740
cctgctatca agaagggcat ccttcagact gttaaggttg tcgatgagct tgtcaaggtt   4800
atgggtcgtc acaagcctga gaacatcgtc atcgagatgg ctcgtgagaa ccagactacc   4860
cagaagggtc agaagaactc gagggagcgc atgaagagga ttgaggaggg tatcaaggag   4920
cttggttctc agatccttaa ggagcaccct gtcgagaaca cccagctcca gaacgagaag   4980
ctctacctct actacctcca gaacggtagg gatatgtacg ttgaccagga gctcgacatc   5040
aacaggcttt ctgactacga cgtcgaccac attgttcctc agtctttcct taaggatgac   5100
```

```
tccatcgaca acaaggtcct cacgaggtcc gacaagaaca ggggtaagtc ggacaacgtc   5160
ccttccgagg aggttgtcaa gaagatgaag aactactgga ggcagcttct caacgctaag   5220
ctcattaccc agaggaagtt cgacaacctc acgaaggctg agaggggtgg cctttccgag   5280
cttgacaagg ctggtttcat caagaggcag cttgttgaga cgaggcagat taccaagcac   5340
gttgctcaga tcctcgattc taggatgaac accaagtacg acgagaacga caagctcatc   5400
cgcgaggtca aggtgatcac cctcaagtcc aagctcgtct ccgacttccg caaggacttc   5460
cagttctaca aggtccgcga gatcaacaac taccaccacg ctcacgatgc ttaccttaac   5520
gctgtcgttg gcaccgctct tatcaagaag taccctaagc ttgagtccga gttcgtctac   5580
ggtgactaca aggtctacga cgttcgtaag atgatcgcca agtccgagca ggagatcggc   5640
aaggccaccg ccaagtactt cttctactcc aacatcatga acttcttcaa gaccgagatc   5700
accctcgcca acggcgagat ccgcaagcgc cctcttatcg agacgaacgg tgagactggt   5760
gagatcgttt gggacaaggg tcgcgacttc gctactgttc gcaaggtcct ttctatgcct   5820
caggttaaca tcgtcaagaa gaccgaggtc cagaccggtg gcttctccaa ggagtctatc   5880
cttccaaaga gaaactcgga caagctcatc gctaggaaga aggattggga ccctaagaag   5940
tacggtggtt tcgactcccc tactgtcgcc tactccgtcc tcgtggtcgc caaggtggag   6000
aagggtaagt cgaagaagct caagtccgtc aaggagctcc tcggcatcac catcatggag   6060
cgctcctcct tcgagaagaa cccgatcgac ttcctcgagg ccaagggcta caaggaggtc   6120
aagaaggacc tcatcatcaa gctccccaag tactctcttt tcgagctcga gaacggtcgt   6180
aagaggatgc tggcttccgc tggtgagctc cagaagggta acgagcttgc tcttccttcc   6240
aagtacgtga acttcctcta cctcgcctcc cactacgaga agctcaaggg ttcccctgag   6300
gataacgagc agaagcagct cttcgtggag cagcacaagc actacctcga cgagatcatc   6360
gagcagatct ccgagttctc caagcgcgtc atcctcgctg acgctaacct cgacaaggtc   6420
ctctccgcct acaacaagca ccgcgacaag cccatccgcg agcaggccga gaacatcatc   6480
cacctcttca cgctcacgaa cctcggcgcc cctgctgctt tcaagtactt cgacaccacc   6540
atcgacagga agcgttacac gtccaccaag gaggttctcg acgctactct catccaccag   6600
tccatcaccg gtctttacga gactcgtatc gacctttccc agcttggtgg tgataagcgt   6660
cctgctgcca ccaaaaaggc cggacaggct aagaaaaaga agtagcctgc aggtcctgct   6720
ttaatgagat atgcgagacg cctatgatcg catgatattt gctttcaatt ctgttgtgca   6780
cgttgtaaaa aacctgagca tgtgtagctc agatccttac cgccggtttc ggttcattct   6840
aatgaatata tcacccgtta ctatcgtatt tttatgaata atattctccg ttcaatttac   6900
tgattgtacc ctactactta tatgtacaat attaaaatga aaacaatata ttgtgctgaa   6960
taggtttata gcgacatcta tgatagagcg ccacaataac aaacaattgc gttttattat   7020
tacaaatcca attttaaaaa aagcggcaga accggtcaaa cctaaaagac tgattacata   7080
aatcttattc aaatttcaaa agtgccccag gggctagtat ctacgacaca ccgagcggcg   7140
aactaataac gctcactgaa gggaactccg gttccccgcc ggcgcgcatg ggtgagattc   7200
cttgaagttg agtattggcc gtccgctcta ccgaaagtta cgggcaccat tcaacccggt   7260
ccagcacggc ggccgggtaa ccgacttgct gccccgagaa ttatgcagca tttttttggt   7320
gtatgtgggc cccaaatgaa gtgcaggtca aaccttgaca gtgacgacaa atcgttgggc   7380
gggtccaggg cgaattttgc gacaacatgt cgaggctcag caggccggcc gtttaaacca   7440
```

-continued actttattat acaaagttgg cattataaaa aagcattgct tatcaatttg ttgcaacgaa 7500
caggtcacta tcagtcaaaa taaaatcatt atttctgggc ctcatgggcc ttccgctcac 7560
tgcccgcttt ccagtcggga aacctgtcgt gccagctgca ttaacatggt catagctgtt 7620
tccttgcgta ttgggcgctc tccgcttcct cgctcactga ctcgctgcgc tcggtcgttc 7680
gggtaaagcc tggggtgcct aatgagcaaa aggccagcaa aaggccagga accgtaaaaa 7740
ggccgcgttg ctggcgtttt tccataggct ccgcccccct gacgagcatc acaaaaatcg 7800
acgctcaagt cagaggtggc gaaacccgac aggactataa agataccagg cgtttccccc 7860
tggaagctcc ctcgtgcgct ctcctgttcc gaccctgccg cttaccggat acctgtccgc 7920
ctttctccct tcgggaagcg tggcgctttc tcatagctca cgctgtaggt atctcagttc 7980
ggtgtaggtc gttcgctcca agctgggctg tgtgcacgaa ccccccgttc agcccgaccg 8040
ctgcgcctta tccggtaact atcgtcttga gtccaacccg gtaagacacg acttatcgcc 8100
actggcagca gccactggta acaggattag cagagcgagg tatgtaggcg gtgctacaga 8160
gttcttgaag tggtggccta actacggcta cactagaaga acagtatttg gtatctgcgc 8220
tctgctgaag ccagttacct tcggaaaaag agttggtagc tcttgatccg gcaaacaaac 8280
caccgctggt agcggtggtt tttttgtttg caagcagcag attacgcgca gaaaaaaagg 8340
atctcaagaa gatcctttga tcttttctac ggggtctgac gctcagtgga acgaaaactc 8400
acgttaaggg attttggtca tgagattatc aaaaaggatc ttcacctaga tccttttaaa 8460
ttaaaaatga agttttaaat caatctaaag tatatatgag taaacttggt ctgacagtta 8520
ccaatgctta atcagtgagg cacctatctc agcgatctgt ctatttcgtt catccatagt 8580
tgcctgactc cccgtcgtgt agataactac gatacgggag ggcttaccat ctggccccag 8640
tgctgcaatg ataccgcgag aaccacgctc accggctcca gatttatcag caataaacca 8700
gccagccgga agggccgagc gcagaagtgg tcctgcaact ttatccgcct ccatccagtc 8760
tattaattgt tgccgggaag ctagagtaag tagttcgcca gttaatagtt tgcgcaacgt 8820
tgttgccatt gctacaggca tcgtggtgtc acgctcgtcg tttggtatgg cttcattcag 8880
ctccggttcc caacgatcaa ggcgagttac atgatccccc atgttgtgca aaaaagcggt 8940
tagctccttc ggtcctccga tcgttgtcag aagtaagttg gccgcagtgt tatcactcat 9000
ggttatggca gcactgcata attctcttac tgtcatgcca tccgtaagat gcttttctgt 9060
gactggtgag tactcaacca agtcattctg agaatagtgt atgcggcgac cgagttgctc 9120
ttgcccggcg tcaatacggg ataataccgc gccacatagc agaactttaa aagtgctcat 9180
cattggaaaa cgttcttcgg ggcgaaaact ctcaaggatc ttaccgctgt tgagatccag 9240
ttcgatgtaa cccactcgtg cacccaactg atcttcagca tcttttactt tcaccagcgt 9300
ttctgggtga gcaaaaacag gaaggcaaaa tgccgcaaaa aagggaataa gggcgacacg 9360
gaaatgttga atactcatac tcttcctttt tcaatattat tgaagcattt atcagggtta 9420
ttgtctcatg agcggataca tatttgaatg tatttagaaa aataaacaaa taggggttcc 9480
gcgcacattt ccccgaaaag tgccac 9506

<210> SEQ ID NO 66
<211> LENGTH: 17930
<212> TYPE: DNA
<213> ORGANISM: Artificial Sequence
<220> FEATURE:
<223> OTHER INFORMATION: Vector RLW137

<400> SEQUENCE: 66

-continued

```
ttatacatag ttgataattc actgggccgg ccgtttaaac ttagttacta atcagtgatc     60
agattgtcgt ttcccgcctt cactttaaac tatcagtgtt tgacaggata tattggcggg    120
taaacctaag agaaaagagc gtttattaga ataatcggat atttaaaagg gcgtgaaaag    180
gtttatccgt tcgtccattt gtatgtcaat attggggggg ggggaaagcc acgttgtgtc    240
tcaaaatctc tgatgttaca ttgcacaaga taaaaatata tcatcatgaa caataaaact    300
gtctgcttac ataaacagta atacaagggg tgttcgccac catgagccat atccagcgtg    360
aaacctcgtg ctcccgcccg cgcctcaatt ccaatatgga tgccgacctt tatggctaca    420
agtgggcgcg cgacaacgtc ggccagtcgg gcgcgaccat ttatcggctt tatggcaaac    480
ccgatgcccc ggaactgttc ctgaagcacg gcaaaggcag cgtcgcaaac gatgtcaccg    540
atgagatggt ccgcctgaac tggcttaccg agttcatgcc gctgccgacg attaagcatt    600
tcatccgtac ccccggacgat gcctggctct tgaccacggc cattccgggc aaaacggcct    660
ttcaggtcct tgaagagtac ccggactccg gtgagaatat cgtggacgcc ctcgcggtct    720
tcctccgccg tttgcatagc atccccgtgt gcaactgccc cttcaactcg gaccgggttt    780
tccgcctggc acaggcccag tcgcgcatga ataacggcct cgttgacgcg agcgatttcg    840
acgatgaacg gaatggctgg ccggtggaac aggtttggaa ggaaatgcac aaactgcttc    900
cgttctcgcc ggattcggtg gtcacgcatg gtgatttttc cctggataat ctgatctttg    960
acgagggcaa gctgatcggc tgcatcgacg tgggtcgcgt cggtatcgcc gaccgctatc   1020
aggacctggc gatcttgtgg aattgcctcg gcgagttctc gccctcgctc cagaagcgcc   1080
tgttccagaa gtacggcatc gacaacccgg atatgaacaa gctccagttc cacctcatgc   1140
tggacgaatt tttttgaaca gaattggtta attggttgta acactggcag agcattacgc   1200
tgacttgacg ggacggcggc tttgttgaat aaatcgaact tttgctgagt tgaaggatcg   1260
atgagttgaa ggaccccgta gaaaagatca aaggatcttc ttgagatcct ttttttctgc   1320
gcgtaatctg ctgcttgcaa acaaaaaaac caccgctacc agcggtggtt tgtttgccgg   1380
atcaagagct accaactctt tttccgaagg taactggctt cagcagagcg cagataccaa   1440
atactgtcct tctagtgtag ccgtagttag gccaccactt caagaactct gtagcaccgc   1500
ctacatacct cgctctgcta atcctgttac cagtggctgc tgccagtggc gataagtcgt   1560
gtcttaccgg gttggactca agacgatagt taccggataa ggcgcagcgg tcgggctgaa   1620
cggggggttc gtgcacacag cccagcttgg agcgaacgac ctacaccgaa ctgagatacc   1680
tacagcgtga gctatgagaa agcgccacgc ttcccgaagg gagaaaggcg gacaggtatc   1740
cggtaagcgg cagggtcgga acaggagagc gcacgaggga gcttccaggg ggaaacgcct   1800
ggtatcttta tagtcctgtc gggtttcgcc acctctgact tgagcgtcga tttttgtgat   1860
gctcgtcagg ggggcggagc ctatggaaaa acgccagcaa cgcggccttt ttacggttcc   1920
tggccttttg ctggcctttt gctcacatgt tctttcctgc gttatcccct gattctgtgg   1980
ataaccgtat taccgccttt gagtgagctg ataccgctcg ccgcagccga acgaccgagc   2040
gcagcgagtc agtgagcgag gaagcggaag agcgcctgat gcggtatttt ctccttacgc   2100
atctgtgcgg tatttcacac cgcataggcc gcgataggcc gacgcgaagc ggcggggcgt   2160
agggagcgca gcgaccgaag ggtaggcgct ttttgcagct cttcggctgt gcgctggcca   2220
gacagttatg cacaggccag gcgggtttta agagttttaa taagttttaa agagttttag   2280
gcggaaaaat cgcctttttt ctcttttata tcagtcactt acatgtgtga ccggttccca   2340
```

-continued

```
atgtacggct ttgggttccc aatgtacggg ttccggttcc caatgtacgg ctttgggttc   2400
ccaatgtacg tgctatccac aggaaagaga ccttttcgac ctttttcccc tgctagggca   2460
atttgcccta gcatctgctc cgtacattag gaaccggcgg atgcttcgcc ctcgatcagg   2520
ttgcggtagc gcatgactag gatcgggcca gcctgccccg cctcctcctt caaatcgtac   2580
tccggcaggt catttgaccc gatcagcttg cgcacggtga aacagaactt cttgaactct   2640
ccggcgctgc cactgcgttc gtagatcgtc ttgaacaacc atctggcttc tgccttgcct   2700
gcggcgcggc gtgccaggcg gtagagaaaa cggccgatgc cggggtcgat caaaaagtaa   2760
tcggggtgaa ccgtcagcac gtccgggttc ttgccttctg tgatctcgcg gtacatccaa   2820
tcagcaagct cgatctcgat gtactccggc cgcccggttt cgctctttac gatcttgtag   2880
cggctaatca aggcttcacc ctcggatacc gtcaccaggc ggccgttctt ggccttcttg   2940
gtacgctgca tggcaacgtg cgtggtgttt aaccgaatgc aggtttctac caggtcgtct   3000
ttctgctttc cgccatcggc tcgccggcag aacttgagta cgtccgcaac gtgtggacgg   3060
aacacgcggc cgggcttgtc tcccttccct tcccggtatc ggttcatgga ttcggttaga   3120
tgggaaaccg ccatcagtac caggtcgtaa tcccacacac tggccatgcc ggcggggcct   3180
gcggaaacct ctacgtgccc gtctggaagc tcgtagcgga tcacctcgcc agctcgtcgg   3240
tcacgcttcg acagacggaa aacggccacg tccatgatgc tgcgactatc gcgggtgccc   3300
acgtcataga gcatcggaac gaaaaaatct ggttgctcgt cgcccttggg cggcttccta   3360
atcgacggcg caccggctgc cggcggttgc cgggattctt tgcggattcg atcagcggcc   3420
ccttgccacg attcaccggg gcgtgcttct gcctcgatgc gttgccgctg ggcggcctgc   3480
gcggccttca acttctccac caggtcatca cccagcgccg cgccgatttg taccgggccg   3540
gatggtttgc gaccgctcac gccgattcct cgggcttggg ggttccagtg ccattgcagg   3600
gccggcagac aacccagccg cttacgcctg gccaaccgcc cgttcctcca cacatggggc   3660
attccacggc gtcggtgcct ggttgttctt gattttccat gccgcctcct ttagccgcta   3720
aaattcatct actcatttat tcatttgctc atttactctg gtagctgcgc gatgtattca   3780
gatagcagct cggtaatggt cttgccttgg cgtaccgcgt acatcttcag cttggtgtga   3840
tcctccgccg gcaactgaaa gttgacccgc ttcatggctg gcgtgtctgc caggctggcc   3900
aacgttgcag ccttgctgct gcgtgcgctc ggacggccgg cacttagcgt gtttgtgctt   3960
ttgctcattt tctctttacc tcattaactc aaatgagttt tgatttaatt tcagcggcca   4020
gcgcctggac ctcgcgggca gcgtcgccct cgggttctga ttcaagaacg gttgtgccgg   4080
cggcggcagt gcctgggtag ctcacgcgct gcgtgatacg ggactcaaga atgggcagct   4140
cgtacccggc cagcgcctcg gcaacctcac cgccgatgcg cgtgcctttg atcgcccgcg   4200
acacgacaaa ggccgcttgt agccttccat ccgtgacctc aatgcgctgc ttaaccagct   4260
ccaccaggtc ggcggtggcc caaatgtcgt aagggcttgg ctgcaccgga atcagcacga   4320
agtcggctgc cttgatcgcg gacacagcca agtccgccgc ctggggcgct ccgtcgatca   4380
ctacgaagtc gcgccggccg atggccttca cgtcgcggtc aatcgtcggg cggtcgatgc   4440
cgacaacggt tagcggttga tcttcccgca cggccgccca atcgcgggca ctgccctggg   4500
gatcggaatc gactaacaga acatcggccc cggcgagttg cagggcgcgg gctagatggg   4560
ttgcgatggt cgtcttgcct gacccgcctt tctggttaag tacagcgata accttcatgc   4620
gttccccttg cgtatttgtt tatttactca tcgcatcata tacgcagcga ccgcatgacg   4680
caagctgttt tactcaaata cacatcacct ttttagatga tcagtgattt tgtgccgagc   4740
```

-continued

```
tgccggtcgg ggagctgttg gctggctggt ggcaggatat attgtggtgt aaacaaattg   4800
acgcttagac aacttaataa cacattgcgg acgtctttaa tgtactgaat ttagttactg   4860
atcactgatt aagtactgat aaatttaatt aacagatctc aactttgtat agaaaagttg   4920
atttaaatga attcaagctt ttaattaact tagccactgc aacaagttct tgaaccttag   4980
cacaatcata ttgtgcatgc acttgtttat tgcaaagaat ggtgcgtagg gaacacgcat   5040
gatttttgaa ttgctggcac ataattttat cattagaaac tggaatgcaa catgtaccct   5100
ttgtcatggt ttctttccga gacattgcac tgtttttttt aatcctatca ttatcataat   5160
gccaagaact ggtcaccaac cagcattttg catcatggtt agttgagctg tccccatgta   5220
tcaataggtg cattgtattg gtccaaaata taaatgcagt ggatgcaacc tatctcatgg   5280
ccgtcaacaa aagaaatcaa aagggaaatg caccatctta tatctccagt ttatatgaac   5340
agattggata agatcataag atcaagtggt ttatattatt ttgaggaata taacatggat   5400
tcatcctaat cactcgtcta ggcagtatgt gtattcatga tggatatggt actatactac   5460
ggagtttttt cttcacaaaa taacctgtta ttttgacctc caaccaaaca cgaattatac   5520
caaaaattgg gttatttcat ctatagtaca actctattat aaacatgcag taaattatcc   5580
tacacatata ccaaaattca agtgtaataa tcctaataca cagacttaaa aaacaaacta   5640
tttccttttt aagaaaagga aaaccatttt tttaacggaa ggaaaacaaa ttcgggtcaa   5700
ggcggaagcc agcgcgccac cccacgtcag cgaatacgga ggcgcggggt tgacggcgtc   5760
acccggtcct aacggcgacc aacaaaccag ccagaagaaa ttacagtaaa aaaaagtaaa   5820
ttgcactttg atccaccttt tattacccaa gtttcaattt ggaccaccct taaacctatc   5880
ttttcaaatt gggccgggtt gtggtttgga ctaccatgaa caacttttcg tcatgtctaa   5940
cttccctttc ggcaaacata tgaaccatat atagaggaga tcggccgtat actagagctg   6000
atgtgtttaa ggtcgttgat tgcacgagaa aaaaaaaatc caaatcgcaa caatagcaaa   6060
tttatctagt tcaaagtgaa aagatatgtt taaaggtagt ccaaagtaaa acttaggggc   6120
tgtttggttc ccagccatac tttaccatta cttgccaaca aaagttgcca caccttgtct   6180
aaggtgaggt gatcaaattg ttagccacaa cttactaagc ctaagggaat cttgccacac   6240
ttttttgagc cattgacacg tgggacttaa tttgttagag ggaaatcttg ccacaactgt   6300
ggctacaacc aaacacctgt caaatttgcc taaccttagg cgtggcaaac tgtggcaaag   6360
tgtggcttac aaccaaacac acccttagat aataaaatgt ggtccaaagc gtaattcact   6420
aaaaaaaaat caacgagacg tgtaccaaac ggagacaaac ggcatcttct cgaaatttcc   6480
caaccgctcg ctcgcccgcc tcgtcttccc ggaaaccgcg gtggtttcag cgtggcggat   6540
tctccaagca gacggagacg tcacggcacg ggactcctcc caccacccaa ccgccataaa   6600
taccagcccc ctcatctcct ctcctcgcat cagctccacc cccgaaaaat ttctccccaa   6660
tctcgcgagg ctctcgtcgt cgaatcgaat cctctcgcgt cctcaagctt ggcatccagg   6720
tacggatccg cgtcccatct ccctcacccc ccgtgttctt cgtgcctgct tctgggtcag   6780
atctgggtgg attcgcggtt gttggatgtg gggggctgtg tttatttgtc ggtggatctg   6840
gttgtctgga tctgcgtttt ctctgtcgta gttagcggat ctgatgaaat gtttagtgtt   6900
cgtgtatact ggtatggtgg atctggtcct aggatgcgtg gaatggatat atgtaggcga   6960
attggaggat ttattttgtg aattttgctg aaatgatagt tctaaacact ggatctgacc   7020
tcgggatgct gttaaatgtg gaaatcatgg tcgatgctgt catgaacatg gtgttcttat   7080
```

-continued

```
ggtagatctg agcaatgtat gtttcaaaat tgtttgtcac atggaaatgc tatggttcta   7140
gatgcaatag aatgatacat gccgagatcc cctctagttg atatgataga tcatgatgtt   7200
ttacagctat gtcatatgaa tatgttcatt tgttaccgat gtatttggat ctacttaaca   7260
tttccaaagc acgccgcgtt ctaattctag atctggtagt catgtttgta cacgtcaccc   7320
acctaataca aatacatatg tctagtgttt ggtgacactg cccgtcagat ctgtttttc    7380
cagatctgtg gaacaaatac tccacgcatg tatggtagtt ttgaaacgat cttgtatctt   7440
ccattgttgt agtaacaact aaataaagta caattgttca attattggga atcgtatttt   7500
ctgtagtgcc gatgtacagc atattcatag atgtctattt aggaactcaa attttaaatt   7560
gaggactagt tatttattgt gggtcagtct tttgaattgt gttatcttgc tgtactggcg   7620
cgccaccatg gccaccgccg ccgccgcgtc taccgcgctc actggcgcca ctaccgctgc   7680
gcccaaggcg aggcgccggg cgcacctcct ggccacccgc cgcgccctcg ccgcgcccat   7740
caggtgctca gcggcgtcac ccgccatgcc gatggctccc ccggccaccc cgctccggcc   7800
gtggggcccc accgatcccc gcaagggcgc cgacatcctc gtcgagtccc tcgagcgctg   7860
cggcgtccgc gacgtcttcg cctaccccgg cggcacgtcc atggagatcc accaggcact   7920
cacccgctcc cccgtcatcg ccaaccacct cttccgccac gagcaagggg aggcctttgc   7980
ggcctccggc tacgcgcgct cctcgggccg cgtcggcgtc tgcatcgcca cctccggccc   8040
cggcgccacc aaccttgtct ccgcgctcgc cgacgcgctg ctcgattccg tccccatggt   8100
cgccatcacg ggacaggtgc cgcgacgcat gattggcacc gacgccttcc aggagacgcc   8160
catcgtcgag gtcacccgct ccatcaccaa gcacaactac ctggtcctcg acgtcgacga   8220
catcccccgc gtcgtgcagg aggctttctt cctcgcctcc tctggtcgac cggggccggt   8280
gcttgtcgac atccccaagg acatccagca gcagatggcg gtgcctgtct gggacaagcc   8340
catgagtctg cctgggtaca ttgcgcgcct tcccaagccc cctgcgactg agttgcttga   8400
gcaggtgctg cgtcttgttg gtgaatcccg gcgccctgtt ctttatgttg gcggtggctg   8460
cgcagcatct ggtgaggagt tgcgacgctt tgtggagctg actggaatcc cggtcacaac   8520
tactcttatg ggcctcggca acttccccag cgacgaccca ctgtctctgc gcatgctagg   8580
tatgcatggc acggtgtatg caaattatgc agtggataag gccgatctgt tgcttgcact   8640
tggtgtgcgg tttgatgatc gtgtgacagg gaagattgag gcttttgcaa gcagggctaa   8700
gattgtgcac gttgatattg atccggctga gattggcaag aacaagcagc cacatgtgtc   8760
catctgtgca gatgttaagc ttgctttgca gggcatgaat gctcttcttg aaggaagcac   8820
atcaaagaag agctttgact ttggctcatg gaacgatgag ttggatcagc agaagaggga   8880
attcccccctt gggtataaaa catctaatga ggagatccag ccacaatatg ctattcaggt   8940
tcttgatgag ctgacgaaag gcgaggccat catcggcaca ggtgttgggc agcaccagat   9000
gtgggcggca cagtactaca cttacaagcg gccaaggcag tggttgtctt cagctggtct   9060
tggggctatg ggatttggtt tgccggctgc tgctggtgct tctgtggcca acccaggtgt   9120
tactgttgtt gacatcgatg gagatggtag ctttctcatg aacgttcagg agctagctat   9180
gatccgaatt gagaacctcc cggtgaaggt ctttgtgcta aacaaccagc acctggggat   9240
ggtggtgcag tgggaggaca ggttctataa ggccaacaga gcgcacacat acttgggaaa   9300
cccagagaat gaaagtgaga tatatccaga tttcgtgacg atcgccaaag ggttcaacat   9360
tccagcggtc cgtgtgacaa agaagaacga agtccgcgca gcgataaaga agatgctcga   9420
gactccaggg ccgtacctct tggatataat cgtcccacac caggagcatg tgttgcctat   9480
```

-continued

```
gatccctaat ggtggggctt tcaaggatat gatcctggat ggtgatggca ggactgtgta   9540
ctagcctgca ggcctaggat cgttcaaaca tttggcaata aagtttctta agattgaatc   9600
ctgttgccgg tcttgcgatg attatcatat aatttctgtt gaattacgtt aagcatgtaa   9660
taattaacat gtaatgcatg acgttattta tgagatgggt ttttatgatt agagtcccgc   9720
aattatacat ttaatacgcg atagaaaaca aaatatagcg cgcaaactag gataaattat   9780
cgcgcgcggt gtcatctatg ttactagatc ggccggccgt ttaaacagcc tgcttttttg   9840
tacaaacttg atttaaatga attcaagctt ttaattaagc atgcgagctc ggcgcgccgg   9900
taccgcgatc gcggatcatg aaccaacggc ctggctgtat ttggtggttg tgtagggaga   9960
tggggagaag aaaagcccga ttctcttcgc tgtgatgggc tggatgcatg cgggggagcg  10020
ggaggcccaa gtacgtgcac ggtgagcggc ccacagggcg agtgtgagcg cgagaggcgg  10080
gaggaacagt ttagtaccac attgcccagc taactcgaac gcgaccaact tataaacccg  10140
cgcgctgtcg cttgtgtgca ttgagtgcta tgctgaggtt ttagagctag aaatagcaag  10200
ttaaaataag gctagtccgt tatcaacttg aaaaagtggc accgagtcgg tgctctgttc  10260
ctcgtgctgg acaagtgtgg tttccagatt ctgcaaccaa gactgcgcag gcattgctgg  10320
acttcaaccg tgaaggatta cctctgttca tcctcgctaa ctggagaggc ttctctggtg  10380
gacaaagaga tctctttgaa ggaattcttc aggctggctc gactattgtt gagaacctta  10440
ggacatacaa tcagcctgcc tttgtctaca ttcccatggc tgcagagcta cgaggagggg  10500
cttgggttgt ggttgatagc aagataaacc cagaccgcat tgagtgctat gctgagagaa  10560
ctgcaaaatc caatgttctg gaaccgcaag ggttaattga gatcaagttc aggtcagagg  10620
aactccagga ttgcatgagt cggcttgacc caacattaat tgatctgaaa gcaaaactcg  10680
aagtagcaaa taaaaatgga agtgctgaca caaaatcgct tcaagaaaat atagaagctc  10740
gaacaaaaca gttgatgcct ctatatactc agattgcgat acggtttgct gaattgcatg  10800
atacatccct cagaatggct gcgaaaggtg tgattaagaa agttgtggac tgggaagaat  10860
cacgatcttt cttttttttg cggccgcccc gggcctgcag gggatcccga tcgggccggc  10920
cgtttaaacc cactttgtac aagaaagctg ggtatttaaa tgaattcaag cttttaatta  10980
atgcagtgca gcgtgacccg gtcgtgcccc tctctagaga taatgagcat tgcatgtcta  11040
agttataaaa aattaccaca tatttttttt gtcacacttg tttgaagtgc agtttatcta  11100
tctttataca tatatttaaa ctttactcta cgaataatat aatctatagt actacaataa  11160
tatcagtgtt ttagagaatc atataaatga acagttagac atggtctaaa ggacaattga  11220
gtattttgac aacaggactc tacagtttta tctttttagt gtgcatgtgt tctccttttt  11280
ttttgcaaat agcttcacct atataatact tcatccattt tattagtaca tccatttagg  11340
gtttagggtt aatggttttt atagactaat ttttttagta catctatttt attctatttt  11400
agcctctaaa ttaagaaaac taaaactcta ttttagtttt tttatttaat agtttagata  11460
taaaatagaa taaaataaag tgactaaaaa ttaaacaaat accctttaag aaattaaaaa  11520
aactaaggaa acatttttct tgtttcgagt agataatgcc agcctgttaa acgccgtcga  11580
cgagtctaac ggacaccaac cagcgaacca gcagcgtcgc gtcgggccaa gcgaagcaga  11640
cggcacggca tctctgtcgc tgcctctgga cccctctcga gagttccgct ccaccgttgg  11700
acttgctccg ctgtcggcat ccagaaattg cgtggcggag cggcagacgt gagccggcac  11760
ggcaggcggc ctcctcctcc tctcacggca ccggcagcta cgggggattc ctttcccacc  11820
```

```
gctccttcgc tttcccttcc tcgcccgccg taataaatag acaccccctc cacaccctct  11880
ttccccaacc tcgtgttgtt cggagcgcac acacacacaa ccagatctcc cccaaatcca  11940
cccgtcggca cctccgcttc aaggtacgcc gctcgtcctc cccccccccc cccctctcta  12000
ccttctctag atcggcgttc cggtccatgg ttagggcccg gtagttctac ttctgttcat  12060
gtttgtgtta gatccgtgtt tgtgttagat ccgtgctgct agcgttcgta cacggatgcg  12120
acctgtacgt cagacacgtt ctgattgcta acttgccagt gtttctcttt ggggaatcct  12180
gggatggctc tagccgttcc gcagacggga tcgatttcat gatttttttt gtttcgttgc  12240
atagggtttg gtttgccctt ttcctttatt tcaatatatg ccgtgcactt gtttgtcggg  12300
tcatcttttc atgctttttt ttgtcttggt tgtgatgatg tggtctggtt gggcggtcgt  12360
tctagatcgg agtagaattc tgtttcaaac tacctggtgg atttattaat tttggatctg  12420
tatgtgtgtg ccatacatat tcatagttac gaattgaaga tgatggatgg aaatatcgat  12480
ctaggatagg tatacatgtt gatgcgggtt ttactgatgc atatacagag atgctttttg  12540
ttcgcttggt tgtgatgatg tggtgtggtt gggcggtcgt tcattcgttc tagatcggag  12600
tagaatactg tttcaaacta cctggtgtat ttattaattt tggaactgta tgtgtgtgtc  12660
atacatcttc atagttacga gtttaagatg gatggaaata tcgatctagg ataggtatac  12720
atgttgatgt gggttttact gatgcatata catgatggca tatgcagcat ctattcatat  12780
gctctaacct tgagtaccta tctattataa taaacaagta tgttttataa ttatttcgat  12840
cttgatatac ttggatgatg gcatatgcag cagctatatg tggatttttt tagccctgcc  12900
ttcatacgct atttatttgc ttggtactgt ttcttttgtc gatgctcacc ctgttgtttg  12960
gtgttacttc tgcagggcgc gccaccatgg ctcctaagaa gaagcggaag gttggtattc  13020
acggggtgcc tgcggctgac aagaagtact ccatcggcct cgacatcggc accaacagcg  13080
tcggctgggc ggtgatcacc gacgagtaca aggtcccgtc caagaagttc aaggtcctgg  13140
gcaacaccga ccgccactcc atcaagaaga acctcatcgg cgccctcctc ttcgactccg  13200
gcgagacggc ggaggcgacc cgcctcaagc gcaccgcccg ccgccgctac acccgccgca  13260
agaaccgcat ctgctacctc caggagatct tctccaacga gatggcgaag gtcgacgact  13320
ccttcttcca ccgcctcgag gagtccttcc tcgtggagga ggacaagaag cacgagcgcc  13380
accccatctt cggcaacatc gtcgacgagg tcgcctacca cgagaagtac cccactatct  13440
accaccttcg taagaagctt gttgactcta ctgataaggc tgatcttcgt ctcatctacc  13500
ttgctctcgc tcacatgatc aagttccgtg gtcacttcct tatcgagggt gaccttaacc  13560
ctgataactc cgacgtggac aagctcttca tccagctcgt ccagacctac aaccagctct  13620
tcgaggagaa ccctatcaac gcttccggtg tcgacgctaa ggcgatcctt tccgctaggc  13680
tctccaagtc caggcgtctc gagaacctca tcgcccagct ccctggtgag aagaagaacg  13740
gtcttttcgg taacctcatc gctctctccc tcggtctgac ccctaacttc aagtccaact  13800
tcgacctcgc tgaggacgct aagcttcagc tctccaagga tacctacgac gatgatctcg  13860
acaacctcct cgctcagatt ggagatcagt acgctgatct cttccttgct gctaagaacc  13920
tctccgatgc tatcctcctt tcggatatcc ttagggttaa cactgagatc actaaggctc  13980
ctctttctgc ttccatgatc aagcgctacg acgagcacca ccaggacctc accctcctca  14040
aggctcttgt tcgtcagcag ctccccgaga agtacaagga gatcttcttc gaccagtcca  14100
agaacggcta cgccggttac attgacggtg gagctagcca ggaggagttc tacaagttca  14160
tcaagccaat ccttgagaag atggatggta ctgaggagct tctcgttaag cttaaccgtg  14220
```

-continued

```
aggacctcct taggaagcag aggactttcg ataacggctc tatccctcac cagatccacc  14280
ttggtgagct tcacgccatc cttcgtaggc aggaggactt ctaccctttc ctcaaggaca  14340
accgtgagaa gatcgagaag atccttactt tccgtattcc ttactacgtt ggtcctcttg  14400
ctcgtggtaa ctcccgtttc gcttggatga ctaggaagtc cgaggagact atcacccctt  14460
ggaacttcga ggaggttgtt gacaagggtg cttccgccca gtccttcatc gagcgcatga  14520
ccaacttcga caagaacctc cccaacgaga aggtcctccc caagcactcc ctcctctacg  14580
agtacttcac ggtctacaac gagctcacca aggtcaagta cgtcaccgag ggtatgcgca  14640
agcctgcctt cctctccggc gagcagaaga aggctatcgt tgacctcctc ttcaagacca  14700
accgcaaggt caccgtcaag cagctcaagg aggactactt caagaagatc gagtgcttcg  14760
actccgtcga gatcagcggc gttgaggacc gtttcaacgc ttctctcggc acctaccacg  14820
atctcctcaa gatcatcaag gacaaggact tcctcgacaa cgaggagaac gaggacatcc  14880
tcgaggacat cgtcctcact cttactctct tcgaggatag ggagatgatc gaggagaggc  14940
tcaagactta cgctcatctc ttcgatgaca aggttatgaa gcagctcaag cgtcgccgtt  15000
acaccggttg gggtaggctc tcccgcaagc tcatcaacgg tatcagggat aagcagagcg  15060
gcaagactat cctcgacttc ctcaagtctg atggtttcgc taacaggaac ttcatgcagc  15120
tcatccacga tgactctctt accttcaagg aggatattca gaaggctcag gtgtccggtc  15180
agggcgactc tctccacgag cacattgcta accttgctgg ttcccctgct atcaagaagg  15240
gcatccttca gactgttaag gttgtcgatg agcttgtcaa ggttatgggt cgtcacaagc  15300
ctgagaacat cgtcatcgag atggctcgtg agaaccagac tacccagaag ggtcagaaga  15360
actcgaggga gcgcatgaag aggattgagg agggtatcaa ggagcttggt tctcagatcc  15420
ttaaggagca ccctgtcgag aacacccagc tccagaacga gaagctctac ctctactacc  15480
tccagaacgg tagggatatg tacgttgacc aggagctcga catcaacagg ctttctgact  15540
acgacgtcga ccacattgtt cctcagtctt tccttaagga tgactccatc gacaacaagg  15600
tcctcacgag gtccgacaag aacaggggta agtcggacaa cgtcccttcc gaggaggttg  15660
tcaagaagat gaagaactac tggaggcagc ttctcaacgc taagctcatt acccagagga  15720
agttcgacaa cctcacgaag gctgagaggg gtggcctttc cgagcttgac aaggctggtt  15780
tcatcaagag gcagcttgtt gagacgaggc agattaccaa gcacgttgct cagatcctcg  15840
attctaggat gaacaccaag tacgacgaga acgacaagct catccgcgag gtcaaggtga  15900
tcaccctcaa gtccaagctc gtctccgact tccgcaagga cttccagttc tacaaggtcc  15960
gcgagatcaa caactaccac cacgctcacg atgcttacct taacgctgtc gttggcaccg  16020
ctcttatcaa gaagtaccct aagcttgagt ccgagttcgt ctacggtgac tacaaggtct  16080
acgacgttcg taagatgatc gccaagtccg agcaggagat cggcaaggcc accgccaagt  16140
acttcttcta ctccaacatc atgaacttct tcaagaccga gatcaccctc gccaacggcg  16200
agatccgcaa gcgccctctt atcgagacga acggtgagac tggtgagatc gtttgggaca  16260
agggtcgcga cttcgctact gttcgcaagg tcctttctat gcctcaggtt aacatcgtca  16320
agaagaccga ggtccagacc ggtggcttct ccaaggagtc tatccttcca aagagaaact  16380
cggacaagct catcgctagg aagaaggatt gggaccctaa gaagtacggt ggtttcgact  16440
cccctactgt cgcctactcc gtcctcgtgg tcgccaaggt ggagaagggt aagtcgaaga  16500
agctcaagtc cgtcaaggag ctcctcggca tcaccatcat ggagcgctcc tccttcgaga  16560
```

agaacccgat cgacttcctc gaggccaagg gctacaagga ggtcaagaag gacctcatca 16620
tcaagctccc caagtactct cttttcgagc tcgagaacgg tcgtaagagg atgctggctt 16680
ccgctggtga gctccagaag ggtaacgagc ttgctcttcc ttccaagtac gtgaacttcc 16740
tctacctcgc ctcccactac gagaagctca agggttcccc tgaggataac gagcagaagc 16800
agctcttcgt ggagcagcac aagcactacc tcgacgagat catcgagcag atctccgagt 16860
tctccaagcg cgtcatcctc gctgacgcta acctcgacaa ggtcctctcc gcctacaaca 16920
agcaccgcga caagcccatc cgcgagcagg ccgagaacat catccacctc ttcacgctca 16980
cgaacctcgg cgcccctgct gctttcaagt acttcgacac caccatcgac aggaagcgtt 17040
acacgtccac caaggaggtt ctcgacgcta ctctcatcca ccagtccatc accggtcttt 17100
acgagactcg tatcgacctt tcccagcttg gtggtgataa gcgtcctgct gccaccaaaa 17160
aggccggaca ggctaagaaa aagaagtagc ctgcaggtcc tgctttaatg agatatgcga 17220
gacgcctatg atcgcatgat atttgctttc aattctgttg tgcacgttgt aaaaaacctg 17280
agcatgtgta gctcagatcc ttaccgccgg tttcggttca ttctaatgaa tatatcaccc 17340
gttactatcg tatttttatg aataatattc tccgttcaat ttactgattg taccctacta 17400
cttatatgta caatattaaa atgaaaacaa tatattgtgc tgaataggtt tatagcgaca 17460
tctatgatag agcgccacaa taacaaacaa ttgcgtttta ttattacaaa tccaatttta 17520
aaaaaagcgg cagaaccggt caaacctaaa agactgatta cataaatctt attcaaattt 17580
caaaagtgcc ccaggggcta gtatctacga cacaccgagc ggcgaactaa taacgctcac 17640
tgaagggaac tccggttccc cgccggcgcg catgggtgag attccttgaa gttgagtatt 17700
ggccgtccgc tctaccgaaa gttacgggca ccattcaacc cggtccagca cggcggccgg 17760
gtaaccgact tgctgccccg agaattatgc agcatttttt tggtgtatgt gggccccaaa 17820
tgaagtgcag gtcaaacctt gacagtgacg acaaatcgtt gggcgggtcc agggcgaatt 17880
ttgcgacaac atgtcgaggc tcagcaggcc ggccgtttaa accaacttta 17930

<210> SEQ ID NO 67
<211> LENGTH: 3734
<212> TYPE: DNA
<213> ORGANISM: Artificial Sequence
<220> FEATURE:
<223> OTHER INFORMATION: Vector CC019

<400> SEQUENCE: 67
cgcggatcat gaaccaacgg cctggctgta tttggtggtt gtgtagggag atggggagaa 60
gaaaagcccg attctcttcg ctgtgatggg ctggatgcat gcgggggagc gggaggccca 120
agtacgtgca cggtgagcgg cccacagggc gagtgtgagc gcgagaggcg ggaggaacag 180
tttagtacca cattgcccag ctaactcgaa cgcgaccaac ttataaaccc gcgcgctgtc 240
gcttgtgtga ctgcaaaagg caatgttcgt tttagagcta gaaatagcaa gttaaaataa 300
ggctagtccg ttatcaactt gaaaaagtgg caccgagtcg gtgctctgtt cctcgtgctg 360
gacaagtgtg gtttccagat tctgcaacca agactgcgca ggcattgctg gacttcaacc 420
gtgaaggatt acctctgttc atcctcgcta actggagagg cttctctggt ggacaaagag 480
atctctttga aggaattctt caggctggct cgactattgt tgagaacctt aggacataca 540
atcagcctgc ctttgtctac attcccatgg ctgcagagct acgaggaggg gcttgggttg 600
tggttgatag caagataaac ccagaccgca ttgagtgcta tgctgagagg actgcaaaat 660
ccaatgttct cgaaccgcaa gggttaattg agatcaagtt caggtcagag gaactccagg 720

-continued

```
attgcatgag tcggcttgac ccaacattaa ttgatctgaa agcaaaactc gaagtagcaa    780
ataaaaatgg aagtgctgac acaaaatcgc ttcaagaaaa tatagaagct cgaacaaaac    840
agttgatgcc tctatatact cagattgcga tacggtttgc tgaattgcat gatacatccc    900
tcagaatggc tgcgaaaggt gtgattaaga aagttgtgga ctgggaagaa tcacgatctt    960
tcttttttt gcggccgccc cggcctgca ggggatcccg atcgggccgg ccgtttaaac    1020
ccactttgta caagaaagtt gaacgagaaa cgtaaaatga tataaatatc aatatattaa   1080
attagatttt gcataaaaaa cagactacat aatactgtaa aacacaacat atgcagtcac   1140
tatgaaccaa ctacttagat ggtattagtg acctgtactg ggcctcatgg gccttccgct   1200
cactgcccgc tttccagtcg ggaaacctgt cgtgccagct gcattaacat ggtcatagct   1260
gtttccttgc gtattgggcg ctctccgctt cctcgctcac tgactcgctg cgctcggtcg   1320
ttcgggtaaa gcctggggtg cctaatgagc aaaaggccag caaaaggcca ggaaccgtaa   1380
aaaggccgcg ttgctggcgt ttttccatag gctccgcccc cctgacgagc atcacaaaaa   1440
tcgacgctca agtcagaggt ggcgaaaccc gacaggacta taaagatacc aggcgtttcc   1500
ccctggaagc tccctcgtgc gctctcctgt tccgaccctg ccgcttaccg gatacctgtc   1560
cgcctttctc ccttcgggaa gcgtggcgct ttctcatagc tcacgctgta ggtatctcag   1620
ttcggtgtag gtcgttcgct ccaagctggg ctgtgtgcac gaaccccccg ttcagcccga   1680
ccgctgcgcc ttatccggta actatcgtct tgagtccaac ccggtaagac acgacttatc   1740
gccactggca gcagccactg gtaacaggat tagcagagcg aggtatgtag gcggtgctac   1800
agagttcttg aagtggtggc ctaactacgg ctacactaga agaacagtat ttggtatctg   1860
cgctctgctg aagccagtta ccttcggaaa aagagttggt agctcttgat ccggcaaaca   1920
aaccaccgct ggtagcggtg gtttttttgt ttgcaagcag cagattacgc gcagaaaaaa   1980
aggatctcaa gaagatcctt tgatcttttc tacggggtct gacgctcagt ggaacgaaaa   2040
ctcacgttaa gggattttgg tcatgagatt atcaaaaagg atcttcacct agatcctttt   2100
aaattaaaaa tgaagtttta aatcaatcta aagtatatat gagtaaactt ggtctgacag   2160
ttaccaatgc ttaatcagtg aggcacctat ctcagcgatc tgtctatttc gttcatccat   2220
agttgcctga ctccccgtcg tgtagataac tacgatacgg gagggcttac catctggccc   2280
cagtgctgca atgataccgc gagaaccacg ctcaccggct ccagatttat cagcaataaa   2340
ccagccagcc ggaagggccg agcgcagaag tggtcctgca actttatccg cctccatcca   2400
gtctattaat tgttgccggg aagctagagt aagtagttcg ccagttaata gtttgcgcaa   2460
cgttgttgcc attgctacag gcatcgtggt gtcacgctcg tcgtttggta tggcttcatt   2520
cagctccggt tcccaacgat caaggcgagt tacatgatcc cccatgttgt gcaaaaaagc   2580
ggttagctcc ttcggtcctc cgatcgttgt cagaagtaag ttggccgcag tgttatcact   2640
catggttatg gcagcactgc ataattctct tactgtcatg ccatccgtaa gatgcttttc   2700
tgtgactggt gagtactcaa ccaagtcatt ctgagaatag tgtatgcggc gaccgagttg   2760
ctcttgcccg gcgtcaatac gggataatac cgcgccacat agcagaactt taaaagtgct   2820
catcattgga aaacgttctt cggggcgaaa actctcaagg atcttaccgc tgttgagatc   2880
cagttcgatg taacccactc gtgcacccaa ctgatcttca gcatctttta ctttcaccag   2940
cgtttctggg tgagcaaaaa caggaaggca aaatgccgca aaaaagggaa taagggcgac   3000
acggaaatgt tgaatactca tactcttcct ttttcaatat tattgaagca tttatcaggg   3060
```

-continued

```
ttattgtctc atgagcggat acatatttga atgtatttag aaaaataaac aaataggggt   3120

tccgcgcaca tttccccgaa aagtgccacc taaattgtaa gcgttaatat tttgttaaaa   3180

ttcgcgttaa atttttgtta aatcagctca ttttttaacc aataggccga aatcggcaaa   3240

atcccttata aatcaaaaga atagaccgag atagggttga gtggccgcta cagggcgctc   3300

ccattcgcca ttcaggctgc gcaactgttg ggaagggcgt ttcggtgcgg gcctcttcgc   3360

tattacgcca gctggcgaaa gggggatgtg ctgcaaggcg attaagttgg gtaacgccag   3420

ggttttccca gtcacgacgt tgtaaaacga cggccagtga gcgcgacgta atacgactca   3480

ctatagggcg aattggcgga aggccgtcaa ggccgcatta caggtcacta ataccatcta   3540

agtagttggt tcatagtgac tgcatatgtt gtgttttaca gtattatgta gtctgttttt   3600

tatgcaaaat ctaatttaat atattgatat ttatatcatt ttacgtttct cgttcaactt   3660

ttttgtacaa acttgattta aatgaattca agcttttaat taagcatgcg agctcggcgc   3720

gccggtaccg cgat                                                      3734
```

<210> SEQ ID NO 68
<211> LENGTH: 17930
<212> TYPE: DNA
<213> ORGANISM: Artificial Sequence
<220> FEATURE:
<223> OTHER INFORMATION: Vector RLW138

<400> SEQUENCE: 68

```
ttatacatag ttgataattc actgggccgg ccgtttaaac ttagttacta atcagtgatc     60

agattgtcgt ttcccgcctt cactttaaac tatcagtgtt tgacaggata tattggcggg    120

taaacctaag agaaaagagc gtttattaga ataatcggat atttaaaagg gcgtgaaaag    180

gtttatccgt tcgtccattt gtatgtcaat attggggggg ggggaaagcc acgttgtgtc    240

tcaaaatctc tgatgttaca ttgcacaaga taaaaatata tcatcatgaa caataaaact    300

gtctgcttac ataaacagta atacaagggg tgttcgccac catgagccat atccagcgtg    360

aaacctcgtg ctcccgcccg cgcctcaatt ccaatatgga tgccgacctt tatggctaca    420

agtgggcgcg cgacaacgtc ggccagtcgg gcgcgaccat ttatcggctt tatggcaaac    480

ccgatgcccc ggaactgttc ctgaagcacg gcaaaggcag cgtcgcaaac gatgtcaccg    540

atgagatggt ccgcctgaac tggcttaccg agttcatgcc gctgccgacg attaagcatt    600

tcatccgtac ccccggacgat gcctggctct tgaccacggc cattccgggc aaaacggcct    660

ttcaggtcct tgaagagtac ccggactccg gtgagaatat cgtggacgcc ctcgcggtct    720

tcctccgccg tttgcatagc atccccgtgt gcaactgccc cttcaactcg gaccgggttt    780

tccgcctggc acaggcccag tcgcgcatga ataacggcct cgttgacgcg agcgatttcg    840

acgatgaacg gaatggctgg ccggtggaac aggtttggaa ggaaatgcac aaactgcttc    900

cgttctcgcc ggattcggtg gtcacgcatg gtgatttttc cctggataat ctgatctttg    960

acgagggcaa gctgatcggc tgcatcgacg tgggtcgcgt cggtatcgcc gaccgctatc   1020

aggacctggc gatcttgtgg aattgcctcg gcgagttctc gccctcgctc cagaagcgcc   1080

tgttccagaa gtacggcatc gacaacccgg atatgaacaa gctccagttc cacctcatgc   1140

tggacgaatt tttttgaaca gaattggtta attggttgta acactggcag agcattacgc   1200

tgacttgacg ggacggcggc tttgttgaat aaatcgaact tttgctgagt tgaaggatcg   1260

atgagttgaa ggaccccgta gaaaagatca aaggatcttc ttgagatcct ttttttctgc   1320

gcgtaatctg ctgcttgcaa acaaaaaaac caccgctacc agcggtggtt tgtttgccgg   1380
```

-continued atcaagagct accaactctt tttccgaagg taactggctt cagcagagcg cagataccaa 1440
atactgtcct tctagtgtag ccgtagttag gccaccactt caagaactct gtagcaccgc 1500
ctacatacct cgctctgcta atcctgttac cagtggctgc tgccagtggc gataagtcgt 1560
gtcttaccgg gttggactca agacgatagt taccggataa ggcgcagcgg tcgggctgaa 1620
cggggggttc gtgcacacag cccagcttgg agcgaacgac ctacaccgaa ctgagatacc 1680
tacagcgtga gctatgagaa agcgccacgc ttcccgaagg gagaaaggcg gacaggtatc 1740
cggtaagcgg cagggtcgga acaggagagc gcacgaggga gcttccaggg ggaaacgcct 1800
ggtatcttta tagtcctgtc gggtttcgcc acctctgact tgagcgtcga tttttgtgat 1860
gctcgtcagg ggggcggagc ctatggaaaa acgccagcaa cgcggccttt ttacggttcc 1920
tggccttttg ctggcctttt gctcacatgt tctttcctgc gttatcccct gattctgtgg 1980
ataaccgtat taccgccttt gagtgagctg ataccgctcg ccgcagccga acgaccgagc 2040
gcagcgagtc agtgagcgag gaagcggaag agcgcctgat gcggtatttt ctccttacgc 2100
atctgtgcgg tatttcacac cgcataggcc gcgataggcc gacgcgaagc ggcggggcgt 2160
agggagcgca gcgaccgaag ggtaggcgct ttttgcagct cttcggctgt gcgctggcca 2220
gacagttatg cacaggccag gcgggtttta agagttttaa taagttttaa agagttttag 2280
gcggaaaaat cgcctttttt ctcttttata tcagtcactt acatgtgtga ccggttccca 2340
atgtacggct ttgggttccc aatgtacggg ttccggttcc caatgtacgg ctttgggttc 2400
ccaatgtacg tgctatccac aggaaagaga ccttttcgac ctttttcccc tgctagggca 2460
atttgcccta gcatctgctc cgtacattag gaaccggcgg atgcttcgcc ctcgatcagg 2520
ttgcggtagc gcatgactag gatcgggcca gcctgccccg cctcctcctt caaatcgtac 2580
tccggcaggt catttgaccc gatcagcttg cgcacggtga aacagaactt cttgaactct 2640
ccggcgctgc cactgcgttc gtagatcgtc ttgaacaacc atctggcttc tgccttgcct 2700
gcggcgcggc gtgccaggcg gtagagaaaa cggccgatgc cggggtcgat caaaaagtaa 2760
tcggggtgaa ccgtcagcac gtccgggttc ttgccttctg tgatctcgcg gtacatccaa 2820
tcagcaagct cgatctcgat gtactccggc cgcccggttt cgctctttac gatcttgtag 2880
cggctaatca aggcttcacc ctcggatacc gtcaccaggc ggccgttctt ggccttcttg 2940
gtacgctgca tggcaacgtg cgtggtgttt aaccgaatgc aggtttctac caggtcgtct 3000
ttctgctttc cgccatcggc tcgccggcag aacttgagta cgtccgcaac gtgtggacgg 3060
aacacgcggc cgggcttgtc tcccttccct tcccggtatc ggttcatgga ttcggttaga 3120
tgggaaaccg ccatcagtac caggtcgtaa tcccacacac tggccatgcc ggcggggcct 3180
gcggaaacct ctacgtgccc gtctggaagc tcgtagcgga tcacctcgcc agctcgtcgg 3240
tcacgcttcg acagacggaa aacggccacg tccatgatgc tgcgactatc gcgggtgccc 3300
acgtcataga gcatcggaac gaaaaaatct ggttgctcgt cgcccttggg cggcttccta 3360
atcgacggcg caccggctgc cggcggttgc cgggattctt tgcggattcg atcagcggcc 3420
ccttgccacg attcaccggg gcgtgcttct gcctcgatgc gttgccgctg ggcggcctgc 3480
gcggccttca acttctccac caggtcatca cccagcgccg cgccgatttg taccgggccg 3540
gatggtttgc gaccgctcac gccgattcct cgggcttggg ggttccagtg ccattgcagg 3600
gccggcagac aacccagccg cttacgcctg gccaaccgcc cgttcctcca cacatggggc 3660
attccacggc gtcggtgcct ggttgttctt gattttccat gccgcctcct ttagccgcta 3720

-continued

```
aaattcatct actcatttat tcatttgctc atttactctg gtagctgcgc gatgtattca   3780
gatagcagct cggtaatggt cttgccttgg cgtaccgcgt acatcttcag cttggtgtga   3840
tcctccgccg gcaactgaaa gttgacccgc ttcatggctg gcgtgtctgc caggctggcc   3900
aacgttgcag ccttgctgct gcgtgcgctc ggacggccgg cacttagcgt gtttgtgctt   3960
ttgctcattt tctctttacc tcattaactc aaatgagttt tgatttaatt tcagcggcca   4020
gcgcctggac ctcgcgggca gcgtcgccct cgggttctga ttcaagaacg gttgtgccgg   4080
cggcggcagt gcctgggtag ctcacgcgct gcgtgatacg ggactcaaga atgggcagct   4140
cgtacccggc cagcgcctcg gcaacctcac cgccgatgcg cgtgcctttg atcgcccgcg   4200
acacgacaaa ggccgcttgt agccttccat ccgtgacctc aatgcgctgc ttaaccagct   4260
ccaccaggtc ggcggtggcc caaatgtcgt aagggcttgg ctgcaccgga atcagcacga   4320
agtcggctgc cttgatcgcg gacacagcca agtccgccgc ctggggcgct ccgtcgatca   4380
ctacgaagtc gcgccggccg atggccttca cgtcgcggtc aatcgtcggg cggtcgatgc   4440
cgacaacggt tagcggttga tcttcccgca cggccgccca atcgcgggca ctgccctggg   4500
gatcggaatc gactaacaga acatcggccc cggcgagttg cagggcgcgg gctagatggg   4560
ttgcgatggt cgtcttgcct gacccgcctt tctggttaag tacagcgata accttcatgc   4620
gttccccttg cgtatttgtt tatttactca tcgcatcata tacgcagcga ccgcatgacg   4680
caagctgttt tactcaaata cacatcacct ttttagatga tcagtgattt tgtgccgagc   4740
tgccggtcgg ggagctgttg gctggctggt ggcaggatat attgtggtgt aaacaaattg   4800
acgcttagac aacttaataa cacattgcgg acgtctttaa tgtactgaat ttagttactg   4860
atcactgatt aagtactgat aaatttaatt aacagatctc aactttgtat agaaaagttg   4920
atttaaatga attcaagctt ttaattaact tagccactgc aacaagttct tgaaccttag   4980
cacaatcata ttgtgcatgc acttgtttat tgcaaagaat ggtgcgtagg gaacacgcat   5040
gatttttgaa ttgctggcac ataattttat cattagaaac tggaatgcaa catgtaccct   5100
ttgtcatggt ttctttccga gacattgcac tgttttttt aatcctatca ttatcataat   5160
gccaagaact ggtcaccaac cagcattttg catcatggtt agttgagctg tccccatgta   5220
tcaataggtg cattgtattg gtccaaaata taaatgcagt ggatgcaacc tatctcatgg   5280
ccgtcaacaa aagaaatcaa aagggaaatg caccatctta tatctccagt ttatatgaac   5340
agattggata agatcataag atcaagtggt ttatattatt ttgaggaata taacatggat   5400
tcatcctaat cactcgtcta ggcagtatgt gtattcatga tggatatggt actatactac   5460
ggagtttttt cttcacaaaa taacctgtta ttttgacctc caaccaaaca cgaattatac   5520
caaaaattgg gttatttcat ctatagtaca actctattat aaacatgcag taaattatcc   5580
tacacatata ccaaaattca agtgtaataa tcctaataca cagacttaaa aaacaaacta   5640
tttcctttt aagaaaagga aaaccatttt tttaacggaa ggaaaacaaa ttcgggtcaa   5700
ggcggaagcc agcgcgccac cccacgtcag cgaatacgga ggcgcggggt tgacggcgtc   5760
acccggtcct aacggcgacc aacaaaccag ccagaagaaa ttacagtaaa aaaaagtaaa   5820
ttgcactttg atccaccttt tattacccaa gtttcaattt ggaccaccct taaacctatc   5880
ttttcaaatt gggccgggtt gtggtttgga ctaccatgaa caacttttcg tcatgtctaa   5940
cttccctttc ggcaaacata tgaaccatat atagaggaga tcggccgtat actagagctg   6000
atgtgtttaa ggtcgttgat tgcacgagaa aaaaaaaatc caaatcgcaa caatagcaaa   6060
tttatctagt tcaaagtgaa aagatatgtt taaaggtagt ccaaagtaaa acttaggggc   6120
```

-continued

```
tgtttggttc ccagccatac tttaccatta cttgccaaca aaagttgcca caccttgtct   6180
aaggtgaggt gatcaaattg ttagccacaa cttactaagc ctaagggaat cttgccacac   6240
ttttttgagc cattgacacg tgggacttaa tttgttagag ggaaatcttg ccacaactgt   6300
ggctacaacc aaacacctgt caaatttgcc taaccttagg cgtggcaaac tgtggcaaag   6360
tgtggcttac aaccaaacac acccttagat aataaaatgt ggtccaaagc gtaattcact   6420
aaaaaaaaat caacgagacg tgtaccaaac ggagacaaac ggcatcttct cgaaatttcc   6480
caaccgctcg ctcgcccgcc tcgtcttccc ggaaaccgcg gtggtttcag cgtggcggat   6540
tctccaagca gacggagacg tcacggcacg ggactcctcc caccacccaa ccgccataaa   6600
taccagcccc ctcatctcct ctcctcgcat cagctccacc cccgaaaaat ttctccccaa   6660
tctcgcgagg ctctcgtcgt cgaatcgaat cctctcgcgt cctcaagctt ggcatccagg   6720
tacggatccg cgtcccatct ccctcacccc ccgtgttctt cgtgcctgct tctgggtcag   6780
atctgggtgg attcgcggtt gttggatgtg gggggctgtg tttatttgtc ggtggatctg   6840
gttgtctgga tctgcgtttt ctctgtcgta gttagcggat ctgatgaaat gtttagtgtt   6900
cgtgtatact ggtatggtgg atctggtcct aggatgcgtg gaatggatat atgtaggcga   6960
attggaggat ttattttgtg aattttgctg aaatgatagt tctaaacact ggatctgacc   7020
tcgggatgct gttaaatgtg gaaatcatgg tcgatgctgt catgaacatg gtgttcttat   7080
ggtagatctg agcaatgtat gtttcaaaat tgtttgtcac atggaaatgc tatggttcta   7140
gatgcaatag aatgatacat gccgagatcc cctctagttg atatgataga tcatgatgtt   7200
ttacagctat gtcatatgaa tatgttcatt tgttaccgat gtatttggat ctacttaaca   7260
tttccaaagc acgccgcgtt ctaattctag atctggtagt catgtttgta cacgtcaccc   7320
acctaataca aatacatatg tctagtgttt ggtgacactg cccgtcagat ctgttttttc   7380
cagatctgtg gaacaaatac tccacgcatg tatggtagtt ttgaaacgat cttgtatctt   7440
ccattgttgt agtaacaact aaataaagta caattgttca attattggga atcgtatttt   7500
ctgtagtgcc gatgtacagc atattcatag atgtctattt aggaactcaa attttaaatt   7560
gaggactagt tatttattgt gggtcagtct tttgaattgt gttatcttgc tgtactggcg   7620
cgccaccatg gccaccgccg ccgccgcgtc taccgcgctc actggcgcca ctaccgctgc   7680
gcccaaggcg aggcgccggg cgcacctcct ggccacccgc cgcgccctcg ccgcgcccat   7740
caggtgctca gcggcgtcac ccgccatgcc gatggctccc ccggccaccc cgctccggcc   7800
gtggggcccc accgatcccc gcaagggcgc cgacatcctc gtcgagtccc tcgagcgctg   7860
cggcgtccgc gacgtcttcg cctaccccgg cggcacgtcc atggagatcc accaggcact   7920
cacccgctcc cccgtcatcg ccaaccacct cttccgccac gagcaagggg aggcctttgc   7980
ggcctccggc tacgcgcgct cctcgggccg cgtcggcgtc tgcatcgcca cctccggccc   8040
cggcgccacc aaccttgtct ccgcgctcgc cgacgcgctg ctcgattccg tccccatggt   8100
cgccatcacg ggacaggtgc cgcgacgcat gattggcacc gacgccttcc aggagacgcc   8160
catcgtcgag gtcacccgct ccatcaccaa gcacaactac ctggtcctcg acgtcgacga   8220
catcccccgc gtcgtgcagg aggctttctt cctcgcctcc tctggtcgac cggggccggt   8280
gcttgtcgac atccccaagg acatccagca gcagatggcg gtgcctgtct gggacaagcc   8340
catgagtctg cctgggtaca ttgcgcgcct tcccaagccc cctgcgactg agttgcttga   8400
gcaggtgctg cgtcttgttg gtgaatcccg gcgccctgtt ctttatgttg gcggtggctg   8460
```

-continued

```
cgcagcatct ggtgaggagt tgcgacgctt tgtggagctg actggaatcc cggtcacaac   8520
tactcttatg ggcctcggca acttccccag cgacgaccca ctgtctctgc gcatgctagg   8580
tatgcatggc acggtgtatg caaattatgc agtggataag gccgatctgt tgcttgcact   8640
tggtgtgcgg tttgatgatc gtgtgacagg gaagattgag gcttttgcaa gcagggctaa   8700
gattgtgcac gttgatattg atccggctga gattggcaag aacaagcagc cacatgtgtc   8760
catctgtgca gatgttaagc ttgctttgca gggcatgaat gctcttcttg aaggaagcac   8820
atcaaagaag agctttgact ttggctcatg gaacgatgag ttggatcagc agaagaggga   8880
attcccctt gggtataaaa catctaatga ggagatccag ccacaatatg ctattcaggt   8940
tcttgatgag ctgacgaaag gcgaggccat catcggcaca ggtgttgggc agcaccagat   9000
gtgggcggca cagtactaca cttacaagcg gccaaggcag tggttgtctt cagctggtct   9060
tggggctatg ggatttggtt tgccggctgc tgctggtgct tctgtggcca acccaggtgt   9120
tactgttgtt gacatcgatg gagatggtag ctttctcatg aacgttcagg agctagctat   9180
gatccgaatt gagaacctcc cggtgaaggt ctttgtgcta aacaaccagc acctggggat   9240
ggtggtgcag tgggaggaca ggttctataa ggccaacaga gcgcacacat acttgggaaa   9300
cccagagaat gaaagtgaga tatatccaga tttcgtgacg atcgccaaag ggttcaacat   9360
tccagcggtc cgtgtgacaa agaagaacga agtccgcgca gcgataaaga agatgctcga   9420
gactccaggg ccgtacctct tggatataat cgtcccacac caggagcatg tgttgcctat   9480
gatccctaat ggtggggctt tcaaggatat gatcctggat ggtgatggca ggactgtgta   9540
ctagcctgca ggcctaggat cgttcaaaca tttggcaata aagtttctta agattgaatc   9600
ctgttgccgg tcttgcgatg attatcatat aatttctgtt gaattacgtt aagcatgtaa   9660
taattaacat gtaatgcatg acgttattta tgagatgggt ttttatgatt agagtcccgc   9720
aattatacat ttaatacgcg atagaaaaca aaatatagcg cgcaaactag gataaattat   9780
cgcgcgcggt gtcatctatg ttactagatc ggccggccgt ttaaacagcc tgcttttttg   9840
tacaaacttg atttaaatga attcaagctt ttaattaagc atgcgagctc ggcgcgccgg   9900
taccgcgatc gcggatcatg aaccaacggc ctggctgtat ttggtggttg tgtagggaga   9960
tggggagaag aaaagcccga ttctcttcgc tgtgatgggc tggatgcatg cgggggagcg  10020
ggaggcccaa gtacgtgcac ggtgagcggc ccacagggcg agtgtgagcg cgagaggcgg  10080
gaggaacagt ttagtaccac attgcccagc taactcgaac gcgaccaact tataaacccg  10140
cgcgctgtcg cttgtgtgac tgcaaaaggc aatgttcgtt ttagagctag aaatagcaag  10200
ttaaaataag gctagtccgt tatcaacttg aaaaagtggc accgagtcgg tgctctgttc  10260
ctcgtgctgg acaagtgtgg tttccagatt ctgcaaccaa gactgcgcag gcattgctgg  10320
acttcaaccg tgaaggatta cctctgttca tcctcgctaa ctggagaggc ttctctggtg  10380
gacaaagaga tctctttgaa ggaattcttc aggctggctc gactattgtt gagaacctta  10440
ggacatacaa tcagcctgcc tttgtctaca ttcccatggc tgcagagcta cgaggagggg  10500
cttgggttgt ggttgatagc aagataaacc cagaccgcat tgagtgctat gctgagagga  10560
ctgcaaaatc caatgttctc gaaccgcaag ggttaattga gatcaagttc aggtcagagg  10620
aactccagga ttgcatgagt cggcttgacc caacattaat tgatctgaaa gcaaaactcg  10680
aagtagcaaa taaaaatgga agtgctgaca caaaatcgct tcaagaaaat atagaagctc  10740
gaacaaaaca gttgatgcct ctatatactc agattgcgat acggtttgct gaattgcatg  10800
atacatccct cagaatggct gcgaaaggtg tgattaagaa agttgtggac tgggaagaat  10860
```

cacgatcttt ctttttttg cggccgcccc gggcctgcag gggatcccga tcgggccggc 10920
cgtttaaacc cactttgtac aagaaagctg ggtatttaaa tgaattcaag cttttaatta 10980
atgcagtgca gcgtgacccg gtcgtgcccc tctctagaga taatgagcat tgcatgtcta 11040
agttataaaa aattaccaca tatttttttt gtcacacttg tttgaagtgc agtttatcta 11100
tctttataca tatatttaaa ctttactcta cgaataatat aatctatagt actacaataa 11160
tatcagtgtt ttagagaatc atataaatga acagttagac atggtctaaa ggacaattga 11220
gtattttgac aacaggactc tacagtttta tctttttagt gtgcatgtgt tctccttttt 11280
ttttgcaaat agcttcacct atataatact tcatccattt tattagtaca tccatttagg 11340
gtttagggtt aatggttttt atagactaat ttttttagta catctatttt attctatttt 11400
agcctctaaa ttaagaaaac taaaactcta ttttagtttt tttatttaat agtttagata 11460
taaaatagaa taaaataaag tgactaaaaa ttaaacaaat accctttaag aaattaaaaa 11520
aactaaggaa acatttttct tgtttcgagt agataatgcc agcctgttaa acgccgtcga 11580
cgagtctaac ggacaccaac cagcgaacca gcagcgtcgc gtcgggccaa gcgaagcaga 11640
cggcacggca tctctgtcgc tgcctctgga cccctctcga gagttccgct ccaccgttgg 11700
acttgctccg ctgtcggcat ccagaaattg cgtggcggag cggcagacgt gagccggcac 11760
ggcaggcggc ctcctcctcc tctcacggca ccggcagcta cgggggattc ctttcccacc 11820
gctccttcgc tttcccttcc tcgcccgccg taataaatag acacccccctc cacaccctct 11880 ttccccaacc tcgtgttgtt cggagcgcac acacacacaa ccagatctcc cccaaatcca 11940
cccgtcggca cctccgcttc aaggtacgcc gctcgtcctc cccccccccc cccctctcta 12000
ccttctctag atcggcgttc cggtccatgg ttagggcccg gtagttctac ttctgttcat 12060
gtttgtgtta gatccgtgtt tgtgttagat ccgtgctgct agcgttcgta cacggatgcg 12120
acctgtacgt cagacacgtt ctgattgcta acttgccagt gtttctcttt ggggaatcct 12180
gggatggctc tagccgttcc gcagacggga tcgatttcat gatttttttt gtttcgttgc 12240
atagggtttg gtttgccctt ttcctttatt tcaatatatg ccgtgcactt gtttgtcggg 12300
tcatcttttc atgctttttt ttgtcttggt tgtgatgatg tggtctggtt gggcggtcgt 12360
tctagatcgg agtagaattc tgtttcaaac tacctggtgg atttattaat tttggatctg 12420
tatgtgtgtg ccatacatat tcatagttac gaattgaaga tgatggatgg aaatatcgat 12480
ctaggatagg tatacatgtt gatgcgggtt ttactgatgc atatacagag atgctttttg 12540
ttcgcttggt tgtgatgatg tggtgtggtt gggcggtcgt tcattcgttc tagatcggag 12600
tagaatactg tttcaaacta cctggtgtat ttattaattt tggaactgta tgtgtgtgtc 12660
atacatcttc atagttacga gtttaagatg gatggaaata tcgatctagg ataggtatac 12720
atgttgatgt gggttttact gatgcatata catgatggca tatgcagcat ctattcatat 12780
gctctaacct tgagtaccta tctattataa taaacaagta tgttttataa ttatttcgat 12840
cttgatatac ttggatgatg gcatatgcag cagctatatg tggatttttt tagccctgcc 12900
ttcatacgct atttatttgc ttggtactgt ttcttttgtc gatgctcacc ctgttgtttg 12960
gtgttacttc tgcagggcgc gccaccatgg ctcctaagaa gaagcggaag gttggtattc 13020
acggggtgcc tgcggctgac aagaagtact ccatcggcct cgacatcggc accaacagcg 13080
tcggctgggc ggtgatcacc gacgagtaca aggtcccgtc caagaagttc aaggtcctgg 13140
gcaacaccga ccgccactcc atcaagaaga acctcatcgg cgccctcctc ttcgactccg 13200

-continued

```
gcgagacggc ggaggcgacc cgcctcaagc gcaccgcccg ccgccgctac acccgccgca  13260
agaaccgcat ctgctacctc caggagatct tctccaacga gatggcgaag gtcgacgact  13320
ccttcttcca ccgcctcgag gagtccttcc tcgtggagga ggacaagaag cacgagcgcc  13380
accccatctt cggcaacatc gtcgacgagg tcgcctacca cgagaagtac cccactatct  13440
accaccttcg taagaagctt gttgactcta ctgataaggc tgatcttcgt ctcatctacc  13500
ttgctctcgc tcacatgatc aagttccgtg gtcacttcct tatcgagggt gaccttaacc  13560
ctgataactc cgacgtggac aagctcttca tccagctcgt ccagacctac aaccagctct  13620
tcgaggagaa ccctatcaac gcttccggtg tcgacgctaa ggcgatcctt tccgctaggc  13680
tctccaagtc caggcgtctc gagaacctca tcgcccagct ccctggtgag aagaagaacg  13740
gtcttttcgg taacctcatc gctctctccc tcggtctgac ccctaacttc aagtccaact  13800
tcgacctcgc tgaggacgct aagcttcagc tctccaagga tacctacgac gatgatctcg  13860
acaacctcct cgctcagatt ggagatcagt acgctgatct cttccttgct gctaagaacc  13920
tctccgatgc tatcctcctt tcggatatcc ttagggttaa cactgagatc actaaggctc  13980
ctctttctgc ttccatgatc aagcgctacg acgagcacca ccaggacctc accctcctca  14040
aggctcttgt tcgtcagcag ctccccgaga agtacaagga gatcttcttc gaccagtcca  14100
agaacggcta cgccggttac attgacggtg gagctagcca ggaggagttc tacaagttca  14160
tcaagccaat ccttgagaag atggatggta ctgaggagct tctcgttaag cttaaccgtg  14220
aggacctcct taggaagcag aggactttcg ataacggctc tatccctcac cagatccacc  14280
ttggtgagct tcacgccatc cttcgtaggc aggaggactt ctaccctttc ctcaaggaca  14340
accgtgagaa gatcgagaag atccttactt tccgtattcc ttactacgtt ggtcctcttg  14400
ctcgtggtaa ctcccgtttc gcttggatga ctaggaagtc cgaggagact atcacccctt  14460
ggaacttcga ggaggttgtt gacaagggtg cttccgccca gtccttcatc gagcgcatga  14520
ccaacttcga caagaacctc cccaacgaga aggtcctccc caagcactcc ctcctctacg  14580
agtacttcac ggtctacaac gagctcacca aggtcaagta cgtcaccgag ggtatgcgca  14640
agcctgcctt cctctccggc gagcagaaga aggctatcgt tgacctcctc ttcaagacca  14700
accgcaaggt caccgtcaag cagctcaagg aggactactt caagaagatc gagtgcttcg  14760
actccgtcga gatcagcggc gttgaggacc gtttcaacgc ttctctcggc acctaccacg  14820
atctcctcaa gatcatcaag gacaaggact tcctcgacaa cgaggagaac gaggacatcc  14880
tcgaggacat cgtcctcact cttactctct tcgaggatag ggagatgatc gaggagaggc  14940
tcaagactta cgctcatctc ttcgatgaca aggttatgaa gcagctcaag cgtcgccgtt  15000
acaccggttg gggtaggctc tcccgcaagc tcatcaacgg tatcagggat aagcagagcg  15060
gcaagactat cctcgacttc ctcaagtctg atggtttcgc taacaggaac ttcatgcagc  15120
tcatccacga tgactctctt accttcaagg aggatattca gaaggctcag gtgtccggtc  15180
agggcgactc tctccacgag cacattgcta accttgctgg ttcccctgct atcaagaagg  15240
gcatccttca gactgttaag gttgtcgatg agcttgtcaa ggttatgggt cgtcacaagc  15300
ctgagaacat cgtcatcgag atggctcgtg agaaccagac tacccagaag ggtcagaaga  15360
actcgaggga gcgcatgaag aggattgagg agggtatcaa ggagcttggt tctcagatcc  15420
ttaaggagca ccctgtcgag aacacccagc tccagaacga gaagctctac ctctactacc  15480
tccagaacgg tagggatatg tacgttgacc aggagctcga catcaacagg ctttctgact  15540
acgacgtcga ccacattgtt cctcagtctt tccttaagga tgactccatc gacaacaagg  15600
```

-continued

```
tcctcacgag gtccgacaag aacaggggta agtcggacaa cgtcccttcc gaggaggttg  15660
tcaagaagat gaagaactac tggaggcagc ttctcaacgc taagctcatt acccagagga  15720
agttcgacaa cctcacgaag gctgagaggg gtggcctttc cgagcttgac aaggctggtt  15780
tcatcaagag gcagcttgtt gagacgaggc agattaccaa gcacgttgct cagatcctcg  15840
attctaggat gaacaccaag tacgacgaga acgacaagct catccgcgag gtcaaggtga  15900
tcaccctcaa gtccaagctc gtctccgact tccgcaagga cttccagttc tacaaggtcc  15960
gcgagatcaa caactaccac cacgctcacg atgcttacct taacgctgtc gttggcaccg  16020
ctcttatcaa gaagtaccct aagcttgagt ccgagttcgt ctacggtgac tacaaggtct  16080
acgacgttcg taagatgatc gccaagtccg agcaggagat cggcaaggcc accgccaagt  16140
acttcttcta ctccaacatc atgaacttct tcaagaccga gatcaccctc gccaacggcg  16200
agatccgcaa gcgccctctt atcgagacga acggtgagac tggtgagatc gtttgggaca  16260
agggtcgcga cttcgctact gttcgcaagg tcctttctat gcctcaggtt aacatcgtca  16320
agaagaccga ggtccagacc ggtggcttct ccaaggagtc tatccttcca aagagaaact  16380
cggacaagct catcgctagg aagaaggatt gggaccctaa gaagtacggt ggtttcgact  16440
cccctactgt cgcctactcc gtcctcgtgg tcgccaaggt ggagaagggt aagtcgaaga  16500
agctcaagtc cgtcaaggag ctcctcggca tcaccatcat ggagcgctcc tccttcgaga  16560
agaacccgat cgacttcctc gaggccaagg gctacaagga ggtcaagaag gacctcatca  16620
tcaagctccc caagtactct cttttcgagc tcgagaacgg tcgtaagagg atgctggctt  16680
ccgctggtga gctccagaag ggtaacgagc ttgctcttcc ttccaagtac gtgaacttcc  16740
tctacctcgc ctcccactac gagaagctca agggttcccc tgaggataac gagcagaagc  16800
agctcttcgt ggagcagcac aagcactacc tcgacgagat catcgagcag atctccgagt  16860
tctccaagcg cgtcatcctc gctgacgcta acctcgacaa ggtcctctcc gcctacaaca  16920
agcaccgcga caagcccatc cgcgagcagg ccgagaacat catccacctc ttcacgctca  16980
cgaacctcgg cgcccctgct gctttcaagt acttcgacac caccatcgac aggaagcgtt  17040
acacgtccac caaggaggtt ctcgacgcta ctctcatcca ccagtccatc accggtcttt  17100
acgagactcg tatcgacctt tcccagcttg gtggtgataa gcgtcctgct gccaccaaaa  17160
aggccggaca ggctaagaaa aagaagtagc ctgcaggtcc tgctttaatg agatatgcga  17220
gacgcctatg atcgcatgat atttgctttc aattctgttg tgcacgttgt aaaaaacctg  17280
agcatgtgta gctcagatcc ttaccgccgg tttcggttca ttctaatgaa tatatcaccc  17340
gttactatcg tatttttatg aataatattc tccgttcaat ttactgattg taccctacta  17400
cttatatgta caatattaaa atgaaaacaa tatattgtgc tgaataggtt tatagcgaca  17460
tctatgatag agcgccacaa taacaaacaa ttgcgtttta ttattacaaa tccaatttta  17520
aaaaaagcgg cagaaccggt caaacctaaa agactgatta cataaatctt attcaaattt  17580
caaaagtgcc ccaggggcta gtatctacga cacaccgagc ggcgaactaa taacgctcac  17640
tgaagggaac tccggttccc cgccggcgcg catgggtgag attccttgaa gttgagtatt  17700
ggccgtccgc tctaccgaaa gttacgggca ccattcaacc cggtccagca cggcggccgg  17760
gtaaccgact tgctgccccg agaattatgc agcatttttt tggtgtatgt gggccccaaa  17820
tgaagtgcag gtcaaacctt gacagtgacg acaaatcgtt gggcgggtcc agggcgaatt  17880
ttgcgacaac atgtcgaggc tcagcaggcc ggccgtttaa accaacttta             17930
```

<210> SEQ ID NO 69
<211> LENGTH: 3755
<212> TYPE: DNA
<213> ORGANISM: Artificial Sequence
<220> FEATURE:
<223> OTHER INFORMATION: Vector CC020

<400> SEQUENCE: 69
cgcggatcat gaaccaacgg cctggctgta tttggtggtt gtgtagggag atggggagaa 60
gaaaagcccg attctcttcg ctgtgatggg ctggatgcat gcgggggagc gggaggccca 120
agtacgtgca cggtgagcgg cccacagggc gagtgtgagc gcgagaggcg ggaggaacag 180
tttagtacca cattgcccag ctaactcgaa cgcgaccaac ttataaaccc gcgcgctgtc 240
gcttgtgtgt gggttattga ttctgttggt tttagagcta gaaatagcaa gttaaaataa 300
ggctagtccg ttatcaactt gaaaaagtgg caccgagtcg gtgcattacg ttcagagctg 360
gatcatttgg cccaagggaa gatgcattct ttgaagctgt taccaaccta gcctgtgaga 420
agaaacttcc tcttatttat ttggcagcaa attctggtgc tcgaattggc atagcagatg 480
aagtgaaatc ttgcttccgt gttgggtggt ctgatgatgg cagccctgaa cgtgggtttc 540
agtacattta tctaagcgaa gaagactatg ctcgtattgg cacttctgtc atagcacata 600
agatgcagct agacagtggt gaaattaggt gggttattga ttctgttgtc ggcaaggaag 660
atggacttgg tgtggagaat ctccatggaa gtgctgctat tgccagtgct tattctaggg 720
catataagga gacatttaca cttacatttg tgactggaag aactgttgga ataggagctt 780
atcttgctcg acttggcatc cggtgcatac agcgtcttga ccagcctatt attcttacag 840
gctattctgc actgaacaag cttcttgggc gggaagtgta cagctcccac atgcagttgg 900
gtggtcccaa aatcatggca actaatggtg ttgtccatct tactgtttca gatgaccttg 960
aaggcgtttc taatatattg aggttttttt tgcggccgcc ccgggcctgc aggggatccc 1020
gatcgggccg gccgtttaaa cccactttgt acaagaaagt tgaacgagaa acgtaaaatg 1080
atataaatat caatatatta aattagattt tgcataaaaa acagactaca taatactgta 1140
aaacacaaca tatgcagtca ctatgaacca actacttaga tggtattagt gacctgtact 1200
gggcctcatg ggccttccgc tcactgcccg ctttccagtc gggaaacctg tcgtgccagc 1260
tgcattaaca tggtcatagc tgtttccttg cgtattgggc gctctccgct tcctcgctca 1320
ctgactcgct gcgctcggtc gttcgggtaa agcctggggt gcctaatgag caaaaggcca 1380
gcaaaaggcc aggaaccgta aaaaggccgc gttgctggcg tttttccata ggctccgccc 1440
ccctgacgag catcacaaaa atcgacgctc aagtcagagg tggcgaaacc cgacaggact 1500
ataaagatac caggcgtttc cccctggaag ctccctcgtg cgctctcctg ttccgaccct 1560
gccgcttacc ggatacctgt ccgcctttct cccttcggga agcgtggcgc tttctcatag 1620
ctcacgctgt aggtatctca gttcggtgta ggtcgttcgc tccaagctgg gctgtgtgca 1680
cgaacccccc gttcagcccg accgctgcgc cttatccggt aactatcgtc ttgagtccaa 1740
cccggtaaga cacgacttat cgccactggc agcagccact ggtaacagga ttagcagagc 1800
gaggtatgta ggcggtgcta cagagttctt gaagtggtgg cctaactacg gctacactag 1860
aagaacagta tttggtatct gcgctctgct gaagccagtt accttcggaa aaagagttgg 1920
tagctcttga tccggcaaac aaaccaccgc tggtagcggt ggtttttttg tttgcaagca 1980
gcagattacg cgcagaaaaa aaggatctca agaagatcct ttgatctttt ctacggggtc 2040
tgacgctcag tggaacgaaa actcacgtta agggattttg gtcatgagat tatcaaaaag 2100

```
gatcttcacc tagatccttt taaattaaaa atgaagtttt aaatcaatct aaagtatata   2160

tgagtaaact tggtctgaca gttaccaatg cttaatcagt gaggcaccta tctcagcgat   2220

ctgtctattt cgttcatcca tagttgcctg actccccgtc gtgtagataa ctacgatacg   2280

ggagggctta ccatctggcc ccagtgctgc aatgataccg cgagaaccac gctcaccggc   2340

tccagattta tcagcaataa accagccagc cggaagggcc gagcgcagaa gtggtcctgc   2400

aactttatcc gcctccatcc agtctattaa ttgttgccgg gaagctagag taagtagttc   2460

gccagttaat agtttgcgca acgttgttgc cattgctaca ggcatcgtgg tgtcacgctc   2520

gtcgtttggt atggcttcat tcagctccgg ttcccaacga tcaaggcgag ttacatgatc   2580

ccccatgttg tgcaaaaaag cggttagctc cttcggtcct ccgatcgttg tcagaagtaa   2640

gttggccgca gtgttatcac tcatggttat ggcagcactg cataattctc ttactgtcat   2700

gccatccgta agatgctttt ctgtgactgg tgagtactca accaagtcat tctgagaata   2760

gtgtatgcgg cgaccgagtt gctcttgccc ggcgtcaata cgggataata ccgcgccaca   2820

tagcagaact ttaaaagtgc tcatcattgg aaaacgttct tcggggcgaa aactctcaag   2880

gatcttaccg ctgttgagat ccagttcgat gtaacccact cgtgcaccca actgatcttc   2940

agcatctttt actttcacca gcgtttctgg gtgagcaaaa acaggaaggc aaaatgccgc   3000

aaaaaaggga ataagggcga cacggaaatg ttgaatactc atactcttcc tttttcaata   3060

ttattgaagc atttatcagg gttattgtct catgagcgga tacatatttg aatgtattta   3120

gaaaaataaa caaatagggg ttccgcgcac atttccccga aaagtgccac ctaaattgta   3180

agcgttaata ttttgttaaa attcgcgtta aatttttgtt aaatcagctc attttttaac   3240

caataggccg aaatcggcaa aatcccttat aaatcaaaag aatagaccga gatagggttg   3300

agtggccgct acagggcgct cccattcgcc attcaggctg cgcaactgtt gggaagggcg   3360

tttcggtgcg ggcctcttcg ctattacgcc agctggcgaa agggggatgt gctgcaaggc   3420

gattaagttg ggtaacgcca gggttttccc agtcacgacg ttgtaaaacg acggccagtg   3480

agcgcgacgt aatacgactc actatagggc gaattggcgg aaggccgtca aggccgcatt   3540

acaggtcact aataccatct aagtagttgg ttcatagtga ctgcatatgt tgtgttttac   3600

agtattatgt agtctgtttt ttatgcaaaa tctaatttaa tatattgata tttatatcat   3660

tttacgtttc tcgttcaact tttttgtaca aacttgattt aaatgaattc aagcttttaa   3720

ttaagcatgc gagctcggcg cgccggtacc gcgat                              3755
```

<210> SEQ ID NO 70
<211> LENGTH: 17951
<212> TYPE: DNA
<213> ORGANISM: Artificial Sequence
<220> FEATURE:
<223> OTHER INFORMATION: Vector RLW139

<400> SEQUENCE: 70

```
ttatacatag ttgataattc actgggccgg ccgtttaaac ttagttacta atcagtgatc     60

agattgtcgt ttcccgcctt cactttaaac tatcagtgtt tgacaggata tattggcggg    120

taaacctaag agaaaagagc gtttattaga ataatcggat atttaaaagg gcgtgaaaag    180

gtttatccgt tcgtccattt gtatgtcaat attggggggg ggggaaagcc acgttgtgtc    240

tcaaaatctc tgatgttaca ttgcacaaga taaaaatata tcatcatgaa caataaaact    300

gtctgcttac ataaacagta atacaagggg tgttcgccac catgagccat atccagcgtg    360
```

-continued

```
aaacctcgtg ctcccgcccg cgcctcaatt ccaatatgga tgccgacctt tatggctaca    420
agtgggcgcg cgacaacgtc ggccagtcgg gcgcgaccat ttatcggctt tatggcaaac    480
ccgatgcccc ggaactgttc ctgaagcacg gcaaaggcag cgtcgcaaac gatgtcaccg    540
atgagatggt ccgcctgaac tggcttaccg agttcatgcc gctgccgacg attaagcatt    600
tcatccgtac cccggacgat gcctggctct tgaccacggc cattccgggc aaaacggcct    660
ttcaggtcct tgaagagtac ccggactccg gtgagaatat cgtggacgcc ctcgcggtct    720
tcctccgccg tttgcatagc atccccgtgt gcaactgccc cttcaactcg gaccgggttt    780
tccgcctggc acaggcccag tcgcgcatga ataacggcct cgttgacgcg agcgatttcg    840
acgatgaacg gaatggctgg ccggtggaac aggtttggaa ggaaatgcac aaactgcttc    900
cgttctcgcc ggattcggtg gtcacgcatg gtgatttttc cctggataat ctgatctttg    960
acgagggcaa gctgatcggc tgcatcgacg tgggtcgcgt cggtatcgcc gaccgctatc   1020
aggacctggc gatcttgtgg aattgcctcg gcgagttctc gccctcgctc cagaagcgcc   1080
tgttccagaa gtacggcatc gacaacccgg atatgaacaa gctccagttc cacctcatgc   1140
tggacgaatt tttttgaaca gaattggtta attggttgta acactggcag agcattacgc   1200
tgacttgacg ggacggcggc tttgttgaat aaatcgaact tttgctgagt tgaaggatcg   1260
atgagttgaa ggaccccgta gaaaagatca aaggatcttc ttgagatcct ttttttctgc   1320
gcgtaatctg ctgcttgcaa acaaaaaaac caccgctacc agcggtggtt tgtttgccgg   1380
atcaagagct accaactctt tttccgaagg taactggctt cagcagagcg cagataccaa   1440
atactgtcct tctagtgtag ccgtagttag gccaccactt caagaactct gtagcaccgc   1500
ctacatacct cgctctgcta atcctgttac cagtggctgc tgccagtggc gataagtcgt   1560
gtcttaccgg gttggactca agacgatagt taccggataa ggcgcagcgg tcgggctgaa   1620
cggggggttc gtgcacacag cccagcttgg agcgaacgac ctacaccgaa ctgagatacc   1680
tacagcgtga gctatgagaa agcgccacgc ttcccgaagg gagaaaggcg gacaggtatc   1740
cggtaagcgg cagggtcgga acaggagagc gcacgaggga gcttccaggg ggaaacgcct   1800
ggtatcttta tagtcctgtc gggtttcgcc acctctgact tgagcgtcga tttttgtgat   1860
gctcgtcagg ggggcggagc ctatggaaaa acgccagcaa cgcggccttt ttacggttcc   1920
tggccttttg ctggcctttt gctcacatgt tctttcctgc gttatcccct gattctgtgg   1980
ataaccgtat taccgccttt gagtgagctg ataccgctcg ccgcagccga acgaccgagc   2040
gcagcgagtc agtgagcgag gaagcggaag agcgcctgat gcggtatttt ctccttacgc   2100
atctgtgcgg tatttcacac cgcataggcc gcgataggcc gacgcgaagc ggcggggcgt   2160
agggagcgca gcgaccgaag ggtaggcgct ttttgcagct cttcggctgt gcgctggcca   2220
gacagttatg cacaggccag gcgggtttta agagttttaa taagttttaa agagttttag   2280
gcggaaaaat cgcctttttt ctcttttata tcagtcactt acatgtgtga ccggttccca   2340
atgtacggct ttgggttccc aatgtacggg ttccggttcc caatgtacgg ctttgggttc   2400
ccaatgtacg tgctatccac aggaaagaga ccttttcgac ctttttcccc tgctagggca   2460
atttgcccta gcatctgctc cgtacattag gaaccggcgg atgcttcgcc ctcgatcagg   2520
ttgcggtagc gcatgactag gatcgggcca gcctgccccg cctcctcctt caaatcgtac   2580
tccggcaggt catttgaccc gatcagcttg cgcacggtga aacagaactt cttgaactct   2640
ccggcgctgc cactgcgttc gtagatcgtc ttgaacaacc atctggcttc tgccttgcct   2700
gcggcgcggc gtgccaggcg gtagagaaaa cggccgatgc cggggtcgat caaaaagtaa   2760
```

-continued

```
tcggggtgaa ccgtcagcac gtccgggttc ttgccttctg tgatctcgcg gtacatccaa   2820
tcagcaagct cgatctcgat gtactccggc cgcccggttt cgctctttac gatcttgtag   2880
cggctaatca aggcttcacc ctcggatacc gtcaccaggc ggccgttctt ggccttcttg   2940
gtacgctgca tggcaacgtg cgtggtgttt aaccgaatgc aggtttctac caggtcgtct   3000
ttctgctttc cgccatcggc tcgccggcag aacttgagta cgtccgcaac gtgtggacgg   3060
aacacgcggc cgggcttgtc tcccttccct tcccggtatc ggttcatgga ttcggttaga   3120
tgggaaaccg ccatcagtac caggtcgtaa tcccacacac tggccatgcc ggcggggcct   3180
gcggaaacct ctacgtgccc gtctggaagc tcgtagcgga tcacctcgcc agctcgtcgg   3240
tcacgcttcg acagacggaa aacggccacg tccatgatgc tgcgactatc gcgggtgccc   3300
acgtcataga gcatcggaac gaaaaaatct ggttgctcgt cgcccttggg cggcttccta   3360
atcgacggcg caccggctgc cggcggttgc cgggattctt tgcggattcg atcagcggcc   3420
ccttgccacg attcaccggg gcgtgcttct gcctcgatgc gttgccgctg ggcggcctgc   3480
gcggccttca acttctccac caggtcatca cccagcgccg cgccgatttg taccgggccg   3540
gatggtttgc gaccgctcac gccgattcct cgggcttggg ggttccagtg ccattgcagg   3600
gccggcagac aacccagccg cttacgcctg gccaaccgcc cgttcctcca cacatggggc   3660
attccacggc gtcggtgcct ggttgttctt gattttccat gccgcctcct ttagccgcta   3720
aaattcatct actcatttat tcatttgctc atttactctg gtagctgcgc gatgtattca   3780
gatagcagct cggtaatggt cttgccttgg cgtaccgcgt acatcttcag cttggtgtga   3840
tcctccgccg gcaactgaaa gttgacccgc ttcatggctg gcgtgtctgc caggctggcc   3900
aacgttgcag ccttgctgct gcgtgcgctc ggacggccgg cacttagcgt gtttgtgctt   3960
ttgctcattt tctctttacc tcattaactc aaatgagttt tgatttaatt tcagcggcca   4020
gcgcctggac ctcgcgggca gcgtcgccct cgggttctga ttcaagaacg gttgtgccgg   4080
cggcggcagt gcctgggtag ctcacgcgct gcgtgatacg ggactcaaga atgggcagct   4140
cgtacccggc cagcgcctcg gcaacctcac cgccgatgcg cgtgcctttg atcgcccgcg   4200
acacgacaaa ggccgcttgt agccttccat ccgtgacctc aatgcgctgc ttaaccagct   4260
ccaccaggtc ggcggtggcc caaatgtcgt aagggcttgg ctgcaccgga atcagcacga   4320
agtcggctgc cttgatcgcg gacacagcca agtccgccgc ctggggcgct ccgtcgatca   4380
ctacgaagtc gcgccggccg atggccttca cgtcgcggtc aatcgtcggg cggtcgatgc   4440
cgacaacggt tagcggttga tcttcccgca cggccgccca atcgcgggca ctgccctggg   4500
gatcggaatc gactaacaga acatcggccc cggcgagttg cagggcgcgg gctagatggg   4560
ttgcgatggt cgtcttgcct gacccgcctt tctggttaag tacagcgata accttcatgc   4620
gttccccttg cgtatttgtt tatttactca tcgcatcata tacgcagcga ccgcatgacg   4680
caagctgttt tactcaaata cacatcacct tttagatga tcagtgattt tgtgccgagc   4740
tgccggtcgg ggagctgttg gctggctggt ggcaggatat attgtggtgt aaacaaattg   4800
acgcttagac aacttaataa cacattgcgg acgtctttaa tgtactgaat ttagttactg   4860
atcactgatt aagtactgat aaatttaatt aacagatctc aactttgtat agaaaagttg   4920
atttaaatga attcaagctt ttaattaact tagccactgc aacaagttct tgaaccttag   4980
cacaatcata ttgtgcatgc acttgtttat tgcaaagaat ggtgcgtagg gaacacgcat   5040
gatttttgaa ttgctggcac ataattttat cattagaaac tggaatgcaa catgtaccct   5100
```

-continued

```
ttgtcatggt ttctttccga gacattgcac tgttttttt aatcctatca ttatcataat   5160
gccaagaact ggtcaccaac cagcattttg catcatggtt agttgagctg tccccatgta   5220
tcaataggtg cattgtattg gtccaaaata taaatgcagt ggatgcaacc tatctcatgg   5280
ccgtcaacaa aagaaatcaa aagggaaatg caccatctta tatctccagt ttatatgaac   5340
agattggata agatcataag atcaagtggt ttatattatt ttgaggaata taacatggat   5400
tcatcctaat cactcgtcta ggcagtatgt gtattcatga tggatatggt actatactac   5460
ggagtttttt cttcacaaaa taacctgtta ttttgacctc caaccaaaca cgaattatac   5520
caaaaattgg gttatttcat ctatagtaca actctattat aaacatgcag taaattatcc   5580
tacacatata ccaaaattca agtgtaataa tcctaataca cagacttaaa aaacaaacta   5640
tttccttttt aagaaaagga aaaccatttt tttaacggaa ggaaaacaaa ttcgggtcaa   5700
ggcggaagcc agcgcgccac cccacgtcag cgaatacgga ggcgcggggt tgacggcgtc   5760
acccggtcct aacggcgacc aacaaaccag ccagaagaaa ttacagtaaa aaaaagtaaa   5820
ttgcactttg atccaccttt tattacccaa gtttcaattt ggaccaccct taaacctatc   5880
ttttcaaatt gggccgggtt gtggtttgga ctaccatgaa caacttttcg tcatgtctaa   5940
cttccctttc ggcaaacata tgaaccatat atagaggaga tcggccgtat actagagctg   6000
atgtgtttaa ggtcgttgat tgcacgagaa aaaaaaaatc caaatcgcaa caatagcaaa   6060
tttatctagt tcaaagtgaa aagatatgtt taaaggtagt ccaaagtaaa acttaggggc   6120
tgtttggttc ccagccatac tttaccatta cttgccaaca aaagttgcca caccttgtct   6180
aaggtgaggt gatcaaattg ttagccacaa cttactaagc ctaagggaat cttgccacac   6240
ttttttgagc cattgacacg tgggacttaa tttgttagag ggaaatcttg ccacaactgt   6300
ggctacaacc aaacacctgt caaatttgcc taaccttagg cgtggcaaac tgtggcaaag   6360
tgtggcttac aaccaaacac acccttagat aataaaatgt ggtccaaagc gtaattcact   6420
aaaaaaaaat caacgagacg tgtaccaaac ggagacaaac ggcatcttct cgaaatttcc   6480
caaccgctcg ctcgcccgcc tcgtcttccc ggaaaccgcg gtggtttcag cgtggcggat   6540
tctccaagca gacggagacg tcacggcacg ggactcctcc caccacccaa ccgccataaa   6600
taccagcccc ctcatctcct ctcctcgcat cagctccacc cccgaaaaat ttctccccaa   6660
tctcgcgagg ctctcgtcgt cgaatcgaat cctctcgcgt cctcaagctt ggcatccagg   6720
tacggatccg cgtcccatct ccctcacccc ccgtgttctt cgtgcctgct tctgggtcag   6780
atctgggtgg attcgcggtt gttggatgtg gggggctgtg tttatttgtc ggtggatctg   6840
gttgtctgga tctgcgtttt ctctgtcgta gttagcggat ctgatgaaat gtttagtgtt   6900
cgtgtatact ggtatggtgg atctggtcct aggatgcgtg gaatggatat atgtaggcga   6960
attggaggat ttattttgtg aattttgctg aaatgatagt tctaaacact ggatctgacc   7020
tcgggatgct gttaaatgtg gaaatcatgg tcgatgctgt catgaacatg gtgttcttat   7080
ggtagatctg agcaatgtat gtttcaaaat tgtttgtcac atggaaatgc tatggttcta   7140
gatgcaatag aatgatacat gccgagatcc cctctagttg atatgataga tcatgatgtt   7200
ttacagctat gtcatatgaa tatgttcatt tgttaccgat gtatttggat ctacttaaca   7260
tttccaaagc acgccgcgtt ctaattctag atctggtagt catgtttgta cacgtcaccc   7320
acctaataca aatacatatg tctagtgttt ggtgacactg cccgtcagat ctgtttttc    7380
cagatctgtg gaacaaatac tccacgcatg tatggtagtt ttgaaacgat cttgtatctt   7440
ccattgttgt agtaacaact aaataaagta caattgttca attattggga atcgtatttt   7500
```

```
ctgtagtgcc gatgtacagc atattcatag atgtctattt aggaactcaa attttaaatt   7560
gaggactagt tatttattgt gggtcagtct tttgaattgt gttatcttgc tgtactggcg   7620
cgccaccatg gccaccgccg ccgccgcgtc taccgcgctc actggcgcca ctaccgctgc   7680
gcccaaggcg aggcgccggg cgcacctcct ggccacccgc cgcgccctcg ccgcgcccat   7740
caggtgctca gcggcgtcac ccgccatgcc gatggctccc ccggccaccc cgctccggcc   7800
gtggggcccc accgatcccc gcaagggcgc cgacatcctc gtcgagtccc tcgagcgctg   7860
cggcgtccgc gacgtcttcg cctaccccgg cggcacgtcc atggagatcc accaggcact   7920
cacccgctcc cccgtcatcg ccaaccacct cttccgccac gagcaagggg aggcctttgc   7980
ggcctccggc tacgcgcgct cctcgggccg cgtcggcgtc tgcatcgcca cctccggccc   8040
cggcgccacc aaccttgtct ccgcgctcgc cgacgcgctg ctcgattccg tccccatggt   8100
cgccatcacg ggacaggtgc cgcgacgcat gattggcacc gacgccttcc aggagacgcc   8160
catcgtcgag gtcacccgct ccatcaccaa gcacaactac ctggtcctcg acgtcgacga   8220
catcccccgc gtcgtgcagg aggctttctt cctcgcctcc tctggtcgac cggggccggt   8280
gcttgtcgac atccccaagg acatccagca gcagatggcg gtgcctgtct gggacaagcc   8340
catgagtctg cctgggtaca ttgcgcgcct tcccaagccc cctgcgactg agttgcttga   8400
gcaggtgctg cgtcttgttg gtgaatcccg gcgccctgtt ctttatgttg gcggtggctg   8460
cgcagcatct ggtgaggagt tgcgacgctt tgtggagctg actggaatcc cggtcacaac   8520
tactcttatg ggcctcggca acttccccag cgacgaccca ctgtctctgc gcatgctagg   8580
tatgcatggc acggtgtatg caaattatgc agtggataag gccgatctgt tgcttgcact   8640
tggtgtgcgg tttgatgatc gtgtgacagg gaagattgag gcttttgcaa gcagggctaa   8700
gattgtgcac gttgatattg atccggctga gattggcaag aacaagcagc cacatgtgtc   8760
catctgtgca gatgttaagc ttgctttgca gggcatgaat gctcttcttg aaggaagcac   8820
atcaaagaag agctttgact ttggctcatg gaacgatgag ttggatcagc agaagaggga   8880
attccccctt gggtataaaa catctaatga ggagatccag ccacaatatg ctattcaggt   8940
tcttgatgag ctgacgaaag gcgaggccat catcggcaca ggtgttgggc agcaccagat   9000
gtgggcggca cagtactaca cttacaagcg gccaaggcag tggttgtctt cagctggtct   9060
tggggctatg ggatttggtt tgccggctgc tgctggtgct tctgtggcca acccaggtgt   9120
tactgttgtt gacatcgatg gagatggtag ctttctcatg aacgttcagg agctagctat   9180
gatccgaatt gagaacctcc cggtgaaggt ctttgtgcta aacaaccagc acctggggat   9240
ggtggtgcag tgggaggaca ggttctataa ggccaacaga gcgcacacat acttgggaaa   9300
cccagagaat gaaagtgaga tatatccaga tttcgtgacg atcgccaaag ggttcaacat   9360
tccagcggtc cgtgtgacaa agaagaacga agtccgcgca gcgataaaga agatgctcga   9420
gactccaggg ccgtacctct tggatataat cgtcccacac caggagcatg tgttgcctat   9480
gatccctaat ggtggggctt tcaaggatat gatcctggat ggtgatggca ggactgtgta   9540
ctagcctgca ggcctaggat cgttcaaaca tttggcaata aagtttctta agattgaatc   9600
ctgttgccgg tcttgcgatg attatcatat aatttctgtt gaattacgtt aagcatgtaa   9660
taattaacat gtaatgcatg acgttattta tgagatgggt ttttatgatt agagtcccgc   9720
aattatacat ttaatacgcg atagaaaaca aaatatagcg cgcaaactag gataaattat   9780
cgcgcgcggt gtcatctatg ttactagatc ggccggccgt ttaaacagcc tgcttttttg   9840
```

-continued

```
tacaaacttg atttaaatga attcaagctt ttaattaagc atgcgagctc ggcgcgccgg   9900
taccgcgatc gcggatcatg aaccaacggc ctggctgtat ttggtggttg tgtagggaga   9960
tggggagaag aaaagcccga ttctcttcgc tgtgatgggc tggatgcatg cgggggagcg  10020
ggaggcccaa gtacgtgcac ggtgagcggc ccacagggcg agtgtgagcg cgagaggcgg  10080
gaggaacagt ttagtaccac attgcccagc taactcgaac gcgaccaact tataaacccg  10140
cgcgctgtcg cttgtgtgtg ggttattgat tctgttggtt ttagagctag aaatagcaag  10200
ttaaaataag gctagtccgt tatcaacttg aaaaagtggc accgagtcgg tgcattacgt  10260
tcagagctgg atcatttggc ccaagggaag atgcattctt tgaagctgtt accaacctag  10320
cctgtgagaa gaaacttcct cttatttatt tggcagcaaa ttctggtgct cgaattggca  10380
tagcagatga agtgaaatct tgcttccgtg ttgggtggtc tgatgatggc agccctgaac  10440
gtgggtttca gtacatttat ctaagcgaag aagactatgc tcgtattggc acttctgtca  10500
tagcacataa gatgcagcta gacagtggtg aaattaggtg ggttattgat tctgttgtcg  10560
gcaaggaaga tggacttggt gtggagaatc tccatggaag tgctgctatt gccagtgctt  10620
attctagggc atataaggag acatttacac ttacatttgt gactggaaga actgttggaa  10680
taggagctta tcttgctcga cttggcatcc ggtgcataca gcgtcttgac cagcctatta  10740
ttcttacagg ctattctgca ctgaacaagc ttcttgggcg ggaagtgtac agctcccaca  10800
tgcagttggg tggtcccaaa atcatggcaa ctaatggtgt tgtccatctt actgtttcag  10860
atgaccttga aggcgtttct aatatattga ggtttttttt gcggccgccc cgggcctgca  10920
ggggatcccg atcgggccgg ccgtttaaac ccactttgta caagaaagct gggtatttaa  10980
atgaattcaa gcttttaatt aatgcagtgc agcgtgaccc ggtcgtgccc ctctctagag  11040
ataatgagca ttgcatgtct aagttataaa aaattaccac atattttttt tgtcacactt  11100
gtttgaagtg cagtttatct atctttatac atatatttaa actttactct acgaataata  11160
taatctatag tactacaata atatcagtgt tttagagaat catataaatg aacagttaga  11220
catggtctaa aggacaattg agtattttga caacaggact ctacagtttt atctttttag  11280
tgtgcatgtg ttctcctttt tttttgcaaa tagcttcacc tatataatac ttcatccatt  11340
ttattagtac atccatttag ggtttagggt taatggtttt tatagactaa tttttttagt  11400
acatctattt tattctattt tagcctctaa attaagaaaa ctaaaactct attttagttt  11460
ttttatttaa tagtttagat ataaaataga ataaaataaa gtgactaaaa attaaacaaa  11520
taccctttaa gaaattaaaa aaactaagga aacatttttc ttgtttcgag tagataatgc  11580
cagcctgtta aacgccgtcg acgagtctaa cggacaccaa ccagcgaacc agcagcgtcg  11640
cgtcgggcca agcgaagcag acggcacggc atctctgtcg ctgcctctgg acccctctcg  11700
agagttccgc tccaccgttg gacttgctcc gctgtcggca tccagaaatt gcgtggcgga  11760
gcggcagacg tgagccggca cggcaggcgg cctcctcctc ctctcacggc accggcagct  11820
acgggggatt cctttcccac cgctccttcg ctttcccttc ctcgcccgcc gtaataaata  11880
gacacccccct ccacaccctc tttccccaac ctcgtgttgt tcggagcgca cacacacaca  11940
accagatctc ccccaaatcc acccgtcggc acctccgctt caaggtacgc cgctcgtcct  12000
cccccccccc ccccctctct accttctcta gatcggcgtt ccggtccatg gttagggccc  12060
ggtagttcta cttctgttca tgtttgtgtt agatccgtgt ttgtgttaga tccgtgctgc  12120
tagcgttcgt acacggatgc gacctgtacg tcagacacgt tctgattgct aacttgccag  12180
tgtttctctt tggggaatcc tgggatggct ctagccgttc cgcagacggg atcgatttca  12240
```

-continued

```
tgattttttt tgtttcgttg catagggttt ggtttgccct tttcctttat ttcaatatat  12300
gccgtgcact tgtttgtcgg gtcatctttt catgcttttt tttgtcttgg ttgtgatgat  12360
gtggtctggt tgggcggtcg ttctagatcg gagtagaatt ctgtttcaaa ctacctggtg  12420
gatttattaa ttttggatct gtatgtgtgt gccatacata ttcatagtta cgaattgaag  12480
atgatggatg gaaatatcga tctaggatag gtatacatgt tgatgcgggt tttactgatg  12540
catatacaga gatgcttttt gttcgcttgg ttgtgatgat gtggtgtggt tgggcggtcg  12600
ttcattcgtt ctagatcgga gtagaatact gtttcaaact acctggtgta tttattaatt  12660
ttggaactgt atgtgtgtgt catacatctt catagttacg agtttaagat ggatggaaat  12720
atcgatctag gataggtata catgttgatg tgggttttac tgatgcatat acatgatggc  12780
atatgcagca tctattcata tgctctaacc ttgagtacct atctattata ataaacaagt  12840
atgttttata attatttcga tcttgatata cttggatgat ggcatatgca gcagctatat  12900
gtggattttt ttagccctgc cttcatacgc tatttatttg cttggtactg tttcttttgt  12960
cgatgctcac cctgttgttt ggtgttactt ctgcagggcg cgccaccatg gctcctaaga  13020
agaagcggaa ggttggtatt cacggggtgc ctgcggctga caagaagtac tccatcggcc  13080
tcgacatcgg caccaacagc gtcggctggg cggtgatcac cgacgagtac aaggtcccgt  13140
ccaagaagtt caaggtcctg ggcaacaccg accgccactc catcaagaag aacctcatcg  13200
gcgccctcct cttcgactcc ggcgagacgg cggaggcgac ccgcctcaag cgcaccgccc  13260
gccgccgcta cacccgccgc aagaaccgca tctgctacct ccaggagatc ttctccaacg  13320
agatggcgaa ggtcgacgac tccttcttcc accgcctcga ggagtccttc ctcgtggagg  13380
aggacaagaa gcacgagcgc caccccatct tcggcaacat cgtcgacgag gtcgcctacc  13440
acgagaagta ccccactatc taccaccttc gtaagaagct tgttgactct actgataagg  13500
ctgatcttcg tctcatctac cttgctctcg ctcacatgat caagttccgt ggtcacttcc  13560
ttatcgaggg tgaccttaac cctgataact ccgacgtgga caagctcttc atccagctcg  13620
tccagaccta caaccagctc ttcgaggaga accctatcaa cgcttccggt gtcgacgcta  13680
aggcgatcct ttccgctagg ctctccaagt ccaggcgtct cgagaacctc atcgcccagc  13740
tccctggtga gaagaagaac ggtcttttcg gtaacctcat cgctctctcc ctcggtctga  13800
cccctaactt caagtccaac ttcgacctcg ctgaggacgc taagcttcag ctctccaagg  13860
atacctacga cgatgatctc gacaacctcc tcgctcagat tggagatcag tacgctgatc  13920
tcttccttgc tgctaagaac ctctccgatg ctatcctcct ttcggatatc cttagggtta  13980
acactgagat cactaaggct cctctttctg cttccatgat caagcgctac gacgagcacc  14040
accaggacct caccctcctc aaggctcttg ttcgtcagca gctccccgag aagtacaagg  14100
agatcttctt cgaccagtcc aagaacggct acgccggtta cattgacggt ggagctagcc  14160
aggaggagtt ctacaagttc atcaagccaa tccttgagaa gatggatggt actgaggagc  14220
ttctcgttaa gcttaaccgt gaggacctcc ttaggaagca gaggactttc gataacggct  14280
ctatccctca ccagatccac cttggtgagc ttcacgccat ccttcgtagg caggaggact  14340
tctacccttt cctcaaggac aaccgtgaga agatcgagaa gatccttact ttccgtattc  14400
cttactacgt tggtcctctt gctcgtggta actcccgttt cgcttggatg actaggaagt  14460
ccgaggagac tatcacccct tggaacttcg aggaggttgt tgacaagggt gcttccgccc  14520
agtccttcat cgagcgcatg accaacttcg acaagaacct ccccaacgag aaggtcctcc  14580
```

-continued

```
ccaagcactc cctcctctac gagtacttca cggtctacaa cgagctcacc aaggtcaagt  14640
acgtcaccga gggtatgcgc aagcctgcct tcctctccgg cgagcagaag aaggctatcg  14700
ttgacctcct cttcaagacc aaccgcaagg tcaccgtcaa gcagctcaag gaggactact  14760
tcaagaagat cgagtgcttc gactccgtcg agatcagcgg cgttgaggac cgtttcaacg  14820
cttctctcgg cacctaccac gatctcctca agatcatcaa ggacaaggac ttcctcgaca  14880
acgaggagaa cgaggacatc ctcgaggaca tcgtcctcac tcttactctc ttcgaggata  14940
gggagatgat cgaggagagg ctcaagactt acgctcatct cttcgatgac aaggttatga  15000
agcagctcaa gcgtcgccgt tacaccggtt ggggtaggct ctcccgcaag ctcatcaacg  15060
gtatcaggga taagcagagc ggcaagacta tcctcgactt cctcaagtct gatggtttcg  15120
ctaacaggaa cttcatgcag ctcatccacg atgactctct taccttcaag gaggatattc  15180
agaaggctca ggtgtccggt cagggcgact ctctccacga gcacattgct aaccttgctg  15240
gttcccctgc tatcaagaag ggcatccttc agactgttaa ggttgtcgat gagcttgtca  15300
aggttatggg tcgtcacaag cctgagaaca tcgtcatcga gatggctcgt gagaaccaga  15360
ctacccagaa gggtcagaag aactcgaggg agcgcatgaa gaggattgag gagggtatca  15420
aggagcttgg ttctcagatc cttaaggagc accctgtcga gaacacccag ctccagaacg  15480
agaagctcta cctctactac ctccagaacg gtagggatat gtacgttgac caggagctcg  15540
acatcaacag gctttctgac tacgacgtcg accacattgt tcctcagtct ttccttaagg  15600
atgactccat cgacaacaag gtcctcacga ggtccgacaa gaacaggggt aagtcggaca  15660
acgtcccttc cgaggaggtt gtcaagaaga tgaagaacta ctggaggcag cttctcaacg  15720
ctaagctcat tacccagagg aagttcgaca acctcacgaa ggctgagagg ggtggccttt  15780
ccgagcttga caaggctggt ttcatcaaga ggcagcttgt tgagacgagg cagattacca  15840
agcacgttgc tcagatcctc gattctagga tgaacaccaa gtacgacgag aacgacaagc  15900
tcatccgcga ggtcaaggtg atcaccctca agtccaagct cgtctccgac ttccgcaagg  15960
acttccagtt ctacaaggtc cgcgagatca acaactacca ccacgctcac gatgcttacc  16020
ttaacgctgt cgttggcacc gctcttatca agaagtaccc taagcttgag tccgagttcg  16080
tctacggtga ctacaaggtc tacgacgttc gtaagatgat cgccaagtcc gagcaggaga  16140
tcggcaaggc caccgccaag tacttcttct actccaacat catgaacttc ttcaagaccg  16200
agatcaccct cgccaacggc gagatccgca agcgccctct tatcgagacg aacggtgaga  16260
ctggtgagat cgtttgggac aagggtcgcg acttcgctac tgttcgcaag gtcctttcta  16320
tgcctcaggt taacatcgtc aagaagaccg aggtccagac cggtggcttc tccaaggagt  16380
ctatccttcc aaagagaaac tcggacaagc tcatcgctag gaagaaggat tgggacccta  16440
agaagtacgg tggtttcgac tcccctactg tcgcctactc cgtcctcgtg gtcgccaagg  16500
tggagaaggg taagtcgaag aagctcaagt ccgtcaagga gctcctcggc atcaccatca  16560
tggagcgctc ctccttcgag aagaacccga tcgacttcct cgaggccaag ggctacaagg  16620
aggtcaagaa ggacctcatc atcaagctcc ccaagtactc tcttttcgag ctcgagaacg  16680
gtcgtaagag gatgctggct tccgctggtg agctccagaa gggtaacgag cttgctcttc  16740
cttccaagta cgtgaacttc ctctacctcg cctcccacta cgagaagctc aagggttccc  16800
ctgaggataa cgagcagaag cagctcttcg tggagcagca caagcactac ctcgacgaga  16860
tcatcgagca gatctccgag ttctccaagc gcgtcatcct cgctgacgct aacctcgaca  16920
aggtcctctc cgcctacaac aagcaccgcg acaagcccat ccgcgagcag gccgagaaca  16980
```

tcatccacct cttcacgctc acgaacctcg gcgcccctgc tgctttcaag tacttcgaca 17040
ccaccatcga caggaagcgt tacacgtcca ccaaggaggt tctcgacgct actctcatcc 17100
accagtccat caccggtctt tacgagactc gtatcgacct ttcccagctt ggtggtgata 17160
agcgtcctgc tgccaccaaa aaggccggac aggctaagaa aaagaagtag cctgcaggtc 17220
ctgctttaat gagatatgcg agacgcctat gatcgcatga tatttgcttt caattctgtt 17280
gtgcacgttg taaaaaacct gagcatgtgt agctcagatc cttaccgccg gtttcggttc 17340
attctaatga atatatcacc cgttactatc gtatttttat gaataatatt ctccgttcaa 17400
tttactgatt gtaccctact acttatatgt acaatattaa aatgaaaaca atatattgtg 17460
ctgaataggt ttatagcgac atctatgata gagcgccaca ataacaaaca attgcgtttt 17520
attattacaa atccaatttt aaaaaaagcg gcagaaccgg tcaaacctaa aagactgatt 17580
acataaatct tattcaaatt tcaaaagtgc cccaggggct agtatctacg acacaccgag 17640
cggcgaacta ataacgctca ctgaagggaa ctccggttcc ccgccggcgc gcatgggtga 17700
gattccttga agttgagtat tggccgtccg ctctaccgaa agttacgggc accattcaac 17760
ccggtccagc acggcggccg ggtaaccgac ttgctgcccc gagaattatg cagcattttt 17820
ttggtgtatg tgggccccaa atgaagtgca ggtcaaacct tgacagtgac gacaaatcgt 17880
tgggcgggtc cagggcgaat tttgcgacaa catgtcgagg ctcagcaggc cggccgttta 17940
aaccaacttt a 17951

<210> SEQ ID NO 71
<211> LENGTH: 10
<212> TYPE: PRT
<213> ORGANISM: Artificial Sequence
<220> FEATURE:
<223> OTHER INFORMATION: Nuclear Localization Signal

<400> SEQUENCE: 71

Met Ser Glu Arg Lys Arg Arg Glu Lys Leu
1 5 10

<210> SEQ ID NO 72
<211> LENGTH: 16
<212> TYPE: PRT
<213> ORGANISM: Artificial Sequence
<220> FEATURE:
<223> OTHER INFORMATION: Nuclear Localization Signal

<400> SEQUENCE: 72

Lys Arg Pro Ala Ala Thr Lys Lys Ala Gly Gln Ala Lys Lys Lys Lys
1 5 10 15

<210> SEQ ID NO 73
<211> LENGTH: 377
<212> TYPE: DNA
<213> ORGANISM: Oryza sativa
<220> FEATURE:
<221> NAME/KEY: misc_feature
<223> OTHER INFORMATION: U3 snRNA promoter

<400> SEQUENCE: 73
aagggatctt taaacatacg aacagatcac ttaaagttct tctgaagcaa cttaaagtta 60
tcaggcatgc atggatcttg gaggaatcag atgtgcagtc agggaccata gcacaggaca 120
ggcgtcttct actggtgcta ccagcaaatg ctggaagccg ggaacactgg gtacgttgga 180
aaccacgtga tgtggagtaa gataaactgt aggagaaaag catttcgtag tgggccatga 240

-continued

```
agcctttcag gacatgtatt gcagtatggg ccggcccatt acgcaattgg acgacaacaa    300

agactagtat tagtaccacc tcggctatcc acatagatca aagctggttt aaaagagttg    360

tgcagatgat ccgtggc                                                   377


<210> SEQ ID NO 74
<211> LENGTH: 76
<212> TYPE: DNA
<213> ORGANISM: Artificial Sequence
<220> FEATURE:
<223> OTHER INFORMATION: Upper sequence from Figure 22 (homology and
      protospacer regions). The first nucleotide, which is only
      partially shown in Figure 22, here corresponds to C at base
      position 1

<400> SEQUENCE: 74

caaataggcg atcgcgggag tgctttattt gaagatcagg ctatcactgc ggtcaataga     60

tttcacaatg tgatgg                                                     76


<210> SEQ ID NO 75
<211> LENGTH: 76
<212> TYPE: DNA
<213> ORGANISM: Artificial Sequence
<220> FEATURE:
<223> OTHER INFORMATION: Lower sequence from Figure 22 (homology and
      protospacer regions), which is given here in 5-prime to
      3-direction. The first nucleotide, which is only partially shown
      in Figure 22, here corresponds to G at base position 76.

<400> SEQUENCE: 75

ccatcacatt gtgaaatcta ttgaccgcag tgatagcctg atcttcaaat aaagcactcc     60

cgcgatcgcc tatttg                                                     76
```

METHODS FOR MODIFICATION OF TARGET NUCLEIC ACIDS

This application is a National Stage application of International Application No. PCT/EP2017/059331, filed Apr. 20, 2017, which claims the benefit of European Patent Application No. 16167773.7, filed Apr. 29, 2016, European Patent Application No. 16167774.5, filed Apr. 29, 2016, and European Patent Application No. 17156018.8, filed Feb. 14, 2017.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "160315_Seqlisting.txt", which was created on Sep. 10, 2018 and is 207,293 bytes in size. The subject matter of the Sequence Listing is incorporated herein in its entirety by reference.

FIELD OF THE INVENTION

The invention is directed to improved methods for modification of target nucleic acids.

DESCRIPTION OF THE INVENTION

The CRISPR (clustered regularly interspaced short palindromic repeats) system was initially identified as an adaptive defense mechanisms of bacteria belonging to the genus of *Streptococcus* (WO2007/025097). Those bacterial CRISPR systems rely on guide RNA (gRNA) in complex with cleaving proteins to direct degradation of complementary sequences present within invading viral DNA. Cas9, the first identified protein of the CRISPR/Cas system, is a large monomeric DNA nuclease guided to a DNA target sequence adjacent to the PAM (protospacer adjacent motif) sequence motif by a complex of two noncoding RNAs: crRNA and trans-activating crRNA (tracrRNA). Later, a synthetic RNA chimera (single guide RNA or gRNA) created by fusing crRNA with tracrRNA was shown to be equally functional (Jinek et. al. 2012).

Several research groups have found that the CRISPR cutting properties could be used to disrupt genes in almost any organism's genome with unprecedented ease (Mali P, et al (2013) Science. 339(6121):819-823; Cong L, et al (2013) Science 339(6121)). Recently it became clear that providing a template for repair allowed for editing the genome with nearly any desired sequence at nearly any site, transforming CRISPR into a powerful gene editing tool (WO/2014/150624, WO/2014/204728).

Gene targeting refers to site specific gene modification by nucleic acid deletion, insertion or replacement via homologous recombination (HR). Targeting efficiency is highly promoted by a double-strand break (DSB) in the genomic target. Also, the direct presence of homology after DSB of chromosomal DNA seems to nearly eliminate non-homologous end joining (NHEJ) repair in favor of homologous recombination.

The invention at hand provides a guide nucleic acid fused to the appropriate donor for HR repair which interacts with a nucleic acid modifying polypeptide (fusion nucleic acid (fuNA) molecule comprising a guide nucleic acid (gNA) molecule covalently linked to at least one donor nucleic acid (doNA) molecule). To improve delivery of donor nucleic acid with homology to target DNA flanking a nuclease cutting site, a gene targeting strategy is presented where the donor nucleic acid (doNA) is covalently linked to the CRISPR components. In this way, the gene editing complex comprises not only the necessary recognition and cutting tools but also the template for modification. Upon recognition by the guide nucleic acid (gNA), the nuclease cleaves the target region, and the immediate synchronized presence of incoming donor will facilitate the HR process, thereby increasing gene repair efficacy.

Many microbial systems lack an efficient NHEJ system [Standage-Beier K, Zhang Q, Wang X (2015) Targeted Large-Scale Deletion of Bacterial Genomes Using CRISPR-Nickases. ACS Synth Biol. 4(11): 1217-1225]. E.g. *Clostridium celluolyticum* which is important for bioenergy research, cannot be engineered easily with CRISPR/Cas9 [Xu T, Li Y, Shi Z, Hemme C L, Li Y, Zhu Y, Van Nostrand J D, He Z, Zhou J (2015) Efficient Genome Editing in *Clostridium cellulolyticum* via CRISPR-Cas9 Nickase. Appl Environ Microbiol. 81(13):4423-31] and attempts to knockout genes by introducing DSBs result in cell death. Another example is *Escherichia coli* which also relies on homologous recombination (HR) for DSB repair. Current techniques for genome editing in such organisms focus on the use of CRISPR/Cas9-based nickases with subsequent inefficient repair via non-fused nucleic acid donors, inducible expression of CRISPR/Cas to coordinate nuclease action and the introduction of nucleic acid donors or recombinases which lack flexibility in addressing custom DNA sequences.

The application of the FusionCRISPR technology, which is the provision and/or application of a CRISPR/Cas or CRISPR/Cas like system comprising a fuNA molecule, will simplify the creation of knockouts in a wide variety of microbial species formerly not amenable to high throughput targeting. By offering the donor nucleic acids promptly upon induction of a double strand break (DSB), the HR repair machinery will successfully ligate the break with accompanying template. The introduction of FusionCRISPR is performed with common techniques otherwise used for the introduction of nicking versions of CRISPR/Cas9, recombinases or any other (trans)genes of interest. These techniques include, but are not limited to electroporation/heat shock of plasmids, viral transduction and conjugation.

Whereas genes in organisms with efficient NHEJ can be knocked out by introducing CRISPR/Cas9 in which the guide RNA consists of (1) spacer matching the target gene (2) essential sequences for correct guide RNA folding (tracrRNA:crRNA commonly combined in one single guide RNA (sgRNA)) with a typical length of ~99 nucleotides, knockouts in DSB-sensitive microbes can be achieved through a simple adaptation of the RNA resulting in the following composition: (1) spacer (2) essential sequences for correct secondary structure (3) at least 15 nucleotides matching the target (4) at least 15 nucleotides matching the target one or more bases downstream from the first at least 15 nucleotides matching the target. Two complementary ssDNA oligonucleotides representing a knockout FusionCRISPR cassette can readily be purchased commercially from any oligo synthesis company. Alternatively, it can be synthesized as dsDNA. Cloning of FusionCRISPR knockout cassettes can proceed similar to the most common method for cloning of 20 nucleotides spacers for an intended target in regular CRISPR cassettes with type IIS restriction enzymes. Thus, access, flexibility and ease of use of controlled gene knockouts through FusionCRISPR is comparable to regular CRISPR/Cas9 and the current invention expands high throughput knockouts to target species in which NHEJ is inefficient or absent.

FusionCRISPR can also be used for knock-ins in any organism. A selectable marker can be knocked in using standard introduction techniques and standard expression vehicles, including simple plasmids. This can be done to interrupt and knockout an endogenous gene while providing easy selection.

Genome-scale knockouts in human and other cells allows the discovery of genes involved in diseases, drug response and normal biological processes and the creation of disease models [Shalem O, Sanjana N E, Hartenian E, Shi X, Scott D A, Mikkelsen T S, Heckl D, Ebert B L, Root D E, Doench J G, Zhang F (2014) Genome-scale CRISPR-Cas9 knockout screening in human cells. Science; 343(6166):84-7]. Knockouts are typically generated by introduction of CRISPR/Cas9 for a specific target and relying on NHEJ to create a "null" for the gene in question. Three major problems arise with this method: (1) Knockouts are often not created because NHEJ repair does not result in a frame shift (or alternative downstream start codons are being used resulting in a truncated gene product), (2) The outcome, i.e. the exact primary DNA sequence, is not known and needs to be determined for each DNA modifying "event" which is costly and time-consuming, (3) in diploid or polyploid organisms the NHEJ repair on each chromosome will occur differently, if successful targeting on all available "substrates" is even achieved in the first place, resulting in complex molecular analysis and/or a forced switch to haploid model lines [Wade M (2015) High-throughput silencing using the CRISPR-Cas9 system: A review of the benefits and challenges. Journal of Biomolecular Screening, Vol. 20(8):1027-39]. FusionCRISPR allows control of the deletion as described above, which leads to a predictable outcome. In diploid and polyploid cell systems any introduced modification on each of the chromosomes will for the majority be identical. The deletion can be designed to be large enough so that alternative transcription possibilities are reduced and by designing the deletion to consist of a number of bases that cannot be divided by three, the risk of still creating a functional protein which merely lacks a short stretch of amino acids will be eliminated.

Methods for the introduction of FusionCRISPR configurations designed to control knockouts in any cell system are identical to methods used for the introduction of CRISPR/Cas9 which is followed by NHEJ repair for creation of knockouts. This includes but is not limited to the use of AAV and lentiviral vectors for human cells to baculovirus expression system for insect cells. No further adaptation to current methods is required other than a short extension of the guideRNA as described above.

Genome editing can be used to treat a variety of genetic disorders. Many genetic disorders involve point mutations which could potentially be corrected by providing a site specific nuclease along with a corrective nucleic acid template containing the required correction(s). One example is sickle cell disease which results from a single DNA base mutation (A>T) in the sixth codon of the β-globin gene [Li C, Ding L, Sun C W, Wu L C, Zhou D, Pawlik K M, Khodadadi-Jamayran A, Westin E, Goldman F D, Townes™ (2016) Novel HDAd/EBV Reprogramming Vector and Highly Efficient Ad/CRISPR-Cas Sickle Cell Disease Gene Correction. Sci Rep. 6:30422]. Correction of mutations in cells by providing nuclease and corrective template separately will often result in uncoordinated initial break in the DNA and local arrival of the corrective template for HDR repair. To compensate for the lack of temporal/spatial coordination nuclease and corrective template concentrations need to be relatively high. Higher nuclease concentrations can lead to higher off-target cleavage with negative consequences (higher patient risk and/or higher costs in molecular analysis). FusionCRISPR will achieve correct gene correction at much lower concentration. Methods for applying FusionCRISPR are identical to current standards in the field [Maeder M L, Gersbach C A (2016) Genome-editing Technologies for Gene and Cell Therapy. Mol Ther. 24(3):430-46] with the sole difference being a slightly longer sgRNA encompassing the desired correction.

FusionCRISPR can be used to alter substrate or product specificity of a variety of enzymes in a variety of different organisms. For example, a single amino acid has been found to be a major determinant in triterpene synthases substrate and product specificity in various plant species [Salmon M, Thimmappa R B, Minto R E, Melton R E, Hughes R K, O'Maille P E, Hemmings A M, Osbourn A (2016) A conserved amino acid residue critical for product and substrate specificity in plant triterpene synthases. Proc Natl Acad Sci USA. 113(30):E4407-14]. Triterpenes are a diverse group of natural products with applications in pharmacy and biotechnology and the ability to influence product specificity opens the door to synthesis of novel or higher quantity biomolecules in a plant of interest. FusionCRISPR allows the modification of critical amino acids in substrate pockets or other domains of an enzyme that influence specificity. The desired amino acid is introduced by including the corresponding codon in the fused template flanked by nucleotide sequences that have homology with the sequences flanking the codon that needs to be replaced in the genome. One example of introducing the FusionCRISPR construct is by *Agrobacterium*-mediated T-DNA transformation in which the T-DNA contains a selectable marker, Cas9 driven by a strong promoter and the FusionCRISPR construct consisting of respectively: (1) an RNA polymerase III promoter, (2) spacer matching the intended target codon or a sequence adjacent to it (find the nearest PAM), (3) essential sequences for correct secondary structure of the guide, (4) homology arm matching one region flanking the break, (5) the novel codon(s) matching the amino acid(s) that affect specificity in the enzyme, (6) the homology arm on the other side of the break and (7) a terminator. Depending on where the cut is made, a silent mutation may have to be included to avoid having a PAM sequence in the donor. Homology arms, intended changes and sequences between intended changes will be contiguous for seamless incorporation of the donor. The selectable marker is used for obtaining plant cells that have stably integrated T-DNA. In these cells, throughout maintenance and regeneration of transformed plants, the FusionCRISPR components have the opportunity to alter the genome at the intended target. These alterations can make their way into the germline and the next generation of seedlings can be screened for the novel endogenous sequence and segregation of the T-DNA.

FusionCRISPR allows the insertion of epitope or other tags at endogenous genes in any organism. The tags can be used for tracking of endogenous gene products at the cellular and subcellular level, identification of protein-protein interactions, ChIP and other molecular interactions and protein purification. Most applications will be in pathway discovery and identification of drug targets. The FusionCRISPR construct will have the nucleic acids encoding for the tags as payload between the stretches of homology as similar described above for introduction of substitutions. Introduction of FusionCRISPR either as DNA or transiently will follow the same protocols as currently used for regular CRISPR/Cas9 in the organisms of interest.

Our yeast experiments have shown that the payload in FusionCRISPR can be at least 731 nucleotides without affecting the full function of the nuclease. A sequence of this or potentially larger size can comprise a strong promoter or promoter with different tissue or environmental cue specific activity compared to the natural promoter. FusionCRISPR can potentially displace the endogenous promoter and allow an alternative method of gene regulation including upregulation.

It is one objective of the invention at hand to simplify the application of the CRISPR/Cas DNA repair system or CRISPR/Cas like DNA repair system.

It is a further objective of the invention at hand to enhance the efficiency of homologous recombination in a target nucleic acid during DNA break repair.

Surprisingly this was achieved by covalently linking a donor nucleic acid molecule and a guide nucleic acid molecule the latter interacting with a site directed nucleic acid modifying polypeptide as elements of a CRISPR/Cas DNA repair system or a CRISPR/Cas like DNA repair system.

DETAILED DESCRIPTION OF THE INVENTION

One embodiment of the invention at hand is a method for modification of a target nucleic acid (target NA) molecule in a cell or composition comprising the steps of a. providing a recombinant fusion nucleic acid (fuNA) molecule comprising a guide nucleic acid (gNA) molecule covalently linked to at least one donor nucleic acid (doNA) molecule, and
b. introducing said fuNA molecule into one or more cells or composition comprising the target NA molecule, and
c. introducing a site directed nucleic acid modifying polypeptide into said one or more cells or composition, and
d. incubating the one or more cells or composition under conditions that allow for homologous recombination in said one or more cells or composition, and optionally
e. isolating one or more cells in which homologous recombination occurred.

Various preferred structures of the fusion nucleic acid molecule according to the invention are depicted in FIG. 1 to 12. The most preferred structure is depicted in FIG. 1.

The target nucleic acid may be modified by introducing a nucleic acid molecule into the target nucleic acid wherein the introduced nucleic acid molecule is heterologous to the target nucleic acid. The sequence between homology arm 1 and homology arm 2 of the donor nucleic acid molecule would in this case comprise the nucleic acid molecule which is supposed to be introduced into the target nucleic acid and which is not present between the regions in the target nucleic acid that are complementary to the homology arms.

The target nucleic acid may also be modified by deleting at least one base from the target nucleic acid. In that case, the sequence between homology arm 1 and homology arm 2 of the donor nucleic acid molecule would comprise a sequence complementary to the target nucleic acid molecule that lacks at least one base compared to the target nucleic acid.

The target nucleic acid may further be modified by replacing at least one base in the target nucleic acid with one or more bases heterologous to the target nucleic acid. In that case the sequence between homology arm 1 and 2 of the donor nucleic acid would comprise at least one mismatch compared to the complementary region in the target nucleic acid.

The target nucleic acid may comprise a "protospacer adjacent motif" (PAM) sequence adjacent to the targeted sequence in the target nucleic acid molecule which is required for some site directed nucleic acid modifying polypeptides for correct target site identification and binding. The sequence of the PAM is specific for the various site directed nucleic acid modifying polypeptides (Doudna and Charpentier, 2014, Science 346 (6213):1258096) and is known to the skilled person.

The method of the invention is preferably applied for target nucleic acid modification in living cells but may also be applied in in vitro systems.

The target nucleic acid molecule may be RNA or DNA, it may be single- or double-stranded. Preferably, the target nucleic acid molecule is DNA, more preferable the target nucleic acid molecule is double-stranded DNA.

The site directed nucleic acid modifying polypeptide may be introduced into the cell or composition as a polypeptide or may be introduced by introduction of an RNA molecule encoding said site directed nucleic acid modifying polypeptide or by introduction of an expression construct expressing said site directed nucleic acid modifying polypeptide wherein the expression construct is comprising a promoter functional in the respective cell or composition functionally linked to a gene encoding said site directed nucleic acid modifying polypeptide. Examples for such site directed nucleic acid modifying polypeptides are shown in Table 1. Further, any functional equivalent to such site directed nucleic acid modifying polypeptide may be used in the method of the invention.

TABLE 1

Examples for site directed nucleic acid modifying polypeptides

| GenBank Acc No. | Bacterium |
|---|---|
| 303229466 | *Veillonella atypica* ACS-134-V-Col7a |
| 34762592 | *Fusobacterium nucleatum* subsp. *vincentii* |
| 374307738 | *Filifactor alocis* ATCC 35896 |
| 320528778 | *Solobacterium moorei* F0204 |
| 291520705 | *Coprococcus catus* GD-7 |
| 42525843 | *Treponema denticola* ATCC 35405 |
| 304438954 | *Peptoniphilus duerdenii* ATCC BAA-1640 |
| 224543312 | *Catenibacterium mitsuokai* DSM 15897 |
| 24379809 | *Streptococcus mutans* UA159 |
| 15675041 | *Streptococcus pyogenes* SF370 |
| 16801805 | *Listeria innocua* Clip11262 |
| 116628213 | *Streptococcus thermophilus* LMD-9 |
| 323463801 | *Staphylococcus pseudintermedius* ED99 |
| 352684361 | *Acidaminococcus intestini* RyC-MR95 |
| 302336020 | *Olsenella uli* DSM 7084 |
| 366983953 | *Oenococcus kitaharae* DSM 17330 |
| 310286728 | *Bifidobacterium bifidum* S17 |
| 258509199 | *Lactobacillus rhamnosus* GG |
| 300361537 | *Lactobacillus gasseri* JV-V03 |
| 169823755 | *Finegoldia magna* ATCC 29328 |
| 47458868 | *Mycoplasma mobile* 163K |
| 284931710 | *Mycoplasma gallisepticum* str. F |
| 363542550 | *Mycoplasma ovipneumoniae* SC01 |
| 384393286 | *Mycoplasma canis* PG 14 |
| 71894592 | *Mycoplasma synoviae* 53 |
| 238924075 | *Eubacterium rectale* ATCC 33656 |
| 116627542 | *Streptococcus thermophilus* LMD-9 |
| 315149830 | *Enterococcus faecalis* TX0012 |
| 315659848 | *Staphylococcus lugdunensis* M23590 |
| 160915782 | *Eubacterium dolichum* DSM 3991 |
| 336393381 | *Lactobacillus coryniformis* subsp. *torquens* |
| 310780384 | *Ilyobacter polytropus* DSM 2926 |
| 325677756 | *Ruminococcus albus* 8 |

TABLE 1-continued

| Examples for site directed nucleic acid modifying polypeptides | |
|---|---|
| GenBank Acc No. | Bacterium |
| 187736489 | *Akkermansia muciniphila* ATCC BAA-835 |
| 117929158 | *Acidothermus cellulolyticus* 11B |
| 189440764 | *Bifidobacterium longum* DJO10A |
| 283456135 | *Bifidobacterium dentium* Bd1 |
| 38232678 | *Corynebacterium diphtheriae* NCTC 13129 |
| 187250660 | *Elusimicrobium minutum* Pei191 |
| 319957206 | *Nitratifractor salsuginis* DSM 16511 |
| 325972003 | *Sphaerocha eta globus* str. Buddy |
| 261414553 | *Fibrobacter succinogenes* subsp. *succinogenes* |
| 60683389 | *Bacteroides fragilis* NCTC 9343 |
| 256819408 | *Capnocytophaga ochracea* DSM 7271 |
| 90425961 | *Rhodopseudomonas palustris* BisB18 |
| 373501184 | *Prevotella micans* F0438 |
| 294674019 | *Prevotella ruminicola* 23 |
| 365959402 | *Flavobacterium columnare* ATCC 49512 |
| 312879015 | *Aminomonas paucivorans* DSM 12260 |
| 83591793 | *Rhodospirillum rubrum* ATCC 11170 |
| 294086111 | *Candidatus Puniceispirillum marinum* IMCC1322 |
| 121608211 | *Verminephrobacter eiseniae* EF01-2 |
| 344171927 | *Ralstonia syzygii* R24 |
| 159042956 | *Dinoroseobacter shibae* DFL 12 |
| 288957741 | *Azospirillum* sp-B510 |
| 92109262 | *Nitrobacter hamburgensis* X14 |
| 148255343 | *Bradyrhizobium* sp-BTAi1 |
| 34557790 | *Wolinella succinogenes* DSM 1740 |
| 218563121 | *Campylobacter jejuni* subsp. *jejuni* |
| 291276265 | *Helicobacter mustelae* 12198 |
| 229113166 | *Bacillus cereus* Rock1-15 |
| 222109285 | *Acidovorax ebreus* TPSY |
| 189485225 | uncultured Termite group 1 |
| 182624245 | *Clostridium perfringens* D str. |
| 220930482 | *Clostridium cellulolyticum* H10 |
| 154250555 | *Parvibaculum lavamentivorans* DS-1 |
| 257413184 | *Roseburia intestinalis* L1-82 |
| 218767588 | *Neisseria meningitidis* Z2491 |
| 15602992 | *Pasteurella multocida* subsp. *multocida* |
| 319941583 | *Sutterella wadsworthensis* 3 1 |
| 254447899 | *gamma proteobacterium* HTCC5015 |
| 54296138 | *Legionella pneumophila* str. Paris |
| 331001027 | *Parasutterella excrementihominis* YIT 11859 |
| 34557932 | *Wolinella succinogenes* DSM 1740 |
| 118497352 | *Francisella novicida* U112 |
| 961512549 | *Francisella tularensis* subsp. *novicida U112* |
| 961512548 | *Acidaminococcus* sp. BV3L6 |

The site directed nucleic acid modifying polypeptide may have a double-stranded nucleic acid digestion function or it may have a nickase function, cutting only one strand of a double-stranded nucleic acid molecule. The nucleic acid restriction or nickase capability of the site directed nucleic acid modifying polypeptide may also be inactivated and the recombinant site directed nucleic acid modifying polypeptide may be linked to other functional groups such as the DNA restriction region of Foki or of a homing endonulcease. Such recombinant site directed nucleic acid modifying polypeptides are for example described in Tsai et al (2014; Nat Biotechnol. 2014 32(6):569-76.) or Guilinger et al (2014; Nat Biotechnol. 2014 32(6):577-82).

The gNA molecule comprises a spacer nucleic acid (spacer NA) molecule comprising at least 12 bases 100% complementary to the target NA molecule. Preferably it comprises at least 13 bases, at least 14 bases or at least 15 bases complementary to the target NA molecule. More preferably it comprises at least 16 bases, at least 17 bases or at least 18 bases complementary to the target NA molecule. Even more preferably it comprises at least 19 bases or at least 20 bases complementary to the target NA.

The gNA molecule further comprises a scaffold nucleic acid (scaffold NA) molecule. The scaffold NA may consist of one nucleic acid molecule, which comprises two regions each comprising at least eight bases being complementary to each other, capable to hybridize and form a hairpin structure. The scaffold NA may consist of two nucleic acid molecules each comprising at least one region of at least eight bases complementary to each other, capable to hybridize and form a double-stranded structure. If said regions are comprising more than eight complementary bases, each region comprises at least eight bases that are complementary to at least eight bases of the other region.

Preferably the scaffold NA consists of one molecule.

The scaffold NA molecule is covalently linked to the spacer NA molecule. In the event, the scaffold NA molecule consists of two independent molecules, at least one of these molecules of the scaffold NA is covalently linked to the spacer NA molecule.

In addition to the two regions comprising at least eight bases being complementary to each other, the scaffold NA molecule comprises a further region forming a secondary structure comprising at least one hairpin, preferably at least two hairpins.

The donor NA molecule comprises two homology arms. Each homology arm of the donor NA molecule comprises at least 15 bases and is at least 5%, preferably at least 10%, more preferably at least 15%, most preferably at least 20% of the size of the additional NA region spacing the homology arms. Homology arm 1 and 2 may have the same length or different length.

The homology arms each comprise at least 15 bases that are 100% complementary to the same number of consecutive bases in target NA molecule. In the event, a homology arm is larger than 15 bases it is preferably at least 60%, preferably at least 70%, more preferably at least 75%, more preferably 80%, more preferably at least 85%, more preferably at least 90%, even more preferably at least 95%, even more preferably at least 98%, even more preferably at least 99% complementary to the target NA molecule. Most preferably each homology arm is 100% complementary to the target NA molecule.

The method of the invention may be applied in cells or compositions comprising the target NA molecule. Preferably the method is applied to cells, wherein the cell is a microbial, animal, human or plant cell, more preferably the method is applied to yeast or plant cells.

The methods of the invention may be applied to any plant cell, for example gymnosperm or angiosperm, preferably angiosperm, for example dicotyledonous or monocotyledonous plant cells. Preferred monocotyledonous plant cells are for example corn, wheat, rice, barley, sorghum, musa, sugarcane, miscanthus and brachypodium, especially preferred monocotyledonous plant cells are corn, wheat and rice. Preferred dicotyledonous plant cells are for example soy, rape seed, canola, linseed, cotton, potato, sugar beet, tagetes and Arabidopsis, especially preferred dicotyledonous plant cells are soy, rape seed, canola and potato.

The method of the invention may also be applied to any microorganism. The microorganism may be a bacteria, the bacterial cell may be any gram-positive bacterium or a gram negative bacterium. Gram positive bacteria include, but not limited to, *Bacillus, Brevibacterium, Corynebacterium, Streptococcus, Streptomyces, Staphylococcus, Enterococcus, Lactobacillus, Lactococcus, Clostridium, Geobacillus*, and *Oceanobacillus.*

Gram negative bacteria include, but not limited to, *E. coli, Pseudomonas, Salmonella, Campylobacter, Helicobacter, Acetobacter, Flavobacterium, Fusobacterium, Gluconobacter*. Preferably, the gram negative cell is an *E. coli* cell.

In the methods of the present invention, the bacterial cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. In a preferred aspect, the bacterial cell is a *Bacillus amyloliquefaciens, Bacillus lentus, Bacillus licheniformis, Bacillus stearothermophilus* or *Bacillus subtilis* cell. In a more preferred aspect, the bacterial cell is a *Bacillus licheniformis* cell or a *Bacillus subtilis* cell, preferably a *Bacillus subtilis* cell.

In the methods of the present invention, the bacterial host cell may be *Lactobacillus acidophilus Lactobacillus plantarum, Lactobacillus gasser, Lactobacillus bulgaricusk, Lactobacillus reuter, Staphylococcus aureus, Corynebacterium*, particularly the species *Corynebacterium glutamicum, Corynebacterium acetoglutamicum, Corynebacterium acetoacidophilum, Corynebacterium callunae, Corynebacterium ammoniagenes, Corynebacterium thermoaminogenes, Corynebacterium melassecola* and *Corynebacterium effiziens, Corynebacterium efficiens, Corynebacterium deserti Brevibacterium flavum, Brevibacterium lactofermentum, Brevibacterium divarecatum, Pseudomonas putida, Pseudomonas syringae, Streptoymyces*, particularly the species *Streptomyces coelicolor, Streptomyces Iividans, Streptomyces albus, Streptomyces avermitils, Gluconobacter oxydans, Gluconobacter morbifer, Gluconobacter thailandicus, Acetobacter acet, Clostridium acetobutylicum, Clostridium saccharobutylicum, Clostridium beijerinck, Streptococcus equisimilis, Streptococcus pyogenes, Streptococcus uberis*, and *Streptococcus equi* subsp. *Zooepidemicus*. Another preferred bacteria is *Basfia succiniciproducens*.

The microorganism may be a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia.*

The target nucleic acid molecule may be endogenous to the cell or it may be heterologous to the cell, such as, for example a transgene or a viral nucleic acid molecule.

The doNA molecule and the gNA molecule are covalently bound to each other forming a fusion nucleic acid (fusion NA) molecule. The donor NA molecule may be covalently bound to the spacer NA part of the gNA molecule or to the scaffold NA part of the gNA molecule.

In a preferred embodiment, the donor NA is covalently linked to the scaffold NA part of the gNA molecule.

Most preferably the fusion NA molecule is one molecule, preferably one continuous RNA molecule, wherein all elements (gNA, scaffold NA and doNA) are covalently linked.

The doNA molecule and guide NA molecule may consist of RNA, DNA, PNA. Preferably they consist of RNA or DNA. More preferably the doNA molecule consists of DNA and the guide NA molecule consists of RNA.

In a most preferred embodiment, both guide and donor NA consist of RNA, wherein at least the doNA and gNA are covalently linked to each other forming a fusion ribonucleic acid molecule (fuRNA).

The fuRNA molecule may be introduced into the cell or composition comprising the target NA molecule as an RNA molecule or as one or more expression constructs encoding said fuRNA molecules.

In another embodiment the doNA molecule and gNA molecule may consist of DNA, wherein the doNA and gNA are covalently linked to each other forming a fusion deoxyribonucleic acid molecule (fuDNA).

The fuDNA molecule may be introduced into the cell or composition comprising the target NA molecule as a DNA molecule by various methods as for example transfection, biolistics, electroporation, photoporation, whiskers, sonication, nanobodies or microfluids. It may also be introduced using an agrobacterium as a vehicle which is capable of transferring a T-DNA molecule into a cell but which is not capable to mediate the integration of said T-DNA molecule into the genomic DNA of the target cell. The T-DNA would comprise or consist of the fuDNA molecule.

A further embodiment of the invention is a recombinant fuNA molecule, for example a fuRNA or fuDNA molecule, comprising a doNA molecule covalently linked to a gNA molecule.

Another embodiment of the invention is a vector comprising an expression construct comprising a promoter functionally linked to a DNA molecule encoding the fuNA molecule of the invention.

A further embodiment of the invention is a cell comprising a fuNA molecule of the invention and a nucleic acid modifying polypeptide.

A further embodiment of the invention is a vector system comprising a. a first vector comprising an expression construct comprising a promoter functionally linked to a DNA molecule encoding the fuNA molecule of the invention and
b. a second vector encoding a site directed nucleic acid modifying polypeptide and optionally
c. a third vector encoding one part of the scaffold NA molecule.

In a preferred embodiment, the vector under a. comprises an expression construct encoding a fuNA molecule comprising a spacerNA, scaffold NA and doNA.

The vector under c. is necessary and part of the vector system of the invention if the scaffold NA is consisting of two molecules and if the vector under a. is encoding a fusion NA molecule comprising only one molecule of the scaffold NA molecule and is not encoding the second molecule of the scaffold NA molecule.

A system for modification of a target NA in a cell comprising

A. a first vector comprising an expression construct comprising a promoter functionally linked to a DNA molecule encoding the fuNA molecule of the invention and
B. a second vector encoding a site directed nucleic acid modifying polypeptide and
C. a cell comprising a target NA molecule and optionally
D. a third vector encoding one part of the scaffold NA molecule.

is another embodiment of the invention. In a preferred embodiment, the vector under A. comprises an expression construct encoding a fuNA molecule comprising a spacerNA, scaffold NA and doNA. The vector under D. is necessary and part of the system of the invention if the scaffold NA is consisting of two molecules and if the vector under A. is encoding a fusion NA molecule comprising only one molecule of the scaffold NA molecule and is not encoding the second molecule of the scaffold NA molecule.

Another embodiment of the invention is a composition comprising a. a first vector comprising an expression construct comprising a promoter functionally linked to a DNA molecule encoding the fuNA molecule of the invention and
b. a second vector encoding a site directed nucleic acid modifying polypeptide and
c. a cell comprising a target NA molecule and optionally
d. a third vector encoding one part of the scaffold NA molecule.

In a preferred embodiment, the vector under a. comprises an expression construct encoding a fuNA molecule comprising a spacerNA, scaffold NA and doNA. The vector under d. is necessary and part of the composition of the invention if the scaffold NA is consisting of two molecules and if the vector under a. is encoding a fusion NA molecule comprising only one molecule of the scaffold NA molecule and is not encoding the second molecule of the scaffold NA molecule.

The use of the vector of the invention, the vector system of the invention, the system of the invention and/or the composition of the invention for modification of a target NA molecule in a cell or composition is also an embodiment of the invention.

Definitions

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Donor NA: the term "donor NA" or "doNA" means a nucleic acid comprising two homology arms each comprising at least 15 bases complementary to two different areas of at least 15 consecutive bases of the target NA, wherein said two homology arms are directly adjacent to each other or are separated by one or more additional bases.

The two different areas of the target NA to which the homology arms are complementary may be directly adjacent to each other or may be separated by additional bases of up to 20 kb, preferably up to 10 kb, preferably up to 5 kb, more preferably up to 3 kb, more preferably up to 2.5 kb, more preferably up to 2 kb.

In the event a homology arm comprises more than 15 bases, it may be 100% complementary to the target NA or it may be at least 75% complementary, preferably at least 80% complementary, more preferably at least 85% complementary, more preferably at least 90% complementary, more preferably at least 95% complementary, more preferably at least 98% complementary to the target NA, wherein the homology arm comprises at least one stretch of at least 15 bases that are 100% complementary to a stretch of the same number of consecutive bases in the target NA, preferably the homology arm comprises at least one stretch of at least 18 bases that are 100% complementary to a stretch of the same number of consecutive bases in the target NA, more preferably the homology arm comprises at least one stretch of at least 20 bases that are 100% complementary to a stretch of the same number of consecutive bases in the target NA, even more preferably the homology arm comprises at least one stretch of at least 25 bases that are 100% complementary to a stretch of the same number of consecutive bases in the target NA, even more preferably the homology arm comprises at least one stretch of at least 50 bases that are 100% complementary to a stretch of the same number of consecutive bases in the target NA.

The homology arms may have the same length and/or the same degree of complementarity to the target NA or may have different length and/or different degrees of complementarity to the target NA.

The homology arms may be directly adjacent to each other or may be separated by a nucleic acid molecule comprising at least one base not present between the regions in the target nucleic acid complementary to the homology arms.

Spacer NA: the term "spacer nucleic acid" or "spacer NA" means a nucleic acid comprising at least 12 bases 100% complementary to the target NA.

In the event the spacer NA comprises more than 12 bases, it may be at least 75% complementary to the target NA, preferably at least 80% complementary, more preferably at least 85% complementary, more preferably at least 90% complementary, more preferably at least 95% complementary, more preferably at least 98% complementary most preferably it is 100% complementary to the target NA, wherein the spacer NA comprises at least one stretch of at least 12 bases that are 100% complementary to a stretch of the same number of consecutive bases in the target NA, preferably the spacer NA comprises at least one stretch of at least 15 bases that are 100% complementary to a stretch of the same number of consecutive bases in the target NA, preferably the spacer NA comprises at least one stretch of at least 18 bases that are 100% complementary to a stretch of the same number of consecutive bases in the target NA, more preferably the spacer NA comprises at least one stretch of at least 20 bases that are 100% complementary to a stretch of the same number of consecutive bases in the target NA, even more preferably the spacer NA comprises at least one stretch of at least 25 bases that are 100% complementary to a stretch of the same number of consecutive bases in the target NA, even more preferably the spacer NA comprises at least one stretch of at least 50 bases that are 100% complementary to a stretch of the same number of consecutive bases in the target NA.

The spacer NA is covalently linked to a scaffold NA. If the scaffold NA is consisting of two nucleic acid molecules, the spacer is covalently linked to one molecule of a scaffold NA.

Scaffold NA: the scaffold nucleic acid or scaffold NA comprises a nucleic acid forming a secondary structure comprising at least one hairpin, preferably at least two hairpins and/or a sequence that is/are bound by the site directed nucleic acid modifying polypeptide. Such site directed nucleic acid modifying polypeptides are known in the art, for example in WO/2014/150624; WO/2014/204728. The scaffold NA further comprises two regions each comprising at least eight bases being complementary to each other, hence capable to hybridize forming a double-stranded structure. If said regions of at least eight bases complementary to each other are comprising more than eight bases, each region comprises at least eight bases that are complementary to at least eight bases of the other region.

The two complementary regions of the scaffold NA may be covalently linked to each other via a linker molecule forming a hairpin structure or may consist of two independent nucleic acid molecules.

Guide NA: the guide nucleic acid or guide NA or gNA comprises a spacer nucleic acid and a scaffold nucleic acid wherein the spacer NA and the scaffold NA are covalently linked to each other. In the event the scaffold NA consists of two molecules, the spacer NA is covalently linked to one molecule of the scaffold NA whereas the other molecule of the scaffold NA molecule hybridizes to the first scaffold NA molecule. Hence, a guide NA molecule may consist of one nucleic acid molecule or may consist of two nucleic acid molecules. Preferably the guide NA consists of one molecule.

Fusion NA: the fusion nucleic acid comprises donor NA and guide NA, wherein the guide NA and the donor NA are covalently linked to each other.

Site directed nucleic acid modifying polypeptide: By "site directed nucleic acid modifying polypeptide" "nucleic acid-binding site directed nucleic acid modifying polypeptide" or "site directed polypeptide" it is meant a polypeptide that binds nucleic acids and is targeted to a specific nucleic acid sequence. A site-directed nucleic acid modifying polypeptide as described herein is targeted to a specific nucleic acid sequence in the target nucleic acid either by mechanism intrinsic to the polypeptide or, preferably by the nucleic acid molecule to which it is bound. The nucleic acid molecule bound by the polypeptide comprises a sequence that is complementary to a target sequence within the target nucleic acid, thus targeting the bound polypeptide to a specific location within the target nucleic acid (the target sequence).

Most site directed nucleic acid modifying polypeptides introduce dsDNA breaks, but they may be modified to have only nicking activity or the nuclease activity may be inactivated. The site directed nucleic acid modifying polypeptides may be bound to a further polypeptide having an activity such as fluorescence or nuclease activity such as the nuclease activity of the FokI polypeptide or a homing endonuclease polypeptide such as I-SceI.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as start codon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, densitometric measurement of nucleic acid concentration in a gel, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS)

can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional fragment: the term "functional fragment" refers to any nucleic acid and/or protein which comprises merely a part of the full length nucleic acid and/or full length polypeptide of the invention but still provides the same function, i.e. the function of an AAT enzyme catalyzing the reaction of acryloyl-CoA and butanol to n-BA and CoA. Preferably, the fragment comprises at least 50%, at least 60%, at least 70%, at least 80%, at least 90% at least 95%, at least 98%, at least 99% of the sequence from which it is derived. Preferably, the functional fragment comprises contiguous nucleic acids or amino acids of the nucleic acid and/or protein from which the functional fragment is derived. A functional fragment of a nucleic acid molecule encoding a protein means a fragment of the nucleic acid molecule encoding a functional fragment of the protein.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., Sambrook J, Fritsch E F and Maniatis T (1989); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self-replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350;

WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41 (% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6. Suitable hybridization conditions are for example hybridizing under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (low stringency) to a nucleic acid molecule comprising at least 50, preferably at least 100, more preferably at least 150, even more preferably at least 200, most preferably at least 250 consecutive nucleotides of the complement of a sequence. Other suitable hybridizing conditions are hybridization in 7% sodium dodecyl sulfate (SDS), 0.5 M $NaPO_4$, 1 mM EDTA at 50° C. with washing in 1×SSC, 0.1% SDS at 50° C. (medium stringency) or 65° C. (high stringency) to a nucleic acid molecule comprising at least 50, preferably at least 100, more preferably at least 150, even more preferably at least 200, most preferably at least 250 consecutive nucleotides of a complement of a sequence. Other suitable hybridization conditions are hybridization in 7% sodium dodecyl sulfate (SDS), 0.5 M $NaPO_4$, 1 mM EDTA at 50° C. with washing in 0.1×SSC, 0.1% SDS at 65° C. (very high stringency) to a nucleic acid molecule comprising at least 50, preferably at least 100, more preferably at least 150, even more preferably at least 200, most preferably at least 250 consecutive nucleotides of a complement of a sequence.

"Identity": "Identity" when used in respect to the comparison of two or more nucleic acid or amino acid molecules means that the sequences of said molecules share a certain degree of sequence similarity, the sequences being partially identical.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs “Gap” and “Needle”, which are both based on the algorithms of Needleman and Wunsch (J. Mol. Biol. 48; 443 (1970)), and “BestFit”, which is based on the algorithm of Smith and Waterman (Adv. Appl. Math. 2; 482 (1981)). “Gap” and “BestFit” are part of the GCG software-package (Genetics Computer Group, 575 Science Drive, Madison, Wis., USA 53711 (1991); Altschul et al., (Nucleic Acids Res. 25, 3389 (1997)), “Needle” is part of the The European Molecular Biology Open Software Suite (EMBOSS) (Trends in Genetics 16 (6), 276 (2000)). Therefore preferably the calculations to determine the percentages of sequence identity are done with the programs “Gap” or “Needle” over the whole range of the sequences. The following standard adjustments for the comparison of nucleic acid sequences were used for “Needle”: matrix: EDNAFULL, Gap_penalty: 10.0, Extend_penalty: 0.5. The following standard adjustments for the comparison of nucleic acid sequences were used for “Gap”: gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program “Needle” with the above parameter set, has a 80% identity. Preferably the identity is calculated on the complete length of the query sequence, for example SEQ ID NO: 1.

Isolated: The term “isolated” as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term “isolated” when used in relation to a nucleic acid molecule, as in “an isolated nucleic acid sequence” refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single- or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Non-coding: The term “non-coding” refers to sequences of nucleic acid molecules that do not encode part or all of an expressed protein. Non-coding sequences include but are not limited enhancers, promoter regions, 3' untranslated regions, and 5' untranslated regions. Nucleic acids and nucleotides: The terms “nucleic acids” and “Nucleotides” refer to naturally occurring or synthetic or artificial nucleic acid or nucleotides. The terms “nucleic acids” and “nucleotides” comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term “nucleic acid” is used interchangeably herein with “gene”, “cDNA, “mRNA”, “oligonucleotide,” and “nucleic acid molecule”. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase “nucleic acid sequence” refers to a single- or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. “Nucleic acid sequence” also refers to a consecutive list of abbreviations, letters, characters or words, which represent nucleotides. In one embodiment, a nucleic acid can be a “probe” which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or -5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with at least one recombinant nucleic acid molecule.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used inter-changeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, dsRNA) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e.g., when the genetic modification affects coding nucleic acid sequences of the microorganism) as compared to the wild type microorganism from which it was derived. A recombinant microorganism comprises at least one recombinant nucleic acid molecule.

The term "recombinant" with respect to nucleic acid molecules refers to nucleic acid molecules produced by man using recombinant nucleic acid techniques. The term comprises nucleic acid molecules which as such do not exist in nature or do not exist in the organism from which the nucleic acid molecule is derived, but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecules" may also comprise a "recombinant construct" which comprises, preferably operably linked, a sequence of nucleic acid molecules not naturally occurring in that order. Preferred methods for producing said recombinant nucleic acid molecules may comprise cloning techniques, directed or non-directed mutagenesis, gene synthesis or recombination techniques.

An example of such a recombinant nucleic acid molecule is a plasmid into which a heterologous DNA-sequence has been inserted or a gene or promoter which has been mutated compared to the gene or promoter from which the recombinant nucleic acid molecule derived. The mutation may be introduced by means of directed mutagenesis technologies known in the art or by random mutagenesis technologies such as chemical, UV light or x-ray mutagenesis or directed evolution technologies.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

FIGURES

FIGS. 1 to 12 depict preferred structures of the fusion nucleic acid molecules of the invention. A site directed nucleic acid modifying polypeptide is directed to the target sequence within the target double-stranded nucleic acid by a guide NA fused to a donor NA (which together form the fuNA molecule).

FIG. 1

Fusion NA molecule comprising from 5' to 3': the guide NA (spacer followed by scaffold), homology arm 1 and 2 optionally separated by an additional nucleic acid region.

FIG. 2

Fusion NA molecule comprising from 5' to 3': homology arm 2 and 1 optionally separated by an additional nucleic acid region, and the guide NA (scaffold followed by spacer)

FIG. 3

Fusion NA molecule comprising from 5' to 3': the guide NA (spacer followed by scaffold), homology arm 2 and 1 optionally separated by an additional nucleic acid region.

FIG. 4

Fusion NA molecule comprising from 5' to 3': homology arm 1 and 2 optionally separated by an additional nucleic acid region, and the guide NA (scaffold followed by spacer).

FIG. 5

Fusion NA molecule comprising from 5' to 3': homology arm 1 and 2 optionally separated by an additional nucleic acid region, and the guide NA (spacer followed by scaffold).

FIG. 6

Fusion NA molecule comprising from 5' to 3': the guide NA (scaffold followed by spacer), homology arm 1 and 2 optionally separated by an additional nucleic acid region.

FIG. 7

Fusion NA molecule comprising from 5' to 3': homology arm 2 and 1 optionally separated by an additional nucleic acid region, and the guide NA (spacer followed by scaffold).

FIG. 8

Fusion NA molecule comprising from 5' to 3': the guide NA (scaffold followed by spacer), homology arm 2 and 1 optionally separated by an additional nucleic acid region.

FIG. 9

Fusion NA molecules comprising from 5' to 3': guide NA (comprising spacer and first molecule of the scaffold), homology arm 1 and 2 optionally separated by an additional nucleic acid region. The second molecule of the scaffold is hybridizing to the first molecule of the scaffold.

FIG. 10

Fusion NA molecules comprising from 5' to 3': homology arm 1 and 2 optionally separated by an additional nucleic acid region, guide NA (comprising first molecule of the scaffold and spacer). The second molecule of the scaffold is hybridizing to the first molecule of the scaffold.

FIG. 11

Fusion NA molecules comprising from 5' to 3': guide NA (comprising spacer and first molecule of the scaffold), homology arm 2 and 1 optionally separated by an additional nucleic acid region. The second molecule of the scaffold is hybridizing to the first molecule of the scaffold.

FIG. 12

Fusion NA molecules comprising from 5' to 3': homology arm 2 and 1 optionally separated by an additional nucleic acid region, guide NA (comprising first molecule of the scaffold, spacer, and second molecule of the scaffold hybridizing to the first molecule of the scaffold).

FIG. 13

Vector RWL121.

FIG. 14

Vector Cas003.

FIG. 15

Vector Cas018.

FIG. 16

Vector Cas006.

FIG. 17

Vector RWL137.

FIG. 18

Vector Cas019.

FIG. 19

Vector RLW138.

FIG. 20

Vector Cas020.

FIG. 21

Vector RLW139.

Figure 22:
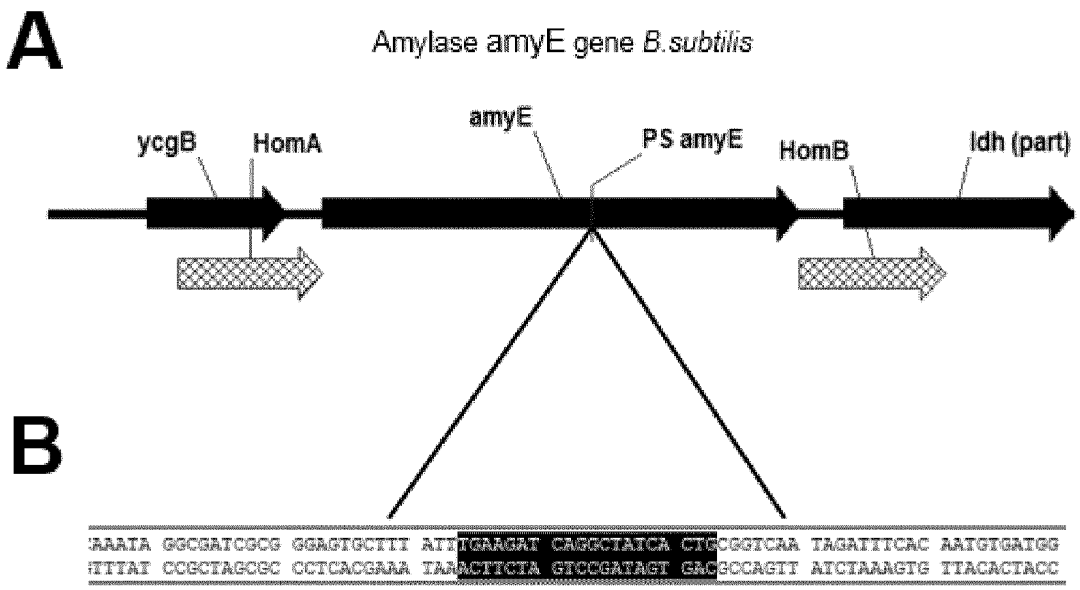

FIG. 22 shows the amylase amyE locus of *B. subtilis* ATCC6051 strain (A) with the location of the homology regions HomA and HomB as indicated. The location of the protospacer sequence PS within in the amyE gene is indicated (A) and the sequence of the PS highlighted (black with white letters, B) (top strand is SEQ ID NO: 74; bottom strand is SEQ ID NO: 75).

FIG. 23 shows the vector map of the pCC004 plasmid—the derivative of the pJOE8999 plasmid carrying the amyE protospacer and the homology regions HomA and HomB of the region adjacent to the amyE gene. PS=protospacer; PvanP*=hemisynthetic promoter; ‘gRNA=guideRNA; lambda T0 terminator; PmanP=promoter of the manP gene *B. subtilis*; Cas9=endonuclease from S. pyrogenes; KanR=kanamycin resistance gene; origin of pUC for replication in *E. coli*, origin of pE194 for replication in *Bacillus*.

Figure 2:
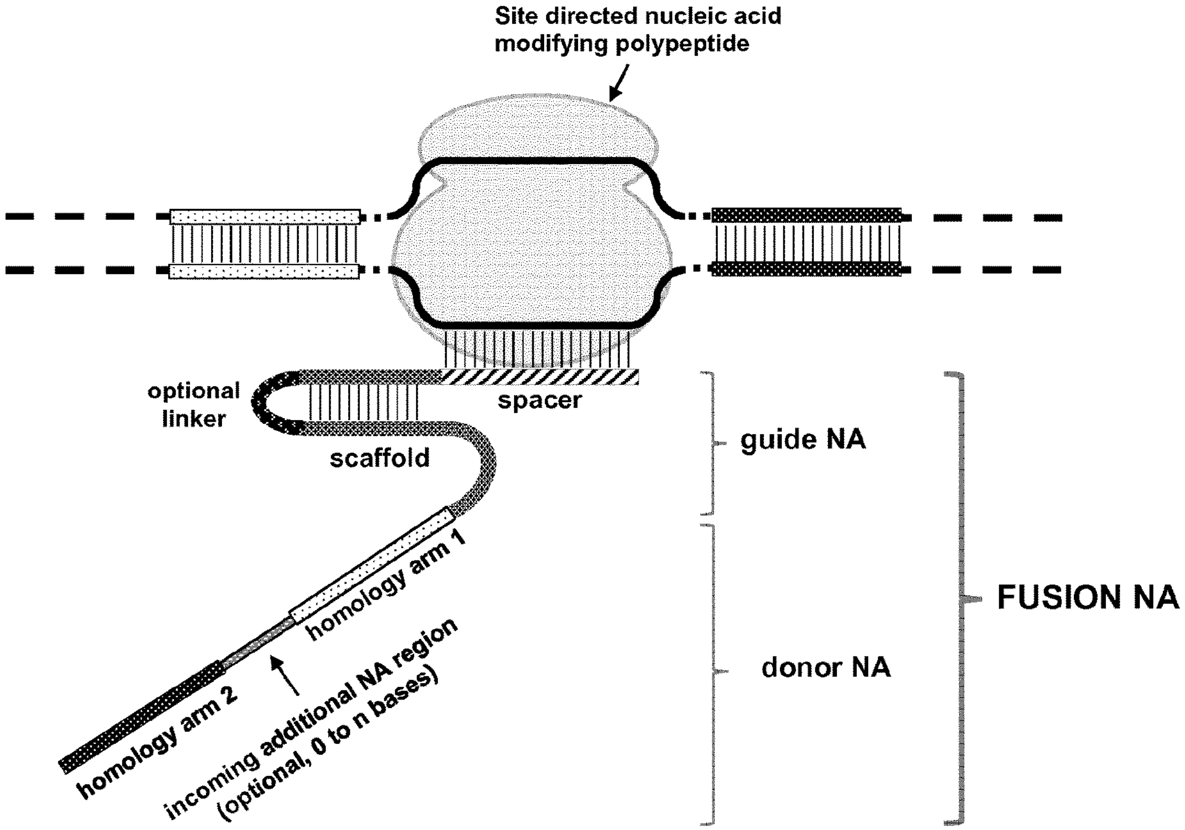
Figure 3:
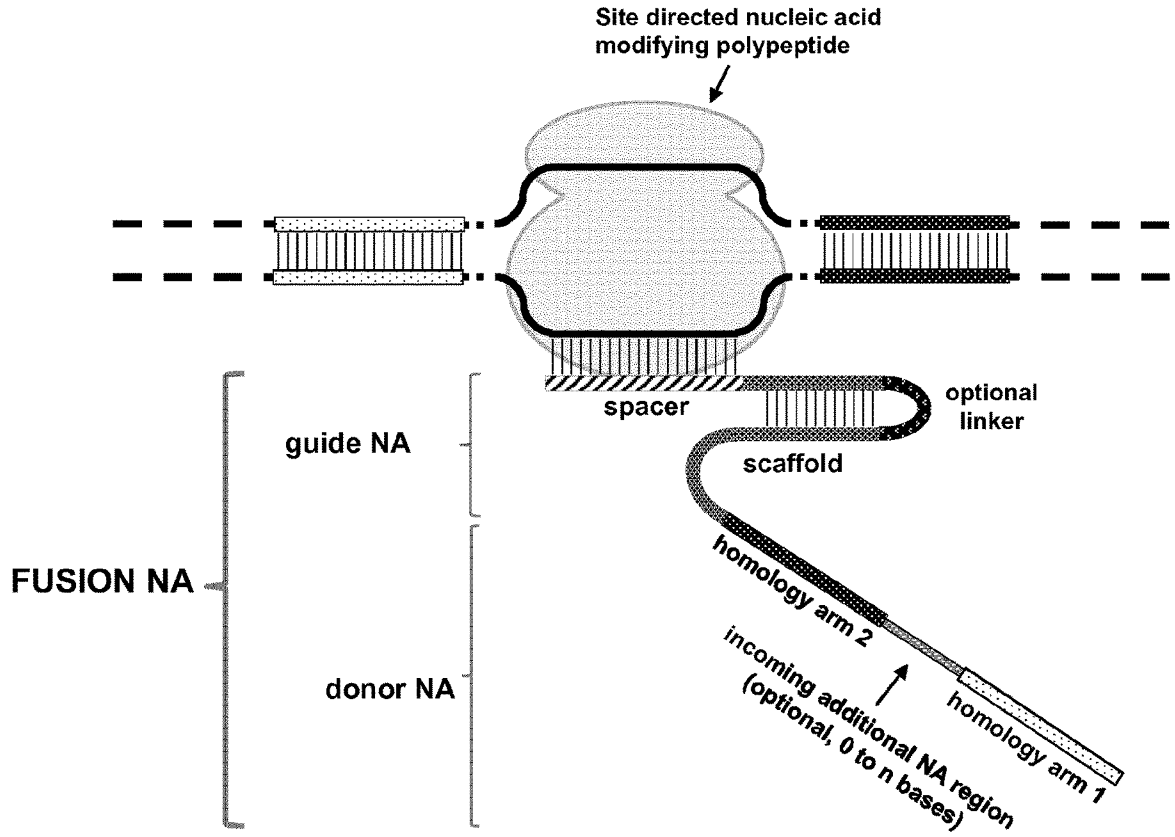
Figure 4:
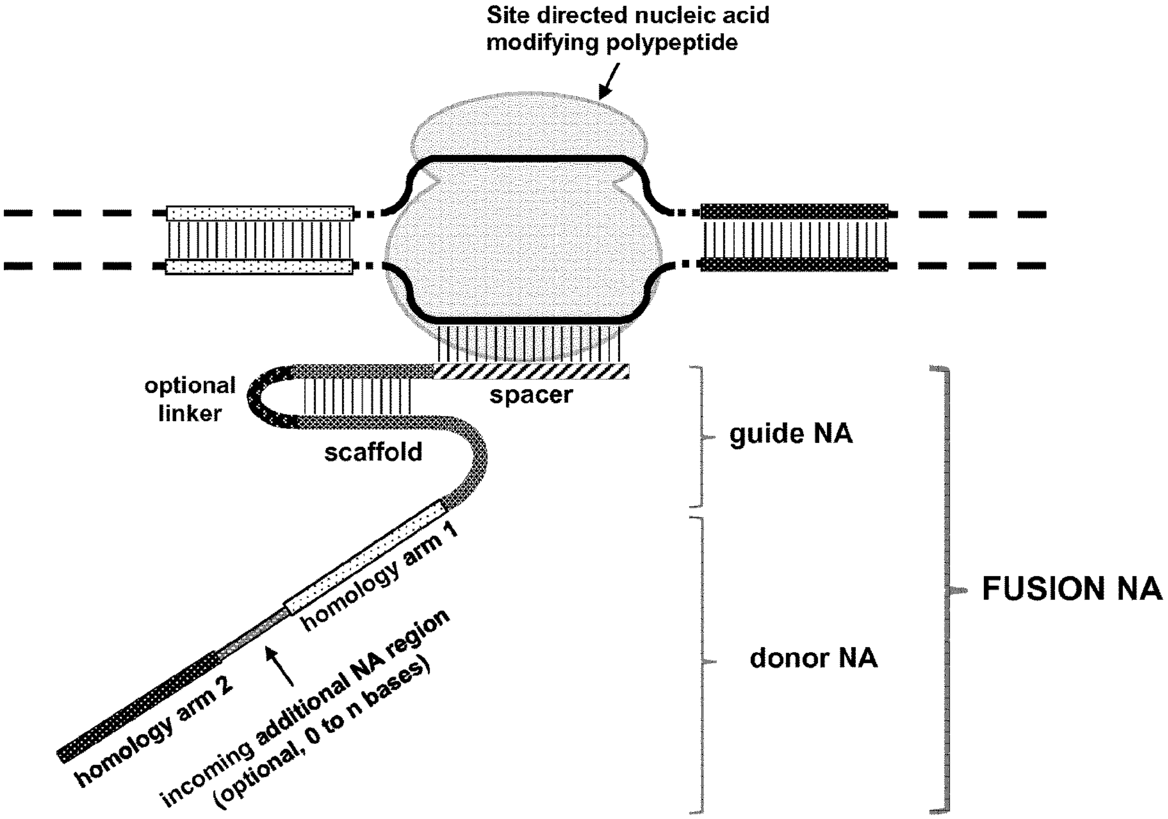
Figure 5:
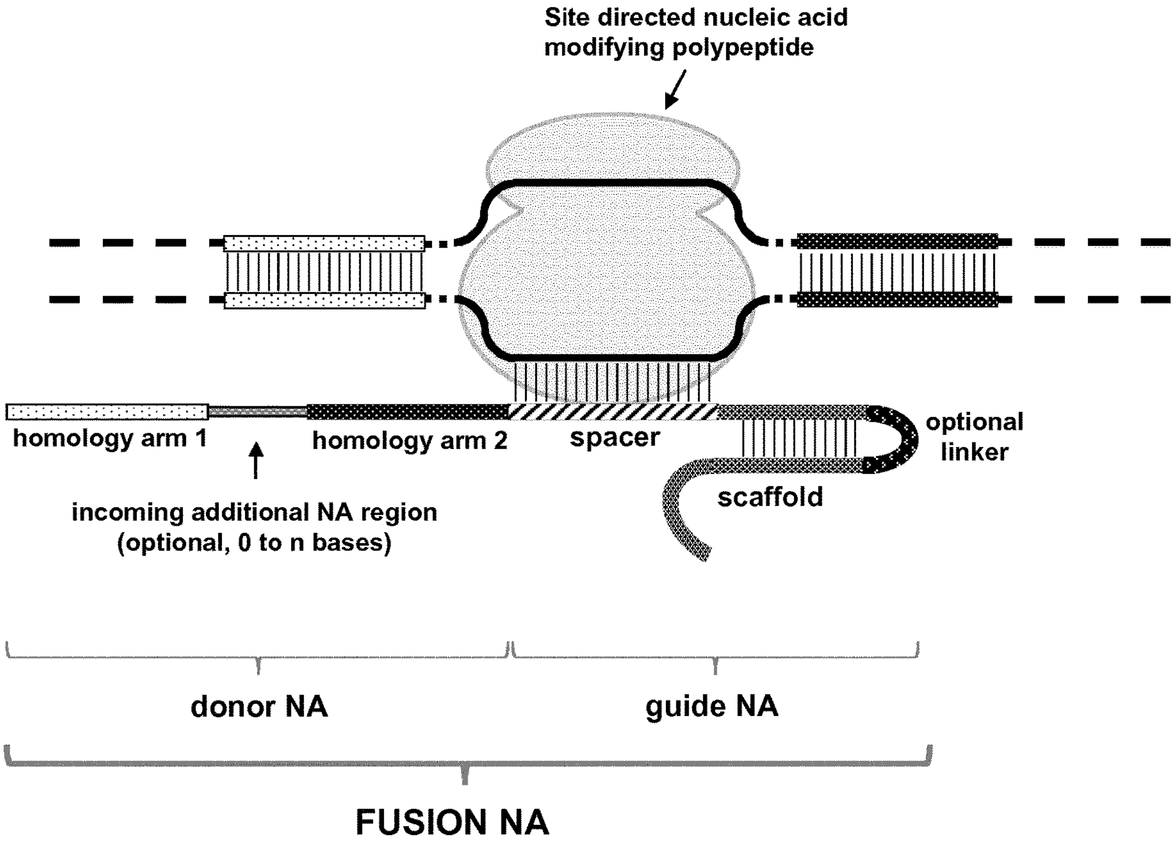
Figure 6:
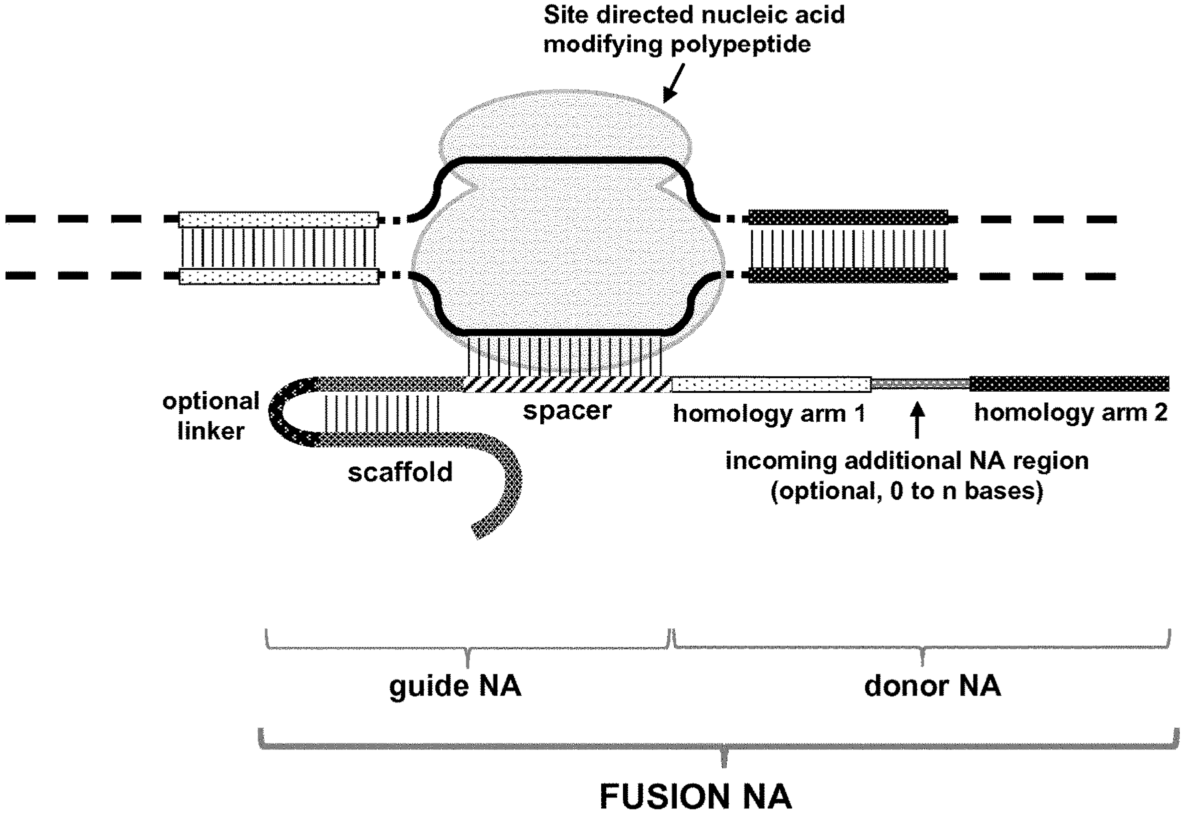
Figure 7:
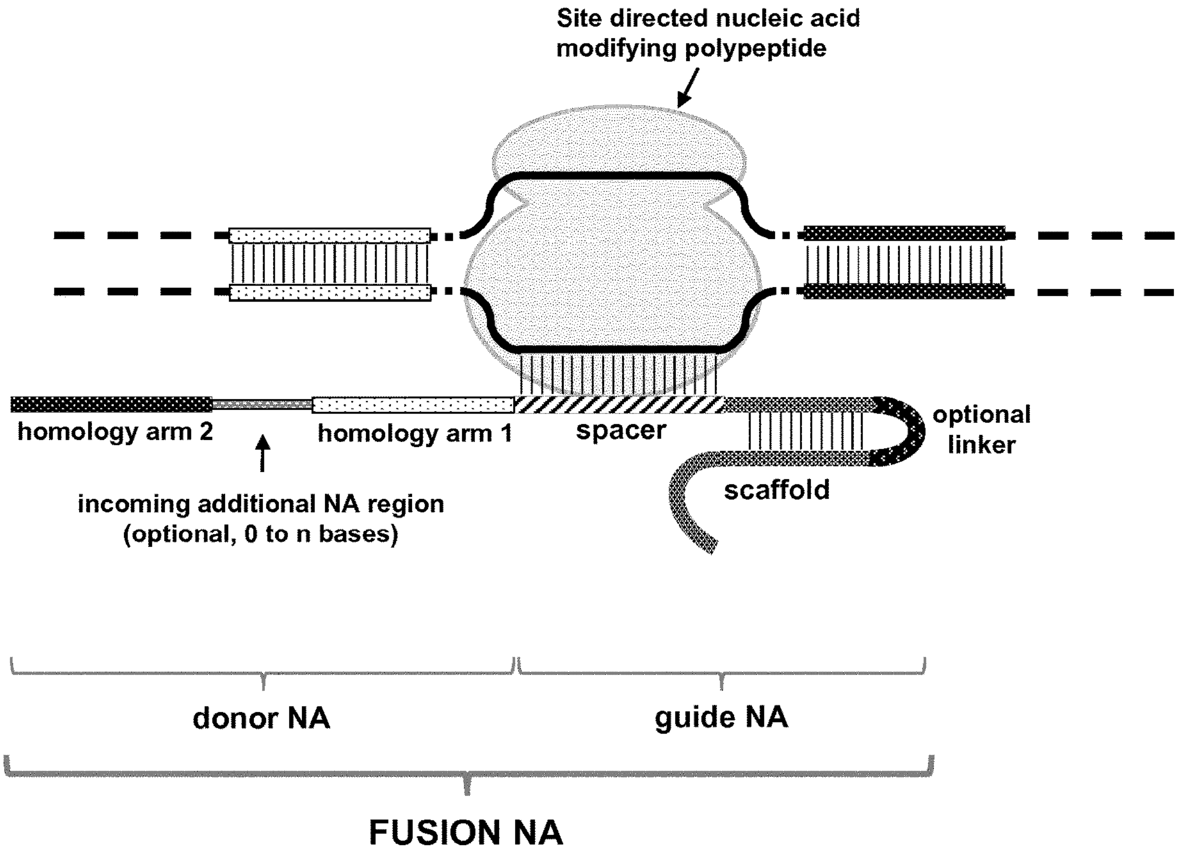
Figure 8:
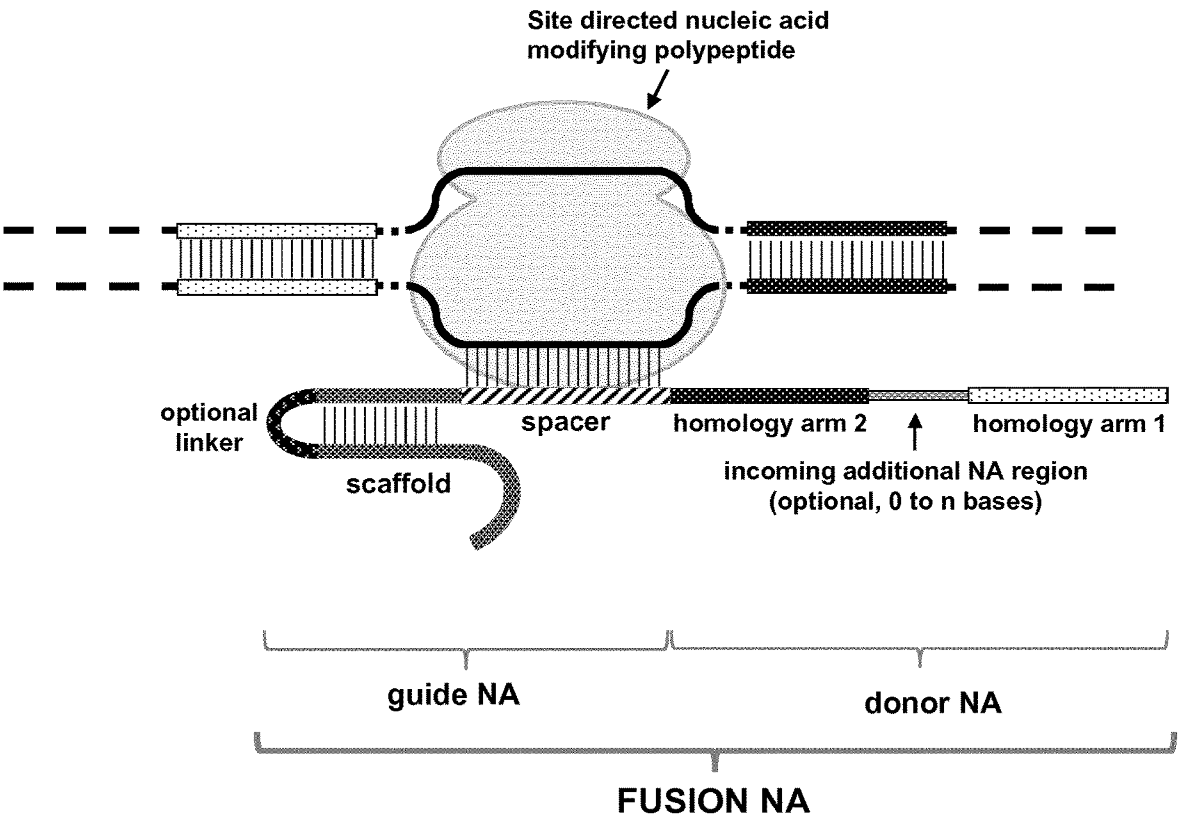
Figure 9:
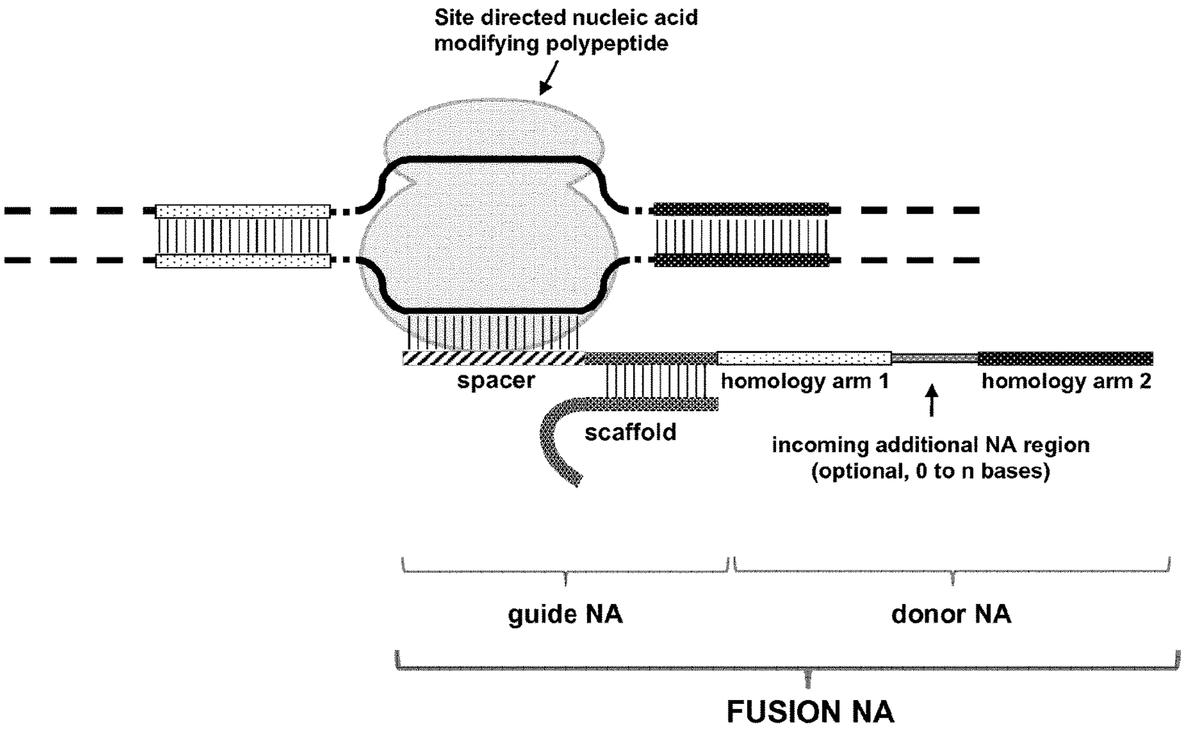
Figure 10:
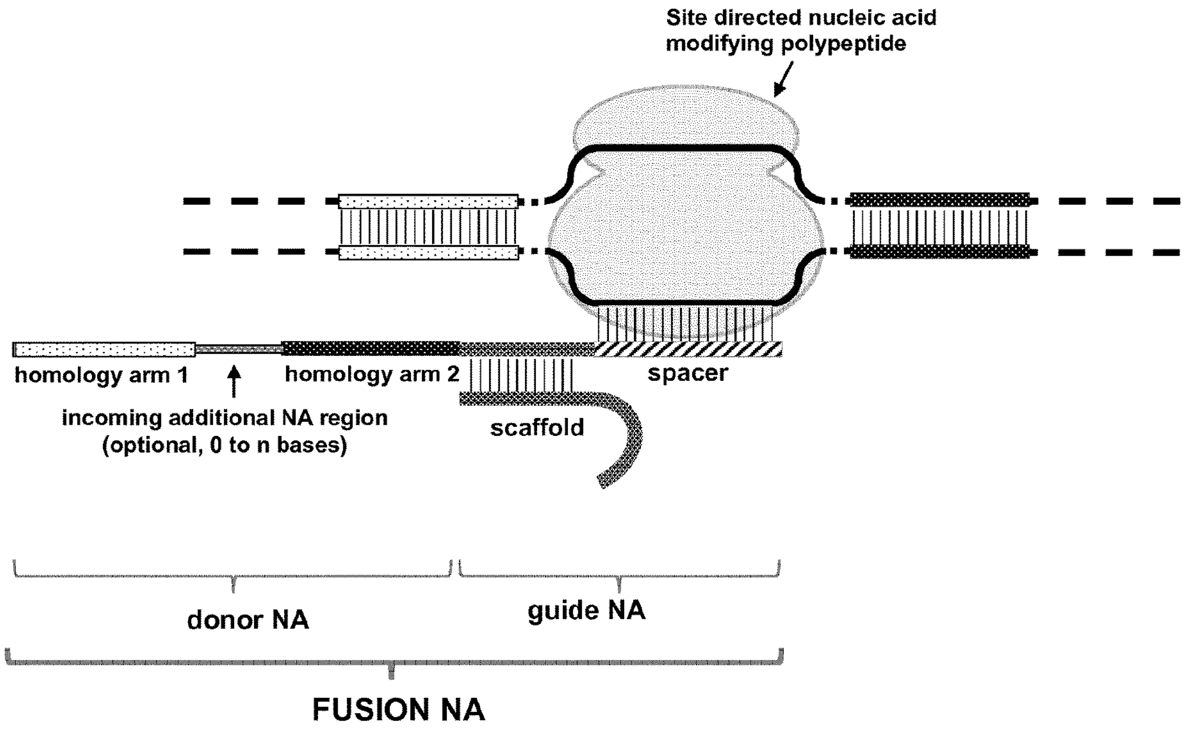
Figure 11:
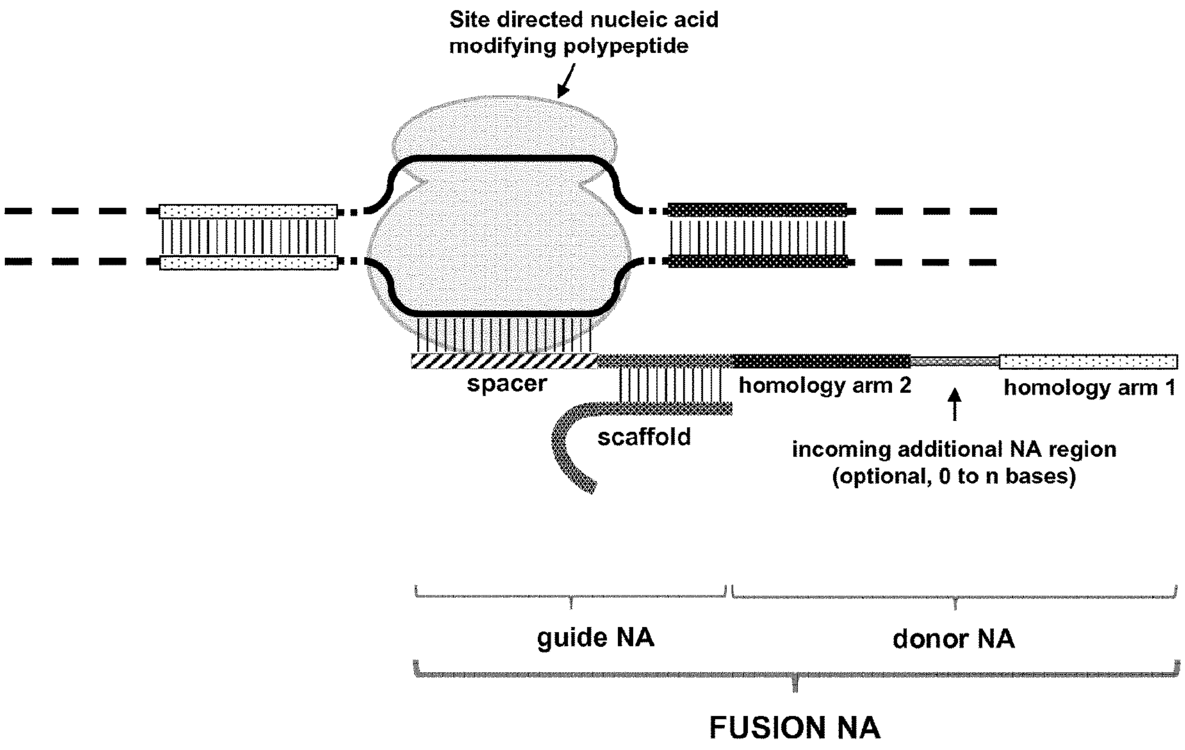
Figure 12:
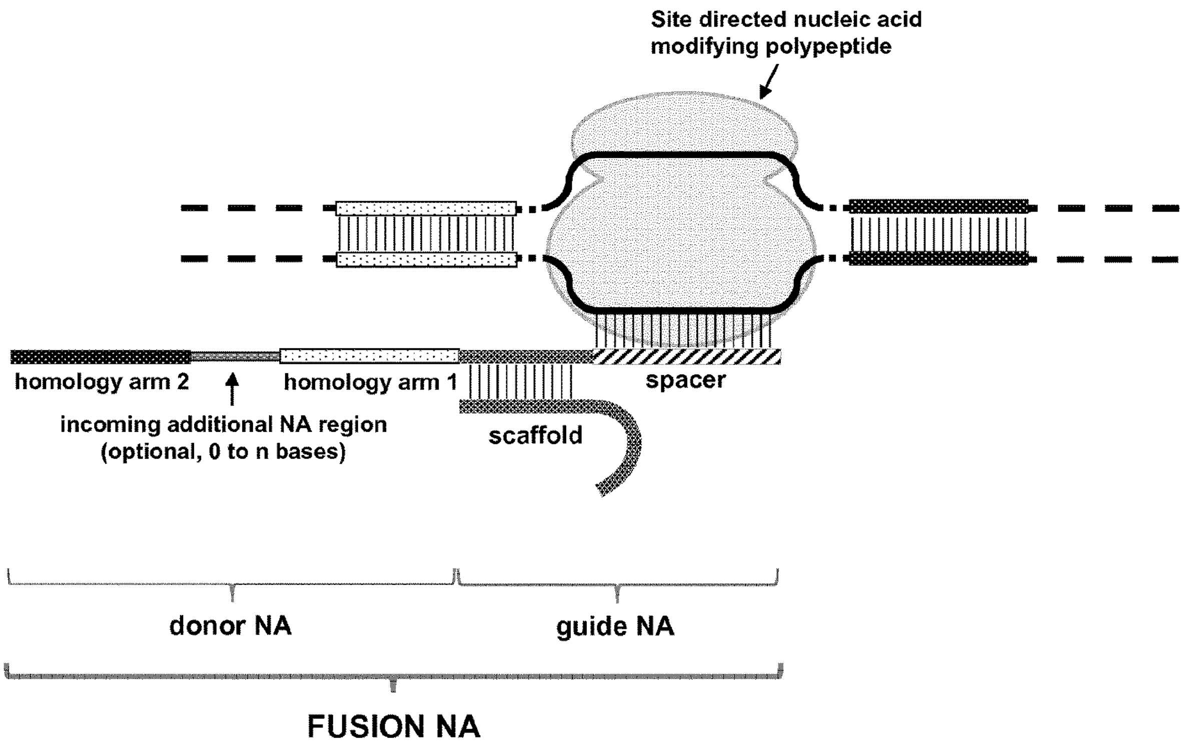
Figure 13:
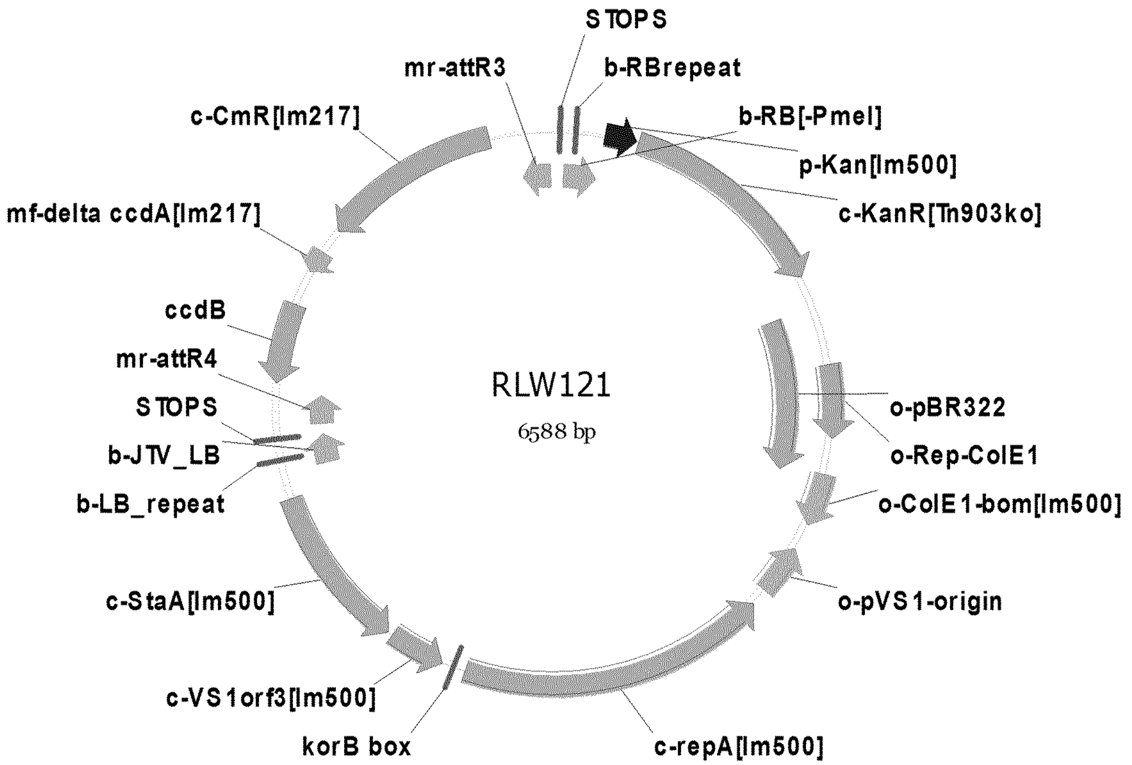
Figure 14:
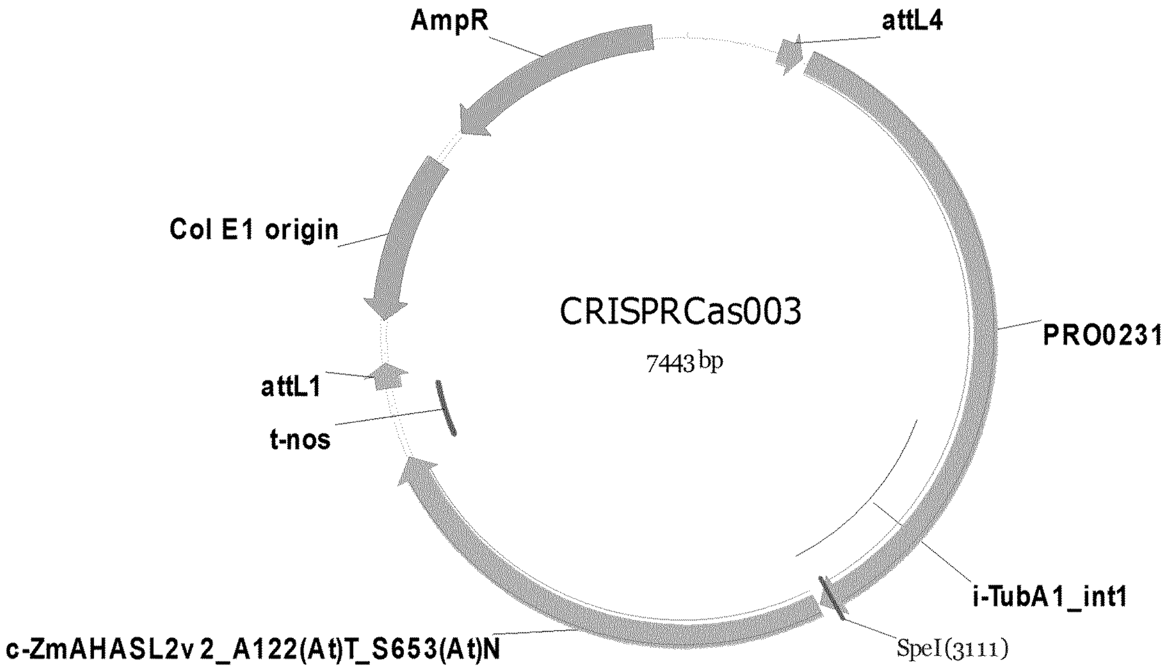
Figure 15:
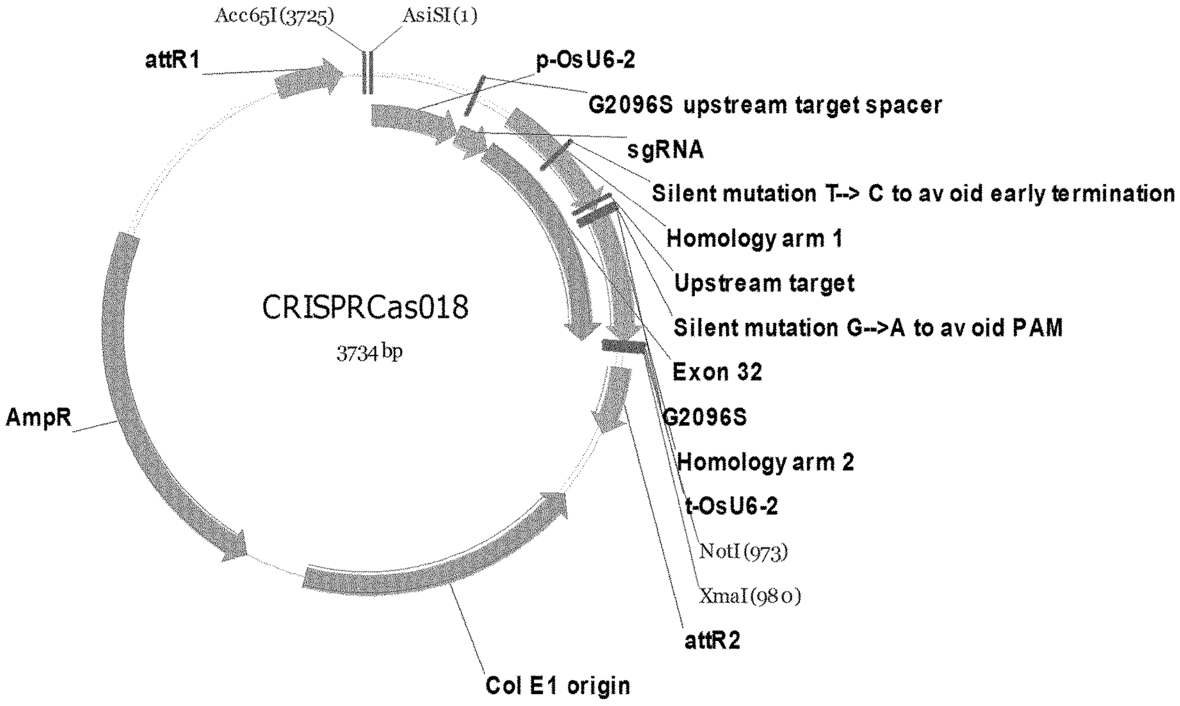
Figure 16:
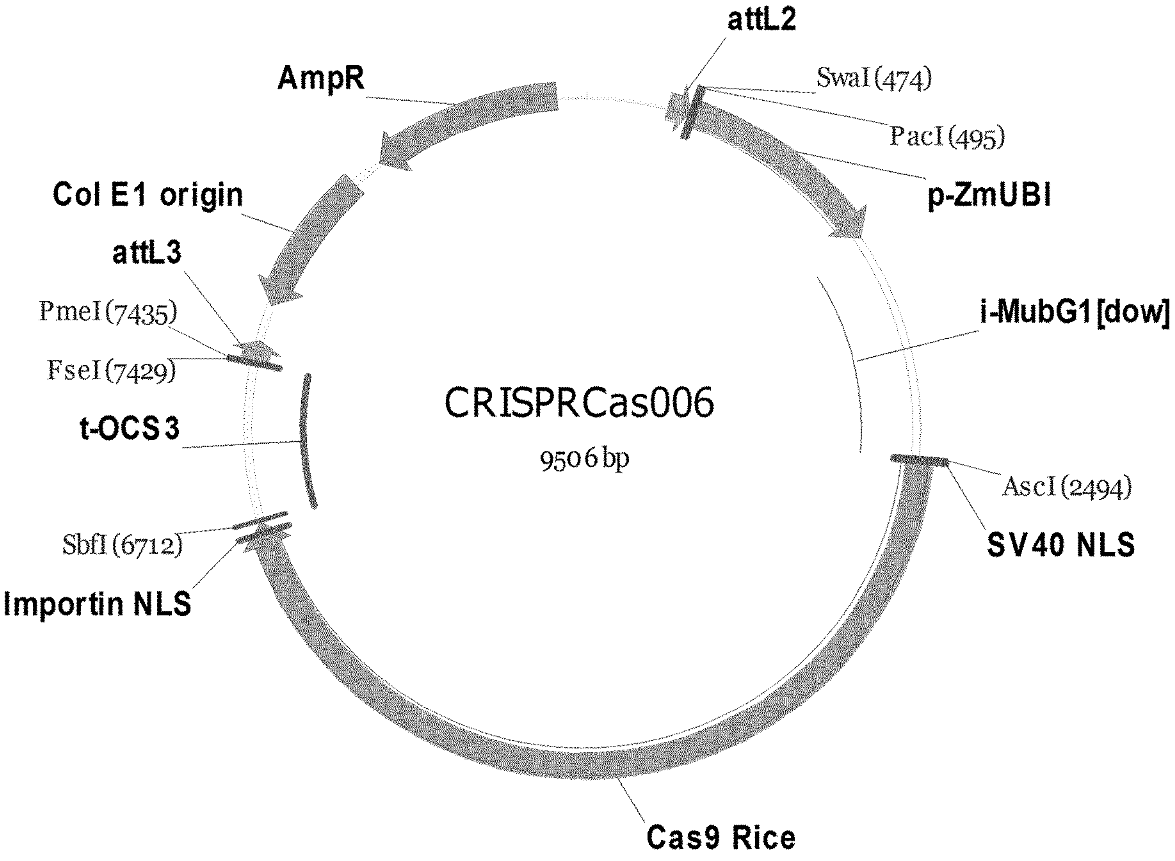
Figure 17:
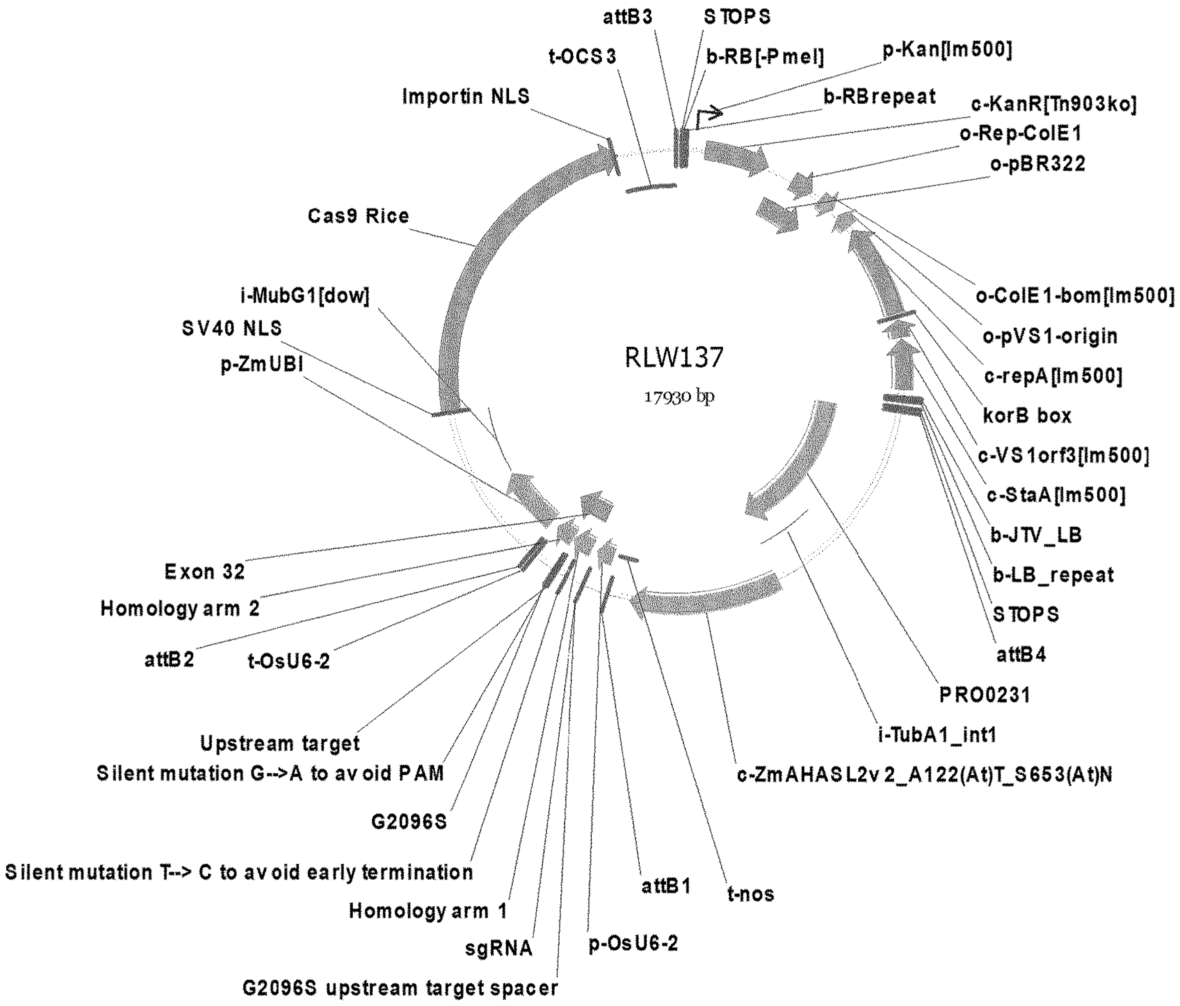
Figure 18:
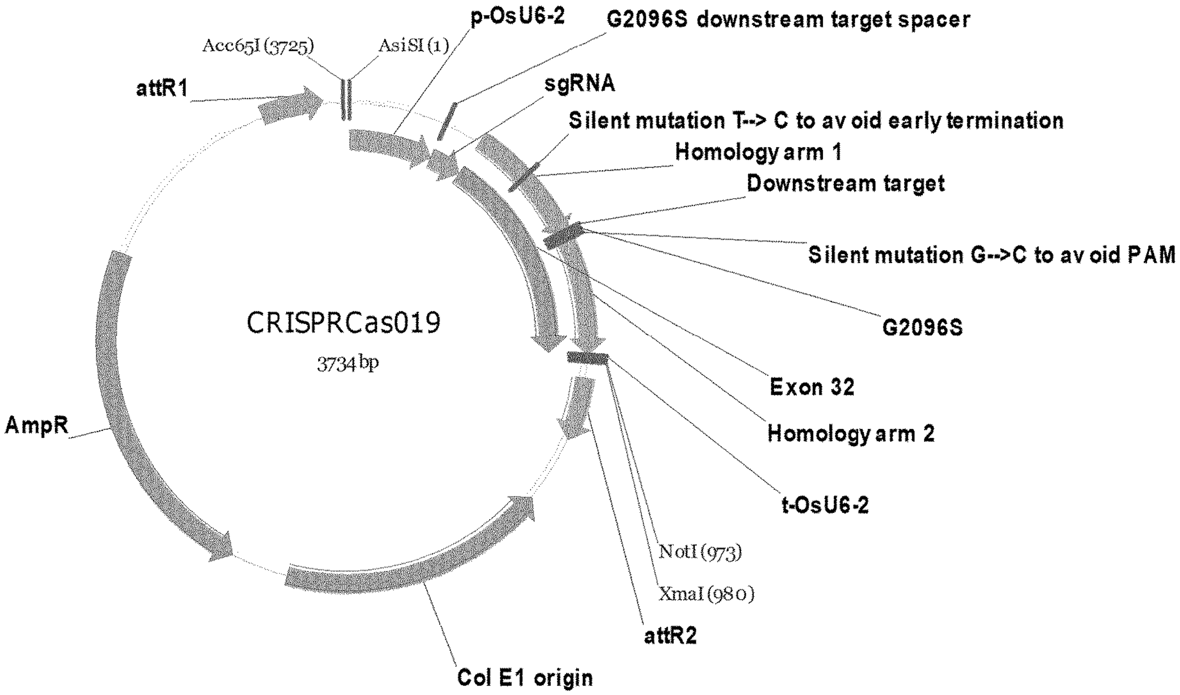
Figure 19:
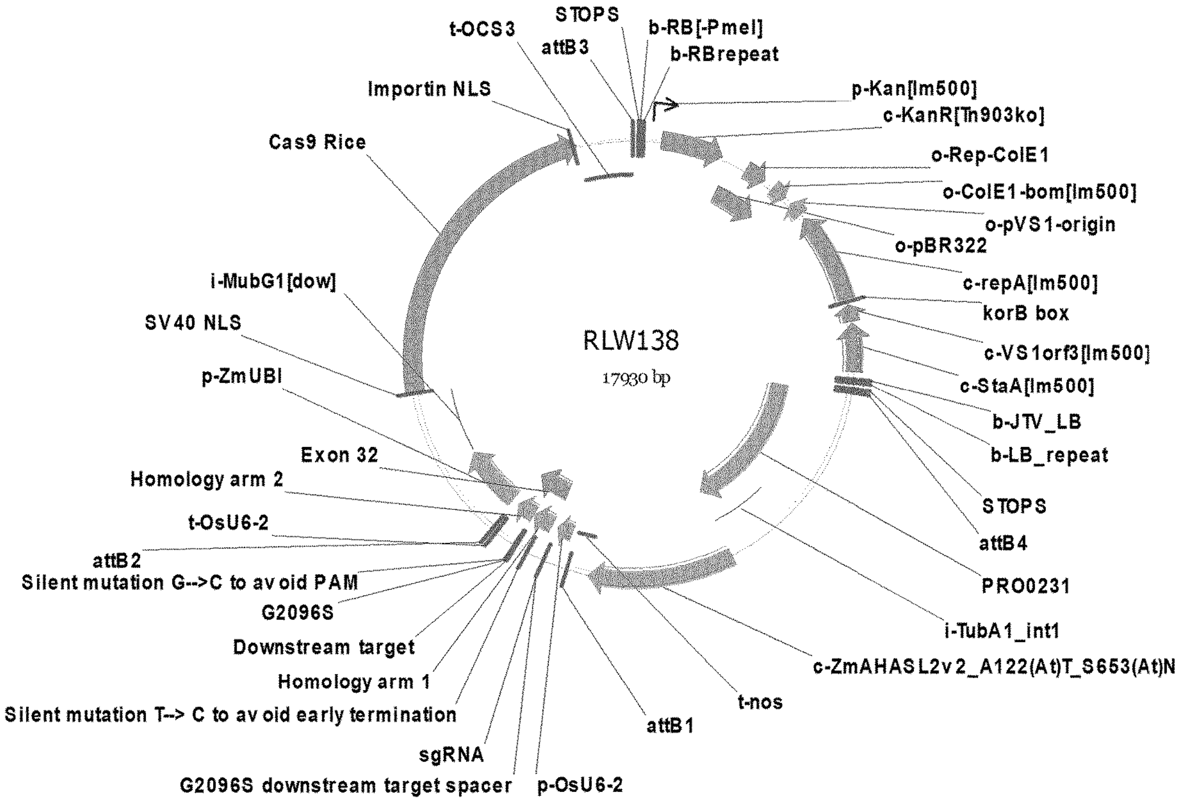
Figure 20:
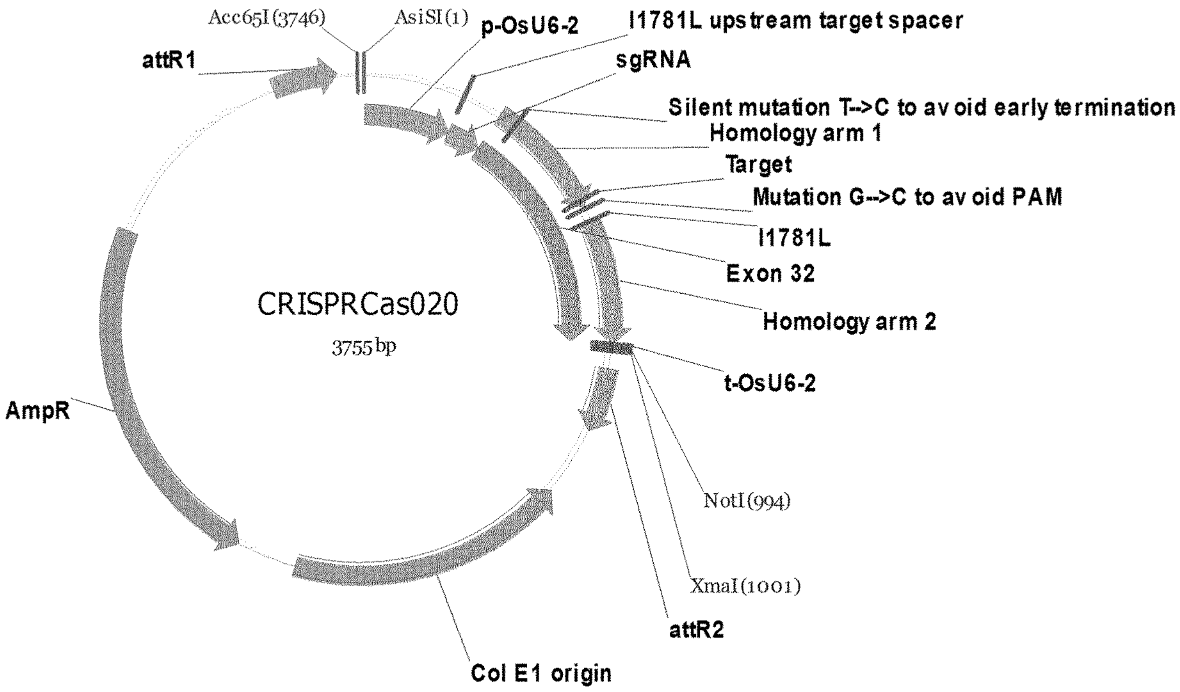
Figure 21:
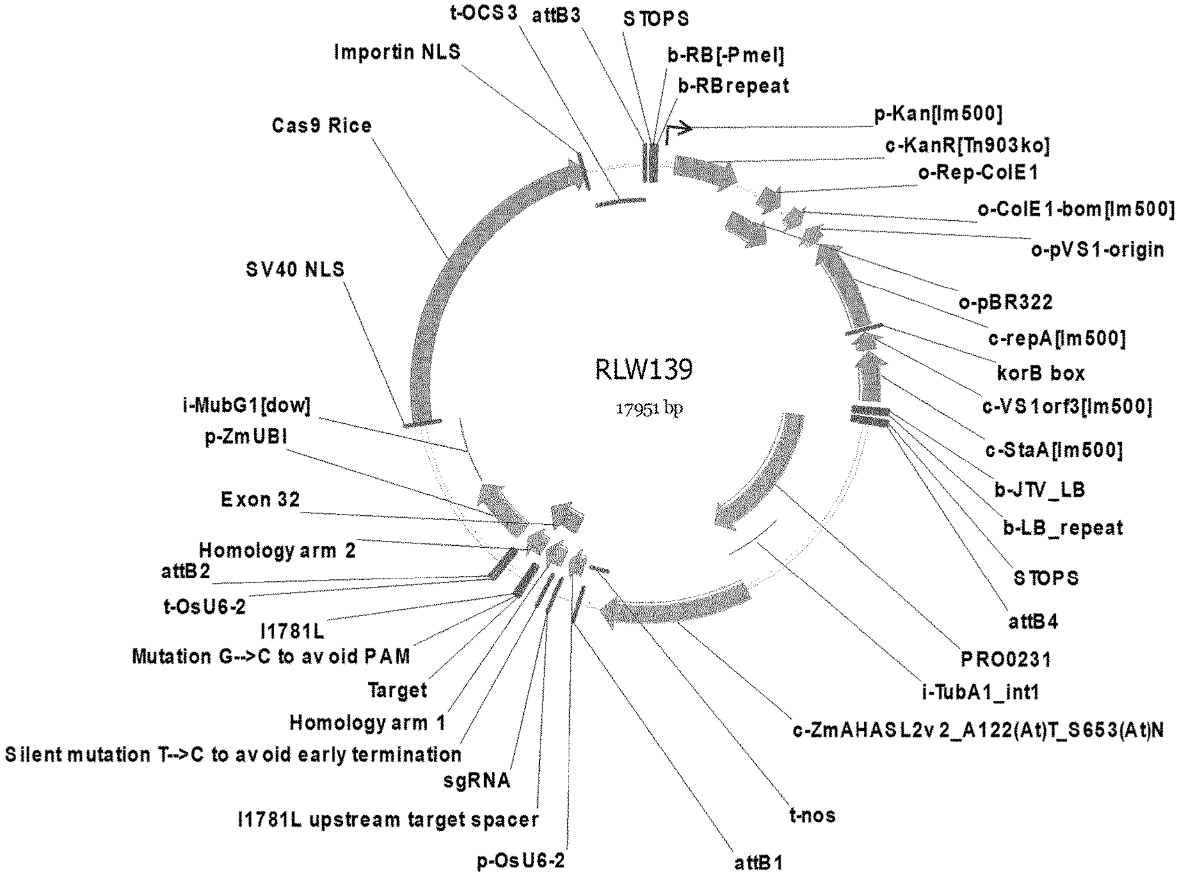

FIG. 24 shows the schematic drawing of the EcoRI/XbaI fragment of the various plasmids used in this study (as exemplified in FIG. 2 with plasmid pCC004). The Cas9 endonuclease, the PmanP promoter and the vector backbone with pUC replication origin, pE194 replication origin, kanamycin resistance gene are not shown. The promoter (Pro) driving the transcription of downstream genetic elements is indicated. PS=Protospacer; gRNA=guide RNA consisting of crRNA-loop-tracrRNA, T=lambda T0 terminator; homology region A and homology region B are depicted as arrows indicative of the orientation of the amyE gene. Detailed description of the plasmid genetic elements by J. Altenbuchner (Altenbuchner J. 2016. Editing of the *Bacillus subtilis* genome by the CRISPR-Cas9 system. Appl Environ Microbiol 82:5421-5).

FIG. 25

The gene knockout efficiency as exemplified for the amylase gene for each gene deletion construct (pJOE8999, pCC005-pCC008) relative to pCC004 is plotted against the deletion constructs as indicated.

FIG. 26 shows 0.8% agarose gels of PCR reactions with oligonucleotides Seq ID NO: 60 and 61 on genomic DNA of 13 individual clones from gene deletion reactions with indicated plasmids pCC004, pCC005, pCC006, pCC007, pCC008. The amplification of a DNA fragment of 1.4 kb indicates gene knockout by recombination whereas a DNA fragment of 3.4 kb indicates amylase gene inactivation by rather a SOS repair mechanism. The 3.4 kb band for WT indicates wildtype amylase locus of B-.*subtilis* WT ATCC6051. C denotes water control with no genomic DNA added. M indicates DNA ladder ‘Perfect plus 1 kb DNA ladder’ (roboklon) with the size of three bands indicated (1.0 kb, 1.5 kb. 4.0 kb).

EXAMPLES

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells are performed as described (Sambrook J, Fritsch E F and Maniatis T (1989)). Sequence analyses of recombinant DNA are performed with a laser fluorescence DNA sequencer (Applied Biosystems, Foster City, Calif., USA) using the Sanger technology (Sanger et al., 1977). Unless described otherwise, chemicals and reagents are obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases are from New England Biolabs (Ipswich, Mass., USA) or Roche Diagnostics GmbH (Penzberg, Germany). Oligonucleotides are synthesized by Eurofins MWG Operon (Ebersberg, Germany).

Introduction to Experimental Procedures

A yeast codon-optimized version of the Cas9 protein bearing a C-terminus SV40 nuclear localization signal (SEQ ID NO: 1) was synthetized and cloned into a yeast expression vector. The same vector included one or more guide RNAs (gRNAs) expressed from the *Saccharomyces cerevisiae* SNR52 polymerase III promoter.

Cas9 binds DNA and cleaves both strands upon recognition of a target sequence by the gRNA, but only if the correct protospacer-adjacent motif (PAM) is present at the 3' end. Theoretically, any sequence of the form GN20GG can be targeted. So, a second vector was constructed for co-expression in yeast of a reporter system (GAL4-UAS (SEQ ID NO: 7)) to be targeted by the designed CRISPR system. gRNA-donor fusions (fusion NA) were used to target and repair several non-functional Gal4 targets (SEQ ID NOs: 9-15).

Gal4 (SEQ ID NO: 8) is a yeast transcriptional activator consisting of two-components: the DNA binding domain located N-terminus and the region for transcriptional activation at C-terminus. Gal4 binds to the specific recognition sequence UAS (upstream activating sequence) of marker genes in the yeast genome, activating their transcription. The MaV203 yeast strain contains single copies of each of three reporter genes (HIS3, URA3 and lacZ) that are stably integrated at different loci in the yeast genome. The promoter regions of URA3, HIS3, and lacZ are unrelated (except for the presence of GAL4 binding sites).

Several non-functional (deleted and/or disrupted by insertion of a STOP codon) versions of Gal4 were synthesized (SEQ ID NOs: 9-15) and transformed into yeast cells, so that they could be targeted and repaired by the co-expressed CRISPR machinery. Restoration of the full-length Gal4 by homologous recombination (HR) with the appropriate repair donor sequence provided with the CRISPR components results in activation of lacZ and HIS3 reporter genes. Gal4 gene repair and consequent transcription activation can be monitored by cell growth on plates lacking histidine, whereas induction of the lacZ gene results in a blue color when assayed with X-gal (5-bromo-4-chloro-3-indolyl-β-D-galactopyranoside).

The employed yeast strain contains two additional auxotrophic mutations (leu2 and trp1) to allow selection for both expression constructs.

To verify repair efficacy increase of the fusion system disclosed here, all experiments were performed in parallel with non-fused cassettes, in which donor and guide RNA are transcribed separately.

Yeast Strain, Media and Cultivation Conditions

The *Saccharomyces cerevisiae* strain used in the examples described is MaV203 (MATα, leu2-3,112, trp1-901, his3Δ200, ade2-101, gal4Δ, gal80Δ, SPAL10::URA3, GAL1::lacZ, HIS3UAS GAL1::HIS3@LYS2, can1R, cyh2R), commercialized by Life Technologies. Yeast was grown in Synthetic Minimal Media (SD Media) based upon Yeast Nitrogen Base supplemented with 2% glucose and lacking the appropriate auxotrophic compounds (ForMedium, United Kingdom). Cultures were grown at 30° C., either in a shaker or incubation oven. *Escherichia coli* was used as propagation microorganism for all the plasmids used in our experiments, as well as for further propagation and maintenance of the modified targets. *E. coli* was grown according standard microbiological practices (Molecular Cloning: A Laboratory Manual, 3rd ed., Vols 1, 2 and 3. J. F. Sambrook and D. W. Russell, ed., Cold Spring Harbor Laboratory Press, 2001). Plasmids containing the Cas9, guide RNA and donor NA included a pUC-based replication origin and ampicillin resistance gene for replication and maintenance in *E. coli*. Whereas GAL4 target plasmids contained a gentamicin resistance gene (Gmr).

Example 1 Plasmid Construction

The Cas9 gene was a yeast codon-optimized version of the *Streptococcus pyogenes* Cas9 (SpCas9; WO2007/025097) originally constructed for expression in eukaryotic cells (Mali et al (2013) Science 339(6121); Cong et al (2013) Science 339(6121)). This Cas9 gene was tagged with a SV40 nuclear localization signal at both ends and synthesised. Also, the gRNA and donor expression cassette containing the SNR52 promoter for in vivo RNA synthesis were synthesised.

The GAL4-AD coding sequence in pDEST22 (Life Technologies) was replaced by the synthetic Cas9 via Seamless Cloning (Life Technologies). This vector contains the constitutive moderate-strength promoter and transcription terminator of the yeast Alcohol Dehydrogenase gene (ADH1) for expression in yeast as well as a TRP1 gene for selection in yeast on medium lacking tryptophan.

The same vector contains two recombination sites, attR1 and attR2, flanking a chloramphenicol resistance gene (Cmr) and a ccdB gene, allowing the designed gRNA and donor expression cassettes (as fusion or dual molecule) to be introduced in the same expression vector via Gateway Cloning (Life Technologies). Following the LR recombination reaction, the Cmr and ccdB genes were replaced by the fusion NA cassette or non-fused donor and guide expression cassettes.

Modified GAL4 coding sequences used as targets for CRISPR repair in yeast were synthesized. The pDEST32 plasmid for expression in yeast (Life Technologies) was cut with HindIII and SacII and the backbone, containing the ADH1 promoter and terminator, was gel purified. The GAL4 synthesized inserts were assembled into the vector using Seamless Cloning. This vector included a LEU2 gene for selection in yeast on medium lacking tryptophan.

Target-sites for recognition by Cas9 in the GAL4 sequence were empirically selected by choosing 20-mer regions preceding potential PAM (NGG) sequences within the GAL4 gene (Sternberg et al (2014); Nature 507(7490)).

To facilitate Cas9 binding and R-loop formation, we chose a single guide RNA design with the secondary structure containing a dangling spacer, an extended hairpin region and a long 3' end, as initially designed by Jinek et al (2012) Science; 337(6096)).

Example 2 Yeast Transformation

Simultaneous transformation of the CRISPR editing tools (Cas9 enzyme and fusion NA expressing cassette) and GAL4 target plasmid was performed by heat-shock as described in the manufacture's protocol (Life Technologies) and propagated in the appropriate synthetic complete (SC) media lacking the auxotrophic compounds complemented by the plasmids being introduced (leucine and tryptophan). The transformed cells were allowed to propagate overnight and equal amounts of transformants (according to OD measurement) were transferred to solid plates containing synthetic complete (SC) media lacking histidine with 100 mM 3-Amino-1,2,4-triazole (3-AT; ForMedium, UK). Expression of HIS3 (for allowing yeast grow in medium without histidine) is GAL4-dependent and therefore transformants are only able to grow if GAL4 repair had occurred. More above, 3-AT is a competitive inhibitor of the product of the HIS3 gene, by applying 3-AT to the yeast transformants which are dependent upon HIS3 to produce histidine, an increased level of HIS3 expression is required in order for the yeast cells to survive.

Additionally the yeast strain used contained a lacZ marker gene under the control of GAL4, which allowed for blue/white selection of GAL4-repaired transformants. Induction of the lacZ gene results in a blue color when assayed with X-gal (5-bromo-4-chloro-3-indolyl-3-D-galactopyranoside).

Example 3 X-Gal Assay

Transformants growing in plates lacking histidine were replica plated onto a nitrocellulose membrane (Hybond, GE Healthcare) placed on the surface of a plate with YPAD medium (Complex yeast media containing a homogeneous blend of Peptone, Yeast Extract and Glucose; ForMedium, UK). Assay was performed after 18-24 h incubation of the YPAD plates containing a membrane. For each membrane, 5 mg X-gal were dissolved in 50 μl DMF and combined with 30 μl 2-mercaptoethanol and 5 ml Z buffer. This solution was used to saturate two round filter papers (Whatman 541) in a 15-cm petri dish. Using forceps, the membrane was carefully remove from the surface of the YPAD plate and completely immersed in liquid nitrogen for about 20 seconds. The frozen membrane was placed on top of the soaked Whatman filters (colony side up). The plates were tightly covered and incubate at 37° C. Appearance of blue color was monitored after 24 hours.

Example 4 Sequencing of Target (CRISPR Repaired) Plasmids

Four each experiment, at least eight GAL4-repaired positive transformants (colonies able to grow in medium without histidine) were sub-cultured overnight in liquid medium and the GAL4 containing plasmid was isolated (using Zymoprep Yeast Plasmid Miniprep II, Zymo Research). The isolated plasmids were introduced in *E. coli* for further propagation and commercial sequencing. GAL4 sequencing allowed verification of the sequence repair and assembly with the donor molecules.

Sanger sequencing of Gal4 gene in the positive clones further validated the sequence specificity of this targeting process, and showed no difference in repair of cells expressing the donor and gRNA as fusion or non-fused, even if cells transformed with fusion NA exhibit a much higher number of successful HR events.

Example 5 Deleting 1nt with 15 bp Homology Arms

Fusion of donor (donor 1; SEQ ID NO: 26) to the guide RNA resulted in repaired transformants (able to grow on medium lacking histidine), whereas no growth was observed for transformants with non-fused guide and donor RNA. The low efficiency of gene repair is consistent with the reduced sequence overlap available for homologous recombination.

Example 6 Deleting 1nt with 50 bp Homology Arms

Fusion of donor (donor 2; SEQ ID NO: 27) to the guide RNA resulted in at least 50 times more transformants than with non-fused donor and guide NA. Sequencing of the Gal4 gene in the positive clones showed that repair results only or very largely from HR (no evidence of NHEJ for all sequenced clones).

Example 7 Inserting 20nt with 50/26 bp Homology Arms

The same fusion NA as above was used to repair a similar target where 20nt were removed (target 3; SEQ ID NO: 11), and as a consequence one homology arm was reduced. Fusion resulted in about 5 times more transformants than with non-fused donor and guide NA. Sequencing of the Gal4 gene in the positive clones showed that repair results exclusively from homologous recombination.

Example 8 Inserting Missing 400 bp with 50 bp Homology Arms (while Testing Two Target Sequences 3nt Apart)

We tested for simultaneous targeting of two sequences (spacer 2 and spacer 3; SEQ ID NOs: 20 and 21) located in close proximity (3nt gap between the two 20 nt target), both independently and together (multiplexed targeting). The multiplex fusion cassette consisted of promoter followed by two tandem fusion NA sequences, resulting in production of a single molecule composed of two gRNAs and repair templates. Our experiments clearly showed that fusion NA is also amenable for targeting two sequences simultaneously.

For both targets repair in the presence of the donor-guide fusion was largely more efficient than with non-fused version (up to 10 times more for targeting with space 2 and five times for spacer 3).

Example 9 Inserting Full GAL4 Gene (960 bp) Except HR Ends with 120 bp Homology Arms In order to test if fusion CRISPR could be effective for introduction full length coding sequences, we have tested introducing the full length GAL4 gene (SEQ ID NO: 7). As example, we have selected for 120 bp homology arms as to keep the ratio of donor/homology arm length already found to be effective in example 4. Insertion of full-length GAL4 gene is about four times more effective with Fusion construct.

Our results show that targeted editing is at least 50 times more efficient when the repair donor sequence was fused to the gRNA. The experiments performed indicate a broad Fusion-related improved effectiveness from a single base removal up to full gene insertion. The examples reported show that this CRISPR fusion system is suitable to carry relatively large Donor molecules fused to the guide RNA.

Example 10a Constructs for Expression in Rice

To accommodate the CRISPR/Cas system to *Agrobacterium*-mediated plant transformation, Gateway binary T-DNA vectors have been designed for co-expression of Cas9 nuclease and guide RNA-donor expression cassette (either as single or dual RNA molecules). A version of the *Streptococcus pyogenes* Cas9 (SpCas9) codon-optimized for expression in rice (*Oryza sativa*), attached to SV40 nuclear localization signals (NLS) at both ends (Seq ID NO: 6), was synthesized The synthesized cassette includes the maize polyubiquitin (Ubi) promoter (Seq ID NO: 32) for constitutive expression located upstream the Cas9, and the nopaline synthase (nos) terminator (Seq ID NO: 33) at the 3'-end. This gene cassette has been cloned via Seamless into a vector, which contained as functional elements within the T-DNA borders: a plant selectable marker; a screenable marker expression cassette; and a Gateway cassette intended for LR recombination with the gRNA-donor expression cassette in an entry clone.

Three gRNA have been designed, which targeted the rice Protoporphyrinogen Oxidase (PPO) gene (WO/2015/092706; WO/2015/022640 (Seq ID NO: 35), resulting in genomic double-strand cleavage at selected target sites (spacer 8, spacer 9 and spacer 10 (Seq ID NO: 36, 37 and 38)). Modifications aim two amino acid substitutions (L419F, F442V; single site mutations and double site mutation), which have been previously identified as potential hotspots for Saflufenacil survival.

The RNA expressing cassette (including gene-specific spacer sequences for the selected locations in the PPO gene) containing either fusion or non-fusion NA were synthesized and cloned into entry vectors, which was cloned (via Gateway) into the destination vector containing the CAS9 expression cassette. RNA expression of gRNA and donor is driven by pol III type promoter of U3 snRNA.

After the LR recombination step, the resulting expression vector is transformed into *Agrobacterium* strain LBA4044 according to methods well known in the art.

Example 10b Constructs for Expression in Rice

An identical vector as described in Example 10a was synthesized with the exception that the NLS derived from SV40 was replaced with plant nuclear localization signals (NLS) (MSERKRREKL, SEQ ID NO: 71) at the N-terminal end and importin NLS (KRPAATKKAGQAKKKK SEQ ID NO: 72) at the C-terminal end and the promoter driving the RNA expression of gRNA and donor was rice pol III type promoter of U3 snRNA (SEQ ID NO: 73).

The RNA expressing cassette (including gene-specific spacer sequences for the selected locations in the PPO gene) containing either fusion or non-fusion NA were synthesized and cloned into entry vectors, which was cloned (via Gateway) into the destination vector containing the CAS9 expression cassette.

The vector used as non fusion control contains PRO0231::U3 RNA pol III promoter::spacer::sg RNA scaffold::TTTTTTTT terminator::U3 RNA pol III promoter::template::TTTTTTTT terminator.

After the LR recombination step, the resulting expression vector is transformed into *Agrobacterium* strain LBA4044 according to methods well known in the art.

Example 11 Rice Transformation and Selection of Herbicide-Tolerant Calli

The *Agrobacterium* containing the expression vector is used to transform scutellum-derived callus of indica rice (*Oryza sativa* L.). Sterilization of mature seeds has been carried out by incubating for one minute in 70% ethanol, followed by 40 minutes in 6% sodium hypochlorite, followed by a 3 to 5 times wash with sterile MQ water. The sterilized seeds are then germinated on a medium containing 2,4-D (callus induction medium). After 6 days of incubation in the light, scutellum-derived calli are incubated for 90 seconds in bacterial solution ($OD_{600}$=0.1), drained, dried on sterile filter paper and then co-cultured with bacteria for 3 days in the dark at 25° C. The co-cultivated calli are transferred to selection medium containing G418 for 4 weeks in the light at 32° C. Antibiotic-resistant callus pieces are transferred to selection medium containing 25 or 50 µM saflufenacil (Kixor™) for 2 weeks in the light at 32° C. These herbicide selection conditions have been established through the analysis of tissue survival in kill curves with saflufenacil. After transfer of herbicide-resistant material to a regeneration medium and incubation in the light, the embryogenic potential is released and shoots developed in the next four to five weeks. Shoots are excised from the calli and incubated for 2 to 3 weeks on an auxin-containing medium until shoots are well rooted for transfer to soil. Hardened shoots are grown under high humidity and short days in a greenhouse.

Example 12 Molecular Characterization of the Herbicide Tolerant Transformants Leaf tissue collected from each individual plant transformant is used for copy number analysis and molecular characterization of PPO gene sequence mutations. Genomic DNA is extracted using a Wizard 96 Magnetic DNA Plant System kit (Promega, U.S. Pat. Nos. 6,027,945 & 6,368,800) as directed by the manufacturer. Isolated DNA was PCR amplified using the appropriate probe, together with forward and reverse primers. Following this quantitative PCR analysis to verify copy number of the T-DNA insert, only low copy transgenic plants that exhibit tolerance to the selection agent are kept for harvest of T1 seeds. Seeds are then harvested three to five months after transplanting.

PCR amplification of PPO genomic sequences is performed using Fusion Taq DNA Polymerase (Thermo Scientific) using thermocycling program as follows: 96° C. for 15 min, followed by 35 cycles (96° C., 30 sec; 58° C., 30 sec; 72° C., 3 min and 30 sec), 10 min at 72° C. PCR products are verified for concentration and fragment size via agarose gel electrophoresis, and send for sequencing using the PCR primers. Sequence analysis is performed on the representative chromatogram trace files and corresponding AlignX alignment with default settings and edited to call secondary peaks.

Mutations identified in several individuals, based on sequence information, show that the technology described in this invention, which involves fusion of NA to the CRISPR components, is applicable to plant organisms. Homologous recombination repair with the provided donors confers tolerance to Saflufenacil (single site mutation and multiple site mutation).

Example 13 Controlled Gene Knockout in *Escherichia coli*

In this example FusionCRISPR is being used to knockout target gene RecA in *E. coli* strain K-12 substr. MG1655. The bacterial strain is inoculated in 10 ml SOB in a 100 ml Erlenmeyer flask and grown overnight at 37° C. (SOB: 2% bacto-tryptone, 0.5% yeast extract, 10 mM NaCl, 2.5 mM KCl, 10 mM $MgCl_2$, 10 mM $MgSO_4$). 3 ml of the overnight culture is diluted in 250 ml SOB in a 1 liter Erlenmeyer flask and grown at 18° C. with vigorous shaking (200-250 rpm) until the $OD_{660}$ nm is 0.6. Subsequently the culture is transfered to precooled 50 ml tubes and centrifuge at 5000 rpm for 5 min at 4° C. The pellet is resuspend in ⅓ of the original volume of ice-cold TB (TB: 250 mM KCl, 10 mM PIPES free acid, 15 mM $CaCl_2.2H_2O$, 55 mM $MnCl_2.2H_2O$) and incubated on ice for 10 min. The cells are centrifuged at 5000 rpm for 5 min at 4° C. and the pellet resuspended in 1/12 of the original volume of ice-cold TB. DMSO is added with gentle mixing to a final concentration of 7%. The competent cells are alliquoted in 200 µl portions and freezed in liquid nitrogen. One aliquot of competent cells is added together with 0.1-0.5 µg of plasmid containing a chloramphenicol selectable marker and Cas9 expression cassette as present in pCas9 [Jiang W, Bikard D, Cox D, Zhang F, Marraffini L (2013) RNA-guided editing of bacterial genomes using CRISPR-Cas systems. Nat Biotechnol] and a cassette for expression of fusion RNA [Zhao D, Yuan S, Xiong B, Sun H, Ye L, Li J, Zhang X, Bi C. (2016) Development of a fast and easy method for *Escherichia coli* genome editing with CRISPR/Cas9. Microb Cell Fact. 15(1):205] with the following FusionCRISPR sequence and RecA spacer:

(SEQ ID NO: 42)

```
gatgtggaaaccatctctacGTTTTAGAGCTAGAAATAGCAAGTTAAAAT
AAGGCTAGTCCGT-TATCAACTTGAAAAAGTGGCACCGAGTCGGTGCTT
TCCATGGATGTGGAAAC-CATCGCTTTCACTGGATATCGCG
```

in which the spacer recognizing RecA is highlighted, the essential sequences for the sgRNA is capitalized, not underlined, homology arm 1 with RecA is double underlined and homology arm 2 with RecA is single underlined. Promoters and terminators for the FusionCRISPR construct and Cas9 can be chosen from world wide web at parts.igem.org/Promoters/Catalog/Constitutive and world wide web at parts.igem.org/Terminators/Catalog. The targeted RecA gene has the following sequence:

(SEQ ID NO: 43)
ATGGCTATCGACGAAAACAAACAGAAAGCGTTGGCGGCAGCACTGGGCCAGATTGA-
GAAACAATTTGGTAAAGGCTCCATCATGCGCCTGGGTGAAGAC-
CGTTCCATGGATGTGGAAACCAT**CTCTAC*CGG*TT**CGCTTTCACTGGATATCGCGCTT-
GGGGCAGGTGGTCTGCCGATGGGCCGTATCGTCGAAATCTACGGACCG-
GAATCTTCCGGTAAAACCACGCTGACGCTGCAGGTGATCGCCGCAGCG-
CAGCGTGAAGGTAAAACCTGTGCGTTTATCGATGCTGAACACGCGCTG-
GACCCAATCTACGCACGTAAACTGGGCGTCGATATCGACAAC-
CTGCTGTGCTCCCAGCCGGACACCGGCGAGCAGGCACTGGAAATCTGTGAC-
GCCCTGGCGCGTTCTGGCGCAGTAGACGTTATCGTCGTTGACTCCGTGGCGGCAC-
TGACGCCGAAAGCGGAAATCGAAGGCGAAATCGGCGACTCTCACATGGGCCTT-
GCGGCACGTATGATGAGCCAGGCGATGCGTAAGCTGGCGGGTAACCTGAAGCAG-
TCCAACACGCTGCTGATCTTCATCAACCAGATCCGTATGAAAATT-
GGTGTGATGTTCGGTAACCCGGAAACCACTACCGGTGGTAACGCGCTGAAATTCTAC-
GCCTCTGTTCGTCTCGACATCCGTCGTATCGGCGCGGTGAAAGAGGGCGAAAAC-
GTGGTGGGTAGCGAAACCCGCGTGAAAGTGGTGAA-
GAACAAAATCGCTGCGCCGTTTAAACAGGCTGAATTCCAGATCCTCTAC-
GGCGAAGGTATCAACTTCTACGGCGAACTGGTTGACCTGGGCGTAAAAGAGAA-
GCTGATCGAGAAAGCAGGCGCGTGGTACAGCTACAAAGGTGAGAA-
GATCGGTCAGGGTAAAGCGAATGCGACTGCCTGGCTGAAAGATAACCCGGAAAC-
CGCGAAAGAGATCGAGAAGAAAGTACGTGAGTTGCTGCTGAG-
CAACCCGAACTCAACGCCGGATTTCTCTGTAGATGATAGCGAAGGCGTAG-
CAGAAACTAACGAAGATTTTTAA in which the PAM sequence is in italics, homology arm 1 is double underlined, homology arm 2 is single underlined, and the protospacer is the following portion of the sequence:

GATGTGGAAACCATCTCTAC.

DNA and cells are kept on ice for 30 minutes prior to a 90 seconds heat shock at 42° C. Cells and DNA are transferred to ice and 1 ml LB is added after 1 minute (LB: 1% tryptone, 1% NaCl, 0.5% yeast extract, pH 7.0). Cells are allowed to recover for 1 hour at 37° C. The recovery phase can be extended to 16 hours to allow the FusionCRISPR components more time to edit the *E. coli* genome. 25 μg/ml chloramphenicol should be added after 1 hour to prevent loss of the plasmid. Cells are plated on LB medium with 25 μg/ml chloramphenicol and incubated at 37° C. for 1 day. Single colonies are selected from plate and grown overnight in LB with chloramphenicol at 37° C. after which genomic DNA is extracted [He, F. (2011) *E. coli* Genomic DNA Extraction. Bio-protocol Bio101: e97]. PCR with a forward primer upstream from the first homology arm (ATGGCTATCGACGAAAACAAA) (SEQ ID NO: 44) and reverse primer downstream from the second homology arm (CGTCAGCGTGGTTTTACCGGA) (SEQ ID NO: 45) is performed to identify colonies in which the 11 nucleotides shown in bold in the RecA sequence (SEQ ID 43) are no longer present due to homologous recombination repair with the FusionCRISPR template. PCR fragments can be sequenced (expected size 220 bp) or, in this case, subjected to AgeI digestions (the deleted sequence around PAM contains the AgeI recognition site ACCGGT) to verify modification of the locus after standard gel electrophoresis. Deletion of 11 nucleotides ensures a disruption of the open reading frame.

Example 14 Controlled Knockout of the PRDM9 Gene in Human-Induced Pluripotent Stem Cells (hiPSCs) and HEK293 Cells Cell culture maintenance, plasmid construction, transfection methods and molecular analysis of genome editing in hiPSCs and HEK293 cells are described in great detail in Yang L, Yang J L, Byrne S, Pan J, Church G (2014) CRISPR/Cas9-directed genome editing of cultured cells. Current Protocols in Molecular Biology 31.1.1-31.1.17. For knockout of the PRDM9 gene, all steps are followed as described therein, with only a minor change in the gRNA plasmid design. The synthesized gRNA should have the following sequence:

(SEQ ID NO: 46)

-continued

*TGTACAAAAAAGCAGGCTTTAAAGGAACCAATTCAGTCGACTGGATCCGGTAC-*

*CAAGGTCGGGCAGGAAGAGGGCCTATTTCCCATGATTCCTTCATATTTGCATATAC-*

*GATACAAGGCTGTTAGAGAGATAATTAGAATTAATTTGACTGTAAACACAAAGA-*

*TATTAGTACAAAATACGTGACGTAGAAAGTAATAATTTCTTGGGTAGTTTGCAG-*

*TTTTAAAATTATGTTTTAAAATGGACTATCATATGCTTACCGTAACTT-*

*GAAAGTATTTCGATTTCTTGGCTTTATATATCTTGTGGAAAGGACGAAACACC*ggcatccctcaggctgggctGTTTTAGAGCTAGAAATAGCAAGTTAAAATAAGGCTAG-

TCCGTTATCAACTTGAAAAAGTGGCACCGAG-

TCGGTGCTGGCCATCAGGCATCCCTCAGTATGGAATGAGGCATCTGATtttttt in which the U6 promoter is shown in italics, the spacer recognizing PRDM9 exon ENSE00001804383 is in lowercase (i.e., ggcatccctcaggctgggct), the essential sequences for the sgRNA is capitalized not underlined or in italics, homology arm 1 with PRDM9 is double underlined, homology arm 2 with PRDM9 is single underlined and the terminator is in small case. The targeted PRDM9 exon ENSE00001804383 has the sequence:

(SEQ ID NO: 47)

ATTGTGAGATGTGTCAGAACTTCTTCATT-

GACAGCTGTGCTGCCCATGGGCCCCCTACATTTGTAAAGGACAGTGCAGTG-

GACAAGGGGCACCCCAACCGTTCAGCCCTCAGTCTGCCCCCAGGGCTGAGAATT-

GGGCCATCAGGCATCCCTCAGGCTGGGCT*TGG*AG-

TATGGAATGAGGCATCTGATCTGCCGCTGGGTCTGCACTTT-

GGCCCTTATGAGGGCCGAATTACAGAAGACGAAGAGGCAGCCAACAATGGA-

TACTCCTGGCTGTGG in which the PAM sequence is in italics, homology arm 1 is double underlined, homology arm 2 is single underlined, and the protospacer is the following portion of the sequence:

GGCATCCCTCAGGCTGGGCT.

The nucleotides shown in boldface are deleted upon homologous recombination with the FusionCRISPR construct resulting in a frame shift as shown using PCR amplifying the respective genomic region from genomic DNA and subsequent sequencing of the resulting PCR products.

Example 15: Introduction of Point Mutations in Rice Plants Leading to Cyclohexanedione (DIM) and/or Aryloxyphenoxypropionate (FOP) in Rice Mutations I1781L and G2096S in plastidic Acetyl Coenzyme A Carboxylase (ACCase) are known to confer tolerance to DIM and FOP herbicides. These mutations can be introduced at the endogenous ACCase locus using the following vectors.

Vector RLW137 SEQ ID NO: 66 The backbone of this vector is the gateway-enabled construct RLW121 SEQ ID NO: 62.

ENTR vectors for RLW137 are vectors CC003 SEQ ID NO: 63 (selectable marker for the incoming T-DNA), CC018 SEQ ID NO: 64 (producing the FusionCRISPR construct which targets and introduces G2096S after cutting upstream from the DNA that corresponds to G2096) and CC006 SEQ ID NO: 65 (providing Cas9).

CC018 (short for CRISPRCas018) contains ~300 nt homology arms flanking the incoming nucleotides (in this case encoding G2096S). Additional mutations are co-introduced to avoid self-cleavage of the T-DNA (mutated PAM, alternatively or in addition the spacer could include many mutations which are preferably silent in parts that correspond with exons and do not affect intron/exon borders if present) and early termination of transcription on long stretches of T present either in the homology arms or incoming nucleotides.

A control vector is synthesized which is identical except that the donor molecule is expressed as separate molecule which is not linked to the guide RNA.

Vector RLW137 and the control vector are transformed into rice using the protocol described above. Initial selection is for the presence of the ZmAHAS A122T S553N marker. Analysis of the transformed plants is performed as described in example 12.

Similar to the procedure described above for RLW137, RLW138 introduces the same mutation, but this time using an alternative, downstream protospacer site. RLW138 consists of the RLW121 backbone with the CC003, CC019 (SEQ ID NO: 67) and CC00006.

The mutation 11781L is introduced by RLW139 (SEQ ID NO: 70) consisting of RLW121, CC003, CC020 (SEQ ID NO: 69) and CC00006.

Example 16 Application of Fusion CRISPR in *Bacillus*

Electrocompetent *Bacillus subtilis* Cells and Electroporation

Transformation of DNA into *B. subtilis* ATCC 6051 is performed via electroporation. Preparation of electrocompetent *B. subtilis* ATCC 6051 cells and transformation of DNA is performed as essentially described by Xue et al (Xue, G.-P., 1999, Journal of Microbiological Methods 34, 183-191) with the following modification: Upon transformation of DNA, cells are recovered in 1 ml LBSPG buffer and incubated for 60 min at 37° C. (Vehmaanperä J., 1989, FEMS Microbio. Lett., 61: 165-170) following plating on selective LB-agar plates. For plasmids containing the temperature-sensitive pE194 replication origin, cells are recovered for 3 h at 33° C.

Plasmid Isolation

Plasmid DNA was isolated from *Bacillus* and *E. coli* cells by standard molecular biology methods described in (Sambrook, J. and Russell, D. W. Molecular cloning. A laboratory manual, 3rd ed, Cold Spring Harbor Laboratory Press, Cold Spring Harbor, N.Y. 2001.) or the the alkaline lysis method (Birnboim, H. C., Doly, J. (1979). Nucleic Acids Res 7(6): 1513-1523). *Bacillus* cells were in comparison to *E. coli* treated with 10 mg/ml lysozyme for 30 min at 37° C. prior to cell lysis.

Annealing of oligonucleotides to form oligonucleotide-duplexes.

Oligonucleotides were adjusted to a concentration of 100 µM in water. 5 µl of the forward and 5 µl of the corresponding reverse oligonucleotide were added to 90 µl 30 mM Hepes-buffer (pH 7.8). The reaction mixture was heated to 95° C. for 5 min following annealing by ramping from 95° C. to 4° C. with decreasing the temperature by 0.1° C./sec (Cobb, R. E., Wang, Y., & Zhao, H. (2015). High-Efficiency Multiplex Genome Editing of *Streptomyces* Species Using an Engineered CRISPR/Cas System. ACS Synthetic Biology, 4(6), 723-728).

Molecular Biology Methods and Techniques

Plasmid pJOE8999:

Altenbuchner J. 2016. Editing of the *Bacillus subtilis* genome by the CRISPR-Cas9 system. Appl Environ Microbiol 82:5421-5.

Plasmid pCC001

The pJOE8999 and the synthetic gene fragment Seq ID 048 provided in a standard *E. coli* cloning vector (pUC derivative) are cut with AvrII and XbaI following isolation of the pJOE8999 plasmid backbone and the smaller AvrII/XbaI fragment of Seq ID 048. The two fragments are ligated using with T4-DNA ligase (NEB) following transformation into *E. coli* XL1-Blue competent cells (Stratagene). The correct plasmid was recovered and named pCC001.

Plasmid pCC002

The pJOE8999 and the synthetic gene fragment Seq ID 049 provided in a standard *E. coli* cloning vector (pUC derivative) are cut with AvrII and XbaI following isolation of the pJOE8999 plasmid backbone and the smaller AvrII/XbaI fragment of Seq ID 049. The two fragments are ligated using with T4-DNA ligase (NEB) following transformation into *E. coli* XL1-Blue competent cells (Stratagene). The correct plasmid was recovered and named pCC002.

Plasmid pCC003

The oligonucleotides SeqID 050 and Seq ID 051 with 5' phosphorylation are annealed to form an oligonucleotide duplex encoding for the protospacer sequence targeting the amylase gene amyE of *B. subtilis* ATCC6051. The plasmid pJOE8999 is cut with BsaI following ligation of the oligonucleotide duplex to recover plasmid pCC003.

Plasmid pCC004

Figure 23:
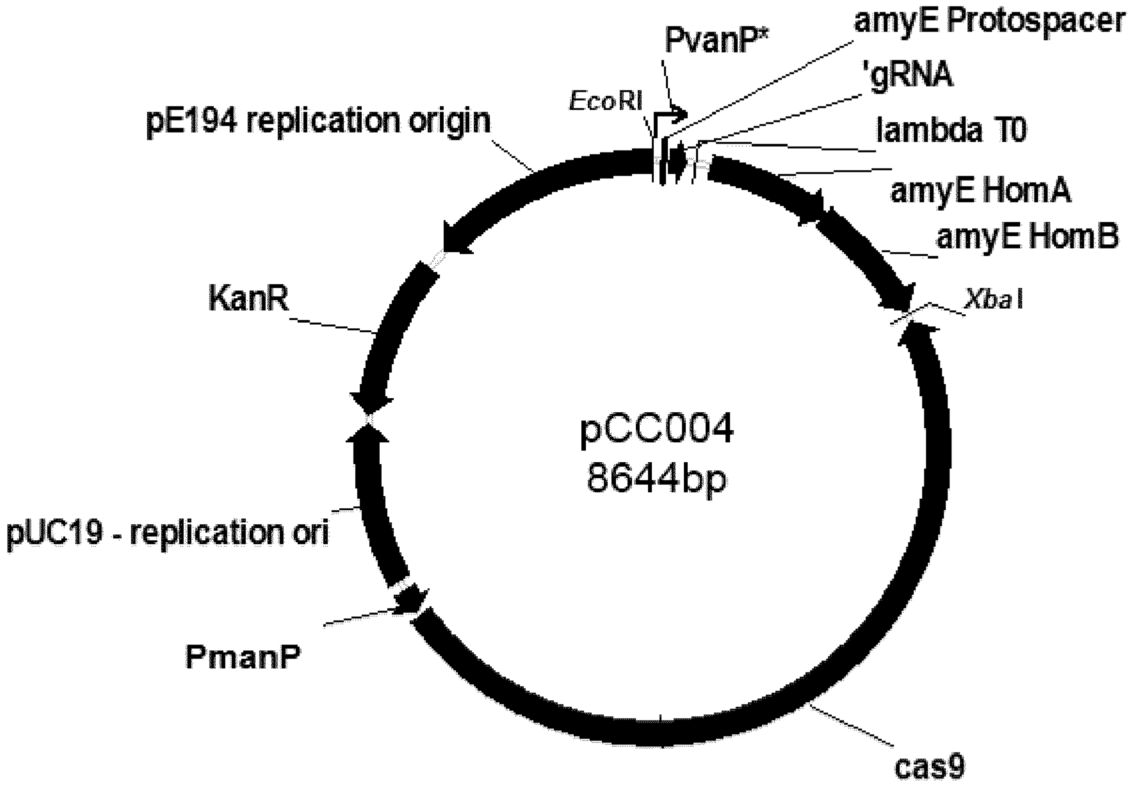
Figure 24:
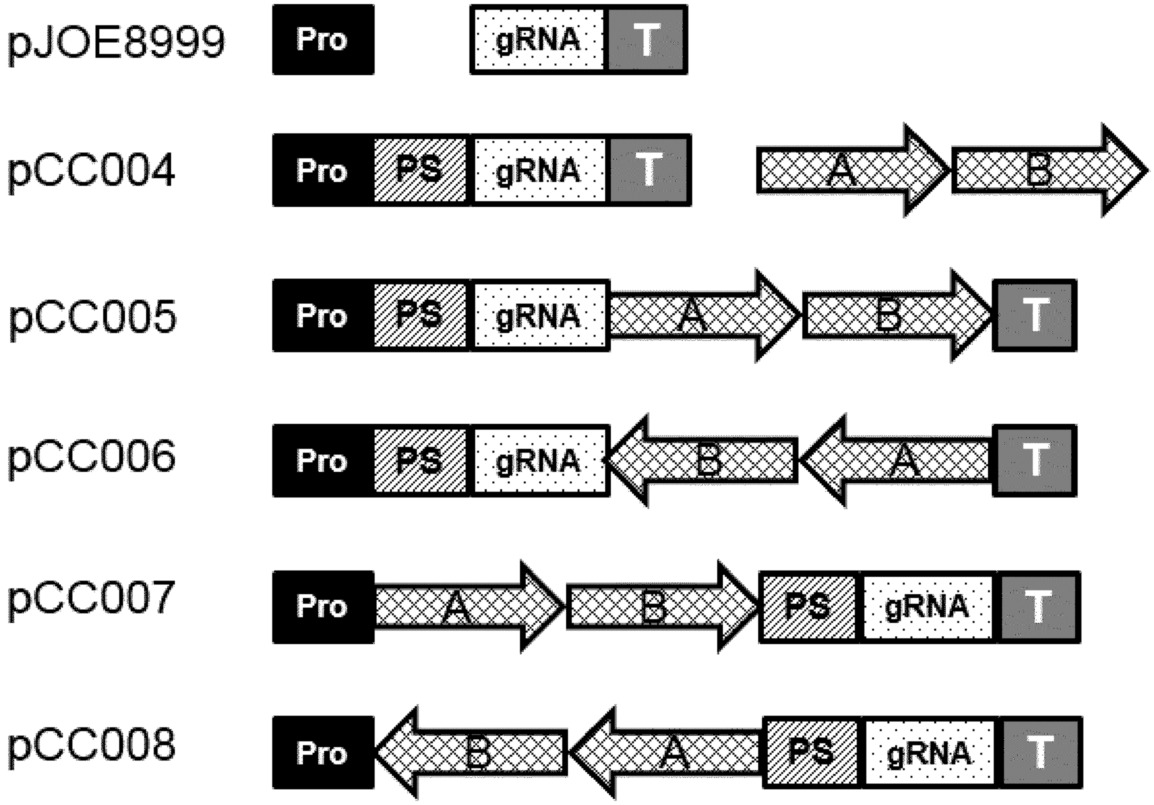

The 5'homology region (also referred to as HomA) and the 3' homology region (also referred to as HomB) adjacent to the amylase amyE gene of *B. subtilis* ATCC6051 were PCR-amplified on isolated genomic DNA with oligonucleotides Seq ID NO: 52, Seq ID NO: 53 and SeqID NO: 54, Seq ID NO: 55 respectively. The two homology regions HomA and HomB were fused and amplified using overlap PCR with oligonucleotides Seq ID NO: 52 and Seq ID NO: 55 to recover the HomAB PCR fragment of the homology regions of the amyE gene. The plasmid pCC003 and the HomAB-amyE PCR fragment were cut with SfiI following ligation with T4-DNA ligase (NEB). The reaction mixture was transformed into *E. coli* XL1-Blue competent cells (Stratagene). The correct plasmid containing the amyE protospacer and the HomAB of amyE was recovered and named pCC004 (FIG. 23).

Plasmid pCC005

The plasmid pCC001 was cut with BsaI following cloning of the amyE protospacer oligonucleotide duplex (SeqID 050/Seq ID051) as described for pCC003. The resulting plasmid and the PCR-fragment of the homology regions HomAB of the amyE gene as described for construction of pCC004 were cut with SfiI following ligation with T4-DNA ligase (NEB). The reaction mixture was transformed into *E. coli* XL1-Blue competent cells (Stratagene). The correct plasmid containing the amyE protospacer and the HomAB of amyE was recovered and named pCC005.

Plasmid pCC006

The 5' homology region (also referred to as HomA) and the 3' homology region (also referred to as HomB) adjacent to the amylase amyE gene of *B. subtilis* ATCC6051 were PCR-amplified on isolated genomic DNA with oligonucleotides Seq ID NO: 56, Seq ID NO: 57 and SeqID NO: 58, Seq ID NO: 59 respectively. The two homology regions HomA and HomB were fused and amplified using overlap PCR with oligonucleotides Seq ID NO: 56 and Seq ID NO: 59 to recover the HomAB PCR fragment of the homology regions of the amyE gene. The plasmid pCC001 was cut with BsaI following ligation of the amyE protospacer oligonucleotide duplex (SeqID NO: 50/Seq ID NO: 51) with T4-DNA ligase (NEB) as described for pCC003. The resulting plasmid and the PCR-fragment of the homology regions HomAB of the amyE gene were cut with SfiI following ligation with T4-DNA ligase (NEB). The reaction mixture was transformed into *E. coli* XL1-Blue competent cells (Stratagene). The correct plasmid containing the amyE protospacer and the HomAB of amyE in reverse orientation compared to pCC005 was recovered and named pCC006.

Plasmid pCC007

The plasmid pCC002 was cut with BsaI following ligation of the amyE protospacer oligonucleotide duplex (SeqID NO: 50/Seq ID NO: 51) with T4-DNA ligase (NEB) as described for pCC003. The resulting plasmid and the PCR-fragment of the homology regions HomAB of the amyE gene as described for construction of pCC004 were cut with SfiI following ligation with T4-DNA ligase (NEB). The reaction mixture was transformed into *E. coli* XL1-Blue competent cells (Stratagene). The correct plasmid containing the HomAB of the amyE gene and the amyE protospacer was recovered and named pCC007.

Plasmid pCC008

The plasmid pCC002 was cut with BsaI following ligation of the amyE protospacer oligonucleotide duplex (SeqID NO: 50/Seq ID NO: 51) with T4-DNA ligase (NEB) as described for pCC003. The resulting plasmid and the PCR-fragment of the homology regions HomAB of the amyE amplified with oligonucleotides Seq ID NO: 56 and Seq ID NO: 59 as described for pCC006 were cut with SfiI following ligation with T4-DNA ligase (NEB). The reaction mixture was transformed into *E. coli* XL1-Blue competent cells (Stratagene). The correct plasmid containing the HomAB of amyE in reverse orientation compared to pCC007 and the amyE protospacer was recovered and named pCC008.

Gene Deletion Using Fusion-CRISPR.

Electrocompetent *B. subtilis* ATCC6051 cells were transformed with 1 μg each of plasmids pJOE8999, pCC004, pCC005, pCC006, pCC007, pCC008 as essentially described by Xue et al (Xue, G.-P., 1999, Journal of Microbiological Methods 34, 183-191) with the following modification: Upon transformation of DNA, cells were recovered in 1 ml LBSPG buffer and incubated for 3 h at 33° C. (Vehmaanperä J., 1989, FEMS Microbio. Lett., 61: 165-170) following plating on LB-Lennox plates supplemented with 20 μg/ml kanamycin and 0.2% D-Mannose for Cas9 induction. Plates were incubated for 20-22 h at 33° C. Up to 10 clones from each plasmid transformation were picked and transferred onto a fresh preheated LB-Lennox-plate following incubation at 50° C. for 18 h. From each large grown colony, cells were picked and 3 strokes on fresh LB-Lennox plates performed to yield single colonies after 7-8 h incubation at 45° C. Single colonies were transferred onto LB-Lennox plates and LB-Lennox plates supplemented with 20 μg/ml kanamycin, following incubation for 16-18 hours at 30° C. Kanamycin-sensitive clones, indicative of plasmid loss, were plated on LB-Lennox plates supplemented with 1% soluble starch following incubation for 20 hours at 30° C. Inactivation of the amylase amyE gene was visualized by covering the plates with iodine containing Lugols solution and analyzed for the presence or absence of a light halo, the latter indicating a successful inactivation.

Figure 25:
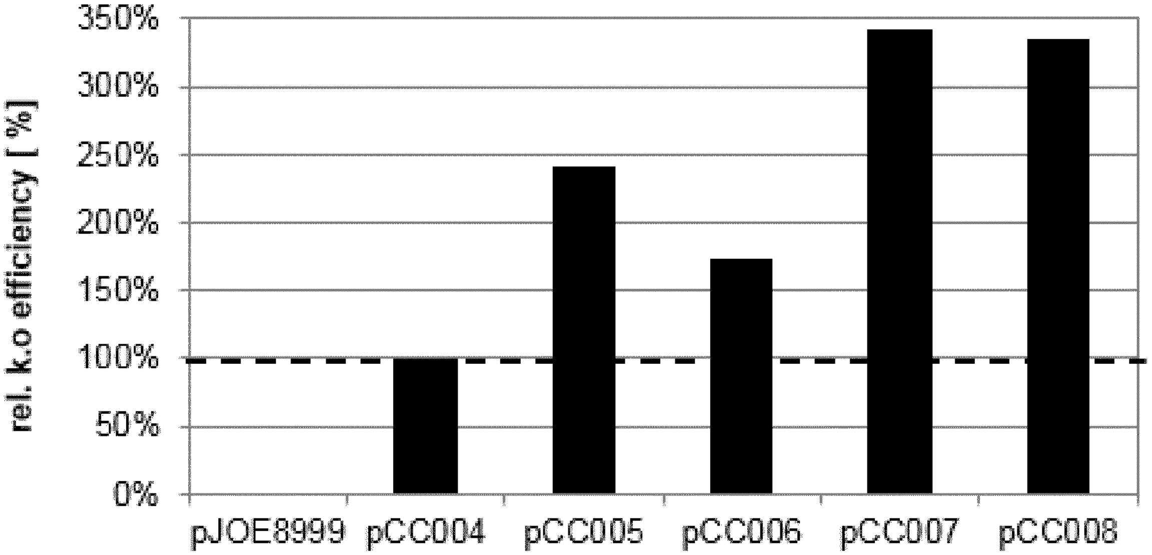
Figure 26:
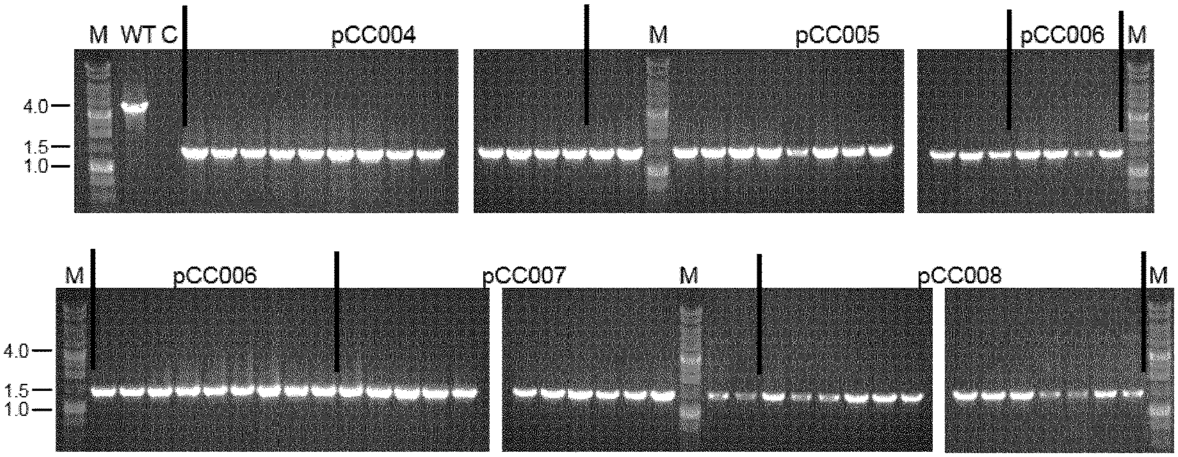

Table 2 summarizes the amount of total clones after plasmid curing, amount of clones with inactivated amylase, the percentage of clones with inactivated amylase relative to total clones and the relative knockout efficiency with the indicated plasmids relative to pCC0004 (FIG. 25)

TABLE 2

| Construct | Subclones total | Subclones Amy. neg. | Subclones Amy. neg. [%] | Relative to pCC004 |
|---|---|---|---|---|
| pJOE8999 | 90 | 0 | 0 | 0 |
| pCC004 | 177 | 42 | 24 | 100 |
| pCC005 | 197 | 113 | 57 | 242 |
| pCC006 | 192 | 79 | 41 | 173 |
| pCC007 | 117 | 95 | 81 | 342 |
| pCC008 | 146 | 116 | 79 | 335 |

What is claimed is:

1. A recombinant fuNA molecule comprising, from 5' to 3', at least one doNA molecule covalently linked to a gNA molecule, wherein the fuNA consists of RNA and the gNA molecule further comprises a scaffold nucleic acid (scaffold NA) molecule.

2. The recombinant fuNA molecule of claim 1, wherein the gNA molecule further comprises a spacer nucleic acid (spacer NA) molecule comprising at least 12 bases complementary to the same number of consecutive bases of the target NA molecule.

3. The recombinant fuNA molecule of claim 2, wherein the spacer NA molecule is 5' to the scaffold NA molecule.

4. The recombinant fuNA molecule of claim 2, wherein the spacer NA molecule is 3' to the scaffold NA molecule.

5. The recombinant fuNA molecule of claim 1, wherein the scaffold NA molecule comprises one nucleic acid molecule, comprising two regions wherein each region comprises at least eight bases being complementary to each other, capable of hybridizing and forming a hairpin structure.

6. The recombinant fuNA molecule of claim 1, wherein the scaffold NA molecule comprises two nucleic acid molecules linked by hybridization, each nucleic acid molecule comprising at least one region of at least eight bases complementary to each other, capable of hybridizing and forming a double-stranded structure.

7. A vector comprising an expression construct comprising a promoter functionally linked to a DNA molecule encoding the fuNA molecule of claim 1.

8. A vector system, comprising a) the vector of claim 7 and b) a vector encoding a site directed nucleic acid modifying polypeptide.

9. A system for modification of a target NA in a cell, comprising a) the vector of claim 7 and b) a vector encoding a site directed nucleic acid modifying polypeptide and c) acell comprising a target NA molecule.

10. A composition, comprising a) the vector of claim 7 and b) a vector encoding a site directed nucleic acid modifying polypeptide and c) a cell comprising a target NA molecule.

11. A method for modification of a target nucleic acid (target NA) molecule in a cell comprising the steps of a) providing a recombinant fusion nucleic acid (fuNA) molecule, wherein said fuNA molecule is an RNA molecule, wherein the fuNA comprises, from 5' to 3', at least one donor nucleic acid (doNA) molecule covalently linked to a guide nucleic acid (gNA) molecule, wherein the gNA molecule further comprises a scaffold nucleic acid (scaffold NA) molecule, b) introducing said fuNA molecule into one or more cells comprising the target NA molecule, c) introducing a site directed nucleic acid modifying polypeptide into said one or more cells, d) incubating the one or more cells under conditions that allow for homologous recombination in said one or more cells, and optionally e) isolating one or more cells in which homologous recombination occurred.

12. The method of claim 11, wherein the gNA molecule further comprises a spacer nucleic acid (spacer NA) molecule comprising at least 12 bases complementary to the same number of consecutive bases of the target NA molecule.

13. The method of claim 12, wherein the spacer NA molecule is 5' to the scaffold NA molecule.

14. The method of claim 12, wherein the spacer NA molecule is 3' to the scaffold NA molecule.

15. The method of claim 11, wherein the scaffold NA molecule is covalently bound to the gNA molecule.

16. The method of claim 11, wherein the scaffold NA molecule comprises one nucleic acid molecule, comprising two regions wherein each region comprises at least eight bases being complementary to each other, capable of hybridizing and forming a hairpin structure.

17. The method of claim 11, wherein the scaffold NA molecule comprises two nucleic acid molecules linked by hybridization, each nucleic acid molecule comprising at least one region of at least eight bases complementary to each other, capable of hybridizing and forming a double-stranded structure.

18. The method of claim 11, wherein the site directed nucleic acid modifying polypeptide is a nucleic acid guided nucleic acid modifying polypeptide or a functional equivalent thereof.

19. The method of claim 11, wherein the fuNA molecule is introduced as one or more expression constructs encoding said fuNA molecule.

20. The method of claim 11, wherein the cell is a microbial, animal, human or plant cell.

* * * * *